(12) United States Patent
Brownlie et al.

(10) Patent No.: US 7,981,427 B2
(45) Date of Patent: Jul. 19, 2011

(54) CANINE RESPIRATORY CORONAVIRUS (CRCV) SPIKE PROTEIN

(75) Inventors: John Brownlie, Hatfield (GB); Victoria Jane Chalker, Hatfield (GB); Kerstin Erles, Hatfield (GB)

(73) Assignee: The Royal Veterinary College, London (GB)

( * ) Notice: Subject to any disclaimer, the term of this patent is extended or adjusted under 35 U.S.C. 154(b) by 286 days.

(21) Appl. No.: 12/239,527

(22) Filed: Sep. 26, 2008

(65) Prior Publication Data

US 2009/0081780 A1     Mar. 26, 2009

Related U.S. Application Data

(62) Division of application No. 10/522,513, filed as application No. PCT/GB2003/002832 on Jul. 1, 2003, now Pat. No. 7,776,340.

(30) Foreign Application Priority Data

Jul. 27, 2002 (GB) .................................. 0217434.0

(51) Int. Cl.
*A61K 39/00*      (2006.01)
*A61K 39/12*      (2006.01)
*A61K 39/215*     (2006.01)
*A01N 63/00*      (2006.01)
*C12N 5/00*       (2006.01)
*C08H 1/00*       (2006.01)
*A61K 39/285*     (2006.01)

(52) U.S. Cl. ............... 424/186.1; 424/184.1; 424/185.1; 424/204.1; 424/221.1; 424/93.1; 435/325; 530/403

(58) Field of Classification Search ........................ None
See application file for complete search history.

(56) References Cited

U.S. PATENT DOCUMENTS

| | | | |
|---|---|---|---|
| 5,672,350 A | 9/1997 | Parker et al. | |
| 5,750,112 A | 5/1998 | Gill | |
| 5,916,570 A | 6/1999 | Kapil | |
| 6,057,436 A | 5/2000 | Miller et al. | |
| 6,280,974 B1 | 8/2001 | Miller et al. | |
| 6,372,224 B1 | 4/2002 | Miller et al. | |

FOREIGN PATENT DOCUMENTS

| | | |
|---|---|---|
| EP | 0510773 | 10/1992 |
| WO | WO 93/23423 A1 | 11/1992 |
| WO | WO 98/16643 A1 | 4/1998 |
| WO | WO 99/25838 A1 | 5/1999 |

OTHER PUBLICATIONS

American Veterinary Medical Association online publication, "Frequently asked questions about canine respiratory coronavirus" Apr. 2008, accessed from http://www.avma.org/animal_health/canine_coronavirus_faq.asp on Dec. 1, 2008.
Decaro, N. and Buonavoglia, C. 2008 "An update on canine Coronaviruses: virul evolution and pathobiology" *Veterinary Medicine* 132:221-234.
Erles, K. and Brownlie, J 2008 "Canine respiratory coronavirus: An emerging pathogen in the canine infectious respiratory disease complex" Vet Clin Small Anim 38:815-825.
Zhang, X. et al. "Comparison of the nucleotide and deduced amino acid sequences of the S genes specified by virulent and avirulent strains of bovine Coronaviruses" *Virology* 183:397-404, 1991.
Appel and Binn 1987 in "Virus infections of carnivores", Appel, Ed., 1$^{st}$ Edition, pp. 201-211, Elsevier Science Publishers, Amsterdam.
Balaguer et al. 1991 "Quantification of DNA sequences obtained by polymerase chain reaction using a bioluminescent adsorbent" *Anal Biochem* 195:105-110.
Becker and Guarente 1991 "High-efficiency transformation of yeast by electroporation" *Methods Enzymol* 194:182-187.
Beggs 1978 "Transformation of yeast by replicating hybrid plasmid" *Nature* 275:104-109.
Bemis et al. 1977 "Naturally occuring respiratory disease in a kennel caused by *Bordetella bronchiseptica*" *Cornell Vet* 67:282-293.
Better et al. 1988 "*Escherichia coli* secretion of an active chimeric antibody fragment" *Science* 240:1041-1047.
Binn et al. 1967 "Viruses recovererd from laboratory dogs with respiratory disease" *Proc Soc Exp Biol Med* 126:140-145.
Binn et al. 1979 "Studies of respiratory disease in random-source laboratory dogs: viral infections in unconditioned dogs" *Lab Anim Sci* 29:48-52.
Bird et al. 1988 "Single chain antigen-binding proteins" *Science* 242:423-426.
Cavanagh et al., pp. 407-411, in "Virus Taxonomy, 6th Report of the International Committee on Taxonomy of Viruses", Murphy et al., Eds., Springer-Verlag Wein, New York.
Chivers et al. 2001 "The effects of coronavirus on human nasal ciliated respiratory epithelium" *Eur Respir J* 18:965-970.
Cohen et al. 1972 "Nonchromosomal antibiotic resistance in bacteria: Genetic transformation of *Escherichia coli* by R-Factor DNA" *Proc Natl Acad Sci USA* 69:2110-2114.
Compton 1991 "Nucleic acid sequence-based amplification" *Nature* 350:91-92.
Coyne and May 1995 "Consideration in using a canine coronavirus vaccine" published as Pfizer Technical Bulletin on the world-wide web at: Pfizer.com/ah/vet/tref/trbull/ccv.html.
DiCesare et al. 1993 "A high-sensitivity electrochemiluminescence-based detection system for automated PCR product quantitation" *BioTechniques* 15:152-157.
Ditchfield et al. 1962 "Association of a canine adenovirus (Toronto A 26/61) with an outbreak of laryngotracheitis ("Kennel cough")" *Can Vet Jour* 3:238-247.

(Continued)

*Primary Examiner* — Bo Peng
*Assistant Examiner* — Benjamin P Blumel
(74) *Attorney, Agent, or Firm* — Knobbe Martens Olson & Bear LLP

(57) ABSTRACT

A canine respiratory coronavirus (CRCV) that is present in the respiratory tract of dogs with canine infectious respiratory disease and which has a low level of homology to the enteric canine coronavirus, but which has a high level of homology to all bovine coronavirus strains (e.g., Quebec and LY138) and human coronavirus strain OC43.

8 Claims, 40 Drawing Sheets

OTHER PUBLICATIONS

Erles et al. 2003 "Detection of a group 2 coronavirus in dogs with canine infectious respiratory disease" *Virology* 310:216-223.
Examination Report dated Jul. 17, 2007 corresponding to New Zealand Patent Application No. NZ 556442.
Felsenstein 1989 Phylip-Phylogeny Inference Package (Version 3.2c), *Cladistics* 5:164-166.
GCG Version 10.3: Section of the Program Manual for the GCG Package, Version 10.3, relating to the GAP alignment (1982-2002), Genetics Computer Group, 575 Science Drive, Madison, Wisconsin US 53711.
GenBank Accession No. AF058942 (2000).
GenBank Accession No. AAM77000 (2005).
GenBank Accession No. AF124985 (1999).
GenBank Accession No. AF124986 (1999).
GenBank Accession No. AF124989 (1999).
GenBank Accession No. AF220295 (2003).
GenBank Accession No. AF481863 (2002).
GenBank Accession No. L07747 (2001).
GenBank Accession No. L14643 (2002).
GenBank Accession No. M76373 (2002).
GenBank Accession No. M84486 (1993).
GenBank Accession No. Z32768 (2002).
GenBank Accession No. AF058944 (2000).
GenBank Accession No. AAF25519, 2000.
GenBank Accession No. AF058944, 2000.
GenBank Accession No. P25191, 2008.
GenBank Accession No. P25194, 2008.
GenBank Accession No. S44240, 1999.
Grand Laboratories Inc. Technical Information on Scour Bos TM 4. On the world-wide-web at grandlab.com/bioproducts (2000).
Hawoksuz et al. (1999) "Antigenic variation among bovine enteric Coronaviruses (BECV) and bovine respiratory coronaviruses (BRCV) detected using monoclonal antibodies" *Archives of Virology* 144:2441-2447.
Houston et al. 1988 "Protein engineering of antibody binding sites: Recovery of specific activity in an anti-digoxin single-chain Fv analogue produced in *Escherichia coli*" *Proc Natl Acad Sci USA* 85:5879-5883.
Iacobelli et al. 1988 "Measurement of a breast cancer associated antigen detected by monoclonal antibody SP-2 in sera of cancer patients" *Breast Cancer Research and Treatment* 11:19-30.
Ignjatovic and Sapats 2000 "Avian infectious bronchitis virus" *Rev Sci Tech* 19:493-508.
Jacobs et al. 1988 "The thermal stability of oligonucleotide duplexes is sequence independent in tetraalkylammonium salt solutions: application to identifying recombinant DNA clones" *Nucl Acids Res* 16:4637-4650.
Jalkanen et al. 1985 "Heparin sulfate proteoglycans from mouse mammary epithelial cells: localization on the cell surface with a monoclonal antibody" *J Cell Biol* 101:976-984.
Jalkanen et al. 1987 "Cell surface proteoglycan of mouse mammary epithelial cells is shed by cleavage of its matrix-binding ectodomain from its membrane-associated domain" *J Cell Biol* 105:3087-3096.
Karpas et al. 1968 "Canine tracheobronchitis: isolation and characterization of the agent with experimental reproduction of the disease (32618)" *Proc Soc Exp Biol Med* 127:45-52.
Keil and Fenwick 1998 "Role of *Bordatella bronchiseptica* in infectious tracheobronchitis in dogs" *J Am Vet Med Assoc* 212:200-207.
Lai and Cavanagh 1997 "The molecular Biology of Coronaviruses" *Adv Vir Res* 48:4-22.
Lou and Wenner 1963 "Natural and experimental infection of dogs with reovirus, type 1: pathogenicity of the strain for other animals" *Am J Hyg* 77:293-304.
Lu et al. 1981 "Improved synthesis of 4-alkoxybenzyl alcohol resin" *J Org Chem* 46:3433-3436.
Luchansky et al. 1998 "Application of electroporation for transfer of plasmid DNA to *Lactobacillus, Lactococcus, Leuconostoc, Listeria, Pediococcus, Bacillus, Staphylococcus, Enterococcus* and *Propionibacterium*" *Mol Microbiol* 2:637-646.
Makela et al. 1998 "Viruses and bacteria in the etiology of the common cold" *J Clin Microbiol* 36:539-542.
Morrison et al. 1984 "Chimeric human antibody molecules: mouse antigen-binding domains with human constant region domains" *Proc Natl Acad Sci USA* 81:6851-6855.
National Office of Animal Health Ltd. (NOAH), Middlesex UK (2001), "Compendium of Data Sheets for Veterinary Products 2002-2003" pp. 216-217, 228-231, 322, 355-363, 448-449, 602-604, 700-706, 703-705 and 759-761.
Neuberger et al. 1988 8th International Biotechnology Symposium Part 2, pp. 792-799.
Page 1996 "TreeView: An application to display Phylogenetic trees on personal computers" *Computer Applications in the Biosciences* 12:357-358.
Pearson and Lipman 1988 "Improved tools for biological sequence comparison" *Proc Natl Acad Sci USA* 85:2444-2448.
Pensaert et al. 1986 "Isolation of a porcine respiratory, non-enteric coronavirus related to transmissible gastroenteritis" *Vet Q* 8:257-261.
Pfizer Animal Health Technical Services. Label Info for Scour Guard 3K. On the world-wide web at americanlivestock.com/showLabelInfo.jsp?productFamilyId=1075.
Randolph et al. 1993 "Prevalence of mycoplasmal and ureaplasmal recovery from tracheobronchial lavages and prevalence of mycoplasmal recovery from pharyngeal swab specimens in dogs with or without pulmonary disease" *Am J Vet Res* 54:387-391.
Saiki et al. 1986 "Analysis of enzymatically amplified β-globin and HLA-DQα DNA with allele-specific oligonucleotide probes" *Nature* 324:163-166.
Schering-Plough Animal Health News Archives 1999 "Schering-Plough Animal Health Secures First EU Approval for one shot calf scours Vaccine" Rotavec TM Corona. On the World-wide-web at spah.com/usa/news/pr/pr41.cfm.
Skerra and Pluckthun 1988 "Assembly of a functional immunoglobulin Fv fragment in *Escherichia coli*" *Science* 240:1038-1041.
Southern 1975 "Detection of specific sequences among DNA fragments separated by gel electrophoresis" *J Mol Biol* 98:503-517.
Spann et al. 1988 "Coronaviruses: Structure and genome expression" *J Gen Virol* 69:2939-2952.
Stephensen et al. 1999 "Phylogenetic analysis of a highly conserved region of the polymerase gene from 11 coronaviruses and development of a consensus polymerase chain reaction assay" *Virus Res* 60:181-189.
Storz et al. 2000 "Coronavirus and *Pasteurella* infections in bovine shipping fever pneumonia and Evans' criteria for causation" *J Clin Microbiol* 38:3291-3298.
Tennant et al. 1993 "Studies on the epizootiology of canine coronavirus" *Vet Rec* 132:7-11.
Thompson et al. 1997 "The CLSTAL_X windows interface: flexible strategies for multiple sequence alignment aided by quality analysis tools" *Nucl Acids Res* 25:4876-4882.
Walker et al. 1992 "Strand displacement amplification-an isothermal, in vitro DNA amplification technique" *Nucl Acids Res* 20:1691-1696.
Ward et al. 1989 "Binding activities of a repertoire of single immunoglobulin variable domains secreted from *Escherichia coli*" *Nature* 341:544-546.
Winter and Milstein 1991 "Man-made antibodies" *Nature* 349:293-299.

FIGURE 1

```
ctcagatgaa tttgaaatat gctattagtg ctaagaatag agcccgcact gttgctggtg    60
tttccatact tagtactatg actggcagaa tgtttcatca aaaatgtttg aaaagtatag   120
cagctacacg tggtgttcct gttgttatag gcaccactaa attttatggc ggctgggatg   180
atatgttacg tcgccttatt aaagatgttg acaatcctgt acttatgggt tgggattatc   240
ctaagtgtga                                                          250
```

FIGURE 2

```
QMNLKYAISA KNRARTVAGV SILSTMTGRM FHQKCLKSIA ATRGVPVVIG TTKFYGGWDD    60
MLRRLIKDVE NPVLMGWDYP KCE                                            84
```

FIGURE 3 (Page 1 of 2)

```
atgtttttga tactttttaat ttccttacca atggcttttg ctgttatagg agatttaaag      60
tgtactacgg tttccatcaa tgatgttgac accggtgctc cttctattag cactgatgtt     120
gtcgatgtta ctaatggttt aggtacttat tatgttttag atcgtgtgta tttaaatact     180
acattgttgc ttaatggtta ttatcctact tcaggttcta catatcgtaa tatggcactg     240
aagggaactt tactattgag cacactatgg tttaaaccac catttctttc tgatttattt     300
gatggtgttt ttgctaaggt aaaaaatacc aaggttatta agatggtgt agtgtatagt      360
gagtttcctg ctataactat aggtagtact tttgtaaata catcctatag tgtggtagta     420
caaccacata ctactaattt agataataaa ttacaaggtc tcttagagat ctctgtttgc     480
cagtatacta tgtgcgatta cccacatacg atgtgtcatc ctaatctggg taataaacgc     540
atagaactat ggcattggga tacaggtgtt gttccctgtt tatataagcg taatttcaca     600
tatgatgtga atgctgatta tttgtattcc cattttttatc aagaaggtgg tactttttat     660
gcatatttta cagacactgg tgttgttact aagtttctgt ttcatgttta tttaggcacg     720
gtgctttcac attattatgt catgcccttg acttgtaata gtgctatgac tttagaatac     780
tgggttacac ctctcacttt taaacaatat ttactcgctt tcaatcaaga tggtgttatt     840
tttaatgctg ttgattgtaa gagtgatttt atgagtgaga ttaagtgtaa acactatct     900
atagcaccat ctactggtgt ttatgaatta aacggttaca ctgttcagcc aattgcagat     960
gtttaccgac gtataccta tcttcccgat tgtaatatag aggcttggct taatgataag    1020
tcggtgcctt ctccattaaa ttgggaacgt aagacctttt caaattgtaa ttttaatatg    1080
agcagcctga tgtcttttat ccaggctgac tcgtttactt gtaataatat tgatgctgct    1140
aagatatacg gtatgtgttt tttcagcata actatagata gtttgctat acccaatggt    1200
aggaaggttg acctacaaat gggcaatttg ggctatttgc agtcttttaa ctatagaatt    1260
gatactactg ctacaagttg tcagttgtat tataatttac ctgctagtaa tgtttctatt    1320
agcaggttta atccttctat ttggaatagg agatttggtt ttacagaaca atctgttttt    1380
aagcctcaac ctgtaggtgt ttttactgat catgatgttg tttatgcaca acattgtttt    1440
aaagctccca caaatttctg tccgtgtaaa ttgaatgggc tttgtgtgt aggtagtggt    1500
tttggtatag atgctggtta taaaaatagt ggtataggca cttgtcctgc aggtactaat    1560
tatttaactt gttataatgc taaccaatgt gattgtttgt gcactccaga ccctatttta    1620
tctaaatcta cagggcctta aagtgccccc caaactaaat acttagttgg cataggtgag    1680
cactgttctg gtcttgctat taaaagtgat tattgtggag gcaatccttg tacttgccaa    1740
ccaaaagcat ttttgggttg gtctgtggac tcttgtttac aagggatag gtgtaatatt    1800
tttgctaatt ttatttgca tggtgttaat agtggtacta cttgttctac tgatttacaa    1860
aaatcaaaca cagacataat tctggtgtt tgtgttaatt atgatcttta tggtattaca    1920
ggccaaggta ttttgttga ggttaatgcg acttattata atagttggca gaaccttta     1980
tatgattcta atggtaatct ctatggtttt agggactact taacaaacag aacttttatg    2040
attcgtagtt gctatagcgg tcgtgtttca gcgggctttc actctaactc ttccgaacca    2100
gcattgctat ttcggaatat taaatgcaat tacgttttta ataatactct ttcacgacag    2160
ctgcaaccta ttaactattt tgatagttat cttggttgtg ttgtcaatgc tgataatagt    2220
```

FIGURE 3 (Page 2 of 2)

```
acttctagtt ctgttcaaac atgtgatctc acagtaggta gtggttactg gggggattac    2280
tctacacaaa gacgaagtcg tagaacgatt accactggtt atcggtttac taattttgag    2340
ccatttactg ttaatccagt aaatgatagt ttacaccctg taggtggttt gtatgaaatt    2400
caaataccct cagagtttac tataggtaat atggaggagt ttattcaaac aagatctcct    2460
aaagttacta ttgattgtcc tgttttgtc tgtggtgatt atgcagcatg taaatcacag    2520
ttggttgaat atggtagttt ttgtgacaat attaatgcta tactcacaga agtaaatgaa    2580
ctacttgaca ctacacagtt gcaagtagct aatagtttaa tgaatggtgt cactcttagc    2640
actaagctta aagatggctt taatttcaat gtagatgaca tcaattttc cctgtatta     2700
ggttgtttag gaagcgaatg taataaagtt tccagtagat ctgctataga ggatttactt    2760
ttttctaaag taaagttatc tgatgttggt tttgttgatg cttataataa ttgtactgga    2820
ggtgccgaaa ttagggacct catttgtgtg caaagttata atggtatcaa agtgttgcct    2880
ccactgctct cagaaaatca gatcagtgga tacactttgg ctgccacctt tgctagtctg    2940
tttcctcctt ggtcagcagc agcaggcgta ccatttatt taaatgttca gtatcgtatt     3000
aatggtattg gtgttaccat ggatgtgcta actcaaaatc aaaagcttat ttctaatgca    3060
tttaacaatg cccttgatgc tattcaggaa gggtttgatg ctaccaattc tgctttagtt    3120
aaaattcaag ctgttgttaa tgcaaatgct gaagctctta ataacttatt gcaacaactc    3180
tctaataaat tggtgctat aagtgcttct ttacaagaaa ttctatctag acttgatgct     3240
cttgaagcgc aagctcagat agacagactt atcaatgggc gtcttaccgc tcttaatgct    3300
tatgtttctc aacagcttag tgattctaca ctagtaaaat ttagtgcagc acaagctatg    3360
gagaaggtta atgaatgtgt caaaagccaa tcatctagga taaattttg tggtaatggt    3420
aatcatatta tatcattagt gcagaatgct ccatatggtt tgtattttat ccactttagc    3480
tatgtcccta ctaagtatgt cactgcgaag gttagtcccg gtctgtgcat ycaggtgat    3540
agaggtatag ctcctaagag tggttatttt gttaatgtaa ataacacttg gatgttcact    3600
ggtagtggtt attactaccc tgaacctata actggaaata atgtggttgt tatgagtacc    3660
tgtgctgtta actatactaa agcaccggat gtaatgctga acatttcaac acccaacctc    3720
cctgatttta aggaagagtt ggatcaatgg tttaaaaacc aaacattaat ggcaccagat    3780
ttgtcacttg attatataaa tgttacattc ttggacctac aagatgaaat gaataggtta    3840
caggaggcaa taaaagtttt aaatcatagc tacatcaatc tcaaggacat tggtacatat    3900
gaatattatg taaaatggcc ttggtatgta tggcttttaa ttggccttgc tggcgtagct    3960
atgcttgttt tactattctt catatgctgt tgtacaggat gtgggactag ttgttttaag    4020
aaatgcggtg gttgttgtga tgattatact ggacatcagg agttagtaat caaaacgtca    4080
catgacgact aa                                                        4092
```

FIGURE 4

```
MFLILLISLP MAFAVIGDLK CTTVSINDVD TGAPSISTDV VDVTNGLGTY YVLDRVYLNT      60
TLLLNGYYPT SGSTYRNMAL KGTLLLSTLW FKPPFLSDFI DGVFAKVKNT KVIKDGVVYS     120
EFPAITIGST FVNTSYSVVV QPHTTNLDNK LQGLLEISVC QYTMCDYPHT MCHPNLGNKR     180
IELWHWDTGV VPCLYKRNFT YDVNADYLYS HFYQEGGTFY AYFTDTGVVT KFLFHVYLGT     240
VLSHYYVMPL TCNSAMTLEY WVTPLTFKQY LLAFNQDGVI FNAVDCKSDF MSEIKCKTLS     300
IAPSTGVYEL NGYTVQPIAD VYRRIPNLPD CNIEAWLNDK SVPSPLNWER KTFSNCNFNM     360
SSLMSFIQAD SFTCNNIDAA KIYGMCFFSI TIDKFAIPNG RKVDLQMGNL GYLQSFNYRI     420
DTTATSCQLY YNLPASNVSI SRFNPSIWNR RFGFTEQSVF KPQPVGVFTD HDVVYAQHCF     480
KAPTNFCPCK LNGSLCVGSG FGIDAGYKNS GIGTCPAGTN YLTCYNANQC DCLCTPDPIL     540
SKSTGPYKCP QTKYLVGIGE HCSGLAIKSD YCGGNPCTCQ PKAFLGWSVD SCLQGDRCNI     600
FANFILHGVN SGTTCSTDLQ KSNTDIILGV CVNYDLYGIT GQGIFVEVNA TYYNSWQNLL     660
YDSNGNLYGF RDYLTNRTFM IRSCYSGRVS AGFHSNSSEP ALLFRNIKCN YVFNNTLSRQ     720
LQPINYFDSY LGCVVNADNS TSSSVQTCDL TVGSGYWGDY STQRRSRRTI TTGYRFTNFE     780
PFTVNPVNDS LHPVGGLYEI QIPSEFTIGN MEEFIQTRSP KVTIDCPVFV CGDYAACKSQ     840
LVEYGSFCDN INAILTEVNE LLDTTQLQVA NSLMNGVTLS TKLKDGFNFN VDDINFSPVL     900
GCLGSECNKV SSRSAIEDLL FSKVKLSDVG FVDAYNNCTG GAEIRDLICV QSYNGIKVLP     960
PLLSENQISG YTLAATFASL FPPWSAAAGV PFYLNVQYRI NGIGVTMDVL TQNQKLISNA    1020
FNNALDAIQE GFDATNSALV KIQAVVNANA EALNNLLQQL SNKFGAISAS LQEILSRLDA    1080
LEAQAQIDRL INGRLTALNA YVSQQLSDST LVKFSAAQAM EKVNECVKSQ SSRINFCGNG    1140
NHIISLVQNA PYGLYFIHFS YVPTKYVTAK VSPGLCIAGD RGIAPKSGYF VNVNNTWMFT    1200
GSGYYYPEPI TGNNVVVMST CAVNYTKAPD VMLNISTPNL PDFKEELDQW FKNQTLMAPD    1260
LSLDYINVTF LDLQDEMNRL QEAIKVLNHS YINLKDIGTY EYYVKWPWYV WLLIGLAGVA    1320
MLVLLFFICC CTGCGTSCFK KCGGCCDDYT GHQELVIKTS HDD                     1363
```

FIGURE 6

```
T101  CTCAGATGAATTTGAAATATGCTATTAGTGCTAAGAATAGAGCCCGCACTGTTGCTGGTG
BCV   CTCAAATGAATTTGAAATATGCTATTAGTGCTAAGAATAGAGCCCGCACTGTTGCTGGTG
OC43  CTCAAATGAATTTGAAATATGCTATTAGTGCTAAGAATAGAGCCCGCACTGTTGCTGGTG
HEV   CTCAAATGAATTTGAAATATGCTATTAGTGCCAAGAATAGAGCCCGCACTGTTGCTGGTG
CCV   CTCAGATGAATTTGAAATATGCTATTTCTGGAAAGGCTAGAGCTCGTACAGTAGGAGGAG
      **** ******************* **   ***   ****** ** ** ** *   ** *

T101  TTTCCATACTTAGTACTATGACTGGCAGAATGTTTCATCAAAAATGTTTGAAAAGTATAG
BCV   TTTCCATACTCAGTACTATGACTGGCAGAATGTTTCATCAAAAATGTTTGAAAAGTATAG
OC43  TTTCCATACTTAGTACTATGACTGGCAGAATGTTTCATCAAAAATGTTTGAAAAGTATAG
HEV   TTTCCATACTTAGTACTATGACTGGCAGAATGTTTCATCAAAAATGCTTGAAAAGTATAG
CCV   TTTCACTTCTTTCTACCATGACTACGAGACAATACCACCAGAAGCATTTGAAGTCAATTG
      ****  *  **    *** ******    ***   *    ** ** **     *****     ** *

T101  CAGCTACACGTGGTGTTCCTGTTGTTATAGGCACCACTAAATTTTATGGCGGCTGGGATG
BCV   CAGCTACACGTGGTGTTCCTGTTGTTATAGGCACCACTAAGTTTTATGGCGGCTGGGATG
OC43  CAGCTACACGTGGTGTTCCTGTAGTTATAGGCACCACTAAATTTTATGGTGGCTGGGATG
HEV   CAGCTACACGTGGCGTTCCTGTGGTTATAGGCACCACTAAATTTTATGGCGGCTGGGATG
CCV   CTGCAACACGCAATGCCACTGTGGTTATTGGCTCAACCAAGTTTTATGGTGGTTGGGATA
      * ** *****       *    **** ****  ***  ** ** ******** ** ******

T101  ATATGTTACGTCGCCTTATTAAAGATGTTGACAATCCTGTACTTATGGGTTGGGATTATC
BCV   ATATGTTACGTCGCCTTATTAAAGATGTTGATAATCCTGTACTTATGGGTTGGGATTATC
OC43  ATATGTTACGCCGCCTTATTAAAGATGTTGACAATCCTGTACTTATGGGTTGGGATTATC
HEV   ATATGTTACGCCGCCTTATTAAAGATGTTGATAATCCTGTACTTATGGGTTGGGATTATC
CCV   ACATGCTTAAAAATTTAATGCGTGATGTTGATAATGGTTGTTTGATGGGATGGGACTATC
      * ***  *           *  *  ******** ***     *  * *****  *****  ****

T101  CTAAGTGTGA
BCV   CTAAGTGTGA
OC43  CTAAGTGTGA
HEV   CAAAGTGTGA
CCV   CTAAGTGTGA
      * ********
```

FIGURE 7

```
protHCVpoly    ---MNLKYAISAKNRARTVAGVSILSTMTGRMFHQKCLKSIAATR
protHEVpoly    ---MNLKYAISAKNRARTVAGVSILSTMTGRMFHQKCLKSIAATR
protBCVpoly    ---MNLKYAISAKNRARTVAGVSILSTMTGRMFHQKCLKSIAATR
protCRCVpol    --QMNLKYAISAKNRARTVAGVSILSTMTGRMFHQKCLKSIAATR
protCECVpol    MTQMNLKYAISGKARARTVGGVSLLSTMTTRQYHQKHLKSIAATR
                 ********.* ***.*:***** * :* ****** protHCVpoly    GVPVVIGTTKFYGGWDDMLRRLIKDVDNPVLMGWDYPKC
protHEVpoly    GVPVVIGTTKFYGGWDDMLRRLIKDVDNPVLMGWDYPKC
protBCVpoly    GVPVVIGTTKFYGGWDDMLRRLIKDVDNPVLMGWDYPKC
protCRCVpol    GVPVVIGTTKFYGGWDDMLRRLIKDVENPVLMGWDYPKC--
protCECVpol    NATVVIGSTKFYGGWDNMLKNLMRDVDNGCLMGWDYPKC---
               ...****:*********:**:.*::**:*  *********
```

FIGURE 8 (Page 1 of 9)

```
CRCVspike    -------------------ATGTTTTTGATACTTTTA------ATTTCCTTACCAATG
CECVspike    ATGATTGTGCTCGTAACTTGCATTTTATTGTTATGTTCATACCACACTGCTTCGAGTACG
                                ** ** *** ** ** *     * * * *      * *

CRCVspike    GCTTTTGCTG-TTATAGGAGATTTAAAGTGTACTACGGTTTC-CATCAATGATGTTGACA
CECVspike    TCAAATAATGATTGTAGACAAGTTAA--CGTAACACAATTAGATGGCAATGAAAACCTCA
              *    *  ** ** ***    *  ****   ***  ** **      ******    **

CRCVspike    CCGGTG-CTCCTTCTATTAGCACTGATGTTGTCGATGTTACTAATGGTTTAGGTACTTAT
CECVspike    TTAGAGACTTTTTGTTTCAAAACTT-TAAAGAAGAAGGAACTGTAGTTGTTGGTGGTTAC
             * * **  ** *  * *    ***   *   *  ** *  ***   * * * ***  ***

CRCVspike    TATGTTTTAGA----TCGTGTG--TATTTAAATACTACA----TTGTTGCTTAATGGTTA
CECVspike    TACCCTACAGAGGTTTGGTATAACTGTTCTAGAACAGCAACAACTACTGCCTA-TGAGTA
             **    * ***      ** *     ** *    **  **     *  ***  **  **

CRCVspike    TTATCCTACTTCAGGTTCTACATATCGTAATATGGCA-CTGAAGGGAACTTTACTATTGA
CECVspike    TTTCAGTAATATACACGCATTCTATTTTGATATGGAAGCCATGGAGAATAGTACTGGTAA
             **  ** *  *  *    ***  * ****** * *   * ***    **** *  * *

CRCVspike    -GCACACTATGG-TTTAAACCACCATTTCTTTCTGATTTTATTGATGGTGTTTTTGCTAA
CECVspike    TGCACGTGGTAAACCTTTATTATTTCATGTTCATGGTGAGCCTGTTAGTGTCATCATATA
              ****      *    *     *  *  * ** **   **  ****   *        *

CRCVspike    GGTAAAAAATACCAAGGTTATTAAAGATGGTGTAGTGTATAG---TGAGTTTCCTGCTAT
CECVspike    CATATCTTATAGAGATGATGTGCAACATAGGCCACTTTTAAAACACGGATTAGTGTGCAT
              **    ***   *  *  ** **  * *  *       *    *  **      **

CRCVspike    AACTATAGGTAGTACTTTTG--TA-AATACATCCTATAGTGTGGTAGTACAACCACATAC
CECVspike    AACTGAAAGTCGCAACATTGACTATAACAGTTTCACCAGTA-GCCAGTGGAATTCCATAT
             ****  * ** *  *  ***  ** **   **   **  ****  *  *** **  ****

CRCVspike    -TACTAATTTAGATAATAAATTACAAGGTCTCTTAGAGATCTCTGTTTGCCAGTATACTA
CECVspike    GTACGGGTAATGACAGAAAAATTCCTT-TCTCTGTCATACCCACGGACAATGGAACAAAA
              ***    *   ** * * *** *    *****  *    *  *       * * *
```

FIGURE 8 (Page 2 of 9)

```
CRCVspike    -TGTGCGATTACCCACATA-CGATGTGTC-ATCCTAATCTGGGT-AATAAACG--CATAG
CECVspike    ATTTATGGTCTTGAGTGGAATGATGAATTTGTTACAGCGTACATTAGTGGTCGTTCTTAT
              *  *   *  *      *  ****  *     *  *    *  *  *   **   *  **

CRCVspike    AACTATGGCATTGGGATACAGGTGTTGTTCCCTGTT-TATATAAGCGTAATTTCACATAT
CECVspike    AATTGGAACATCAATAATAATTGGTTTAACAATGTCACGCTTCTGTATAGTCGCTCAAGC
             ** *    ***     *   *     ***  *  ***         *   ** *  * **

CRCVspike    GATGTGA-ATGCTGATTATTTGTATTCCCATTTTTATCAAGAAGGTGGTACTTT---TTA
CECVspike    ACTGCCACATGGCAACACAGTGC-TGCATACGTTTACCAAGGTGTTTCTAACTTCACTTA
              ** * ***    *       **  * *  *  **** ****  *  **  **    ***

CRCVspike    TGCATATTTTACAGACACTGGTGTTGTTACTAAGTTTCTGTTTCATGTTTAT-TTAGGCA
CECVspike    TTACAAGTTAAATAACACCAATGGTCTAA--AAACCTATGAATTATGTGAAGATTATGAA
              *    * ** *    ****  **  * * *    *  **  * ****   *  *** * *

CRCVspike    CGGTGCTTT---CACATTATTA-TGTCATGCCCTTGACTTGTAATAGTGCTATGACTTTA
CECVspike    TATTGCACTGGCTACGCCACTAACATCTTTGCCCCAACTGTGGGAGGTTACATACCTGAT
                 ***  *   **    *** *  *** ** *   ** *    **    **  **  **

CRCVspike    GAATACTGGGTTA-----CACCTCTCACTTTTAAACAATATTTACTCGCTTTCAATCAAG
CECVspike    GGATTTAGTTTTAACAATTGGTTTTTGCTTACAAACAGCTCCACTTTTGTTAGTGGCAGA
             * **   *  ***         *   *  *** *****      *    **     **

CRCVspike    ATGGTGTTATTTTTAATGCTGTTGATTGTAAGAGTGATTTTATGAGTGAGATTAAGTGT-
CECVspike    TTTGTAACAAATCAACCATTATTAGTTAATTGCTTGTGGCCAGTTCCTAGTTTTGGTGTT
              * **    *    *    *  **  *   **    *   *      ** **  ****

CRCVspike    --AAAACACTATCTATAGCACCATCTACTGGTGTTTATGAATTAAACGGTTACACTGTTC
CECVspike    GCAGCACAAGAATTTTGTTTTGAAGGTGCACAGTTTAGCCAATGTAATGGTGTGTTTTA
               *  ***  *  *  *        *     *****    *  *  *  *      * **

CRCVspike    AGCCA-ATTGCAGATGTTTACCGACGTATACCTAATCTTCCCG--ATTGTAATATAGAGG
CECVspike    AATAACACAGTAGATGTCATTAGATTCAACCTTAATTTTACTGCAGATGTACAATCTGGC
              *  *  *  ******    *  *  *  * *  ***  * *   **** **   *
```

FIGURE 8 (Page 3 of 9)

```
CRCVspike    CTTGGCTTAATGATAAGT-CGGTGCCTTCTCCATTAAATTGGGAACGTAAGACCTTTTCA
CECVspike    ATGGGTGCTACAGTATTTTCACTGAATACAACAGGTGGTTGCATTCTTGAGATTTCTT--
              * **     *  **  * *  **   * * **       ***    * * ***   * **

CRCVspike    AATTGTAATTTTAATATGAGCAGCCTGATGTCTTTTATCCAGGCTGACTCGTTTACTTGT
CECVspike    -GTTATAATGATATAGTGAGCGAGTCAAGTTTCTACAGTTATGGTGA---AATTCCCTTC
              ** **** **  ***** *   *   *   *    * *  * * ***   ** * *

CRCVspike    AATAATATTGATGCTGCTAAGATATACGGTATGTGTTTTTTCA--GCATAACTATAGATA
CECVspike    GGCGTAACTGATGG-ACCGCGTTAT-TGTTATGTCCTCTATAATGGCACAGCTCTTAAGT
              *  *****  *    *  * ***  * *****  *   *   ***  ** * **  *   *

CRCVspike    AGTTTGCTA---TACCCAATGGTAGGAAGGTTGACCTACAAATGGGCAATTTGGGCTATT
CECVspike    ATTTCGGCACATTACCCCCTAGTGTCAAGG--AAATTGCTATTAG-TAAGTGGGGCCAAT
              * **  *   *      *****  * **   ****   *  *  * *  **  * **** *  *

CRCVspike    TGCAGTCTTTTAACTATAGAATTGATACTACTGCTACAAGTTGTCAGTTGTATTATAATT
CECVspike    TTTATATTAATGGTTACAATTTCTTTAGCACTTTTCCTATTGATTGTATATCTTTTAACT
              *   *   *   *   ** *   *    ** ***  * * * *   * * ** *** *

CRCVspike    TACCTGCTAGTAATGTTTCTATTAGCAGGTTTAATCCTTCTATTTGGAATA--GGAGATT
CECVspike    TAACCACTGGTGATAGTGGAGCATTTTGGACAATTGCTTACACATCGTACACTGAAGCAT
              ** *   ** **  **     *           **   * * ***  *  *   *  * **  *

CRCVspike    TGGTTTTA-CAGAACAATCTGTTTTTAAGCCT-CAACCTGTAGGTGTTTTTACTGATCAT
CECVspike    TAGTACAAGTTGAAAACACAGCCATTAAAAAGGTGACGTATTGTAACAGTCAC-ATTAAT
              * **    *   *** *  *  *   ****            **  **   *  *  * **

CRCVspike    GATGTTGTTTATGCACAACATTGTTTTAAAGCTCCCACAAATTTCTGTCCG-----TGTA
CECVspike    AACATCAAATGTTCTCAACTTACTGCTAATTTGCAAAATGGCTTTTATCCTGTTGCTTCA
              *  *    *  *  * *** **  *  *        *   **   **  ***        *  *

CRCVspike    AATTGAATGGGTCTTTGTGTGTAGGTAGTGGTTTTGGTA--TAGATGCTGGTTATAAA--
CECVspike    AGTGAAGTTGGTCTTGTCAATAAGAGTGTTGTGTTACTACCTAGTTTCTATTCACATACC
              * *   * * * ******      **  *** **  **   * ***  *  * ** *    * * * *
```

FIGURE 8 (Page 4 of 9)

```
CRCVspike    AATAGTGGTATAGGCACTTGTCCTGCAGGTACTAATTATTTAACTTGTTATAATGCTAAC
CECVspike    AGTGTTAATATAACTATTGATCTTG---GTATGAAGCGTAGTGGTTATGGTCAACCCA--
              *  *   ****   *  *  ** **    ***  **    *   ** *  *  *   * *

CRCVspike    CAATGTGATTGTTTGTGCACTCCAGAC--CCTATTTTATCTAAATCTACAGGGCCTTA-T
CECVspike    TAGCCTCAACACTAAGTAACATCACACTACCAATGCAGGATAATAACACCGATGTGTACT
              *   * *    *     **  ** **  ** **       ***   ** *      ** *

CRCVspike    AAGTGCCCCCAAACTAAATACTTAGTTGGCATAGGTGAGCACTGTTCTGGTCTTGCTATT
CECVspike    GTATTCGTTCTAACCAATT-CTCAGTTTATGTTCACTCCACTTGCAAAAGTTCTTTATGG
              *  *    *  ***  ** *  ** ****    *        **     **    **  *

CRCVspike    AAAAGTGATTATTGTGGAGGCAATCCTTGTACTTGCCAACCAAAAGCATTTTTGGG--TT
CECVspike    GACAACAATTTTAATCAAGATTGCACAGATGTTTTATATGCCACAGCTGTTATAAAAACT
              *  *    *** *    *   **        *    *   **    *  * *** ** *        *

CRCVspike    GGTCTGTGGAC--TCTTGTTTACAAGG--GGATAGGTGTAATATTTTTGCTAA-TTTTAT
CECVspike    GGTACTTGCCCCTTCTCATTTGATAAATTGAATAATTACTTAACTTTTAACAAGCTTTGT
             ***   **  *     *** ***    *   * *** *     * ****  **  *** *

CRCVspike    TTTGCATGGTGT--TAATAGTG------GTACTACTTGTTCTACTGATT-TACAAAAATC
CECVspike    TTGTCGTTGAATCCTACTGGTGCCAACTGTAAGTTTGATGTTGCTGCCCGTACAAGAACC
              **  *  *  *   *  ** * ***   ***        *  * ***   ***** ** *

CRCVspike    AAACACAGACATAATTCTTGGTGTTTGTGTTAATTATGATCTTTATGGTATTACAGGCCA
CECVspike    AA-TGAGCAGGTTGTTAGAAGTTTATATGTAATATATGAAGAAGGAGACAACATAGTGGG
             **       *   *   **    **  * *** *  ****             *  * **

CRCVspike    AGGTATTTTTGTTGA----GGTTAATGCGACTTATTATAATAGTTGGCAGAACCTTTTAT
CECVspike    TGTACCGTCTGATAATAGTGGTCTTCACGATTTGTCAGTGTTACACTTAGACTCCTGTAC
               *   * ** * *      *** *  *** **  * * **   *      *** * * **

CRCVspike    ATGATTCTAATG---GTAATCTCTATGGTTTTAGGGACTACTTAACAAACAGA-ACTTTT
CECVspike    A-GATTACAATATATATGGTAGAACTGGTGTT-GGTATTATTAGACAAACTAACAGCACA
             * ****  ***    *  *  **** ** *  *  ****** *  * *
```

FIGURE 8 (Page 5 of 9)

```
CRCVspike    ATGATTCGTAGTTGCTATAGCG-GTCGTGTTTCAGCGGGCTTTCA---CTCTAACTCTTC
CECVspike    ATACTTAGTGGCTTACATTATACATCACTATCAGGTGATTTATTAGGTTTTAAAAATGTT
             **  ** ** * *   **      **    *   * *   * * *     *  **    *

CRCVspike    CGAACCAGCATTG-CTATTTCGGAATATTAAATGCAATTACGTTTTTAATAATACTCTTT
CECVspike    AGTGATGGTGTTGTCTATTCTGTGACACCATGTGATGTAAGCGCACAAGCGGCTGTTATT
              *     *  *** *****  *  *  *    *  **   *  *        *  ** **

CRCVspike    CACG-----ACAGCTGCAACCTATTAACTATTTTGATAGTTATCTTGGTTGTGTTGTCAA
CECVspike    GATGGGGCCATAGTTGGAGC-TATGACTTCCATTAATAGTGAACT-GTTAGGTCTAACAC
             * *         * ** **  * *** *   * * ***** * *  ** * *     **

CRCVspike    TGCTGATAATAGTAC-----TTCTAGTTCTGTTCAAACATGTGATCTCACAGTAGGTAGT
CECVspike    ATTGGACAACAACACCAAATTTTTATTACTACTCTA-TATATAAT---ACAACAAATGAG
              ** **  *  **   ** ** * **  ** *  ** * *  **   *** *   * *

CRCVspike    GGTTACTGGGGGGATTACTCTACACAAAGACGAAGT----CGTAGAACGATTACCACTGG
CECVspike    AGA-ACTCGTGGCACTGCAATCGACAGTAACGATGTAGATTGTGAACCTATCATAACCTA
              *  *** * **     * **  * *  ***  **    **** *  *** *   **

CRCVspike    TT-----ATCGGTTT----ACTAATTTTGAGCCATTTACTGTTAATCCAGTAAATGATAG
CECVspike    TTCTAACATAGGTGTTTGTAAAAATGGTGCGTTGGTTTTTATTAACGTCACACATTCTGA
             **      * ***  *     *  ** **  *      * ** *** * **  *

CRCVspike    TTTACACCCTGTAGGTGGTTTGTAT--GAAAT-TCA-AATACCTTCAGAGTTTACTATAG
CECVspike    TGGAGATGTT-CAACCAATTAGCACTGGCAATGTCACGATACCCACAAACTTTACCATAT
             *  *  * *      * *        *  ***  ** * **** ** *  ***** ***

CRCVspike    GTAATATGGAGGAGTTTATTCAAACAAGATCTCCTAAAGTTACTATTGATTGTCCTGTTT
CECVspike    CTGTGCAAGTTGAATACATCCAGGTTTACACTACACCGGTGTCAATAGATTGTTCTAGAT
               *    *   ** **  **  **     **   * ** * *  * ***** **   *

CRCVspike    TTGTCTGTGGTGATTATGCAGCATGTAAATCACAGTTGGTTGAATATGGTAGTTTTTGTG
CECVspike    ACGTTTGTAATGGTAACCCTAGATGTAATAAATTGTTAACACAATATGTTTCTGCATGTC
              **  ***  **   *  * *  *****  *  *** *  * *  ***** *  * * *
```

FIGURE 8 (Page 6 of 9)

```
CRCVspike    ACAATATTAATGCTATACTCACAG-AAGT----------AAATGAACTACTTGACACTA
CECVspike    AAACTATTGAGCAAGCGCTTGCAATGAGTGCCAGCCTTGAAAACATGGAAGTTGATTCCA
             *  *  ****  *            **  **   ***            ***      *  ****   *  *

CRCVspike    CACAGTTGCAAGTAGCTAATAGTTTAATGAATGGTGTCACTCTTAGCACTAAGCTTAAAG
CECVspike    TGTTGTTTGTTTCAGAAAATGCCCTTA-AATTGGCATCTGTTGAGGCGTTCAATAGTACA
                    ***       **   ***     *  *   ***   **    *    **    *  *            *

CRCVspike    ATGGCTTTAATTTCAATGTAGATGACAT----CAATTT---TTCCCCTGTATTAGGTTGT
CECVspike    GAACATTTAGATCCTATTTACAAAGAATGGCCTAACATAGGTGGTTCTTGGCTAGGAGGT
                ****  *  *  **  **  *     **         **     *    *     **     ****   **

CRCVspike    TTAGGAAGCGAAT---------GTAATAA-AGTTTCCAGTA--GATCTGCTATAGAGGAT
CECVspike    CTAAAAGACATACTTCCGTCCCATAATAGCAAACGTAAGTATCGTTCTGCTATAGAAGAC
             **    *     *   *                *****    *         ****    *  **********   **

CRCVspike    TTACTTTTTTCTAAAGTAAAGTTATCTGATGTTGGTTTTGTTGATGC---TTATAATAAT
CECVspike    TTGCTTTTTGATAAAGTTGTAACTTCTGGTCTAGGTACAGTTGATGAAGATTATAAACGT
             **  ******  ******       ****  *  *  ***   ******       ******    *

CRCVspike    TGTACTGGAGGTGCCGAAATTAGGGACCTCATTTGTGTGCAAAGTTATAATGGTATCAAA
CECVspike    TGTACAGGTGGTTATGACATAGCTGACTTAGTTTGTGCACAATATTACAATGGCATCATG
             *****  **  ***    **   **       ***  *   ******   ***   ***  *****  ****

CRCVspike    GTGTTGCCTC-CACTGCTCTCAGAAAATCAGATCAGTGGATACACTTTGGCTGCCACCTT
CECVspike    GTTCTACCTGGTGTTGCTAAT-GATGACAAGATGACTATGTACACAGCCTCTCTTGCAGG
             **  *  ***     ****   **  *  ****  *  *    *****        **     *

CRCVspike    TGCTAGTCTGTTTCCTCC-TTGGTCAGCAGCA--GCAGGCGTACCATTTTATTTAAATGT
CECVspike    TGGTATAGCATTAGGTGCACTAGGTGGTGGCGCCGTGGCTATACCTTTTGCAGTAGCAGT
             **  **       **     *  *  *    *   *   **    *    *     ****  ***      **    **

CRCVspike    TCAGTATCGTATTAATGGTATTGGTGTTACCATGGATGTGCTAACTCAAAATCAAAAGCT
CECVspike    TCAGGCTAGACTTAATTATGTTGCTCTACAAACTGATGTATTGAACAAAAACCAGCAGAT
             ****    *  *  *****  *  ***  *  *        *  *****   *    ****  **   **  *
```

FIGURE 8 (Page 7 of 9)

```
CRCVspike      TATTTCTAATGCATTTAACAATGCCCTTGATGCTATT---------CAGGAAGGGTT--
CECVspike      CCTGGCTAATGCTTTCAACCAAGCTATTGGTAACATTACACAGGCATTTGGTAAGGTTAA
                *  ******* ** *** * **  *** *    ***           ** * ****

CRCVspike      TGATGCTA----------------------CCAATTCTGCT------TTAGTTAAAAT
CECVspike      TGATGCTATACATCAAACATCACAAGGTCTTGCCACTGTTGCTAAAGCATTGGCAAAAGT
               ********                       ***  *  ****      ** *  *** *

CRCVspike      TCAAGCTGTTGTTAATGCAAATGCTGAAGCTCTTAATAACTTATTGCAACAACTCTCTAA
CECVspike      GCAAGATGTTGTTAACACACAAGGGCAAGCTTTAAGCCACCTAACAGTACAACTGCAAAA
                **** ********* **  *      ***** *    **  *      ****** **

CRCVspike      TAAATTTGGTGCTATAAGTGCTTCTTTACAAGAAATTCTATCTAGACTTGATGCTCTTGA
CECVspike      TAGCTTCCAAGCCATTAGTAGTTCTATTAGTGACATTTATAATAGGCTTGATGAACTGAG
                **  **    ** ** ***  **** *    ** ***       *** ******* **

CRCVspike      AGCGCAAGCTCAGATAGACAGACTTATCAATGGGCGTCTTACCGCTCTTAATGCTTATGT
CECVspike      TGCTGATGCACAAGTTGATAGGCTGATTACAGGTAGACTTACAGCACTTAATGCATTTGT
                **  * ** **    *  ** **  ** ** **  * **  *** ** ******** * ***

CRCVspike      TTCTCAACAGCTTAGTGATTCTACACTAGTAAAATTTAGTGCAGCACAAGCTATGGAGAA
CECVspike      ATCTCAGACTCTAACCAGACAAGCGGAGGTTAGGGCTAGTAGACAACTTGCCAAAGACAA
                *****      **  *       *      ** *    ****   **  * ** **

CRCVspike      GGTTAATGAATGTGTCAAAAGCCAATCATCTAGGATAAATTTTTGTGGTAATGGTAATCA
CECVspike      GGTTAATGAATGTGTTAGGTCTCAGTCTCAGAGATTTGGATTTTGTGGTAATGGTACACA
               *************** *   **  **     **  * *    ***************  **

CRCVspike      TATTATATCATTAGTGCAGAATGCTCCATATGGTTTGTATTTTATCCACTTTA-GCTATG
CECVspike      TTTGTTTTCACTTGCAAATGCAGCACCAAATGGCATGGTTTTCTTTCACACAGTGCTAT-
                * *  *** * *    *   **  ***   ****  ***  *  *  **        *****

CRCVspike      TCCCTACTAAGTATGTCACTGCGAAGGTTAGTCCCGGTCTGTGCATYGCAGGTGATAGAG
CECVspike      TACCAACAGCTTATGAAACTGTAACAGCTTGGTCAGGTATTTGTGCTTCAGATGGCGATC
                *  **  ****  ****  *    *      *  *     * ***  **  *** **
```

FIGURE 8 (Page 8 of 9)

```
CRCVspike      GTA---------TAGCTCCTAAGAGTGGTTATTT-----TGTT----AATGTAAATAACA
CECVspike      GCACTTTTGGACTTGTCGTTAAAGATGTTCAGTTGACGTTGTTTCGTAATCTAGATGACA
               * *            * *     ***  ** * **      ****    *** ** ** ***

CRCVspike      CTTGGATGTTCACTGGTAGTGGTTATTACTACCCTGAACCTATAACTGGAAATAATGTGG
CECVspike      AGTTCTATTTGACTCCCAGAACTATGTATCAGCCTAGAGCTGCAACTAGTTCTGATTTTG
                 *     ** ***  **   *   **   * ***  * **  ****  *  * ** * *

CRCVspike      TTGTTATGAGTACCTGTGCTGTTAACTATACTAAAGCACCGGATGTAATGCTGAACATTT
CECVspike      TTCAGATTGAGGGGTGCGACGTGTTGTTTGTCAATGCAACTGTAATTGACTTGCCTAGTA
               **    **      ** *  ** *   *  ** *** * *      **    * *  * *

CRCVspike      CAACACCCAACCTCCCTGATTTTAAGGAAG-------AGTTGGATCAATGGTTTAAAAAC
CECVspike      TTATACCTGACTATATCGACATTAATCAGACTGTTCAAGACATATTAGAAAACTACAGAC
                 * ***  **     **  ****   *          **    ** *    ** * **

CRCVspike      CAAACATTAATGGCACCAGATTTGTCACTTGATTATATAAATGTTACATTCTTGGACCTA
CECVspike      CAAAC-TGGACTGTACCTGAATTGACAATTGACATTTTTAACGCAACCTATTTAAATCTG
               ***** *    *  *  ***  ** *** ** ****    * *  ** * *  *   **

CRCVspike      CAAGATGAAATGAATAGGTTACAGG--AGGCAATAAAAGTT---TTAAATCATAGC----
CECVspike      ACTGGTGAAATTGATGACTTAGAATTTAGGTCAGAAAAGCTACATAACACCACAGTAGAG
                 * ****** **  *** *  **   ***  * * ***** * *  *  ** **

CRCVspike      ----------------------------TACAT----CAATCTCAAGGACATTGGTACA
CECVspike      CTTGCCATTCTCATTGACAATATTAACAATACATTAGTCAATCTTGAATGGCTCAATAGA
                                           *****    ******  *    *    ** *

CRCVspike      TATGAATATTATGTAAAATGGCCTTGGTATGTATGGCTTTTAATTGGCCTTGCTGGCGTA
CECVspike      ATTGAAACTTATGTGAAATGGCCTTGGTATGTGTGGCTACTAATAGGC-TTAGTAGTAGT
                 ** *  ****** ****************** ***    ***  **  **  *  * *

CRCVspike      GCTATGCTTGTT-TTACTATTCTTCATATGCTGTTGTACAGGATG---TGGGACTAGTTG
CECVspike      GTTTTGCATACCGCTATTGCTATTTTGCTGTTGTAGTACAGGTTGCTGTGGATGCATAGG
               * * *  *     **   ** *    ** *** ******* **   ***    *   *
```

FIGURE 8 (Page 9 of 9)

```
CRCVspike    TTTTAAGAAATGCGGTGGTTGTTGTGATGATTATACTGGACA--TCAGGAGTTAGTAATC
CECVspike    TTGTTTGGGAAGTTGTTGTCATTCTATTTGTAGTAGAAGACAATTTGAAAATTACGAACC
             ** *   * *  ** **  ** *   *   *  **     ****    *  * *** ** *

CRCVspike    AA----AACGTCACATGACGACTAA-----------------------------------
CECVspike    AATTGAAAAGTGCATGTCCACTAAA-----------------------------------
             **    **    **** * *****
```

FIGURE 9 (Page 1 of 12)

```
BCVspike           ATGTTTTTGATACTTTTAATTTCCTTACCAATGGCTCTTGCTGTTATAG
HCVspike  -----------ATGTTTTTGATACTTTTAATTTCCTTACCAACGGCTTTTGCTGTTATAG
CRCVspike -----------ATGTTTTTGATACTTTTAATTTCCTTACCAATGGCTTTTGCTGTTATAG
HEVspike  -------  ATGTTTTTTATACTTTTAATCACCCTGCCTTCTGTTTTTGCAGTTATAG
                   ******* **********  ** * **      * * **** *******

BCVspike  GAGATTTAAAGTGTACTACGGTTTCCATTAATGATGTTGACACCGGTGTTCCTTCTGTTA
HCVspike  GAGATTTAAAGTGTACTACGGTTTCCATTAATGATATTGACACCGGTGCTCCTTCTATTA
CRCVspike GAGATTTAAAGTGTACTACGGTTTCCATCAATGATGTTGACACCGGTGCTCCTTCTATTA
HEVspike  GGGATTTAAAGTGTAATACTTCATCAATTAATGACGTTGACACTGGTGTGCCATCTATTA
          * *************  ***    ** ** *****  ******* ****  ** *** ***

BCVspike  GCACTGATACTGTCGATGTTACTAATGGTTTAGGTACTTATTATGTTTTAGATCGTGTGT
HCVspike  GCACTGATATTGTCGATGTTACTAATGGTTTAGGTACTTATTATGTTTTAGATCGTGTGT
CRCVspike GCACTGATGTTGTCGATGTTACTAATGGTTTAGGTACTTATTATGTTTTAGATCGTGTGT
HEVspike  GCTCTGAAGTTGTTGATGTCACTAATGGTTTGGGGACTTTCTATGTTTTAGATCGTGTCT
          ** ****    *** ***** ********** ** ****   ***************** *

BCVspike  ATTTAAATACTACGTTGTTGCTTAATGGTTACTACCCTACTTCAGGTTCTACATATCGTA
HCVspike  ATTTAAATACTACGTTGTTGCTTAATGGTTACTACCCTACTTCAGGTTCTACATATCGTA
CRCVspike ATTTAAATACTACATTGTTGCTTAATGGTTATTATCCTACTTCAGGTTCTACATATCGTA
HEVspike  ATTTAAATACCACATTGTTGCTCAATGGTTATTACCCAATTTCAGGTGCTACATTTCGTA
          **********  ** ********  ** **  ** ** * ******* ****** *****

BCVspike  ATATGGCACTGAAGGGAACTTTACTATTGAGCACACTATGGTTTAAACCACCTTTTCTTT
HCVspike  ATATGGCACTGAAGGGAACTTTACTATTGAGCAGACTATGGTTTAAACCACCTTTTCTTT
CRCVspike ATATGGCACTGAAGGGAACTTTACTATTGAGCACACTATGGTTTAAACCACCATTTCTTT
HEVspike  ATGTGGCTCTGAAAGGAACTCGATTATTGAGCACCTTGTGGTTTAAGCCGCCTTTTTTAT
          ** **** ***** ****** *    * ********     * ******** ** *** * *

BCVspike  CTGATTTTATTAATGGTATTTTTGCTAAGGTCAAAAATACCAAGGTTATTAAAAATGGTG
HCVspike  CTGATTTTATTAATGGTATTTTTGCTAAGGTCAAAAATACCAAGGTTATTAAAAAGGGTG
CRCVspike CTGATTTTATTGATGGTGTTTTTGCTAAGGTAAAAAATACCAAGGTTATTAAAGATGGTG
HEVspike  CACCTTTTAATGATGGTATTTTTGCCAAGGTTAAAAACAGCAGATTTTCTAAACATGGTG
          *    ***** * ***** ******  ***** ***** **  **    ** ** * ****
```

FIGURE 9 (Page 2 of 12)

```
BCVspike     TAATGTATAGTGAGTTTCCTGCTATAACTATAGGTAGTACTTTTGTAAATACATCCTATA
HCVspike     TAATGTATAGTGAGTTTCCTGCTATAACTATAGGTAGTACTTTTGTAAATACATCCTATA
CRCVspike    TAGTGTATAGTGAGTTTCCTGCTATAACTATAGGTAGTACTTTTGTAAATACATCCTATA
HEVspike     TTATTTATAGTGAGTTTCCTGCTATTACTATAGGTAGTACTTTTGTAAATACTTCCTATA
              *  * ******************* ************************* *******

BCVspike     GTGTGGTAGTACAACCACATACTACCAATTTAGATAATAAATTACAAGGTCTCTTAGAGA
HCVspike     GTGTGGTAGTACAACCACATACTACCAATTTGGATAATAAATTACAAGGTCTCTTAGAGA
CRCVspike    GTGTGGTAGTACAACCACATACTACTAATTTAGATAATAAATTACAAGGTCTCTTAGAGA
HEVspike     GCATAGTAGTAAAGCCTCATACCTCATTTATTAATGGTAATTTACAAGGTTTTTTGCAAA
              *  * ****** *  ** ***** *    *  **   ***  ********* * **  * *

BCVspike     TCTCTGTTTGCCAGTATACTATGTGCGAGTACCCACATACGATTTGTCATCCTAATTTGG
HCVspike     TCTCTGTTTGCCAGTATACTATGTGCGAGTACCCACATACGATTTGTCATCCTAATCTGG
CRCVspike    TCTCTGTTTGCCAGTATACTATGTGCGATTACCCACATACGATGTGTCATCCTAATCTGG
HEVspike     TTTCTGTTTGTCAATATACTATGTGTGAATACCCACAGACTATTTGTCATCCTAATTTGG
              * ******** **  ********** **  ******* **  ** ************ ***

BCVspike     GTAATCGGCGCATAGAACTATGGCATTGGGATACAGGTGTTGTTTCCTGTTTATATAAGC
HCVspike     GTAATCGACGCGTAGAACTATGGCATTGGGATACAGGTGTTGTTTCCTGTTTATATAAGC
CRCVspike    GTAATAAACGCATAGAACTATGGCATTGGGATACAGGTGTTGTTCCCTGTTTATATAAGC
HEVspike     GTAATCAACGCATAGAATTATGGCATCATGACACAGATGTTGTTTCTTGTTTATACAGGC
              *****   *** ***** ********   *    ****  ******* * ******** * **

BCVspike     GTAATTTCACATATGATGTGAATGCTGATTATTTGTATTTCCATTTTTATCAAGAAGGTG
HCVspike     GTAATTTCACATATGATGTGAATGCTGATTACTTGTATTTCCATTTTTATCAAGAAGGTG
CRCVspike    GTAATTTCACATATGATGTGAATGCTGATTATTTGTATTCCCATTTTTATCAAGAAGGTG
HEVspike     GTAATTTCACATATGATGTGAATGCTGATTATTTATATTTTCACTTTTATCAGGAAGGTG
             ***************************** ** *****   **  ********* *******

BCVspike     GTACTTTTTATGCATATTTTACAGACACTGGTGTTGTTACTAAGTTTCTGTTTAATGTTT
HCVspike     GTACTTTTTATGCATATTTTACAGACACTGGTGTTGTTACTAAGTTTCTGTTTAATGTTT
CRCVspike    GTACTTTTTATGCATATTTTACAGACACTGGTGTTGTTACTAAGTTTCTGTTTCATGTTT
HEVspike     GCACTTTTTATGCATACTTTACAGATACTGGTTTTGTGACCAAGTTTCTGTTTAAGTTGT
              * ************* ******** *******  **** **  ********* *    * *
```

FIGURE 9 (Page 3 of 12)

```
BCVspike    ATTTAGGCACGGTGCTTTCACATTATTATGTCATGCCTTTGACTTGTAATAGTGCTATGA
HCVspike    ATTTAGGCACGGTGCTTTCACATTATTATGTCCTGCCTTTGACTTGTAATAGTGCTATGA
CRCVspike   ATTTAGGCACGGTGCTTTCACATTATTATGTCATGCCCTTGACTTGTAATAGTGCTATGA
HEVspike    ATTTAGGCACTGTGCTGTCACACTATTATGTTATGCCATTGACTTGTGATAGCGCTTTAT
            ********** ***** ***** *******  **** ********* **** *** *

BCVspike    CTTTAGAATATTGGGTTACACCTCTCACTTCTAAACAATATTTACTCGCTTTCAATCAAG
HCVspike    CTTTAGAATATTGGGTTACACCTCTCACTTCTAAACAATATTTACTAGCTTTCAATCAAG
CRCVspike   CTTTAGAATACTGGGTTACACCTCTCACTTTTAAACAATATTTACTCGCTTTCAATCAAG
HEVspike    CTTTAGAATATTGGGTTACACCTCTCACTACTAGACAATTTCTTCTAGCCTTTGACCAGG
            ********** ******************  ** *****   *  ** ** **    ** *

BCVspike    ATGGTGTTATTTTTAATGCTGTTGATTGTAAGAGTGATTTTATGAGTGAGATTAAGTGTA
HCVspike    ATGGTGTTATTTTTAATGCTGTTGATTGTAAGAGTGATTTTATGAGTGAGATTAAGTGTA
CRCVspike   ATGGTGTTATTTTTAATGCTGTTGATTGTAAGAGTGATTTTATGAGTGAGATTAAGTGTA
HEVspike    ATGGTGTTTTATACCATGCTGTTGATTGTGCTAGTGATTTTATGAGTGAGATTATGTGTA
            ******** * *  ************* *  ********************** *****

BCVspike    AAACACTATCTATAGCACCATCTACTGGTGTTTATGAATTAAACGGTTACACTGTTCAGC
HCVspike    AAACACTATCTATAGCACCATCTACTGGTGTTTATGAATTAAACGGTTACACTGTTCAGC
CRCVspike   AAACACTATCTATAGCACCATCTACTGGTGTTTATGAATTAAACGGTTACACTGTTCAGC
HEVspike    AAACTTCTTCAATTACACCACCTACTGGTGTTTATGAACTAAACGGTTACACAGTTCAAC
            ****   ** ** ***** ****************** ************* ***** *

BCVspike    CAATTGCAGATGTTTACCGACGTATACCTAATCTTCCCGATTGTAATATAGAGGCTTGGC
HCVspike    CAATTGCAGATGTTTACCGACGTATACCTAATCTTCCCGATTGTAATATAGAGGCTTGGC
CRCVspike   CAATTGCAGATGTTTACCGACGTATACCTAATCTTCCCGATTGTAATATAGAGGCTTGGC
HEVspike    CTGTTGCCACTGTGTATCGTAGAATACCTGACTTACCCAATTGCGATATCGAAGCTTGGC
            *  ****   *** ** ** *  ******  * * ***  *** * *****  ******

BCVspike    TTAATGATAAGTCTGTGCCCTCTCCATTAAATTGGGAACGTAAGACCTTTTCAAATTGTA
HCVspike    TTAATGATAAGTCGGTGCCCTCTCCATTAAATTGGGAACGTAAGACCTTTTCAAATTGTA
CRCVspike   TTAATGATAAGTCGGTGCCTTCTCCATTAAATTGGGAACGTAAGACCTTTTCAAATTGTA
HEVspike    TTAATTCTAAGACCGTTTCTTCGCCTCTTAATTGGGAACGTAAAATTTTTTCTAATTGTA
            ***** ****  **  * ** *  ** *************   ***** *  *******
```

FIGURE 9 (Page 4 of 12)

```
BCVspike    ATTTTAATATGAGCAGCCTGATGTCTTTTATTCAGGCAGACTCATTTACTTGTAATAATA
HCVspike    ATTTTAATATGAGCAGCCTGATGTCTTTTATTCAGGCAGACTCATTTACTTGTAATAATA
CRCVspike   ATTTTAATATGAGCAGCCTGATGTCTTTTATCCAGGCTGACTCGTTTACTTGTAATAATA
HEVspike    ATTTTAACATGGGCAGGCTGATGTCTTTTATTCAGGCTGACTCTTTTGGTTGTAACAATA
            ******* *** ****  ************** ***** ***** ***  ****** ****

BCVspike    TTGATGCAGCTAAGATATATGGTATGTGTTTTTCCAGCATAACTATAGATAAGTTTGCTA
HCVspike    TTGATGCTGCTAAGATATATGGTATGTGTTTTTCCAGCATAACTATAGATAAGTTTGCTA
CRCVspike   TTGATGCTGCTAAGATATACGGTATGTGTTTTTTCAGCATAACTATAGATAAGTTTGCTA
HEVspike    TTGATGCTTCTCGCTTATATGGTATGTGTTTTGGTAGCATTACTATTGACAAGTTTGCTA
            ******* **    **** ************    ***** ***** ** **********

BCVspike    TACCCAATGGTAGGAAGGTTGACCTACAATTGGGCAATTTGGGCTATTTGCAGTCTTTTA
HCVspike    TACCCAATGGTAGGAAGGTTGACCTACAATTGGGCAATTTGGGCTATTTGCAGTCTTTTA
CRCVspike   TACCCAATGGTAGGAAGGTTGACCTACAAATGGGCAATTTGGGCTATTTGCAGTCTTTTA
HEVspike    TACCCAATAGTAGAAAGGTTGATCTGCAAGTGGGTAAATCTGGTTATTTACAATCTTTTA
            ******** **** ******* ** ***  *** *  ** ***  ***** ** ******

BCVspike    ACTATAGAATTGATACTACTGCTACAAGTTGTCAGTTGTATTATAATTTACCTGCTGCTA
HCVspike    ACTATAGAATTGATACTACTGCTACAAGTTGTCAGTTGTATTATAATTTACCTGCTGCTA
CRCVspike   ACTATAGAATTGATACTACTGCTACAAGTTGTCAGTTGTATTATAATTTACCTGCTAGTA
HEVspike    ATTATAAGATTGACACTGCTGTTAGCAGTTGTCAACTCTATTATAGTTTGCCTGCAGCAA
            * ****  *****  *** *** **  ********   * ******  *** ****** *

BCVspike    ATGTTTCTGTTAGCAGGTTTAATCCTTCTACTTGGAATAGGAGATTTGGTTTTACAGAAC
HCVspike    ATGTTTCTGTTAGCAGGTTTAATCCTTCTACTTGGAATAGGAGATTTGGTTTTACAGAAC
CRCVspike   ATGTTTCTATTAGCAGGTTTAATCCTTCTATTTGGAATAGGAGATTTGGTTTTACAGAAC
HEVspike    ACGTATCTGTCACTCATTATAATCCTTCATCTTGGAACAGAAGGTATGGGTTTAT----T
            * ** *** *    *    * ********   ****** ** ** * *** ****

BCVspike    AATCTGTTTTTAAGCCTCAACCTGTAGGTGTTTTTACTGATCATGATGTTGTTTATGCAC
HCVspike    AATCTGTTTTTAAGCCTCAACCTGTAGGTGTTTTTACTCATCATGATGTTGTTTATGCAC
CRCVspike   AATCTGTTTTTAAGCCTCAACCTGTAGGTGTTTTTACTGATCATGATGTTGTTTATGCAC
HEVspike    AATCAGAGTTTTGGTTCCAG-----AGGC-CTT--------CATGATGCTGTATATTCAC
            **** *  ***  *  * **     ***  **         ******* *** *** ***
```

FIGURE 9 (Page 5 of 12)

```
BCVspike    AACATTGTTTTAAAGCTCCCACAAATTTCTGTCCGTGTAAATTGGATGGGTCTTTGTGTG
HCVspike    AACATTGTTTTAAAGCTCCCACAAATTTCTGTCCGTGTAAATTGGATGGGTCTTTGTGTG
CRCVspike   AACATTGTTTTAAAGCTCCCACAAATTTCTGTCCGTGTAAATTGAATGGGTCTTTGTGTG
HEVspike    AGCAATGTTTTAATACACCTAATACATATTGTCCTTGTA----GAACAAGTC--AATGCA
            * ** ********  * **  *   *  *  ***** ****    * *   ***   **

BCVspike    TAGGTAGTGGTTCTGGTATAGATGCTGGTTATAAAAATAGTGGTATAGGCACTTGTCCTG
HCVspike    TAGGTAATGGTCCTGGTATAGATGCTGGTTATAAAAATAGTGGTATAGGCACTTGTCCTG
CRCVspike   TAGGTAGTGGTTTTGGTATAGATGCTGGTTATAAAAATAGTGGTATAGGCACTTGTCCTG
HEVspike    TAGGTGGTG---CTGGCACAGGAACTTGTCCTGTAGGCACCACTGTGCGCAAGTGTTTTG
            ***** **    ***  *  **  ** **   *    *  *  *** *** **

BCVspike    CAGGTACTAATTATTTAACTTGTCATAATGCTGCCCAATGTAATTGTTTGTGCACTCCAG
HCVspike    CAGGTACTAATTATTTAACTTGCCATAATGCTGCCCAATGTGATTGTTTGTGCACTCCCG
CRCVspike   CAGGTACTAATTATTTAACTTGTTATAATGCTAACCAATGTGATTGTTTGTGCACTCCAG
HEVspike    CTG---C-AGTTAC--A---------AACGCTACTAAGTGTACTTGCTGGTGTCAACCAG
             *    *  * ***   *          ** ***  * *** *** * ***     ** *

BCVspike    ACCCCATTACATCTAAATCTACAGGGCCTTATAAGTGCCCCCAAACTAAATATTTAGTTG
HCVspike    ACCCCATTACATCTAAATCTACAGGGCCTTACAAGTGCCCCCAAACTAAATACTTAGTTG
CRCVspike   ACCCTATTTTATCTAAATCTACAGGGCCTTATAAGTGCCCCCAAACTAAATACTTAGTTG
HEVspike    ATCCTTCCACATATAAAGGTGTAAATGCCTGGACTTGTCCGCAATCTAAAGTTTCTATAC
            * **        **  *       *     *   ** **  ***  **** *   *

BCVspike    GCATAGGTGAGCACTGTTCGGGTCTTGCTATTAAAAGTGATTATTGTGGAGGTAATCCTT
HCVspike    GCATAGGTGAGCACTGTTCGGGTCTTGCTATTAAAAGTGATTATTGTGGAGGTAATCCTT
CRCVspike   GCATAGGTGAGCACTGTTCTGGTCTTGCTATTAAAAGTGATTATTGTGGAGGCAATCCTT
HEVspike    AACCAGGTCAGCATTGCCCTGGCTTGGGTCTTGTGGAGGATGATTGCTCTGGTAATCCTT
              *  *** **** **  * ** ** *  *   *  * ***  **  ** *******

BCVspike    GTACTTGCCAACCACAAGCATTTTTGGGTTGGTCTGTTGATTCTTGTTTACAAGGGGATA
HCVspike    GTACTTGCCAACCACAAGCATTTTTGGGTTGGTCTGTTGACTCTTGTTTACAAGGGGATA
CRCVspike   GTACTTGCCAACCAAAAGCATTTTTGGGTTGGTCTGTGGACTCTTGTTTACAAGGGGATA
HEVspike    GCACTTGTAAACCACAGGCTTTCATAGGCTGGAGTTCAGAAACTTGTTTGCAAAATGGTA
            * *****  ***** ** **  *  ** *** ** **   * ******  *** * *
```

FIGURE 9 (Page 6 of 12)

```
BCVspike    GGTGTAATATCTTTGCTAATTTTATTTTGCATGATGTTAATAGTGGTACTACTTGTTCTA
HCVspike    GGTGTAATATTTTTGCTAATTTTATTTTGCATGATGTTAATAGTGGTACTACTTGTTCTA
CRCVspike   GGTGTAATATTTTTGCTAATTTTATTTTGCATGGTGTTAATAGTGGTACTACTTGTTCTA
HEVspike    GGTGTAATATTTTTGCTAATTTTATTTTGAATGATGTTAATAGCGGTACTACCTGTTCTA
            ********* ***************** *** ******** ******* *******

BCVspike    CTGATTTACAAAAATCAAACACAGACATAATTCTTGGTGTTTGTGTTAATTATGATCTTT
HCVspike    CTGATTTACAAAAATCAAACACAGACATAATTCTTGGTGTTTGTGTTAATTATGATCTTT
CRCVspike   CTGATTTACAAAAATCAAACACAGACATAATTCTTGGTGTTTGTGTTAATTATGATCTTT
HEVspike    CTGATTTACAACAGGGTAATACTAATATTACTACTGATGTTTGTGTTAATTATGACCTAT
            ********** *   ** **  * ** * *  ** ******************** ** *

BCVspike    ATGGTATTACAGGCCAAGGTATTTTTGTTGAGGTTAATGCGACTTATTATAATAGTTGGC
HCVspike    ATGGTATTACAGGCCAAGGTATTTTTGTTGAGGTTAATGCGCCTTATTATAATAGTTGGC
CRCVspike   ATGGTATTACAGGCCAAGGTATTTTTGTTGAGGTTAATGCGACTTATTATAATAGTTGGC
HEVspike    ATGGCATTACAGGCCAGGGCATACTTATAGAAGTTAATGCCACGTATTATAATAGTTGGC
            **** *********** ** **  **  *  ********  * ****************

BCVspike    AGAACCTTTTATATGATTCTAATGGTAATCTCTATGGTTTTAGAGACTACTTAACAAACA
HCVspike    AGAACCTTTTATATGATTCTAATGGTAATCTCTATGGTTTTAGAGACTACTTAACAAACA
CRCVspike   AGAACCTTTTATATGATTCTAATGGTAATCTCTATGGTTTTAGGGACTACTTAACAAACA
HEVspike    AGAATCTTCTTTATGATTCTAGTGGTAATCTCTATGGCTTTAGAGATTATTTATCAAATA
            **** *** * ********** *************** ***** ** ** ** *** *

BCVspike    GAACTTTTATGATTCGTAGTTGCTATAGCGGTCGTGTTTCAGCGGCCTTTCATGCTAATT
HCVspike    GAACTTTTATGATTCGTAGTTGCTATAGCGGTCGTGTTTCAGCGGCCTTTCATGCTAACT
CRCVspike   GAACTTTTATGATTCGTAGTTGCTATAGCGGTCGTGTTTCAGCGGGCTTTCACTCTAACT
HEVspike    GAACCTTTCTTATTCGTAGCTGCTATAGTGGAAGAGTTTCAGCAGTCTTTCATGCTAACT
            **** *** * ******** ******** **   * ******* *  ****** **** *

BCVspike    CTTCCGAACCAGCATTGCTATTTCGGAATATTAAATGCAATTACGTTTTAATAATACTC
HCVspike    CTTCCGAACCAGCATTGCTATTTCGGAATATTAAATGCAGTTACGTTTTAATAATACTC
CRCVspike   CTTCCGAACCAGCATTGCTATTTCGGAATATTAAATGCAATTACGTTTTAATAATACTC
HEVspike    CTTCTGAACCAGCTTTGATGTTTCGTAATCTTAAATGCAGCCACGTTTTTAATTATACCA
            **** ******** *** * ***** ***  ********   ********** ****
```

FIGURE 9 (Page 7 of 12)

```
BCVspike     TTTCACGACAGCTGCAACCTATTAACTATTTTGATAGTTATCTTGGTTGTGTTGTCAATG
HCVspike     TTTCACGACAGCTGCAACCTATTAACTATTTTGATAGTTATCTTGGTTGTGTTGTCAATG
CRCVspike    TTTCACGACAGCTGCAACCTATTAACTATTTTGATAGTTATCTTGGTTGTGTTGTCAATG
HEVspike     TTTTAAGACAAATACAGCTTGTTAATTATTTTGATAGTTACCTTGGTTGTGTTGTTAATG
             *** * ****  * ** * * **** **************  ************** ****

BCVspike     CTGATAATAGTACTTCTAGTGCTGTTCAAACATGTGATCTCACAGTAGGTAGTGGTTACT
HCVspike     CTGATAATAGTACTTCTAGTGTTGTTCAAACATGTGATCTCACAGTAGGTAGTGGTTACT
CRCVspike    CTGATAATAGTACTTCTAGTTCTGTTCAAACATGTGATCTCACAGTAGGTAGTGGTTACT
HEVspike     CTTATAATAATACAGCTAGTGCTGTAAGTACTTGTGATTTAACCGTTGGTAGCGGCTATT
             ** ****** ***  *****   ***       ** ****** *  ** ***** ** ** *

BCVspike     GTGTGGATTACTCTACAAAAAGACGAAGTCGTAGAGCGATTACCACTGGTTATCGGTTTA
HCVspike     GTGTGGATTACTCTACAAAAAGACGAAGTCGTAGAGCGATTACCACTGGTTATCGGTTTA
CRCVspike    GGGGGGATTACTCTACACAAAGACGAAGTCGTAGAACGATTACCACTGGTTATCGGTTTA
HEVspike     GTGTTGATTATGTTACAGCACTTAGATCACGTAGATCTTTTACTACAGGTTATCGCTTTA
             * * ***** ****   *     **   *****  *    **** ** ******** ****

BCVspike     CTAATTTTGAGCCATTTACTGTTAATTCAGTAAATGATAGTTTAGAACCTGTAGGTGGTT
HCVspike     CTAATTTTGAGCCATTTACTGTTAATTCAGTAAATGATAGTTTAGAACCTGTAGGTGGTT
CRCVspike    CTAATTTTGAGCCATTTACTGTTAATCCAGTAAATGATAGTTTACACCCTGTAGGTGGTT
HEVspike     CTAATTTTGAACCATTTGCCGCTAATTTGGTAAATGATAGTATAGAACCTGTTGGTGGTT
             ********** ****** *  * ****    ************ ** * ***** *******

BCVspike     TGTATGAAATTCAAATACCTTCAGAGTTTACTATAGGTAATATGGAGGAGTTTATTCAAA
HCVspike     TGTATGAAATTCAAATACCTTCAGAGTTTACTATAGGTAATATGGAGGAGTTTATTCAAA
CRCVspike    TGTATGAAATTCAAATACCTTCAGAGTTTACTATAGGTAATATGGAGGAGTTTATTCAAA
HEVspike     TGTATGAAATACAGATACCTTCAGAGTTTACCATTGGTAATTTAGAAGAATTCATTCAAA
             ********** ** ***************** ** ****** * ** ** ** *******

BCVspike     TAAGCTCTCCTAAAGTTACTATTGATTGTTCTGCTTTTGTCTGTGGTGATTATGCAGCAT
HCVspike     CAAGCTCTCCTAAAGTTACTATTGATTGTTCTGCTTTTGTCTGTGGTGATTATGCAGCAT
CRCVspike    CAAGATCTCCTAAAGTTACTATTGATTGTCCTGTTTTTGTCTGTGGTGATTATGCAGCAT
HEVspike     CGAGTTCCCCTAAGGTTACTATAGATTGTGCTACATTTGTTTGTGGTGACTATGCTGCAT
             * ** ***** ******** ****** **    ***** ********* ***** ****
```

FIGURE 9 (Page 8 of 12)

```
BCVspike    GTAAATCACAGTTGGTTGAATATGGTAGTTTCTGTGACAATATTAATGCTATACTCACAG
HCVspike    GTAAATCACAGTTGGTTGAATATGGTAGCTTCTGTGACAATATTAATGCTATACTCACAG
CRCVspike   GTAAATCACAGTTGGTTGAATATGGTAGTTTTTGTGACAATATTAATGCTATACTCACAG
HEVspike    GTAGACAACAGTTAGCTGAGTATGGTAGTTTTTGTGAGAACATTAATGCTATACTCATAG
            *** *  ****** * *** ******* ** ***** ** **************** **

BCVspike    AAGTAAATGAACTACTTGACACTACACAGTTGCAAGTAGCTAATAGTTTAATGAATGGTG
HCVspike    AAGTAAATGAACTACTTGACACTACACAGTTGCAAGTAGCTAATAGTTTAATGAATGGTG
CRCVspike   AAGTAAATGAACTACTTGACACTACACAGTTGCAAGTAGCTAATAGTTTAATGAATGGTG
HEVspike    AAGTAAATGAACTACTTGACACTACACAGTTGCAAGTAGCTAATAGTTTAATGAATGGAG
            *********************************************************** *

BCVspike    TCACTCTTAGCACTAAGCTTAAAGATGGCGTTAATTTCAATGTAGACGACATCAATTTTT
HCVspike    TCACTCTTAGCACTAAGCTTAAAGATGGCGTTAATTTCAATGTAGACGACATCAATTTTT
CRCVspike   TCACTCTTAGCACTAAGCTTAAAGATGGCTTTAATTTCAATGTAGATGACATCAATTTTT
HEVspike    TCACCCTTAGTACTAAGATTAAGGATGGATTAATTTCAATGTTGACGATATCAACTTCT
            ****  **** ****** ****  *****    ************* ** ** ***** ** *

BCVspike    CCCCTGTATTAGGTTGTTTAGGAAGCGATTGTAATAAAGTTTCCAGTAGATCTGCTATAG
HCVspike    CCCCTGTATTAGGTTGTTTAGGAAGCGCTTGTAATAAAGTTTCCAGCAGATCTGCTATAG
CRCVspike   CCCCTGTATTAGGTTGTTTAGGAAGCGAATGTAATAAAGTTTCCAGTAGATCTGCTATAG
HEVspike    CCTCTGTATTAGGTTGTTTAGGAAGCGAATGTAACAGAGCTTCCACTAGATCTGCTATAG
            ** ********************** *****  * ** *****   ************

BCVspike    AGGATTTACTTTTTTCTAAAGTAAAGTTATCTGATGTCGGTTTTGTTGAGGCTTATAATA
HCVspike    AGGATTTACTTTTTTCTAAAGTAAAGTTATCTGATGTCGGTTTCGTTGAGGCTTATAATA
CRCVspike   AGGATTTACTTTTTTCTAAAGTAAAGTTATCTGATGTTGGTTTTGTTGATGCTTATAATA
HEVspike    AGGATTTACTTTTTGATAAAGTAAAATTGTCTGATGTCGGTTTTGTACAGGCCTATAATA
            **************  ******** ** ********  *****  **   * ** *******

BCVspike    ATTGTACTGGAGGTGCCGAAATTAGGGACCTCATTTGTGTGCAAAGTTATAATGGTATCA
HCVspike    ATTGTACTGGAGGTGCCGAAATTAGGGACCTCATTTGTGTGCAAAGTTATAATGGTATCA
CRCVspike   ATTGTACTGGAGGTGCCGAAATTAGGGACCTCATTTGTGTGCAAAGTTATAATGGTATCA
HEVspike    ACTGCACTGGAGGAGCCGAAATTAGGGATCTCATTTGTGTGCAAAGTTATAATGGTATCA
            * ** ******** ************** *******************************
```

FIGURE 9 (Page 9 of 12)

```
BCVspike    AAGTGTTGCCTCCACTACTCTCAGAAAATCAGATCAGTGGATACACTTTGGCTGCTACCT
HCVspike    AAGTGTTGCCTCCACTGCTCTCAGTAAATCAGATCAGTGGATACACTTTGGCTGCCACCT
CRCVspike   AAGTGTTGCCTCCACTGCTCTCAGAAAATCAGATCAGTGGATACACTTTGGCTGCCACCT
HEVspike    AAGTGTTGCCTCCATTGTTATCTGAAAATCAGATTAGTGGTTACACTTCGGCAGCCACCG
            ************** * * ** * ********* ***** ******* *** ** ***

BCVspike    CTGCTAGTCTGTTTCCTCCTTGGTCAGCAGCAGCAGGCGTACCATTTTATTTAAATGTTC
HCVspike    CTGCTAGTCTGTTTCCTCCTTGGTCAGCAGCAGCAGGTGTACCATTTTATTTAAATGTTC
CRCVspike   TTGCTAGTCTGTTTCCTCCTTGGTCAGCAGCAGCAGGCGTACCATTTTATTTAAATGTTC
HEVspike    CTGCTAGCCTATTTCCTCCCTGGACAGCTGCAGCAGGTGTACCATTTTATTTAAATGTTC
            ****** ** ******** *** **** ******* ********************

BCVspike    AGTATCGTATTAATGGGATTGGTGTTACCATGGATGTTCTAAGTCAAAATCAAAAGCTTA
HCVspike    AGTATCGTATTAATGGGATTGGTGTTACCATGGATGTGTTAAGTCAAAATCAAAAGCTTA
CRCVspike   AGTATCGTATTAATGGTATTGGTGTTACCATGGATGTGCTAACTCAAAATCAAAAGCTTA
HEVspike    AGTATCGTATAAATGGGCTTGGCGTCACCATGGATGTGCTAAGCCAAAACCAAAAGCTTA
            ********** *****  **** ** **********  ***  ***** **********

BCVspike    TTGCTAATGCATTTAACAATGCCCTTGATGCTATTCAGGAAGGGTTTGATGCTACCAATT
HCVspike    TTGCTAATGCATTTAGCAATGCTCTTGATGCTATTCAGGAAGGGTTTGATGCTACCAATT
CRCVspike   TTTCTAATGCATTTAACAATGCCCTTGATGCTATTCAGGAAGGGTTTGATGCTACCAATT
HEVspike    TTGCTAGTGCATTTAACAACGCTCTTGATTCTATCCAGGAAGGGTTCGACGCAACCAATT
            ** *** ******** *** ** ****** **** *********** ** ** *******

BCVspike    CTGCTTTAGTTAAAATTCAAGCTGTTGTTAATGCAAATGCTGAAGCTCTTAATAACTTAT
HCVspike    CTGCTTTAGTTAAAATTCAAGCTGTTGTTAATGCAAATGCTGAAGCTCTTAATAACTTAT
CRCVspike   CTGCTTTAGTTAAAATTCAAGCTGTTGTTAATGCAAATGCTGAAGCTCTTAATAACTTAT
HEVspike    CTGCTTTAGTTAAAATTCAGGCTGTTGTTAATGCAAATGCTGAAGCACTTAATAACTTAT
            ******************* ****************************** *********

BCVspike    TGCAACAACTCTCTAATAGATTTGGTGCTATAAGTTCTTCTTTACAAGAAATTCTATCTA
HCVspike    TGCAACAACTCTCTAATAGATTTGGTGCTATAGGTTCTTCTTTACAAGAAATTCTATCTA
CRCVspike   TGCRACAACTCTCTAATAAATTTGGTGCTATAAGTGCTTCTTTACAAGAAATTCTATCTA
HEVspike    TGCAGCAACTCTCTAACAGATTTGGTGCCATAAGTGCCTCTTTACAAGAAATTTTATCCA
            ***  ********** * ********* *** **   ************* *  ****  
```

FIGURE 9 (Page 10 of 12)

```
BCVspike    GACTTGATGCTCTTGAAGCGCAAGCTCAGATAGACAGACTTATTAATGGGCGTCTTACCG
HCVspike    GACTGGATGCTCTTGAAGCGCAAGCTCAGATAGACAGACTTATTAATGGGCGTCTTACCG
CRCVspike   GACTTGATGCTCTTGAAGCGCAAGCTCAGATAGACAGACTTATCAATGGGCGTCTTACCG
HEVspike    GGCTCGATGCTCTTGAAGCTAAAGCTCAGATAGACAGACTTATTAATGGGCGTCTCACCG
            * ** ************* ********************* ********** ****

BCVspike    CTCTTAATGCTTATGTTTCTCAACAGCTTAGTGATTCTACACTAGTAAAATTTAGTGCAG
HCVspike    CTCTTAATGCTTATGTTTCTCAACAGCTTAGTGATTCTACACTAGTAAAATTTAGTGCAG
CRCVspike   CTCTTAATGCTTATGTTTCTCAACAGCTTAGTGATTCTACACTAGTAAAATTTAGTGCAG
HEVspike    CTCTTAATGCTTATGTTTCTCAGCAGCTTAGTGATTCTACACTAGTAAAATTTAGTGCAG
            ********************** *************************************

BCVspike    CACAAGCTATGGAGAAGGTTAATGAATGTGTCAAAAGCCAATCATCTAGGATAAATTTTT
HCVspike    CACAAGCTATGGAGAAGGTTAATGAATGTGTCAAAAGCCAATCATCTAGGATAAATTTTT
CRCVspike   CACAAGCTATGGAGAAGGTTAATGAATGTGTCAAAAGCCAATCATCTAGGATAAATTTTT
HEVspike    CACAAGCTATTGAGAAAGTTAATGAATGTGTTAAAAGCCAATCATCTAGGATAAATTTCT
            ********** ***** ************** ***************************  *

BCVspike    GTGGTAATGGTAATCATATTATATCATTAGTGCAGAATGCTCCATATGGTTTGTATTTTA
HCVspike    GTGGTAATGGTAATCATATTATATCATTAGTGCAGAATGCTCCATATGGTTTGTATTTTA
CRCVspike   GTGGTAATGGTAATCATATTATATCATTAGTGCAGAATGCTCCATATGGTTTGTATTTTA
HEVspike    GTGGTAATGGTAATCATATTATATCATTAGTACAGAATGCTCCATATGGTTTGTATTTTA
            ******************************* ****************************

BCVspike    TCCACTTTAGCTATGTCCCTACTAAGTATGTCACTGCGAAGGTTAGTCCCGGTCTGTGCA
HCVspike    TCCACTTTAGCTATGTCCCTACTAAGTATGTCACTGCGAAGGTTAGTCCCGGTCTGTGCA
CRCVspike   TCCACTTTAGCTATGTCCCTACTAAGTATGTCACTGCGAAGGTTAGTCCCGGTCTGTGCA
HEVspike    TCCATTTTAGCTATGTCCCCACCAAGTATGTTACAGCAAAGGTTAGTCCTGGTTTGTGCA
            **** ************** ** ******** ** ** *********** *** ******

BCVspike    TTGCTGGTGATAGAGGTATAGCCCCTAAGAGTGGTTATTTTGTTAATGTAAATAACACTT
HCVspike    TTGCTGGTGATAGAGGTATAGCCCCTAAGAGTGGTTATTTTGTTAATGTAAATAATACTT
CRCVspike   TYGCAGGTGATAGAGGTATAGCTCCTAAGAGTGGTTATTTTGTTAATGTAAATAACACTT
HEVspike    TTGCTGGCGATATAGGAATATCGCCTAAGAGTGGTTATTTTATTAATGTAAATAACTCTT
            * ** ** **** *** *** * * ******************* ************* ***
```

FIGURE 9 (Page 11 of 12)

```
BCVspike    GGATGTTCACTGGTAGTGGTTATTACTACCCTGAACCTATAACTGGAAATAATGTTGTTG
HCVspike    GGATGTTCACTGGTAGTGGTTATTACTACCCTGAACCCATAACTGGAAATAATGTTGTTG
CRCVspike   GGATGTTCACTGGTAGTGGTTATTACTACCCTGAACCTATAACTGGAAATAATGTGGTTG
HEVspike    GGATGTTCACTGGTAGTGGCTATTACTACCCTGAACCTATAACCCAAAATAATGTTGTTG
            ****************** ****************** *****   ********  ****

BCVspike    TTATGAGTACCTGTGCTGTTAATTACACTAAAGCACCGGATGTAATGCTGAACATTTCAA
HCVspike    TTATGAGTACCTGTGCTGTTAACTATACTAAAGCGCCGGATGTAATGCTGAACATTTCAA
CRCVspike   TTATGAGTACCTGTGCTGTTAACTATACTAAAGCACCGGATGTAATGCTGAACATTTCAA
HEVspike    TGATGAGTACGTGTGCTGTTAATTATACTAAAGCACCGGATCTAATGCTGAACACATCGA
            * ******** *********** ** ******** ****** ************  ** *

BCVspike    CACCCAACCTCCCTGATTTTAAGGAAGAGTTGGATCAATGGTTTAAAAACCAAACATCAG
HCVspike    CACCCAACCTCCATGATTTTAAGGAAGAGTTGGATCAATGGTTTAAAAACCAAACATCAG
CRCVspike   CACCCAACCTCCCTGATTTTAAGGAAGAGTTGGATCAATGGTTTAAAAACCAAACATTAA
HEVspike    CACCCAACCTTCCTGATTTCAAGGAAGAATTGTATCAATGGTTTAAAAACCAATCTTCAT
            ********** *  ****** *** ******  **** *** *** *** **** * * *

BCVspike    TGGCACCAGATTTGTCACTTGATTATATAAATGTTACATTCTTGGACCTACAAGATGAAA
HCVspike    TGGCACCAGATTTGTCACTTGATTATATAAATGTTACATTCTTGGACCTACAAGATGAAA
CRCVspike   TGGCACCAGATTTGTCACTTGATTATATAAATGTTACATTCTTGGACCTACAAGATGAAA
HEVspike    TGGCACCAGATTTGTCATTTGATTATATTAATGTTACGTTCTTGGACCTACAAGATGAAA
            ***************** ********** ******** **********************

BCVspike    TGAATAGGTTACAGGAGGCAATAAAAGTTTTAAATCAGAGCTACATCAATCTCAAGGACA
HCVspike    TGAATAGGTTACAGGAGGCAATAAAAGTTTTAAATCAGAGCTACATCAATCTCAAGGACA
CRCVspike   TGAATAGGTTACAGGAGGCAATAAAAGTTTTAAATCATAGCTACATCAATCTCAAGGACA
HEVspike    TGAATAGGTTACAAGAAGCTATAAAAGTTCTAAATCATAGCTACATCAATCTCAAGGACA
            ************* ** ** ********* ******* **********************

BCVspike    TTGGTACATATGAGTATTATGTAAAATGGCCTTGGTATGTATGGCTTTTAATTGGCCTTG
HCVspike    TTGGTACATATGAGTATTATGTAAAATGGCCTTGGTATGTATGGCTTTTAATTGGCTTTG
CRCVspike   TTGGTACATATGAATATTATGTAAAATGGCCTTGGTATGTATGGCTTTTAATTGGCCTTG
HEVspike    TTGGTACATATGAGTATTATGTGAAATGGCCTTGGTATGTATGGCTTTTAATTTGCCTTG
            ************* ******* *********************** ************ * ***
```

FIGURE 9 (Page 12 of 12)

```
BCVspike     CTGGTGTAGCTATGCTTGTTTTACTATTCTTCATATGCTGTTGTACAGGATGTGGGACTA
HCVspike     CTGGTGTAGCTATGCTTGTTTTACTATTCTTCATATGCTGTTGTACAGGATGTGGGACTA
CRCVspike    CTGGCGTAGCTATGCTTGTTTTACTATTCTTCATATGCTGTTGTACAGGATGTGGGACTA
HEVspike     CTGGTGTAGTTATGCTTGTTTTACTATTCTTCATATGCTGCTGTACAGGATGTGGGACTA
             **** **** ****************************** ******************

BCVspike     GTTGTTTTAAGAAATGTGGTGGTTGTTGTGATGATTATAC--------------------
HCVspike     GTTGTTTTAAGATATGTGGTGGTTGTTGTGATGATTATACTGGACACCAGG---------
CRCVspike    GTTGTTTTAAGAAATGCGGTGGTTGTTGTGATGATTATACTGGACATCAGG---------
HEVspike     GTTGTTTTAAGAAATGTGGCGGTTGTTTTGATGATTATACTGGACACCAGGAGTTTGTAA
             *********** *** ** ******* ************

BCVspike     ----------------------------
HCVspike     ----------------------------
CRCVspike    ----------------------------
HEVspike     TCAAAACTTCACATGACGATTAATTTCGT
```

FIGURE 10 (Page 1 of 5)

```
BCVspikepro    ----MFLILLISLPMALAVIGDLKCTTVSINDVDTGVPSVSTDTVDVTNGLGTYYVLDRV
HCVspikepro    ----MFLILLISLPTAFAVIGDLKCTTVSINDIDTGAPSISTDIVDVTNGLGTYYVLDRV
CRCVspikepr    ----MFLILLISLPMAFAVIGDLKCTTVSINDVDTGAPSISTDVVDVTNGLGTYYVLDRV
HEVspikepro    ----MFFILLITLPSVFAVIGDLKCNTSSINDVDTGVPSISSEVVDVTNGLGTFYVLDRV
CECVspikepr    MIVLVTCILLLCSYHTASSTSNNDCRQVNVTQLDGNENLIRDFLFQNFKEEGTVVVGG--
                   : ***:     .: .: .* .:.::*.   :    .: : ** *  .

/103
BCVspikepro    YLNTTLLLNGYYPTSGSTYRNMALKGTLLLSTLWFKPPFLSDFINGIFAKVKNTKVIKNG
HCVspikepro    YLNTTLLLNGYYPTSGSTYRNMALKGTLLLSRLWFKPPFLSDFINGIFAKVKNTKVIKKG
CRCVspikepr    YLNTTLLLNGYYPTSGSTYRNMALKGTLLLSTLWFKPPFLSDFIDGVFAKVKNTKVIKDG
HEVspikepro    YLNTTLLLNGYYPISGATFRNVALKGTRLLSTLWFKPPFLSPFNDGIFAKVKNSRFSKHG
CECVspikepr    YYPTEVWYNCSRTATTTAYEYFSNIHAFYFDMEAMENSTGNARGKPLLFHVHGEPVS--V
                *  *  : *   . : :::. .:  :   :.   ::  .  . :: :*:.  .

/118                                   /166  /171
BCVspikepro    VMYSEFPAITIGSTFVNTSYSVVVQPHTTNLDNKLQGLLEISVCQYTMCEYPHTICHPNL
HCVspikepro    VMYSEFPAITIGSTFVNTSYSVVVQPHTTNLDNKLQGLLEISVCQYTMCEYPHTICHPNL
CRCVspikepr    VVYSEFPAITIGSTFVNTSYSVVVQPHTTNLDNKLQGLLEISVCQYTMCDYPHTMCHPNL
HEVspikepro    VIYSEFPAITIGSTFVNTSYSIVVKPHTSFINGNLQGFLQISVCQYTMCEYPQTICHPNL
CECVspikepr    IIYISYRDDVQHRPLLKHGLVCITESRNIDYN-SFTSSQWNSICTGNDRKIPFSVIPTDN
               ::* .:      .:::    .  :..:.       :  .:    *:*  . . *  :: .:

/179           /192                  /210
BCVspikepro    GNRRIELWHWDTGVVSCLYKRNFTYDVN------ADYLYFHFYQEGGTFYAYFTDTGVVT
HCVspikepro    GNRRVELWHWDTGVVSCLYKRNFTYDVN------ADYLYFHFYQEGGTFYAYFTDTGVVT
CRCVspikepr    GNKRIELWHWDTGVVPCLYKRNFTYDVN------ADYLSHFYQEGGTFYAYFTDTGVVT
HEVspikepro    GNQRIELWHHDTDVVSCLYRRNFTYDVN------ADYLYFHFYQEGGTFYAYFTDTGFVT
CECVspikepr    GTKIYGLEWNDEFVTAYISGRSYNWNINNNWFNNVTLLYSRSSTATWQHSAAYVYQGVSN
                *.:    *    *   *...  :  *.:.:::*      . ** :     .  *  :.   *. .

/235                               /267
BCVspikepro    KFLFNVYLGTVLSHYYVMP---------LTCNSAMTLEYWVTPLTSKQYLLAFNQDGVIF
HCVspikepro    KFLFNVYLGTVLSHYYVLP---------LTCNSAMTLEYWVTPLTSKQYLLAFNQDGVIF
CRCVspikepr    KFLFHVYLGTVLSHYYVMP---------LTCNSAMTLEYWVTPLTFKQYLLAFNQDGVIF
HEVspikepro    KFLFKLYLGTVLSHYYVMP---------LTCDSALSLEYWVTPLTTRQFLLAFDQDGVLY
CECVspikepr    FTYYKLNNTNGLKTYELCEDYEYCTGYATNIFAPTVGGYIPDGFSNNWFLLTNSSTFVS
                :::   . *. * :          . :.    *    :: .:::*  :... .:
```

FIGURE 10 (Page 2 of 5)

```
BCVspikepro   NAVDCKSDFMSEIKCKTLSIAPSTGVYELNGYTVQPIADVYRR-IPNLPDCNIEAWLNDK
HCVspikepro   NAVDCKSDFMSEIKCKTLSIAPSTGVYELNGYTVQPIADVYRR-IPNLPDCNIEAWLNDK
CRCVspikepr   NAVDCKSDFMSEIKCKTLSIAPSTGVYELNGYTVQPIADVYRR-IPNLPDCNIEAWLNDK
HEVspikepro   HAVDCASDFMSEIMCKTSSITPPTGVYELNGYTVQPVATVYRR-IPDLPNCDIEAWLNSK
CECVspikepr   GRFVTNQPLLVNCLWPVPSFGVAAQEFCFEGAQFSQCNGVFLNNTVDVIRFNLNFTADVQ
                . .::  :  . .*: .: : ::*  ..  *: .  ::  :::   : :
                                                                   388
BCVspikepro   SVPSPLNWERKTFSNCNFNMSSLMSFIQADSFTCN------NIDAAKIYGMCFSSITIDK
HCVspikepro   SVPSPLNWERKTFSNCNFNMSSLMSFIQADSFTCN------NIDAAKIYGMCFSSITIDK
CRCVspikepr   SVPSPLNWERKTFSNCNFNMSSLMSFIQADSFTCN------NIDAAKIYGMCFFSITIDK
HEVspikepro   TVSSPLNWERKIFSNCNFNMGRLMSFIQADSFGCN------NIDASRLYGMCFGSITIDK
CECVspikepr   SGMGATVFSLNTTGGCILEISCYNDIVSESSFYSYGEIPFGVTDGPRYCYVLYNGTALKY
              :  ..    :. :   ..* :::.   .::. .**  .      *...:   :  . ::.
                              407                 436  440    447
BCVspikepro   FAIPNGRKVDLQLGNLGYLQSFNYRIDTTATSCQLYYNLPAAN-VSVSRFNPSTWNRRFG
HCVspikepro   FAIPNGRKVDLQLGNLGYLQSFNYRIDTTATSCQLYYNLPAAN-VSVSRFNPSTWNRRFG
CRCVspikepr   FAIPNGRKVDLQMGNLGYLQSFNYRIDTTATSCQLYYNLPASN-VSISRFNPSIWNRRFG
HEVspikepro   FAIPNSRKVDLQVGKSGYLQSFNYKIDTAVSSCQLYYSLPAAN-VSVTHYNPSSWNRRYG
CECVspikepr   FGTLPPSVKEIAISKWGQFYINGYNFFSTFPIDCISFNLTTGDSGAFWTIAYTSYTEALV
              *.           :: :.:  * :   .*.: ::  .  : :..*.:.:  :.     :  :...
                                                                   501
BCVspikepro   FTEQSVFKPQPVGVFTDHDVVYAQHCFKAPTNFCPCKLDGSLCVGSGSGIDAGYKNSGIG
HCVspikepro   FTEQSVFKPQPVGVFTHHDVVYAQHCFKAPTNFCPCKLDGSLCVGNGPGIDAGYKNSGIG
CRCVspikepr   FTEQSVFKPQPVGVFTDHDVVYAQHCFKAPTNFCPCKLNGSLCVGSGFGIDAGYKNSGIG
HEVspikepro   FINQS------FGSRGLHDAVYSQQCFNTPNTYCPCRT--SQCIGG---------AGTG
CECVspikepr   QVENTAIKKVTYCNSHINNIKCSQLTANLQNGFYPVASSEVGLVNKSVVLLPSFYSHTSV
              :::            :: ::  :*    :  . : *            :.
                          525   528    540
BCVspikepro   TCPAGTNYLTCH----NAAQCNCLCTPDPITSKSTGPYKCPQTKYLVGIGEHCSGLAIKS
HCVspikepro   TCPAGTNYLTCH----NAAQCDCLCTPDPITSKSTGPYKCPQTKYLVGIGEHCSGLAIKS
CRCVspikepr   TCPAGTNYLTCY----NANQCDCLCTPDPILSKSTGPYKCPQTKYLVGIGEHCSGLAIKS
HEVspikepro   TCPVGTTVRKCFAAVTNATKCTCWCQPDPSTYKGVNAWTCPQSKVSIQPGQHCPGLGLVE
CECVspikepr   NITIDLGMKRSGYG--QPIASTLSNITLPMQDNNTDVYCIRSNQFSVYVHSTCKSSLWDN
               . . .     .   :. .    . *  :... :    ..:  :    . * .    .
```

FIGURE 10 (Page 3 of 5)

```
                           582               608
BCVspikepro    DYCGGNPCTCQPQAFLGWSVDSCLQGDRCN--IFANFILHDVNSGTTCSTDLQKSNTDII
HCVspikepro    DYCGGNPCTCQPQAFLGWSVDSCLQGDRCN--IFANFILHDVNSGTTCSTDLQKSNTDII
CRCVspikepr    DYCGGNPCTCQPKAFLGWSVDSCLQGDRCN--IFANFILHGVNSGTTCSTDLQKSNTDII
HEVspikepro    DDCSGNPCTCKPQAFIGWSSETCLQNGRCN--IFANFILNDVNSGTTCSTDLQQGNTNIT
CECVspikepr    NFNQDCTDVLYATAVIKTGTCPFSFDKLNNYLTFNKLCLSLNPTGANCKFDVAARTRTNE
               :    . . . .*.: . .  .  *  * :: *    :*:.*. *:   .

BCVspikepro    LGVCVNYDLYGITGQGIFVEVNATYYNSWQNLLYDSNGNLYGFRDYLTNRTFMIRSCYSG
HCVspikepro    LGVCVNYDLYGITGQGIFVEVNAPYYNSWQNLLYDSNGNLYGFRDYLTNRTFMIRSCYSG
CRCVspikepr    LGVCVNYDLYGITGQGIFVEVNATYYNSWQNLLYDSNGNLYGFRDYLTNRTFMIRSCYSG
HEVspikepro    TDVCVNYDLYGITGQGILIEVNATYYNSWQNLLYDSSGNLYGFRDYLSNRTFLIRSCYSG
CECVspikepr    QVVRSLYVIYEEGDNIVGVPSDNSGLHDLSVLHLDSCTDYN---IYGRTGVGIIRQTNST
                *    *  *:*  .: : : :. . :. .  *  **  :      *  . .:**. *

692  695
BCVspikepro    RVSAAFHANSSEPALLFRNIKCNYVFNNTLSRQLQPINYFDSYLGCVVNADNSTSSAVQT
HCVspikepro    RVSAAFHANSSEPALLFRNIKCSYVFNNTLSRQLQPINYFDSYLGCVVNADNSTSSVVQT
CRCVspikepr    RVSAGFHSNSSEPALLFRNIKCNYVFNNTLSRQLQPINYFDSYLGCVVNADNSTSSSVQT
HEVspikepro    RVSAVFHANSSEPALMFRNLKCSHVFNYTILRQIQLVNYFDSYLGCVVNAYNNTASAVST
CECVspikepr    ILSGLHYTSLSGDLLGFKNVSDGVVYSVTPCDVSAQAAVIDGAIVGAMTSINSELLGLTH
               :*.  .::. *   * *:*:.. .*:. *       :*. :  .:.: *.       :

757 758  763   769          786
BCVspikepro    CDLTVGSGYCVDYSTKRRSRRAITTGYRFTNFEPFTVNS---------------VNDS
HCVspikepro    CDLTVGSGYCVDYSTKRRSRRAITTGYRFTNFEPFTVNS---------------VNDS
CRCVspikepr    CDLTVGSGYWGDYSTQRRSRRTITTGYRFTNFEPFTVNP---------------VNDS
HEVspikepro    CDLTVGSGYCVDYVTALRSRRSFTTGYRFTNFEPFAANL---------------VNDS
CECVspikepr    WTTTPNFYYYSIYNTTNERTRGTAIDSNDVDCEPIITYSNIGVCKNGALVFINVTHSDGD
                 * .  *  *   *  . * :  . : . . .: **:.                :..

792              818 827  828
BCVspikepro    LEPVGGLYEIQIPSEFTIGNMEEFIQISSPKVTIDCSAFVCGDYAACKSQLVEYGSFCDN
HCVspikepro    LEPVGGLYEIQIPSEFTIGNMEEFIQTSSPKVTIDCSAFVCGDYAACKSQLVEYGSFCDN
CRCVspikepr    LHPVGGLYEIQIPSEFTIGNMEEFIQTRSPKVTIDCPVFVCGDYAACKSQLVEYGSFCDN
HEVspikepro    IEPVGGLYEIQIPSEFTIGNLEEFIQTSSPKVTIDCATFVCGDYAACRQQLAEYGSFCEN
CECVspikepr    VQPIS-TGNVTIPTNFTISVQVEYIQVYTTPVSIDCSRYVCNGNPRCNKLLTQYVSACQT
               :.*:.   ::  **::***.  *:**  :.****. .**.. . *.. *.:* * *:.
```

FIGURE 10 (Page 4 of 5)

```
                        887
BCVspikepro   INAILTEVNELLDTTQLQVANSLMNGVTLSTKLKDGVNFNVDDIN----------FSPVL
HCVspikepro   INAILTEVNELLDTTQLQVANSLMNGVTLSTKLKDGVNFNVDDIN----------FSPVL
CRCVspikepr   INAILTEVNELLDTTQLQVANSLMNGVTLSTKLKDGFNFNVDDIN----------FSPVL
HEVspikepro   INAILIEVNELLDTTQLQVANSLMNGVTLSTKIKDGINFNVDDIN----------FSSVL
CECVspikepr   IEQALAMSASLENMEVDSMLFVSENALKLASVEAFNSTEHLDPIYKEWPNIGGSWLGGLK
              *:  *    .* :    .:       *.:.*::    . . ::* *         :. :

933
BCVspikepro   GCLGSDCNKVSSRSAIEDLLFSKVKLSDVG-FVEAYNNCTGGAEIRDLICVQSYNGIKVL
HCVspikepro   GCLGSACNKVSSRSAIEDLLFSKVKLSDVG-FVEAYNNCTGGAEIRDLICVQSYNGIKVL
CRCVspikepr   GCLGSECNKVSSRSAIEDLLFSKVKLSDVG-FVDAYNNCTGGAEIRDLICVQSYNGIKVL
HEVspikepro   GCLGSECNRASTRSAIEDLLFDKVKLSDVG-FVQAYNNCTGGAEIRDLICVQSYNGIKVL
CECVspikepr   DILPSHNSKRKYRSAIEDLLFDKVVTSGLGTVDEDYKRCTGGYDIADLVCAQYYNGIMVL
              . * *    .: . ********.**  *.:*   . : *:.**** :* **:*.* **** **
                      977                                       1011 1018
BCVspikepro   PPLLSENQISGYTLAATSASLFPPWS-AAAGVPFYLNVQYRINGIGVTMDVLSQNQKLIA
HCVspikepro   PPLLSVNQISGYTLAATSASLFPPWS-AAAGVPFYLNVQYRINGIGVTMDVLSQNQKLIA
CRCVspikepr   PPLLSENQISGYTLAATFASLFPPWS-AAAGVPFYLNVQYRINGIGVTMDVLTQNQKLIS
HEVspikepro   PPLLSENQISGYTSAATAASLFPPWT-AAAGVPFYLNVQYRINGLGVTMDVLSQNQKLIA
CECVspikepr   PGVANDDKMTMYTASLAGGIALGALGGGAVAIPFAVAVQARLNYVALQTDVLNKNQQILA
              *  :  .  :::: ** : :   . .    .*..:** : ** *:* :.: ***.:**::::

1063
BCVspikepro   NAFNNALDAIQEGFDATN--------------SALVKIQAVVNANAEALNNLLQQLSNRF
HCVspikepro   NAFSNALDAIQEGFDATN--------------SALVKIQAVVNANAEALNNLLQQLSNRF
CRCVspikepr   NAFNNALDAIQEGFDATN--------------SALVKIQAVVNANAEALNNLLQQLSNKF
HEVspikepro   SAFNNALDSIQEGFDATN--------------SALVKIQAVVNANAEALNNLLQQLSNRF
CECVspikepr   NAFNQAIGNITQAFGKVNDAIHQTSQGLATVAKALAKVQDVVNTQGQALSHLTVQLQNSF
              .**.:*:.. *  :.*. .*              .**.:* ***:::..**.:* **.* *

BCVspikepro   GAISSSLQEILSRLDALEAQAQIDRLINGRLTALNAYVSQQLSDSTLVKFSAAQAMEKVN
HCVspikepro   GAIGSSLQEILSRLDALEAQAQIDRLINGRLTALNAYVSQQLSDSTLVKFSAAQAMEKVN
CRCVspikepr   GAISASLQEILSRLDALEAQAQIDRLINGRLTALNAYVSQQLSDSTLVKFSAAQAMEKVN
HEVspikepro   GAISASLQEILSRLDALEAKAQIDRLINGRLTALNAYVSQQLSDSTLVKFSAAQAIEKVN
CECVspikepr   QAISSSISDIYNRLDELSADAQVDRLITGRLTALNAFVSQTLTRQAEVRASRQLAKDKVN
              **..:*:..:* .*** *.*.**:*****.*********:*** :*::.  :**.* *  * :***
```

FIGURE 10 (Page 5 of 5)

```
BCVspikepro    ECVKSQSSRINFCGNGNHIISLVQNAPYGLYFIHFSYVPTKYVTAKVSPGLCIAGDRGIA
HCVspikepro    ECVKSQSSRINFCGNGNHIISLVQNAPYGLYFIHFSYVPTKYVTAKVSPGLCIAGDRGIA
CRCVspikepr    ECVKSQSSRINFCGNGNHIISLVQNAPYGLYFIHFSYVPTKYVTAKVSPGLCIAGDRGIA
HEVspikepro    ECVKSQSSRINFCGNGNHIISLVQNAPYGLYFIHFSYVPTKYVTAKVSPGLCIAGDIGIS
CECVspikepr    ECVRSQSQRFGFCGNGTHLFSLANAAPNGMVFFHTVLLPTAYETVTAWSGICASDGDRTF
               ***:***.*:.*****.*::**.: ** *: *:*    :** * *..  .*:* :..

BCVspikepro    ------PKSGYFVNVNNTWMFTGSGYYYPEPITGNNVVVMSTCAVNYTKAPDVMLNISTP
HCVspikepro    ------PKSGYFVNVNNTWMFTGSGYYYPEPITGNNVVVMSTCAVNYTKAPDVMLNISTP
CRCVspikepr    ------PKSGYFVNVNNTWMFTGSGYYYPEPITGNNVVVMSTCAVNYTKAPDVMLNISTP
HEVspikepro    ------PKSGYFINVNNSWMFTGSGYYYPEPITQNNVVVMSTCAVNYTKAPDLMLNTSTP
CECVspikepr    GLVVKDVQLTLFRNLDDKFYLTPRTMYQPRAATSSDFVQIEGCDVLFVNATVIDLPSIIP
               :  * *:::.: :*    * *.. * .:.* :. * * :..:*. : *         *
```
                       1256        1257
```
BCVspikepro    NLPDFKEELDQWFKNQTS--VAPDLSLDYINVTFLDLQDEMN---------------RLQE
HCVspikepro    NLHDFKEELDQWFKNQTS--VAPDLSLDYINVTFLDLQDEMN---------------RLQE
CRCVspikepr    NLPDFKEELDQWFKNQTL--MAPDLSLDYINVTFLDLQDEMN---------------RLQE
HEVspikepro    NLPDFKEELYQWFKNQSS--LAPDLSFDYINVTFLDLQDEMN---------------RLQE
CECVspikepr    DYIDINQTVQDILENYRPNWTVPELTIDIFNATYLNLTGEIDDLEFRSEKLHNTTVELAI
               :  *::: : : ::*        .*:*:* :*.*:*:* .*::              .*

BCVspikepro    AIKVLNQSYINLKDIGTYEYYVKWPWYVWLLIGLAGVAMLVLLFFICCCTGCGTSCFKKC
HCVspikepro    AIKVLNQSYINLKDIGTYEYYVKWPWYVWLLIGFAGVAMLVLLFFICCCTGCGTSCFKIC
CRCVspikepr    AIKVLNHSYINLKDIGTYEYYVKWPWYVWLLIGLAGVAMLVLLFFICCCTGCGTSCFKKC
HEVspikepro    AIKVLNHSYINLKDIGTYEYYVKWPWYVWLLICLAGVVMLVLLFFICCCTGCGTSCFKKC
CECVspikepr    LIDNINNTLVNLEWLNRIETYVKWPWYVWLLIGLVVVFCIPLLLFCCCSTGCCG-CIGCL
                *. :*:: :**: :.  * ***********  :. *  : **:* **.***   *:

BCVspikepro    GGCCDDYTGHQELVIKTSHDD---------------------------------------
HCVspikepro    GGCCDDYTGHQELVIKTSHDD---------------------------------------
CRCVspikepr    GGCCDDYTGHQELVIKTSHDD---------------------------------------
HEVspikepro    GGCFDDYTGHQEFVIKTSHDD---------------------------------------
CECVspikepr    GSCCHSICSRRQFENYEPIEKVHVH-----------------------------------
               *.*  ..  .::::     . :.
```

FIGURE 13

```
TATCGCAGCC TTACTTTTGT TAATGTACCA TATGTTTATA ATGGCTCTGC ACAATCTACA  60
GCTCTTTGTA AATCTGGTAG TTTAGTTCTT AATAACCCTG CATATATAGC TCGTGAAGCT 120
AATTTTGGGG ATTATTATTA TAAGGTTGAA GCTGATTTCT ATTTGTCAGG TTGTGACGAG 180
TATATCGTAC CACTTTGTAT TTTTAACGGC AAGTTTTTGT CGAATACAAA GTATTATGAT 240
GATAGTCAAT ATTATTTTAA TAAAGACACT GGTGTTATTT ATGGTTTCAA TTCTACTGAA 300
ACCATTAACA CTGGTTTTGA TTTTAATTGT CATTATTTAC TTTTACCCTC TGGTAATTAT 360
TTAGCCATTT CAAATGAGCT ATTGTTAACT GTTCCTACGA AAGCAATCTG TCTTAATAAG 420
CGTAAGGATT TTACGCCTGT ACAGGTTGTT GACTCGCGGT GGAACAATGC CAGGCAGTCT 480
GATAACATGA CGGCGG                                                 497
```

FIGURE 14

```
YRSLTFVNVP YVYNGSAQST ALCKSGSLVL NNPAYIAREA NFGDYYKVE  ADFYLSGCDE  60
YIVPLCIFNG KFLSNTKYYD DSQYYFNKDT GVIYGFNSTE TINTGFDFNC HYLLLPSGNY 120
LAISNELLLT VPTKAICLNK RKDFTPVQVV DSRWNNARQS DNMTA                 165
```

FIGURE 15 (Page 1 of 2)

```
CRCV    TATCGCAGCCTTACTTTTGTTAATGTACCATATGTTTATAATGGCTCTGCACAATCTACA
BCV     TATCGCAGCCTTACTTTTGTTAATGTACCATATGTTTATAATGGCTCTGCACAATCTACA
OC43    TATCGCAGCCTTACTTTTGTTAATGTACCATATGTTTATAATGGCTCTGCACAATCTACA
HECV    TATCGCAGCCTTACTTTTGTTAATGTACCATATGTTTACAATGGCTCTGCACAATCTACA
HEV     TATCGCAGTCTTACTTTAGTTAATGTGCCATACGTTTACAATGGGTCAGCTCAACCCACC
        ******** ******* ******* ***** ***** ***** ** ** *** * **

CRCV    GCTCTTTGTAAATCTGGTAGTTTAGTTCTTAATAACCCTGCATATATAGCTCGTGAAGCT
BCV     GCTCTTTGTAAATCTGGTAGTTTAGTTCTTAATAACCCTGCATATATAGCTCGTGAAGCT
OC43    GCTCTTTGTAAATCTGGTAGTTTAGTCCTTAATAACCCTGCATATATAGCTCCTCAAGCT
HECV    GCTCTTTGTAAATCTGGTAGTTTAGTTCTTAATAACCCTGCATATATAGCTCGTGAAGCT
HEV     GCACTTTGTAAGTCTGGCAGTTTAATTCTTAACAATCCTGCATATATAGCCCGTGAGGCT
        ** ******** ***** ****** * ***** ** ************** * * ***

CRCV    AATTTTGGGGATTATTATTATAAGGTTGAAGCTGATTTCTATTTGTCAGGTTGTGACGAG
BCV     AATTTTGGGGATTATTATTATAAGGTTGAAGCTGATTTTTATTTGTCAGGTTGTGACGAG
OC43    AACTCTGGGGATTATTATTATAAGGTTGAAGCTGATTTTTATTTGTCAGGTTGTGACGAG
HECV    AATTTTGGGGATTATTATTATAAGGTTGAAGCTGATTTTTATTTGTCAGGTTGTGACGAG
HEV     AATGTGGGTGATTATTATTATAAGTCTGAAGCAGATTTTTCTCTCTCAGGTTGTGACGAG
        **    ** ************** * ***** ***** *  * *  **************

CRCV    TATATCGTACCACTTTGTATTTTTAACGGCAAGTTTTTGTCGAATACAAAGTATTATGAT
BCV     TATATCGTACCACTTTGTATTTTTAACGGCAAGTTTTTGTCGAATACAAAGTATTATGAT
OC43    TATATCGTACCACTTTGTATTTTTAACGGCAAGTTTTTGTCGAATACAAAGTATTATGAT
HECV    TATATCGTACCACTTTGTATTTTTAACGGCAAGTTTTTGTCGAATACAAAGTATTATGAT
HEV     TATATCGTACCACTTTGTATTTTTAATGGCAAGTTTTTGTCGAATACAAAGTATTATGAT
        ************************* **********************************

CRCV    GATAGTCAATATTATTTTAATAAAGACACTGGTGTTATTTATGGTTTCAATTCTACTGAA
BCV     GATAGTCAATATTATTTTAATAAAGACACTGGTGTTATTTATGGTCTCAATTCTACTGAA
OC43    GATAGTCAATATTATTTTAATAAAGACACTGGTGTTATTTATGGTCTCAATTCTACAGAA
HECV    GATAGTCAATATTATTTTAATAAAGACACTGGTGTTATTTATGGTCTCAATTCTACTGAA
HEV     GATAGTCAATATTATTTTAATAAAGACACTGGTGTTATTTATGGTCTCAATTCTACTGAA
        ********************************************* ********** ***

CRCV    ACCATTAACACTGGTTTTGATTTTAATTGTCATTATTTACTTTTACCCTCTGGTAATTAT
BCV     ACCATTACCACTGGTTTTGATTTTAATTGTCATTATTTAGTTTTACCCTCTGGTAATTAT
OC43    ACCATTACCACTGGTTTTGATCTTAATTGTTATTATTTAGTTTTACCCTCTGGTAATTAT
HECV    ACCATTACCACTGGTTTTGATTTTAATTGTCATTATTTAGTTCTACCCTCTGGCAATTAT
HEV     ACCATTACCACTGGTTTTGATTTTAATTGTCATTATTTAGTTCTACCCTCTGGTAATTAT
        ****** * ************ ******** ********  * ********* ******

CRCV    TTAGCCATTTCAAATGAGCTATTGTTAACTGTTCCTACGAAAGCAATCTGTCTTAATAAG
BCV     TTAGCCATTTCAAATGAGCTATTGTTAACTGTTCCTACGAAAGCAATCTGTCTTAATAAG
OC43    TTAGCCATTTCAAATGAGCTATTGTTAACTGTTCCTACGAAAGCAATCTGTCTTAATAAG
HECV    TTAGCCATTTCAAATGAGCTATTGTTAACTGTTCCTACTAAAGCAATCTGTCTTAATAAG
HEV     CTAGCCATTTCAAATGAGCTATTGTTAACTGTTCCTACTAAAGCAATCTGTCTTAATAAG
         ************************************* ********************
```

FIGURE 15 (Page 2 of 2)

```
CRCV    CGTAAGGATTTTACGCCTGTACAGGTTGTTGACTCGCGGTGGAACAATGCCAGGCAGTCT
BCV     CGTAAGGATTTTACGCCTGTACAGGTTGTTGACTCTCGGTGGAACAATGCCAGGCAGTCT
OC43    CGTAAGGATTTTACGCCTGTACAGGTTGTTGATTCGCGGTGGAACAATGCCAGGCAGTCT
HECV    CGTAAGGATTTTACGCCTGTACAGGTTGTTGACTCGCGGTGGAACAATGCCAGGCAGTCT
HEV     CGTAAGGTTTTACGCCTGTACAGGTTGTTGATTCGCGGTGGAACAATGCCAGGCAATCT
        ******* *********************** ** ****************** ***

CRCV    GATAACATGACGGCGGT
BCV     GATAACATGACGGCGGT
OC43    GATAACATGACGGCGGT
HECV    GATAACATGACGGCAGT
HEV     GATAACATGACGGCAGT
        ************** **
```

FIGURE 16

```
CRCV    YRSLTFVNVPYVYNGSAQSTALCKSGSLVLNNPAYIAREANFGDYYYKVEADFYLSGCDE
BCV     YRSLTFVNVPYVYNGSAQSTALCKSGSLVLNNPAYIAREANFGDYYYKVEADFYLSGCDE
OC43    YRSLTFVNVPYVYNGSAQSTALCKSGSLVLNNPAYIAPQANSGDYYYKVEADFYLSGCDE
HECV    YRSLTFVNVPYVYNGSAQSTALCKSGSLVLNNPAYIAREANFGDYYYKVEADFYLSGCDE
HEV     YRSLTLVNVPYVYNGSAQPTALCKSGSLILNNPAYIAREANVGDYYYKSEADFSLSGCDE
        *****:************.********:********  :** ****** **** ******

CRCV    YIVPLCIFNGKFLSNTKYYDDSQYYFNKDTGVIYGFNSTETINTGFDFNCHYLLLPSGNY
BCV     YIVPLCIFNGKFLSNTKYYDDSQYYFNKDTGVIYGLNSTETITTGFDFNCHYLVLPSGNY
OC43    YIVPLCIFNGKFLSNTKYYDDSQYYFNKDTGVIYGLNSTETITTGFDLNCYYLVLPSGNY
HECV    YIVPLCIFNGKFLSNTKYYDDSQYYFNKDTGVIYGLNSTETITTGFDFNCHYLVLPSGNY
HEV     YIVPLCIFNGKFLSNTKYYDDSQYYFNKDTGVIYGLNSTETITTGFDFNCHYLVLPSGNY
        ********************************** :****** ****.****:**:******

CRCV    LAISNELLLTVPTKAICLNKRKDFTPVQVVDSRWNNARQSDNMTA
BCV     LAISNELLLTVPTKAICLNKRKDFTPVQVVDSRWNNARQSDNMTA
OC43    LAISNELLLTVPTKAICLNKRKDFTPVQVVDSRWNNARQSDNMTA
HECV    LAISNELLLTVPTKAICLNKRKDFTPVQVVDSRWNNARQSDNMTA
HEV     LAISNELLLTVPTKAICLNKRKVFTPVQVVDSRWNNARQSDNMTA
        ********************* ***********************
```

CANINE RESPIRATORY CORONAVIRUS (CRCV) SPIKE PROTEIN

RELATED APPLICATIONS

This application is a divisional of application Ser. No. 10/522,513, filed Jun. 22, 2006, now issued as U.S. Pat. No. 7,776,340, which is U.S. National Phase of international Application PCT/GB2003/002832, filed Jul. 1, 2003, which claims priority to British Patent Application No. 0217434.0 filed Jul. 27, 2002.

BACKGROUND OF THE INVENTION

1. Field of the Invention

The present invention relates to biological material, and in particular to a canine respiratory coronavirus that is present in dogs having canine infectious respiratory disease.

2. Description of the Related Art

Canine infectious respiratory disease (CIRD) is a highly contagious disease common in dogs housed in crowded conditions such as re-homing centres and boarding or training kennels. Many dogs suffer only from a mild cough and recover after a short time, however in some cases a severe bronchopneumonia can develop (Appel and Binn, 1987).

The pathogenesis of CIRD is considered to be multifactorial, involving several viruses and bacteria. The infectious agents considered to be the major causative pathogens of CIRD are canine parainfluenzavirus (CPIV) (Binn et al., 1967), canine adenovirus type 2 (CAV-2) (Ditchfield et al., 1962) and the bacterium *Bordetella bronchiseptica* (Bemis et al., 1977, Keil et al., 1998). Also, canine herpesvirus, human reovirus and mycoplasma species have been isolated from dogs with symptoms of CIRD (Karpas et al., 1968, Lou and Wenner 1963, Randolph et al., 1993) Additional factors like stress may also be important.

CIRD is rarely fatal but it delays re-homing of dogs at rescue centres and it causes disruption of schedules in training kennels as well as considerable treatment costs.

Vaccines are available against some of the infectious agents associated with this disease, namely *Bordetella bronchiseptica* as well as CPIV and CAV-2. However, despite the use of these vaccines, CIRD is still prevalent in kennels world-wide, which is possibly due to the vaccines not providing protection against all the infectious agents involved in CIRD.

We have discovered a novel coronavirus, which we have called canine respiratory coronavirus (CRCV), in a large kennelled dog population with a history of endemic respiratory disease, and we have shown that this virus is associated with CIRD.

Some members of the family coronaviridae are known to cause respiratory disease in humans, cattle, swine and poultry (Mäkelä et al., 1998, Pensaert et al., 1986, Ignjatovic and Sapats 2000). For example, bovine respiratory coronavirus is associated with shipping fever in cattle which is a multifactorial respiratory disease (Storz et al., 2000).

However, coronaviruses were not suspected to have a role in the pathogenesis of CIRD. Indeed, with only a single exception, canine coronaviruses have been reported to be enteric viruses and to cause acute diarrhea mainly in young dogs (for example, Tennant et al., 1993). In a large study of viruses involved in canine respiratory diseases, Binn et al. (1979) reported the detection of a canine coronavirus in the lung of a single dog that was also infected with SV5 and canine adenovirus 2, two other viruses that are associated with canine respiratory disease.

There are 30-40 dog vaccines commercially available in the UK for use against a number of pathogens that can cause a range of diseases, such as neurological, enteric, hepatic and respiratory diseases. Most of these vaccines contain microbial agents such as Distemper virus, Canine Adenovirus-2, Canine parvovirus, canine parainfluenza virus and *Leptospira canicola* and *L. icterohaemorrhagiae*. None of these vaccines contain canine coronaviruses.

The dog vaccines for use against canine respiratory diseases are marketed as vaccines for "kennel-cough" (see below). All of the vaccines contain *Bordetella bronchiseptica*, which is a bacterium associated with "kennel cough".

Coyne M. J. & May S. W., (1995) in their article entitled "Considerations in using a canine coronavirus vaccine" (published as a Pfizer Technical Bulletin on the Internet at http://www.pfizer.com/ah/vet/tref/trbull/ccv.html), lists over 20 commercially available vaccines against either canine coronaviruses alone or against canine coronaviruses together with other organisms. Each of these vaccines is for canine enteric disease, and there is no suggestion that a canine coronavirus may be associated with respiratory disease.

U.S. Pat. Nos. 6,057,436 and 6,372,224, both to Miller et al and assigned to Pfizer, Inc., describe the spike gene of the enteric canine coronavirus and uses therefor, including its use as a vaccine against gastroenteritis. Neither of these two patents suggest that a canine coronavirus may be involved in CIRD.

BRIEF DESCRIPTION OF THE DRAWINGS

FIG. 1. Partial nucleotide sequence (250 residues) of the CRCV polymerase (pol) cDNA (SEQ ID NO: 1).

FIG. 2. Partial amino acid sequence (83 residues) of the CRCV pol protein (SEQ ID NO: 2), derived from the nucleotide sequence of FIG. 1.

FIG. 3. Nucleotide sequence (4092 residues) of the CRCV Spike (S) cDNA (SEQ ID NO: 3). The Y at position 3531 refers to either C or T.

FIG. 4. Amino acid sequence (1363 residues) of the CRCV S protein (SEQ ID NO: 4), derived from the nucleotide sequence of FIG. 3.

FIG. 6. CLUSTAL X (1.8) multiple sequence alignment of the 250 nucleotide partial sequence of the pol cDNA of CRCV (sample T101, SEQ ID NO: 1), BCV (SEQ ID NO: 5), HCV strain OC43 (SEQ ID NO: 6), HEV (SEQ ID NO: 7) and CCV (enteric CCV, SEQ ID NO: 8).

FIG. 7. CLUSTAL X (1.8) multiple sequence alignment of the 83 amino acid partial sequence of the pol protein of CRCV (protCRCVpol, SEQ ID NO: 2) with HCV (protHCVpoly, SEQ ID NO: 9), HEV (protHEVpoly, SEQ ID NO: 10), BCV (protBCVpoly, SEQ ID NO: 11) and CECV (enteric CCV, protCECVpol, SEQ ID NO: 12).

FIG. 8. CLUSTAL X (1.8) sequence alignment of the nucleotide sequence of the CRCV spike cDNA (CRCVspike, SEQ ID NO: 3) and enteric CCV spike cDNA (CECVspike, SEQ ID NO: 13).

FIG. 9. CLUSTAL X (1.8) multiple sequence alignment of the 4092 nucleotides of the CRCV spike cDNA (CRCVspike, SEQ ID NO: 3) sequence with BCV (BCVspike, SEQ ID NO: 14), HCV (HCVspike, SEQ ID NO: 15) and HEV (HEVspike, SEQ ID NO: 16) spike cDNAs. The Y at position 3531 in the CRCV sequence refers to either C or T.

FIG. 10. CLUSTAL X (1.8) multiple sequence alignment of the 1363 amino acid sequence of the CRCV spike protein (CRCVspikepr, SEQ ID NO: 4) with BCV (BCVspikepro, SEQ ID NO: 17), HCV (HCVspikepro, SEQ ID NO: 18), HEV (HEVspikepro, SEQ ID NO: 19) and enteric CCV (CECVspikepr, SEQ ID NO: 20) spike proteins.

FIG. 13. Partial nucleotide sequence (497 residues) of the CRCV hemagglutinin/esterase (HE) gene (SEQ ID NO: 21). The sequence corresponds to nucleotides 418 to 914 of the HE genes of BCV (GenBank M84486) and HCV OC43 (GenBank Accession No. M76373).

FIG. 14. Partial amino acid sequence (165 residues) of the CRCV HE protein (SEQ ID NO: 22), derived from the nucleotide sequence of FIG. 13. This sequence corresponds to amino acid residues 140 to 304 of BCV (GenBank M84486) and HCV OC43 (GenBank Accession No. M76373).

FIG. 15. CLUSTAL X (1.8) multiple sequence alignment of a 497 nucleotide partial sequence of the hemagglutinin/esterase (HE) gene of CRCV (canine respiratory coronavirus, SEQ ID NO: 21) with BCV (bovine coronavirus strain LY138, (SEQ ID NO: 23, taken from Genbank Accession No. AF058942), OC43 (human coronavirus strain OC43, SEQ ID NO: 24 taken from Genbank Accession No. M76373), HECV (human enteric coronavirus, SEQ ID NO: 25, taken from Genbank Accession No. L07747), and HEV (hemagglutinating encephalomyelitis virus, SEQ ID NO: 26, taken from Genbank Accession No. AF481863).

FIG. 16. CLUSTAL X (1.8) multiple sequence alignment of a 165 amino acid partial sequence of the HE protein of CRCV (canine respiratory coronavirus, (SEQ ID NO: 22) with BCV (bovine coronavirus strain LY138, SEQ ID NO: 27, taken from Genbank Accession No. AF058942), OC43 (human coronavirus strain OC43, SEQ ID NO: 28, taken from Genbank Accession No. M76373), HECV (human enteric coronavirus, SEQ ID NO: 29, taken from Genbank Accession No. L07747), and HEV (hemagglutinating encephalomyelitis virus, SEQ ID NO: 30, taken from Genbank Accession No. AF481863). The three CRCV-specific amino acids F, N and L are indicated in bold and are underlined.

Figure 5:
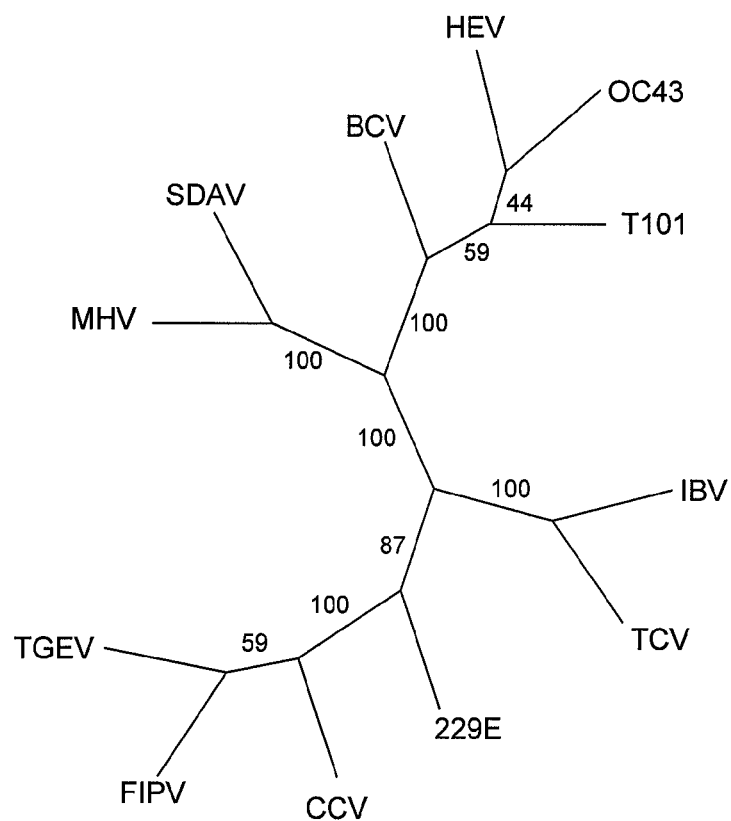
FIG. 5. Consensus tree for cDNA sequences from a 250 nucleotide region of the polymerase gene of 12 coronaviruses. The sequence obtained from the canine respiratory coronavirus is designated T101. The numbers indicate bootstrap values obtained by analysis of 100 data sets. BCV: bovine coronavirus, CCV: canine coronavirus, FIPV: feline infectious peritonitis virus, HEV: hemagglutinating encephalomyelitis virus, IBV: infectious bronchitis virus, MHV: mouse hepatitis virus, OC43: human coronavirus strain OC43, SDAV: sialodacryoadenitis virus, TCV: turkey coronavirus, TGEV: transmissible gastroenteritis virus, 229E: human coronavirus strain 229E, T101: canine respiratory coronavirus (PCR product from tracheal sample T101)

DETAILED DESCRIPTION OF THE PREFERRED EMBODIMENT

Members of the family coronaviridae are enveloped viruses, 80-160 nm in diameter, containing a linear positive-stranded RNA genome. The structural proteins of coronaviruses are the spike glycoprotein (S), the membrane glycoprotein (M) and the nucleocapsid protein (N). The hemagglutinin/esterase glycoprotein (HE) is found only on the surface of group II coronaviruses (e.g. bovine coronavirus and murine hepatitis virus) (Spaan et al, 1988). Further details of the structure of coronoviruses may be found in the chapter by Cavanagh et al entitled "Coronviridae" p 407-411, in "Virus Taxonomy, 6*th* Report of the International Committee on Taxonomy of Viruses", pub. Springer-Verlag Wein, New York, Eds. Murphy et al, which is incorporated herein by reference.

The canine respiratory coronavirus (CRCV) of the invention may be characterised as a coronavirus present in the respiratory tracts of dogs with infectious respiratory disease. To further characterise CRCV, we have determined the sequence of 250 nucleotide residues of the CRCV polymerase (pol) cDNA (FIG. 1 and SEQ ID NO: 1) which corresponds to an 83 amino acid partial sequence of the pol protein (FIG. 2 and SEQ ID NO: 2). We have also cloned and determined the sequence of the 4092 nucleotide residues of the CRCV spike (S) cDNA (FIG. 3 and SEQ ID NO: 3), corresponding to 1363 amino acids (FIG. 4 and SEQ ID NO: 4). We have also determined the sequence of 497 nucleotide residues of the CRCV hemagglutinin/esterase (HE) gene (FIG. 13 and SEQ ID NO: 21), corresponding to 165 amino acids (FIG. 14 and SEQ ID NO: 22). We have identified that CRCV has a surprisingly low homology to the enteric canine coronavirus (CCV) while it has an unexpectedly high level of homology to bovine coronavirus (strain LY138 or Quebec) and human coronavirus (strain OC43).

The CRCV spike, polymerase and hemagglutinin/esterase cDNA and protein partial sequences are listed in FIGS. 1 to 4, 13 and 14.

A culture of "Spike D-1 CRCV", which is XL1-Blue *E. coli* (Stratagene) containing a pT7Blue2 plasmid (Novagen) whose insert contains a portion of the CRCV spike cDNA, has been deposited under the Budapest Treaty at NCIMB Ltd under Accession number NCIMB 41146 on 25 Jul. 2002. The depositor of NCIMB 41146 is the Royal Veterinary College, Royal College Street, London NW1 OTU, UK. The address of NCIMB Ltd is 23 St. Machar Drive, Aberdeen, Scotland, AB24 3RY, UK.

The phylogenetic relationship of CRCV to eleven known coronaviruses was determined based upon a comparison of the 250 nucleotide sequence from the CRCV pol gene and the corresponding regions of the other viruses (FIG. 5). The bovine coronavirus (BCV), human coronavirus (HCV) strain OC43 and hemagglutinating encephalomyelitis virus (HEV) were found to be most closely related to CRCV, while the enteric CCV was found to be only distantly related to CRCV.

Over the 250 sequenced residues of the pol cDNA, corresponding to 83 amino acids, CRCV has only 68.5% and 75.9% sequence identity at the nucleotide and amino acid levels, respectively, with the equivalent region of the enteric CCV (strain 1-71) pol gene (Genbank Accession No. AF124986), as shown in FIGS. 6 and 7.

Over the 4092 sequenced nucleotide residues of the CRCV S gene, corresponding to 1363 amino acids, CRCV has 45% and 21.2% sequence identity at the nucleotide (FIG. 8) and amino acid levels, respectively, with the equivalent region of the enteric CCV (strain 1-71) S gene.

Enteric CCV is not a group II coronavirus and does not possess an HE gene, hence it is not possible to determine the extent of sequence identity between this gene in CRCV and in enteric CCV.

Except as described below, the percentage identity between two nucleotide or two amino acid sequences was determined using FASTA version 34 (Pearson W R. (1990) "Rapid and sensitive sequence comparison with FASTP and FASTA". *Methods Enzymol.;* 183:63-98). FASTA settings were Gap open penalty-16 and Gap extension penalty-4.

The percentage identity between the CRCV and enteric CCV spike sequences was determined using GCG version 10 (Genetics Computer Group, (1991), Program Manual for the GCG Package, Version 7, April 1991, 575 Science Drive, Madison, Wis., USA 53711). The GCG parameters used were: Gap creation penalty 50, gap extension penalty 3 for DNA, and Gap creation penalty 8 and Gap extension penalty 2 for Protein.

Sequence alignments were performed using ClustalX (Thompson et al., 1997).

By contrast, over the 250 sequenced residues of the pol cDNA, CRCV has 98.8% sequence identity with the equivalent region of the BCV strain Quebec pol gene (Genbank Accession No. AF220295), 98.4% sequence identity with the BCV strain LY138 pol gene (Genbank Accession No. AF124985) and 98.4% sequence identity with the HCV OC43 pol gene (Genbank Accession No. AF124989).

There was only a single amino acid difference between the CRCV pol protein over the 83 sequenced amino acids and the BCV, HCV and HEV pol proteins which is that CRCV has E (Glu) as opposed to D (Asp) at the position corresponding to position 4975 in the BCV genome (Accession No. SWALL: Q91A29). Thus the CRCV pol protein is 99% identical to the BCV, HCV and HEV pol proteins over this region.

The one and three letter amino acid codes of the IUPAC-IUB Biochemical Nomenclature Commission are used herein.

Over the 497 sequenced nucleotide residues, corresponding to 165 amino acids, of the HE gene, CRCV has 98.994% and 98.2% sequence identity with the equivalent region of the BCV strain LY138 HE gene (Genbank Accession No. AF058942) at the nucleotide and amino acid levels respectively. CRCV has 98.189% (nucleotide) and 98.2% (amino acid) sequence identity with human enteric coronavirus (HECV) HE gene (Genbank Accession No. L07747); 97.4% (nucleotide) and 95.2% (amino acid) sequence identity with the HCV OC43 HE gene (Genbank Accession No. M76373); and 92.0% (nucleotide) and 93.9% (amino acid) identity with HEV (Genbank Accession Nos. AF481863), as shown in FIGS. 15 and 16.

As shown in FIG. 16 and Table 3, the three amino acids that are different between the CRCV HE protein and each of the BCV, HECV, HCV and HEV S proteins, within the 165 amino acids of the CRCV HE protein, are F (Phe) as opposed to L (Leu), N (Asn) as opposed to T (Thr), and L (Leu) as opposed to V (Val) at positions corresponding to position 235, 242 and 253, respectively, in the BCV, HECV, HCV OC43 and HEV HE genes (FIG. 16). Thus F at position 235, N at position 242 and L at position 253 could be said to be CRCV HE protein-specific amino acids.

Over the 4092 sequenced nucleotide residues, corresponding to 1363 amino acids, of the CRCV S gene, CRCV has 97.3% and 96% identity with the equivalent region of BCV strain LY138 (Genbank Accession No. AF058942) at the nucleotide and amino acid levels respectively. CRCV has 96.9% (nucleotide) and 95.2% (amino acid) identity with HCV strain OC43 (Genbank Accession No. Z32768), and 83.8% (nucleotide) and 80.4% (amino acid) identity with HEV (Genbank Accession Nos. AF481863 (cDNA) and AAM 77000 (protein)) as shown in FIGS. 9 and 10.

The amino acids that are different between the CRCV S protein and each of the BCV, HCV and HEV S proteins, within the 1363 amino acids of the CRCV S protein, are listed in Table 1 below. Thus the amino acids listed in Table 1 could be said to be CRCV S protein-specific amino acids. The amino acids are numbered from the initial M residue at the start of the CRCV protein, as shown in FIG. 4.

TABLE 1

List of 39 amino acids specific to the CRCV S protein that are not present in the BCV, HCV and HEV S proteins.

| Position | Amino acid |
|---|---|
| 103 | V |
| 118 | V |
| 166 | D |
| 171 | M |
| 179 | K |
| 192 | P |
| 210 | S |
| 235 | H |
| 267 | F |
| 388 | F |
| 407 | M |
| 436 | S |
| 440 | I |
| 447 | I |
| 501 | F |
| 525 | Y |
| 528 | N |
| 540 | L |
| 582 | K |
| 608 | G |
| 692 | G |
| 695 | S |
| 757 | W |
| 758 | G |
| 763 | Q |
| 769 | T |
| 786 | P |
| 792 | H |
| 818 | R |
| 827 | P |
| 828 | V |
| 887 | F |
| 933 | D |
| 977 | F |
| 1011 | T |
| 1018 | S |
| 1063 | K |
| 1256 | L |
| 1257 | M |

A first aspect of the invention provides a coronavirus S protein, or fragment thereof, having at least 75% amino acid sequence identity with the CRCV S protein whose amino acid sequence is listed in FIG. 4, and having at least one of V at position 103; V at position 118; D at position 166; M at position 171; K at position 179; P at position 192; S at position 210; H at position 235; F at position 267; F at position 388; M at position 407; S at position 436; I at position 440; I at position 447; F at position 501; Y at position 525; N at position 528; L at position 540; K at position 582; G at position 608; G at position 692; S at position 695; W at position 757; G at position 758; Q at position 763; T at position 769; P at position 786; H at position 792; R at position 818; P at position 827; V at position 828; F at position 887; D at position 933; F at position 977; T at position 1011; S at position 1018; K at position 1063; L at position 1256; and M at position 1257. The amino acids are numbered from the initial M at the start of the CRCV S protein, as listed in FIG. 4 (SEQ ID NO: 4).

It is appreciated that the partial nucleotide sequence of CRCV S can be readily determined by a person or ordinary skill in the art by sequencing the insert of the plasmid contained in *E. coli* strain D-1 CRCV, that has been deposited under the Budapest Treaty at NCIMB Ltd. under Accession number NCIMB 41146 on 25 Jul. 2002. Furthermore, this DNA can be used as a hybridisation probe, or as the basis for the design of probes, in the isolation of CRCV nucleic acid in dogs.

For the avoidance of doubt, the invention includes a coronavirus S protein, or fragment thereof, having at least 75% amino acid sequence identity with the CRCV S protein (SEQ ID NO: 4), and comprising at least one of the amino acids specific for the CRCV S protein at the position listed in Table 1.

By "protein" we also include the meaning glycoprotein. The amino acid sequence of a glycoprotein refers to the amino acid sequence of the polypeptide backbone of the glycoprotein, irrespective of the type, number, sequence and position of the sugars attached thereto.

Typically, the invention includes an isolated or recombinant protein, and not an unmodified CRCV protein present as a CRCV component.

The invention includes a coronavirus S protein, or fragment thereof, having at least 76% amino acid sequence identity with the CRCV S protein (SEQ ID NO: 4), or at least 77%, or at least 78%, or at least 79%, or at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99% amino acid sequence identity with the CRCV S protein, and comprising at least one of the amino acids specific for the CRCV S protein at the position listed in Table 1.

The invention also includes a coronavirus S protein, or fragment thereof, having at least 75%, or at least 80%, or at least 85% or at least 90% or at least 95% amino acid sequence identity with the CRCV S protein (SEQ ID NO: 4), and comprising at least 2, or at least 3, or at least 4, or at least 5, or at least 6, or at least 7, or at least 8, or at least 9, or at least 10, or at least 11, or at least 12, or at least 13, or at least 14, or at least 15, or at least 16, or at least 17, or at least 18, or at least 19, or at least 20, or at least 21, or at least 22, or at least 23, or at least 24, or at least 25, or at least 26, or at least 27, or at least 28, or at least 29, or at least 30, or at least 31, or at least 32, or at least 33, or at least 34, or at least 35, or at least 36, or at least 37, or at least 38 of the amino acids specific for CRCV S protein at the positions listed in Table 1.

Preferably, the coronavirus S protein, or fragment thereof comprises all 39 of the amino acid residues specific for CRCV S protein at the positions listed in Table 1.

Thus the invention includes a BCV, HCV or HEV S protein or fragment thereof, that has been modified at least one position listed in Table 1 to resemble the CRCV S protein.

Preferably, the coronavirus S protein of the invention is a CRCV S protein that comprises or consists of the sequence listed in FIG. 4 (SEQ ID NO: 4), or a variant thereof with at least 97% identity with the sequence listed in FIG. 4. Preferably, the variant has at least 98%, or at least 99% amino acid sequence identity with the sequence listed in FIG. 4. More preferably the variant has at least 99.1%, or at least 99.2%, or at least 99.3%, or at least 99.4%, or at least 99.5%, or at least 99.6%, or at least 99.7%, or at least 99.8%, or at least 99.9% amino acid sequence identity with the sequence listed in FIG. 4.

Thus the variant of the coronavirus S protein of the invention includes a protein that comprises or consists of the sequence listed in FIG. 4 (SEQ ID NO: 4) but has between 1 and 40 amino acid differences from the sequence listed in FIG. 4. Preferably, the variant has less than 40 amino acid differences from the sequence listed in FIG. 4. More preferably the variant has less than 35, less than 30, or less than 25, or less than 20, or less than 15, or 10 or 9 or 8 or 7 or 6 or 5 or 4 or 3 or 2 amino acid differences, or a single amino acid difference, from the sequence listed in FIG. 4.

The invention also includes a CRCV S protein fragment comprising a fragment of the sequence listed in FIG. 4 (SEQ ID NO: 4) which comprises at least one of the amino acids specific for CRCV S protein at the position listed in Table 1.

The invention includes a coronavirus S protein, or fragment thereof, having at least 75% amino acid sequence identity with BCV strain LY138 S protein (SEQ ID NO: 14, Genbank Accession No. AF058942), and comprising at least one of V at position 103; V at position 118; D at position 166; M at position 171; K at position 179; P at position 192; S at position 210; H at position 235; F at position 267; F at position 388; M at position 407; S at position 436; I at position 440; I at position 447; F at position 501; Y at position 525; N at position 528; L at position 540; K at position 582; G at position 608; G at position 692; S at position 695; W at position 757; G at position 758; Q at position 763; T at position 769; P at position 786; H at position 792; R at position 818; P at position 827; V at position 828; F at position 887; D at position 933; F at position 977; T at position 1011; S at position 1018; K at position 1063; L at position 1256 and M at position 1257.

For the avoidance of doubt, the invention includes a coronavirus S protein, or fragment thereof, having at least 75% amino acid sequence identity with BCV strain LY138 S protein (SEQ ID NO: 14), and comprising at least one of the amino acids specific for CRCV S protein at the position listed in Table 1.

The invention includes a coronavirus S protein, or fragment thereof, having at least 76% amino acid sequence identity with BCV strain LY138 S protein, or at least 77%, or at least 78%, or at least 79%, or at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99% amino acid sequence identity with BCV strain LY138 S protein, and having at least one of the amino acids specific for CRCV S protein at the position listed in Table 1.

The invention also includes a coronavirus S protein, or fragment thereof, having at least 75%, or at least 80%, or at least 85%, or at least 90%, or at least 95% amino acid sequence identity with BCV strain LY138 S protein (SEQ ID NO: 14), and comprising at least 2, or at least 3, or at least 4, or at least 5, or at least 6, or at least 7, or at least 8, or at least 9, or at least 10, or at least 11, or at least 12, or at least 13, or at least 14, or at least 15, or at least 16, or at least 17, or at least 18, or at least 19, or at least 20, or at least 21, or at least 22, or at least 23, or at least 24, or at least 25, or at least 26, or at least 27, or at least 28, or at least 29, or at least 30, or at least 31, or at least 32, or at least 33, or at least 34, or at least 35, or at least 36, or at least 37, or at least 38 of the amino acids specific for CRCV S protein at the positions listed in Table 1.

Preferably, the coronavirus S protein, or fragment thereof comprises all 39 of the amino acid residues specific for CRCV S protein at the positions listed in Table 1.

A second aspect of the invention provides a coronavirus pol protein, or fragment thereof, having at least 90% amino acid sequence identity with the BCV pol protein (SEQ ID NO: 5) and comprising the amino acid E at the position corresponding to position 4975 in the BCV genome (Accession No. SWALL: Q91A29).

The invention includes a coronavirus pol protein, or fragment thereof, having at least 91% amino acid sequence identity with BCV strain LY138 pol protein, or at least 92%, or at least 93%, or at least 94%, or at least 95%, or at least 96%, or at least 97%, or at least 98%, or at least 99% amino acid sequence identity with BCV strain LY138 pol protein, and having the amino acid E at the position corresponding to position 4975 in the BCV genome (Accession No. SWALL: Q91A29).

Preferably, the coronavirus pol protein, or fragment thereof is a CRCV pol protein or fragment thereof that comprises or consists of the amino acid sequence listed in FIG. 2.

Thus the invention includes a BCV, HCV or HEV pol protein or fragment thereof, that has been modified at the amino acid corresponding to position 4975 in the BCV genome, to resemble the CRCV pol protein.

The invention also includes a CRCV pol protein fragment comprising a fragment of the sequence listed in FIG. 2 (SEQ ID NO: 2) and having the amino acid E at the position corresponding to position 4975 in the BCV genome.

A third aspect of the invention provides a coronavirus HE protein, or fragment thereof, having at least 90% amino acid sequence identity with the BCV LY138 HE protein (Genbank Accession No. AF058942), and having at least one of F at position 235; N at position 242; and L at position 253. The amino acid positions are numbered from the initial M (which is number 1) at the start of the BCV HE protein.

The invention includes a coronavirus HE protein, or fragment thereof, having at least 91% amino acid sequence identity with BCV strain LY138 HE protein, or at least 92%, or at least 93%, or at least 94%, or at least 95%, or at least 96%, or at least 97%, or at least 98%, or at least 99% amino acid sequence identity with BCV strain LY138 HE protein, and having at least one of F at position 235; N at position 242; and L at position 253. The amino acid positions are numbered from the initial M (which is number 1) at the start of the BCV HE protein.

The invention also includes a coronavirus HE protein, or fragment thereof, having at least 90%, or at least 91%, or at least 92%, or at least 93%, or at least 94%, or at least 95%, or at least 96%, or at least 97%, or at least 98%, or at least 99% amino acid sequence identity with BCV strain LY138 HE protein, and having two of F at position 235; N at position 242; and L at position 253. The amino acid positions are numbered from the initial M (which is number 1) at the start of the BCV HE protein.

The invention further includes a coronavirus HE protein, or fragment thereof, having at least 90%, or at least 91%, or at least 92%, or at least 93%, or at least 94%, or at least 95%, or at least 96%, or at least 97%, or at least 98%, or at least 99% amino acid sequence identity with BCV strain LY138 HE protein, and having all three of F at position 235; N at position 242; and L at position 253. The amino acid positions are numbered from the initial M (which is number 1) at the start of the BCV HE protein.

Preferably, the coronavirus HE protein, or fragment thereof is a CRCV HE protein or fragment thereof that comprises or consists of the amino acid sequence listed in FIG. 14 (SEQ ID NO: 22).

Thus the invention includes a BCV, HCV, HECV or HEV HE protein or fragment thereof, that has been modified at one or more of the amino acids corresponding to position 235, 242; and 253 to resemble the CRCV HE protein.

The invention also includes a CRCV HE protein fragment comprising a fragment of the sequence listed in FIG. 14 (SEQ ID NO: 22) and having one or more of the amino acid F at position 235, N at position 242, and L at position 253. The numbering of these amino acid positions corresponds to that of BCV LY138 HE protein (Genbank Accession No. AF058942) in which residue number 1 is the initial M at the start of the BCV LY138 HE protein.

The coronavirus S, pol and HE proteins as defined above in the first, second and third aspects of the invention may be termed herein "CRCV" or "CRCV-like" proteins.

A "CRCV S protein" is an S protein or fragment thereof that has the native CRCV S amino acid sequence as listed in FIG. 4 (SEQ ID NO: 4), or a fragment thereof which comprises at least one of the amino acids specific for a CRCV S protein at the positions listed in Table 1.

A "CRCV pol protein" is a pol protein or fragment thereof that has the native CRCV pol amino acid sequence as listed in FIG. 2 (SEQ ID NO: 2), or a fragment thereof which comprises the amino acid E at the position corresponding to position 4975 in the BCV genome.

A "CRCV HE protein" is an HE protein or fragment thereof that has the native CRCV HE amino acid sequence as listed in FIG. 14 (SEQ ID NO: 22), or a fragment thereof which comprises one or more of the amino acid F at position 235, N at position 242, and L at position 253. The numbering of these amino acid positions corresponds to that of BCV LY138 HE protein (Genbank Accession No. AF058942) in which residue number 1 is the initial M at the start of the BCV LY138 HE protein.

A "CRCV-like S protein" is an S protein or fragment thereof that does not have an amino acid sequence identical to the native CRCV S amino acid sequence (FIG. 4 and SEQ ID NO: 4), but has at least 75% sequence identity with the corresponding region of the CRCV or BCV strain LY138 S protein, and has at least one of the amino acids specific for a CRCV S protein at the positions listed in Table 1.

A "CRCV-like S protein" also includes an S protein that does not have an amino acid sequence identical to the native CRCV S amino acid sequence (FIG. 4 and SEQ ID NO: 4), but that comprises or consists of a variant of the sequence listed in FIG. 4 with at least 97% identity with the sequence listed in FIG. 4. Preferably, the variant has at least 98%, or at least 99% amino acid sequence identity with the sequence listed in FIG. 4. More preferably the variant has at least 99.1%, or at least 99.2%, or at least 99.3%, or at least 99.4%, or at least 99.5%, or at least 99.6%, or at least 99.7%, or at least 99.8%, or at least 99.9% amino acid sequence identity with the sequence listed in FIG. 4.

A "CRCV-like pol protein" is a pol protein or fragment thereof that does not have an amino acid sequence identical to the native CRCV pol amino acid sequence, but has at least 90% sequence identity with the corresponding BCV strain LY138 pol protein, and which has an E at the position corresponding to position 4975 in the BCV genome.

A "CRCV-like HE protein" is an HE protein or fragment thereof that does not have an amino acid sequence identical to the native CRCV HE amino acid sequence, but has at least 90% sequence identity with the corresponding BCV strain LY138 HE protein, and which has one or more of the amino acid F at position 235, N at position 242, and L at position 253. The numbering of these three amino acid positions corresponds to that of BCV LY138 HE protein (Genbank Accession No. AF058942) in which residue number 1 is the initial M at the start of the BCV LY138 HE protein.

Preferably, the CRCV or CRCV-like protein, or fragment thereof, is at least 10 amino acids in length. More preferably, the CRCV or CRCV-like protein, or fragment thereof, is at least 20, or at least 30, or at least 40, or at least 50, or at least 100, or at least 200, or at least 300, or at least 400, or at least 500, or at least 600, or at least 700, or at least 800, or at least 900, or at least 1,000, or at least 1,100, or at least 1,200 amino acids in length.

Preferably, the CRCV or CRCV-like protein, or fragment thereof, is less than about 1,300 amino acids in length. More preferably, the CRCV or CRCV-like protein, or fragment thereof, is less than about 1,200, or less than about 1,100, or less than about 1,000, or less than about 900, or less than about 800, or less than about 700, or less than about 600, or less than about 500, or less than about 400, or less than about 300, or less than about 200, or less than about 100, or less than about 50 amino acids in length.

CRCV proteins may be isolated from CRCV, or may be made using protein chemistry techniques for example using partial proteolysis of isolated proteins (either exolytically or endolytically), or by de novo synthesis. Alternatively, the CRCV proteins, as well as CRCV-like proteins, may be made by recombinant DNA technology. Suitable techniques for cloning, manipulation, modification and expression of nucleic acids, and purification of expressed proteins, are well known in the art and are described for example in Sambrook et al (2001) "*Molecular Cloning, a Laboratory Manual*", 3$^{rd}$ edition, Sambrook et al (eds), Cold Spring Harbor Laboratory Press, Cold Spring Harbor, N.Y., USA, incorporated herein by reference.

Shorter fragments of CRCV and CRCV-like proteins, ie peptides, may be synthesised using standard techniques. Peptides may be synthesised by the Fmoc-polyamide mode of solid-phase peptide synthesis as disclosed by Lu et al (1981) *J. Org. Chem.* 46, 3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1-hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesised. Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiochem (UK) Ltd, Nottingham NG7 2QJ, UK. Purification may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino-acid analysis after acid hydrolysis and by fast atom bombardment (FAB) mass spectrometric analysis.

A fourth aspect of the invention provides a polynucleotide that encodes a CRCV or CRCV-like S, pol or HE protein according to the first, second and third aspects of the invention, or the complement thereof.

Preferably, the polynucleotide encodes a CRCV S protein according to the first aspect of the invention, or the complement thereof.

More preferably, the polynucleotide encoding the CRCV S protein comprises or consists of the sequence listed in FIG. 3 (SEQ ID NO: 3).

It is appreciated that the sequence listed in FIG. 3 (SEQ ID NO: 3) contains a Y at position 3531, which refers to either C or T. In both cases the corresponding amino acid is Ile. Thus the invention includes a polynucleotide encoding a CRCV S protein which comprises or consists of the sequence listed in FIG. 3, and having C at position 3531. The invention also includes a polynucleotide encoding a CRCV S protein which comprises or consists of the sequence listed in FIG. 3, and having T at position 3531.

The invention also includes a CRCV S polynucleotide comprising a fragment of the sequence listed in FIG. 3 (SEQ ID NO: 3), that encodes a protein having at least one of the amino acids specific for CRCV S protein at the position listed in Table 1, or the complement thereof.

Preferably, the polynucleotide encoding the pol protein comprises or consists of the sequence listed in FIG. 1 (SEQ ID NO: 1), or the complement thereof.

The invention also includes a CRCV pol polynucleotide comprising a fragment of the sequence listed in FIG. 1 (SEQ ID NO: 1) that encodes a protein having E at the position corresponding to position 4975 in the BCV genome, or the complement thereof.

Preferably, the polynucleotide encoding the HE protein comprises or consists of the sequence listed in FIG. 13 (SEQ ID NO: 21), or the complement thereof.

The invention also includes a CRCV HE polynucleotide comprising a fragment of the sequence listed in FIG. 13 (SEQ ID NO: 21) that encodes a protein having one or more of the amino acid F at position 235, N at position 242, and L at position 253. The numbering of these three amino acid positions corresponds to that of BCV LY138 HE protein (Genbank Accession No. AF058942) in which residue number 1 is the initial M at the start of the BCV LY138 HE protein.

The polynucleotides as defined above are referred to herein as CRCV or CRCV-like polynucleotides of the invention.

A "CRCV-like polynucleotide" is a polynucleotide that does not have a base sequence identical to all or a fragment of the native CRCV cDNA sequence as listed in FIGS. 1, 3 and 13 (SEQ ID NOS: 1, 3 and 21), but that encodes a CRCV or CRCV-like S pol or HE protein as defined above, or the complement thereof.

The CRCV is a positive strand RNA virus. The polynucleotide of the invention may be DNA or RNA. The RNA may be positive or negative strand RNA. The DNA may be single or double stranded DNA.

Suitable techniques for cloning and sequencing a cDNA from a positive strand RNA virus such as CRCV are well known in the art and are described for example in Sambrook et al 2001, incorporated herein by reference.

The CRCV or CRCV-like polynucleotides of the invention may be any suitable size. However, for certain purposes, such as probing or amplifying, it is preferred if the nucleic acid has fewer than 3,000, more preferably fewer than 1000, more preferably still from 10 to 100, and in further preference from 15 to 30 base pairs (if the nucleic acid is double-stranded) or bases (if the nucleic acid is single stranded). As is described more fully below, single-stranded DNA oligonucleotides, suitable for use as hybridisation probes or as primers in a polymerase chain reaction, are particularly preferred.

Oligonucleotides that can specifically amplify, or hybridise to CRCV S, pol or HE polynucleotides, as opposed to BCV, HCV, HEV or enteric CCV S, pol or HE polynucleotides, are particularly preferred. Suitable oligonucleotides can be determined by a person of skill in the art by reference to the nucleotide sequence comparisons in FIGS. 6, 8, 9 and 15.

It is appreciated that the CRCV or CRCV-like oligonucleotides may, even under highly stringent conditions, hybridise to nucleic acid, whether RNA or DNA, from HCV, BCV, and HEV as well as from CRCV. However, it is preferred if the CRCV or CRCV-like oligonucleotides hybridise to nucleic acid from CRCV under more stringent conditions than to nucleic acid from HCV, BCV or HEV. This can either be determined experimentally or by a comparison of the oligonucleotide sequence with the respective CRCV, HCV, BCV and HEV sequences, as is well known to one of skill in the art (Sambrook et al 2001).

It is also appreciated that the CRCV or CRCV-like oligonucleotides may hybridise to nucleic acid, whether RNA or DNA, from the enteric CCV as well as from CRCV. However, it is preferred if the CRCV or CRCV-like oligonucleotides hybridise to nucleic acid from CRCV under more stringent conditions than to nucleic acid from enteric CCV. This can either be determined experimentally or by a comparison of the oligonucleotide sequence with the respective sequences, as is well known to one of skill in the art (Sambrook et al 2001). Preferably, the oligonucleotides do not hybridise to nucleic acid from enteric CCV at all under stringent conditions (see below).

Conveniently, the CRCV or CRCV-like polynucleotides or oligonucleotides further comprise a detectable label.

By "detectable label" is included any convenient radioactive label such as $^{32}$P, $^{33}$P or $^{35}$S which can readily be incorporated into a nucleic acid molecule using well known methods; any convenient fluorescent or chemiluminescent label which can readily be incorporated into a nucleic acid is also included. In addition the term "detectable label" also includes a moiety which can be detected by virtue of binding to another moiety (such as biotin which can be detected by binding to streptavidin); and a moiety, such as an enzyme, which can be detected by virtue of its ability to convert a colourless compound into a coloured compound, or vice versa (for example, alkaline phosphatase can convert colourless o-nitrophenylphosphate into coloured o-nitrophenol). Conveniently, the nucleic acid probe may occupy a certain position in a fixed array and whether a nucleic acid hybridises to it can be determined by reference to the position of hybridisation in the fixed array.

Labelling with [$^{32}$P]dCTP may be carried out using a Rediprime® random primer labelling kit supplied by Amersham.

Primers which are suitable for use in a polymerase chain reaction (PCR; Saiki et al (1988) *Science* 239, 487-491) are preferred. Suitable PCR primers may have the following properties:

It is well known that the sequence at the 5' end of the oligonucleotide need not match the target sequence to be amplified.

It is usual that the PCR primers do not contain any complementary structures with each other longer than 2 bases, especially at their 3' ends, as this feature may promote the formation of an artefactual product called "primer dimer". When the 3' ends of the two primers hybridise, they form a "primed template" complex, and primer extension results in a short duplex product called "primer dimer".

Internal secondary structure should be avoided in primers. For symmetric PCR, a 40-60% G+C content is often recommended for both primers, with no long stretches of any one base. The classical melting temperature calculations used in conjunction with DNA probe hybridization studies often predict that a given primer should anneal at a specific temperature or that the 72° C. extension temperature will dissociate the primer/template hybrid prematurely. In practice, the hybrids are more effective in the PCR process than generally predicted by simple $T_m$ calculations.

Optimum annealing temperatures may be determined empirically and may be higher than predicted. Taq DNA polymerase does have activity in the 37-55° C. region, so primer extension will occur during the annealing step and the hybrid will be stabilised. The concentrations of the primers are equal in conventional (symmetric) PCR and, typically, within 0.1- to 1 μM range.

It will further be appreciated that if a control amplification reaction is to be carried out, for example using primers complementary to an ubiquitously expressed gene, that it may be beneficial for the products of the control and CRCV or CRCV-like products to be of different sizes, such that the two products may be distinguished by the detection means employed, for example by mobility on agarose gel electrophoresis. However, it may be desirable for the two products to be of similar size, for example both between 100 and 1000, or between 100 and 600 nucleotides long. This may aid simultaneous analysis of the products, for example by gel electrophoresis, and may also mean that the control and CRCV or CRCV-like amplification reactions may have similar performance characteristics, in terms, for example, of relative rates of accumulation of product at different stages during the reaction.

Any of the nucleic acid amplification protocols can be used in the method of the invention including the polymerase chain reaction, QB replicase and ligase chain reaction. Also, NASBA (nucleic acid sequence based amplification), also called 3SR, can be used as described in Compton (1991) *Nature* 350, 91-92 and *AIDS* (1993), Vol 7 (Suppl 2), S108 or SDA (strand displacement amplification) can be used as described in Walker et al (1992) *Nucl. Acids Res.* 20, 1691-1696. The polymerase chain reaction is particularly preferred because of its simplicity.

When a pair of suitable nucleic acids of the invention are used in a PCR it is convenient to detect the product by gel electrophoresis and ethidium bromide staining. As an alternative, it is convenient to use a labelled oligonucleotide capable of hybridising to the amplified DNA as a probe. When the amplification is by PCR the oligonucleotide probe hybridises to the interprimer sequence as defined by the two primers. The oligonucleotide probe is preferably between 10 and 50 nucleotides long, more preferably between 15 and 30 nucleotides long. It may be longer than the amplified DNA or include one or both of the primers, but in this case, the hybridisation conditions should be such that the probe should not hybridise to the primers alone, but only to an amplified product that also contains interprimer sequence that is capable of hybridising to the probe.

The probe may be labelled with a radionuclide such as $^{32}P$, $^{33}P$ and $^{35}S$ using standard techniques, or may be labelled with a fluorescent dye. When the oligonucleotide probe is fluorescently labelled, the amplified DNA product may be detected in solution (see for example Balaguer et al (1991) "Quantification of DNA sequences obtained by polymerase chain reaction using a bioluminescence adsorbent" *Anal. Biochem.* 195, 105-110 and Dilesare et al (1993) "A high-sensitivity electrochemiluminescence-based detection system for automated PCR product quantitation" *BioTechniques* 15, 152-157.

PCR products can also be detected using a probe which may have a fluorophore-quencher pair or may be attached to a solid support or may have a biotin tag or they may be detected using a combination of a capture probe and a detector probe.

Fluorophore-quencher pairs are particularly suited to quantitative measurements of PCR reactions (eg RT-PCR). Fluorescence polarisation using a suitable probe may also be used to detect PCR products.

The invention also includes a vector comprising the CRCV or CRCV-like polynucleotide of the fourth aspect of the invention.

Typical prokaryotic vector plasmids are: pUC18, pUC19, pBR322 and pBR329 available from Biorad Laboratories (Richmond, Calif., USA); pTrc99A, pKK223-3, pKK233-3, pDR540 and pRIT5 available from Pharmacia (Piscataway, N.J., USA); pBS vectors, Phagescript vectors, Bluescript vectors, pNH8A, pNH16A, pNH18A, pNH46A available from Stratagene Cloning Systems (La Jolla, Calif. 92037, USA).

A typical mammalian cell vector plasmid is pSVL available from Pharmacia (Piscataway, N.J., USA). This vector uses the SV40 late promoter to drive expression of cloned genes, the highest level of expression being found in T antigen-producing cells, such as COS-1 cells. An example of an inducible mammalian expression vector is pMSG, also available from Pharmacia (Piscataway, N.J., USA). This vector uses the glucocorticoid-inducible promoter of the mouse mammary tumour virus long terminal repeat to drive expression of the cloned gene.

Useful yeast plasmid vectors are pRS403-406 and pRS413-416 and are generally available from Stratagene Cloning Systems (La Jolla, Calif. 92037, USA). Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (YCps).

Generally, the CRCV or CRCV-like polynucleotide of the invention is inserted into an expression vector, such as a plasmid, in proper orientation and correct reading frame for expression. It may be linked to the appropriate transcriptional and translational regulatory control nucleotide sequences recognised by the desired host prior to insertion into the vector, although such controls are generally available in the expression vector. Thus, the polynucleotide of the invention insert may be operatively linked to an appropriate promoter. Eukaryotic promoters include the CMV immediate early promoter, the HSV thymidine kinase promoter, the early and late SV40 promoters and the promoters of retroviral LTRs. Other suitable promoters will be known to the skilled artisan. The expression constructs desirably also contain sites for transcription initiation and termination, and in the transcribed region, a ribosome binding site for translation (Hastings et al, International Patent No. WO 98/16643).

Methods well known to those skilled in the art can be used to construct expression vectors containing the coding sequence and, for example appropriate transcriptional or translational controls. One such method involves ligation via homopolymer tails. Homopolymer polydA (or polydC) tails are added to exposed 3' OH groups on the DNA fragment to be cloned by terminal deoxynucleotidyl transferases. The fragment is then capable of annealing to the polydT (or polydG) tails added to the ends of a linearised plasmid vector. Gaps left following annealing can be filled by DNA polymerase and the free ends joined by DNA ligase.

Another method involves ligation via cohesive ends. Compatible cohesive ends can be generated on the DNA fragment and vector by the action of suitable restriction enzymes. These ends will rapidly anneal through complementary base pairing and remaining nicks can be closed by the action of DNA ligase.

A further method uses synthetic molecules called linkers and adaptors. DNA fragments with blunt ends are generated by bacteriophage T4 DNA polymerase or *E. coli* DNA polymerase I which remove protruding 3' termini and fill in recessed 3' ends. Synthetic linkers, pieces of blunt-ended double-stranded DNA which contain recognition sequences for defined restriction enzymes, can be ligated to blunt-ended DNA fragments by T4 DNA ligase. They are subsequently digested with appropriate restriction enzymes to create cohesive ends and ligated to an expression vector with compatible termini. Adaptors are also chemically synthesised DNA fragments which contain one blunt end used for ligation but which also possess one preformed cohesive end.

Synthetic linkers containing a variety of restriction endonuclease sites are commercially available from a number of sources including International Biotechnologies Inc, New Haven, Conn., USA.

A desirable way to modify the polynucleotide of the invention is to use the polymerase chain reaction as disclosed by Saiki et al (1988) *Science* 239, 487-491. In this method the DNA to be enzymatically amplified is flanked by two specific oligonucleotide primers which themselves become incorporated into the amplified DNA. The specific primers may contain restriction endonuclease recognition sites which can be used for cloning into expression vectors using methods known in the art.

The invention also includes a host cell transformed with the vector comprising the CRCV or CRCV-like polynucleotide. The host cell can be either prokaryotic or eukaryotic. If the CRCV or CRCV-like polynucleotide, in the vector, is to be expressed as a glycoprotein, the host cell is a eukaryotic host cell, and preferably a mammalian host cell.

Bacterial cells are preferred prokaryotic host cells and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast and mammalian cells, preferably vertebrate cells such as those from a mouse, rat, monkey or human fibroblastic cell line. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, and monkey kidney-derived COS-1 cells available from the ATCC as CRL 1650. Preferred insect cells are Sf9 cells which can be transfected with baculovirus expression vectors.

Transformation of appropriate cell hosts with a vector is accomplished by well known methods that typically depend on the type of vector used. With regard to transformation of prokaryotic host cells, see, for example, Cohen et al (1972) *Proc. Natl. Acad. Sci. USA* 69, 2110 and Sambrook et al (2001) *Molecular Cloning, A Laboratory Manual*, 3$^{rd}$ Ed. Cold Spring Harbor Laboratory, Cold Spring Harbor, N.Y. Transformation of yeast cells is described in Sherman et al (1986) *Methods In Yeast Genetics, A Laboratory Manual*, Cold Spring Harbor, N.Y. The method of Beggs (1978) *Nature* 275, 104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming cells and is well known in the art for transforming yeast cell, bacterial cells and vertebrate cells.

For example, many bacterial species may be transformed by the methods described in Luchansky et al (1988) *Mol. Microbiol.* 2, 637-646 incorporated herein by reference. The greatest number of transformants is consistently recovered following electroporation of the DNA-cell mixture suspended in 2.5×PEB using 6250V per cm at 25 µFD.

Methods for transformation of yeast by electroporation are disclosed in Becker & Guarente (1990) *Methods Enzymol.* 194, 182.

Physical methods may be used for introducing DNA into animal and plant cells. For example, microinjection uses a very fine pipette to inject DNA molecules directly into the nucleus of the cells to be transformed. Another example involves bombardment of the cells with high-velocity microprojectiles, usually particles of gold or tungsten that have been coated with DNA.

Successfully transformed cells, ie cells that contain a CRCV or CRCV-like DNA construct, can be identified by well known techniques. For example, one selection technique involves incorporating into the expression vector a DNA sequence (marker) that codes for a selectable trait in the transformed cell. These markers include dihydrofolate reductase, G418 or neomycin resistance for eukaryotic cell culture, and tetracyclin, kanamycin or ampicillin resistance genes for culturing in *E. coli* and other bacteria. Alternatively, the gene for the selectable trait can be on another vector, which is used to co-transform the desired host cell.

The marker gene can be used to identify transformants but it is desirable to determine which of the cells contain recombinant DNA molecules and which contain self-ligated vector molecules. This can be achieved by using a cloning vector where insertion of a DNA fragment destroys the integrity of one of the genes present on the molecule. Recombinants can therefore be identified because of loss of function of that gene.

Another method of identifying successfully transformed cells involves growing the cells resulting from the introduction of an expression construct of the present invention to produce the CRCV or CRCV-like S, pol or HE protein. Cells can be harvested and lysed and their DNA content examined for the presence of the DNA using a method such as that described by Southern (1975) *J. Mol. Biol.* 98, 503 or Berent et al (1985) *Biotech.* 3, 208. Alternatively, the presence of the protein in the supernatant can be detected using antibodies as described below.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, in addition to the transformed host cells themselves, the present invention also contemplates a culture of those cells, preferably a monoclonal (clonally homogeneous) culture, or a culture derived from a monoclonal culture, in a nutrient medium.

Host cells that have been transformed by the recombinant CRCV or CRCV-like polynucleotide, typically in a vector as described above, are then cultured for a sufficient time and under appropriate conditions known to those skilled in the art in view of the teachings disclosed herein to permit the expression of the CRCV or CRCV-like protein encoded by the CRCV or CRCV-like polynucleotide, which can then be recovered.

The CRCV or CRCV-like protein can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

For example, for expression in a baculovirus system, recombinant DNA encoding the CRCV spike gene may be cloned into a suitable transfer vector such as pMelBac (Invitrogen). Co-transfection with baculovirus DNA (eg Bac-N-Blue/Invitrogen) results in a recombinant baculovirus encoding the spike gene. Infection of a suitable insect cell line (e.g. Sf9, Sf21, High Five/Invitrogen) at an appropriate multiplicity of infection leads to expression of the recombinant spike protein. Protein expression is confirmed by western blotting or ELISA using appropriate reagents (e.g. convalescent canine serum or other virus specific antiserum).

The invention thus includes a method of obtaining a CRCV or CRCV-like protein encoded by the CRCV or CRCV-like polynucleotide of the present invention. The method comprises culturing the host cell comprising the CRCV or CRCV-like polynucleotide, typically in a vector; expressing the protein in the host cell, and purifying the protein. The invention further includes the protein obtainable by this method.

The invention thus also includes a method of obtaining a glycosylated CRCV or CRCV-like protein, typically an S protein, encoded by the CRCV or CRCV-like polynucleotide of the present invention. The method comprises culturing a eukaryotic, or more preferably mammalian, host cell comprising the CRCV or CRCV-like polynucleotide, typically in a vector; expressing the protein in the host cell; and purifying the glycosylated protein. The invention further includes the glycosylated protein obtainable by this method.

In a fifth aspect, the invention provides a method of making an anti-CRCV antibody comprising raising an immune response to a CRCV or CRCV-like S protein of the invention as described above in the first aspect of the invention in an animal, and preparing an antibody from the animal or from an immortal cell derived therefrom. Alternatively, the method may comprise selecting an antibody from an antibody-display library using a CRCV or CRCV-like S protein of the invention as described above in the first aspect of the invention.

Methods and techniques for producing a monoclonal antibody are well known to a person of skill in the art, for example those disclosed in "*Monoclonal Antibodies: A manual of techniques*", H Zola (CRC Press, 1988) and in "*Monoclonal Hybridoma Antibodies: Techniques and Applications*", J G R Hurrell (CRC Press, 1982), incorporated herein by reference.

Optionally, the method further comprises determining whether the antibody thus obtained has greater affinity for the CRCV S protein than for the BCV S protein, and preferably also whether the antibody has a greater affinity for the CRCV S protein than for the HCV and HEV S proteins. Methods for determining the relative affinity of antibodies for antigens are known in the art.

The invention also includes an anti-CRCV antibody obtainable by the method of the fifth aspect of the invention, that has greater affinity for the CRCV S protein than for the BCV S protein. Preferably, the antibody also has a greater affinity for the CRCV S protein than for the HCV and HEV S proteins.

The invention also includes a method of making an anti-CRCV antibody comprising raising an immune response to a CRCV or CRCV-like HE protein of the invention as described above in the third aspect of the invention in an animal, and preparing an antibody from the animal or from an immortal cell derived therefrom. Alternatively, the method may comprise selecting an antibody from an antibody-display library using a CRCV or CRCV-like HE protein of the invention as described above in the third aspect of the invention.

Optionally, the method further comprises determining whether the antibody thus obtained has greater affinity for the CRCV HE protein than for the BCV HE protein, and preferably also whether the antibody has a greater affinity for the CRCV HE protein than for the HCV and HEV HE proteins. Methods for determining the relative affinity of antibodies for antigens are known in the art.

The invention also includes an anti-CRCV antibody obtainable by the method of the fifth aspect of the invention, that has greater affinity for the CRCV HE protein than for the BCV HE protein. Preferably, the antibody also has a greater affinity for the CRCV HE protein than for the HCV and HEV HE proteins.

Preferably, the antibody is a monoclonal antibody. However, the invention includes a monospecific anti-CRCV antibody. The antibody may be an antibody fragment, as described below.

The monoclonal or monospecific antibody may be a chimaeric antibody, as discussed by Neuberger et al (1988, 8*th International Biotechnology Symposium* Part 2, 792-799). The monoclonal or monospecific antibody may also be a "caninised" antibody, for example by inserting the CDR regions of mouse antibodies into the framework of canine antibodies.

The invention also includes anti-CRCV antibody fragments. The variable heavy ($V_H$) and variable light ($V_L$) domains of antibodies are involved in antigen recognition, a fact first recognised by early protease digestion experiments. Further confirmation was found by "humanisation" of rodent antibodies, in which variable domains of rodent origin may be fused to constant domains of human origin such that the resultant antibody retains the antigenic specificity of the rodent parented antibody (Morrison et al (1984) *Proc. Natl. Acad. Sci. USA* 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) *Science* 240, 1041); Fv molecules (Skerra et al (1988) *Science* 240, 1038); single-chain Fv (ScFv) molecules where the $V_H$ and $V_L$ partner domains are linked via a flexible oligopeptide (Bird et al (1988) *Science* 242, 423; Huston et al (1988) *Proc. Natl. Acad. Sci. USA* 85, 5879) and single domain antibodies (dAbs) comprising isolated V domains (Ward et al (1989) *Nature* 341, 544). A general review of the techniques involved in the synthesis of antibody fragments which retain their specific binding sites is to be found in Winter & Milstein (1991) *Nature* 349, 293-299.

By "ScFv molecules" we mean molecules wherein the $V_H$ and $V_L$ partner domains are linked via a flexible oligopeptide.

The advantages of antibody fragments, rather than whole antibodies, are several-fold. The smaller size of the fragments may lead to improved pharmacological properties, such as better penetration of solid tissue. Effector functions of whole antibodies, such as complement binding, are removed. Fab, Fv, ScFv and dAb antibody fragments can all be expressed in and secreted from *E. coli*, thus allowing the facile production of large amounts of the fragments.

Whole antibodies, and F(ab')$_2$ fragments are "bivalent". By "bivalent" we mean that the antibodies and F(ab')$_2$ fragments have two antigen combining sites. In contrast, Fab, Fv, ScFv and dAb fragments are monovalent, having only one antigen combining sites.

In a sixth aspect, the invention provides a method of determining whether a dog has been exposed to CRCV. The method comprises obtaining a suitable sample from the dog, and identifying CRCV or an anti-CRCV antibody in the sample. The method may be used as an aid in the diagnosis of whether a dog has CIRD.

The invention includes a method of detecting, in a sample obtained from a dog, past exposure of the dog to CRCV, the method comprising obtaining a suitable sample from the dog, and identifying anti-CRCV antibodies in the sample.

In one preferred embodiment, the suitable sample can be any antibody containing sample such as serum, saliva, tracheal wash or bronchiolar lavage.

Preferably, the anti-CRCV antibody can be detected using a BCV, HCV, HEV or CRCV antigen, more preferably, using a BCV or CRCV antigen.

More preferably, identifying an anti-CRCV antibody in the sample comprises identifying an antibody that selectively binds to an S protein whose amino acid sequence is at least 75% identical with the amino acid sequence of the CRCV S protein (FIG. 4 and SEQ ID NO: 4); an S protein whose amino acid sequence is at least 75% identical with the amino acid sequence of the BCV S protein (Genbank Accession No. AF058942); HCV S protein (Genbank Accession No. L14643); to a coronavirus having an S protein at least 75% identical with BCV S protein (Genbank Accession No. AF058942), or a fragment thereof; or to a coronavirus having an S protein at least 75% identical with the CRCV S protein, or a fragment thereof.

More preferably, identifying an antibody that selectively binds to an S protein whose amino acid sequence is at least 75% identical with the amino acid sequence of the BCV S protein, comprises identifying an antibody that selectively binds to an S protein whose amino acid sequence is at least 80% identical, or at least 85% identical, or at least 90% identical, or at least 95% identical with the amino acid sequence of the BCV S protein (Genbank Accession No. AF058942) or a fragment thereof.

More preferably, identifying an anti-CRCV antibody in the sample comprises identifying an antibody that selectively binds to the BCV S protein (Genbank Accession No. AF058942).

Even more preferably, identifying an antibody that selectively binds to an S protein whose amino acid sequence is at least 75% identical with the amino acid sequence of the CRCV S protein, comprises identifying an antibody that selectively binds to an S protein whose amino acid sequence is at least 80% identical, or at least 85% identical, or at least 90% identical, or at least 95% identical with the amino acid sequence of the CRCV S protein (FIG. 4 and SEQ ID NO: 4) or a fragment thereof.

Yet more preferably, identifying an anti-CRCV antibody in the sample comprises identifying an antibody that selectively binds to a CRCV or CRCV-like S protein as defined in the first aspect of the invention.

Most preferably, identifying an anti-CRCV antibody in the sample comprises identifying an antibody that selectively binds to the CRCV S protein as listed in FIG. 4 (SEQ ID NO: 4), or a fragment thereof.

Similarly, identifying an anti-CRCV antibody in the sample may comprise identifying an antibody that selectively binds to an HE protein whose amino acid sequence is at least 90% identical with the partial amino acid sequence of the CRCV HE protein (FIG. 14 and SEQ ID NO: 22); to an HE protein whose amino acid sequence is at least 90% identical with the amino acid sequence of the BCV HE protein (Genbank Accession No. AF058942) or the HECV HE protein (Genbank Accession No. L07747); to a coronavirus having an S protein at least 90% identical with BCV HE protein (Genbank Accession No. AF058942), or a fragment thereof; or to a coronavirus having an HE protein at least 90% identical with the CRCV HE protein, or a fragment thereof.

More preferably, identifying an antibody that selectively binds to an HE protein whose amino acid sequence is at least 90% identical with the amino acid sequence of the BCV HE protein, comprises identifying an antibody that selectively binds to an HE protein whose amino acid sequence is at least 91% identical, or at least 92% identical, or at least 93% identical, or at least 94% identical, or at least 95% identical, or at least 96% identical, or at least 97% identical, or at least 98% identical, or at least 99% identical with the amino acid sequence of the BCV HE protein (Genbank Accession No. AF058942) or a fragment thereof.

More preferably, identifying an anti-CRCV antibody in the sample comprises identifying an antibody that selectively binds to the BCV HE protein (Genbank Accession No. AF058942).

Even more preferably, identifying an antibody that selectively binds to an HE protein whose amino acid sequence is at least 90% identical with the partial amino acid sequence of the CRCV HE protein, comprises identifying an antibody that selectively binds to an HE protein whose partial amino acid sequence is at least 91% identical, or at least 92% identical, or at least 93% identical, or at least 94% identical, or at least 95% identical, or at least 96% identical, or at least 97% identical, or at least 98% identical, or at least 99% identical with the partial amino acid sequence of the CRCV HE protein (FIG. 13) or a fragment thereof.

Yet more preferably, identifying an anti-CRCV antibody in the sample comprises identifying an antibody that selectively binds to a CRCV or CRCV-like HE protein as defined in the third aspect of the invention.

Most preferably, identifying an anti-CRCV antibody in the sample comprises identifying an antibody that selectively binds to the CRCV HE protein whose partial amino acid sequence is listed in FIG. 14 (SEQ ID NO: 22), or a fragment thereof.

The invention includes a method of detecting CRCV in a sample obtained from a dog, the method comprising obtaining a suitable sample from the dog, and identifying CRCV in the sample.

It is appreciated that there may be some naturally occurring sequence variation between different isolates of CRCV. The invention thus includes identifying CRCV isolates whose S, pol and HE genes and proteins have some sequence variation from the sequences provided in FIGS. 1 to 4 and 13 and 14. It is appreciated, however, that the same methods will be used to detect the variant isolates of CRCV, as well as the isolate characterised by the sequences listed in FIGS. 1 to 4 and 13 and 14.

In a preferred embodiment, the suitable sample can be a lung wash, tracheal wash, tonsillar swab or a biopsy or post-mortem sample from the respiratory tract of the dog.

Preferably, in this embodiment, identifying CRCV comprises identifying a nucleic acid component of CRCV.

Typically, this will be performed by extracting RNA from the sample, and obtaining cDNA therefrom, for example as is described in Example 1. Thereafter, a CRCV nucleic acid component is identified in the cDNA, for example using techniques involving high stringency hybridisation, specific amplification, and nucleotide sequencing, as are well known to a person of skill in the art (Sambrook et al (2001) supra).

Preferably, identifying CRCV comprises identifying a polynucleotide that hybridises at high stringency to the BCV genome, such as the LY138 strain genome (Genbank Accession No. AF058942) or a portion thereof.

Further preferably, identifying CRCV comprises identifying a polynucleotide that hybridises at high stringency to the CRCV S, pol or HE polynucleotides (FIGS. 1, 3 and 13) or a portion thereof.

By "hybridising at high stringency" is meant that the polynucleotide and the nucleic acid to which it hybridises have sufficient nucleotide sequence similarity that they can hybridise under highly stringent conditions. As is well known in the art, the stringency of nucleic acid hybridisation depends on factors such as length of nucleic acid over which hybridisation occurs, degree of identity of the hybridising sequences and on factors such as temperature, ionic strength and CG or AT content of the sequence.

Nucleic acids which can hybridise at high stringency to the CRCV cDNA molecule include nucleic acids which have >90% sequence identity, preferably those with >95% or >96% or >97% or >98, more preferably those with >99% sequence identity, over at least a portion of the CRCV cDNA.

Typical highly stringent hybridisation conditions which lead to selective hybridisation are known in the art, for example those described in Sambrook et al 2001 (supra), incorporated herein by reference.

An example of a typical hybridisation solution when a nucleic acid is immobilised on a nylon membrane and the probe nucleic acid is >500 bases is:

6×SSC (saline sodium citrate)
0.5% sodium dodecyl sulphate (SDS)
100 μg/ml denatured, fragmented salmon sperm DNA
The hybridisation is performed at 68° C. The nylon membrane, with the nucleic acid immobilised, may be washed at 68° C. in 0.1×SSC.

20×SSC may be prepared in the following way. Dissolve 175.3 g of NaCl and 88.2 g of sodium citrate in 800 ml of H$_2$O. Adjust the pH to 7.0 with a few drops of a 10 N solution of NaOH. Adjust the volume to 1 liter with H$_2$O. Dispense into aliquots. Sterilise by autoclaving.

An example of a typical hybridisation solution when a nucleic acid is immobilised on a nylon membrane and the probe is an oligonucleotide of between 15 and 50 bases is:

3.0 M trimethylammonium chloride (TMACl)
0.01 M sodium phosphate (pH 6.8)
1 mm EDTA (pH 7.6)
0.5% SDS
100 μg/ml denatured, fragmented salmon sperm DNA
0.1% non-fat dried milk The optimal temperature for hybridisation is usually chosen to be 5° C. below the $T_i$ for the given chain length. $T_i$ is the irreversible melting temperature of the hybrid formed between the probe and its target sequence. Jacobs et al (1988) *Nucl. Acids Res.* 16, 4637 discusses the determination of $T_i$s. The recommended hybridization temperature for 17-mers in 3M TMACl is 48-50° C.; for 19-mers, it is 55-57° C.; and for 20-mers, it is 58-66° C.

Preferably, identifying CRCV comprises using a polynucleotide having at least 80%, or at least 85%, or at least 90%, or at least 95% identity with a portion of the BCV genome (Genbank Accession No. AF058942).

More preferably, identifying CRCV comprises using a polynucleotide having at least 80%, or at least 85%, or at least 90%, or at least 95% identity with a portion of the CRCV S polynucleotide (FIG. 3), or having at least 90%, or at least 95% identity with a portion of the CRCV pol polynucleotide (FIG. 1), or having at least 90%, or at least 95% identity with a portion of the CRCV HE polynucleotide (FIG. 13).

More preferably, identifying CRCV comprises identifying a CRCV polynucleotide as defined above with respect to the fourth aspect of the invention.

Most preferably, identifying CRCV comprises identifying a CRCV polynucleotide comprising or consisting of a sequence listed in FIG. 1 or FIG. 3 or FIG. 13, or a fragment thereof.

In another preferred embodiment, identifying CRCV comprises identifying a protein component of CRCV.

Preferably, identifying a protein component of CRCV comprises identifying a CRCV protein as defined above in the first or second or third aspects of the invention.

Most preferably, identifying a protein component of CRCV comprises identifying a CRCV protein comprising or consisting of the amino acid sequence listed in FIG. 2 or FIG. 4 or FIG. 14, or a fragment thereof.

Assaying a protein component of CRCV in a biological sample can occur using any art-known method. Preferred for assaying CRCV protein levels in a biological sample are antibody-based techniques.

Preferably, identifying a protein component of CRCV comprises using an antibody reactive with CRCV.

More preferably, the antibody reactive with CRCV is an anti-BCV antibody, an anti-HCV antibody, an anti-HEV antibody, or an anti-CRCV antibody obtainable or obtained by the methods of the fifth aspect of the invention.

For example, CRCV protein expression can be studied with classical immunohistological methods. In these, the specific recognition is provided by the primary antibody (polyclonal or monoclonal) but the secondary detection system can utilise fluorescent, enzyme, or other conjugated secondary antibodies. As a result, an immunohistological staining of tissue section for pathological examination is obtained. Tissues can also be extracted, e.g., with urea and neutral detergent, for the liberation of CRCV protein for Western-blot or dot/slot assay (Jalkanen, M., et al, *J. Cell. Biol.* 101:976-985 (1985); Jalkanen, M., et al, *J. Cell. Biol.* 105:3087-3096 (1987)). In this technique, which is based on the use of cationic solid phases, quantitation of CRCV protein can be accomplished using isolated CRCV protein as a standard. This technique can also be applied to body fluid samples.

Other antibody-based methods useful for detecting CRCV protein expression include immunoassays, such as the enzyme linked immunosorbent assay (ELISA) and the radioimmunoassay (RIA). For example, a CRCV reactive monoclonal antibody can be used both as an immunoadsorbent and as an enzyme-labeled probe to detect and quantify the CRCV protein. The amount of CRCV protein present in the sample can be calculated by reference to the amount present in a standard preparation using a linear regression computer algorithm. Such an ELISA for detecting a tumour antigen is described in Iacobelli et al, *Breast Cancer Research and Treatment* 11: 19-30 (1988). In another ELISA assay, two distinct specific monoclonal antibodies can be used to detect CRCV protein in a body fluid. In this assay, one of the antibodies is used as the immunoadsorbent and the other as the enzyme-labeled probe.

The above techniques may be conducted essentially as a "one-step" or "two-step" assay. The "one-step" assay involves contacting CRCV protein with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulfur ($^{35}$S), tritium ($^3$H), indium ($^{112}$In), and technetium ($^{99}$mTc), and fluorescent labels, such as fluorescein and rhodamine, and biotin.

In a seventh aspect, the invention provides an immunosorbent assay for detecting anti-CRCV S or HE antibodies. The assay comprises a solid phase coated with a CRCV or CRCV-like S or HE protein, or coated with both CRCV or CRCV-like S and HE proteins as defined in the first and third aspects of the invention, or obtainable using the methods of the fourth aspect of the invention, or an antigenic fragment thereof, wherein anti-CRCV S or HE antibodies in a sample exposed to the solid phase will bind to the protein; and a detectable label conjugate which will bind to the anti-CRCV antibodies bound to the solid phase.

It is appreciated that an antigenic fragment of the CRCV or CRCV-like S protein that coats the solid phase is of sufficient size to be bound by an anti-CRCV S antibody, and which comprises at least one of the amino acids specific for CRCV S protein as listed in Table 1.

It is also appreciated that an antigenic fragment of the CRCV or CRCV-like HE protein that coats the solid phase is of sufficient size to be bound by an anti-CRCV HE antibody, and which comprises at least one of the three amino acids specific for CRCV HE protein as defined above.

Preferably, the CRCV or CRCV-like S or HE protein, or antigenic fragment thereof, that coats the solid phase is at least 10 amino acids in length. More preferably, the CRCV or CRCV-like S protein, or antigenic fragment thereof, is at least 20, or at least 30, or at least 40, or at least 50, or at least 100, or at least 200, or at least 300, or at least 400 amino acids in length. The CRCV or CRCV-like S protein may be at least 500, or at least 600, or at least 700, or at least 800, or at least 900, or at least 1,000 amino acids in length.

Preferably, the CRCV or CRCV-like S protein, or antigenic fragment thereof, that coats the solid phase is less than about 1200 amino acids in length. More preferably, the CRCV or CRCV-like S protein, or antigenic fragment thereof, is less than about 1,100, or less than about 1,000, or less than about 900, or less than about 800, or less than about 700, or less than about 600, or less than about 500 amino acids in length. The CRCV or CRCV-like S or HE protein may be less than about 400, or less than about 300, or less than about 200, or less than about 100, or less than about 50 amino acids in length.

Preferably, the solid phase is a microtitre well.

Further preferably, the conjugate comprises anti-dog antibody.

Preferably, the conjugate comprises an enzyme, for example horseradish peroxidase. Further preferably, the immunosorbent assay also comprises a substrate for the enzyme.

Further details of suitable immunosorbent assays and ELISAs are provided above.

The invention includes a kit of parts which include the components of the immunosorbent assay. The kit of parts may thus include a solid phase such as a microtitre plate, CRCV or CRCV-like S or HE protein or both for coating the solid phase, a detectable label conjugate, such as an anti-dog antibody, which will bind to anti-CRCV antibodies bound to the solid phase. If the detectable label conjugate is an enzyme, the kit of parts may also include a substrate for the enzyme. The kit may also include a positive control sample that contains an anti-CRCV S or HE protein antibody, such as those described with reference to the fifth aspect of the invention, and a negative control sample.

The invention thus includes a solid substrate with a CRCV or CRCV-like S or HE protein as defined in the first and third aspects of the invention, or obtainable using the methods of the fourth aspect of the invention, or an antigenic fragment thereof, attached thereto, for capturing anti-CRCV S or HE antibodies or both from a liquid sample, wherein anti-CRCV S or HE antibodies in a sample exposed to the solid substrate will bind to the S or HE protein.

Typically, protein is coated on microtitre plates overnight at 4° C. to 37° C., depending on the stability of the antigen. Unbound protein is washed off with a wash buffer such as phosphate buffered saline or Tris buffered saline. Serum or other samples are incubated on the plate, typically at 37° C. for between 1 and several hours. Unbound material is washed off, the plates are incubated with enzyme-labelled (e.g. horseradish peroxidase) antibody, such as anti-canine IgG or IgM for serum samples, or anti-canine IgA for lung washes, for 1 to several hours at 37° C. Unbound antibody is washed off and plates are incubated with a substrate such as OPD for about 10 min, and the optical density measured in a photometer.

Preferably, the solid substrate is a microtitre well.

In an eighth aspect, the invention provides a vaccine composition for vaccinating dogs comprising (i) a coronavirus having an S protein with at least 75% amino acid identity with CRCV S protein, or (ii) a coronavirus having an S protein with at least 75% amino acid identity with BCV S protein, or (iii) a coronavirus having an HE protein with at least 90% amino acid identity with CRCV HE protein, or (iv) a coronavirus having an HE protein with at least 90% amino acid identity with BCV HE protein, or (v) a coronavirus protein having at least 75% amino acid identity with a CRCV protein or an immunogenic fragment thereof, or (vi) a coronavirus protein having at least 75% amino acid identity with a BCV protein or an immunogenic fragment thereof, or (vii) a nucleic acid encoding said coronaviral protein or immunogenic fraction thereof.

Preferably, the vaccine is packaged and presented for use in dogs.

When the vaccine comprises a coronavirus protein, or an immunogenic fragment thereof, the protein preferably has at least 80%, or at least 85%, or at least 90%, or at least 95% amino acid identity with the corresponding portion of a BCV or CRCV protein.

Preferably, the coronavirus protein is a BCV, HCV, HEV or CRCV protein, or a modification thereof.

Typical protein modifications include amino acid substitutions to improve the antigenicity of the vaccine. BCV, HCV and HEV proteins may be modified to be more like a CRCV protein. For example, the spike protein of BCV, HCV or HEV may be modified to include a CRCV amino acid at any of differences shown in the comparison in FIG. 10, or listed in Table 1. Additionally or alternatively, the HE protein of BCV, HCV or HEV may be modified to include a CRCV amino acid at any of the three CRCV-specific residues as defined above.

Proteins in which one or more of the amino acid residues are chemically modified, may be used providing that the function of the protein, namely the production of specific antibodies in vivo, remains substantially unchanged. It is appreciated that synthesised proteins may be suitably modified before or after their synthesised. Such modifications include forming salts with acids or bases, especially physiologically acceptable organic or inorganic acids and bases, forming an ester or amide of a terminal carboxyl group, and attaching amino acid protecting groups such as N-t-butoxycarbonyl. Such modifications may protect the peptide from in vivo metabolism.

The protein may be present as single copies or as multiples, for example tandem repeats. Such tandem or multiple repeats may be sufficiently antigenic themselves to obviate the use of a carrier. It may be advantageous for the protein to be formed as a loop, with the N-terminal and C-terminal ends joined together, or to add one or more Cys residues to an end to increase antigenicity and/or to allow disulphide bonds to be formed. If the protein is covalently linked to a carrier, preferably a polypeptide, then the arrangement is preferably such that the protein of the invention forms a loop.

According to current immunological theories, a carrier function should be present in any immunogenic formulation in order to stimulate, or enhance stimulation of, the immune system. It is thought that the best carriers embody (or, together with the antigen, create) a T-cell epitope. The peptides may be associated, for example by cross-linking, with a separate carrier, such as serum albumins, myoglobins, bacterial toxoids and keyhole limpet haemocyanin. More recently developed carriers which induce T-cell help in the immune response include the hepatitis-B core antigen (also called the nucleocapsid protein), presumed T-cell epitopes such as Thr-Ala-Ser-Gly-Val-Ala-Glu-Thr-Thr-Asn-Cys (SEQ ID NO: 52), beta-galactosidase and the 163-171 peptide of interleukin-1. The latter compound may variously be regarded as a carrier or as an adjuvant or as both. Alternatively, several copies of the same or different proteins of the invention may be cross-linked to one another; in this situation there is no separate carrier as such, but a carrier function may be provided by such cross-linking. Suitable cross-linking agents include those listed as such in the Sigma and Pierce catalogues, for example glutaraldehyde, carbodiimide and succinimidyl 4-(N-maleimidomethyl)cyclohexane-1-carboxylate, the latter agent exploiting the —SH group on the C-terminal cysteine residue (if present).

If the protein is prepared by expression of a suitable nucleotide sequence in a suitable host, then it may be advantageous to express it as a fusion product with a peptide sequence which acts as a carrier. Kabigen's "Ecosec" system is an example of such an arrangement.

It is appreciated that the coronavirus component of the vaccine may be linked to other antigens to provide a dual effect.

Preferably, the coronavirus protein in the vaccine composition is an S protein. More preferably, the S protein is a CRCV or CRCV-like S protein as defined above in the first aspect of the invention or obtainable by the methods of the fourth aspect of the invention, a BCV S protein, an HCV S protein, an HEV S protein, or an immunogenic fragment thereof.

Most preferably, the vaccine composition contains a CRCV S protein that comprises or consists of the amino acid sequence listed in FIG. 4, or an immunogenic fragment thereof having at least 97% identity with the sequence listed in FIG. 4. Preferably, the variant has at least at least 98%, or at least 99% amino acid sequence identity with the sequence listed in FIG. 4. More preferably the variant has at least 99.1%, or at least 99.2%, or at least 99.3%, or at least 99.4%, or at least 99.5%, or at least 99.6%, or at least 99.7%, or at least 99.8%, or at least 99.9% amino acid sequence identity with the sequence listed in FIG. 4.

Additionally or alternatively, the vaccine composition may comprise coronavirus proteins such as a hemagglutinin-esterase protein (HE) or an integral membrane protein (M), or the small membrane protein (E) (Lai MMC & Cavanagh D, (1997) "The molecular biology of coronaviruses" *Adv. Vir. Res*, 48: 1-100).

In one embodiment, the HE, E or M proteins are BCV, HCV or HEV proteins. In another embodiment, the HE, E or M proteins are CRCV proteins.

Preferably, the HE protein is a CRCV or CRCV-like HE protein as defined above in the third aspect of the invention or obtainable by the methods of the fourth aspect of the invention, or an immunogenic fragment thereof.

More preferably, the vaccine composition contains a CRCV HE protein that comprises or consists of the partial amino acid sequence listed in FIG. 14, or an immunogenic fragment thereof having at least 97% identity with the sequence listed in FIG. 14. Preferably, the variant has at least at least 98%, or at least 99% amino acid sequence identity with the sequence listed in FIG. 14. More preferably the variant has at least 99.1%, or at least 99.2%, or at least 99.3%, or at least 99.4%, or at least 99.5%, or at least 99.6%, or at least 99.7%, or at least 99.8%, or at least 99.9% amino acid sequence identity with the sequence listed in FIG. 14.

When the vaccine comprises a coronavirus, preferably the coronavirus comprises an S protein with at least 80%, or at least 85%, or at least 90%, or at least 95% amino acid identity with the BCV S protein. More preferably, the coronavirus comprises an S protein with at least 80%, or at least 85%, or at least 90%, or at least 95% amino acid identity with the CRCV S protein.

Additionally or alternatively, when the vaccine comprises a coronavirus, preferably the coronavirus comprises an HE protein with at least 90% or at least 95% amino acid identity with the BCV HE protein. More preferably, the coronavirus comprises an HE protein with at least 96%, or at least 97%, or at least 98%, or at least 99% amino acid identity with the CRCV HE protein.

In another preferred embodiment, the vaccine composition comprises a virus selected from BCV, HCV, HEV and CRCV, or a modification thereof.

It is appreciated that dog vaccines effective against a canine virus may be derived from a non-canine virus. For example U.S. Pat. No. 5,750,112 to Gill, and assigned to Solvay Animal Health Inc, discloses a vaccine against enteric canine coronavirus containing inactivated feline enteric coronavirus. The disclosure of U.S. Pat. No. 5,750,112 is incorporated herein by reference.

In one preferred embodiment, the virus is an inactivated virus. Methods for inactivating viruses for use in vaccines are well known in the art. Suitable methods include chemical methods, such as the use of beta proprio-lactone (BPL). Suitable inactivated bovine coronavirus vaccines may include inactivated BCV which is a component of bovine vaccines such as "Rotovec Corona" from Schering-Plough (http://www.ukvet.co.uk/rotovec/scour.htm); "Lactovac" by Hoechst Roussel Vet Ltd, (Veterinary Formulary 5th Edition of the Veterinary Data Sheet Compendium); "First Defense" by Immuncell Corp, USA; "Scour Bos 4" by Grand Laboraotries and "Scour Guard 3K" by Pfizer.

In an alternative embodiment, the virus is an attenuated virus. Methods for attenuating viruses for use in vaccines are well known in the art.

Preferably, the vaccine composition also comprises a pharmaceutically acceptable adjuvant.

Preferably, when the vaccine comprises a nucleic acid, the nucleic acid encoding the coronaviral protein or immunogenic fraction thereof, for use as a vaccine is a CRCV or CRCV-like S polynucleotide, or a CRCV or CRCV-like HE polynucleotide or both a CRCV or CRCV-like S and HE polynucleotide. More preferably, the nucleic acid comprises or consists of the nucleotide sequence listed in FIG. 3 or FIG. 13, or fractions thereof.

For vaccine use, the CRCV or CRCV-like S or HE nucleic acid can be delivered in various replicating (e.g. recombinant adenovirus vaccine) or non-replicating (DNA vaccine) vectors.

In a preferred embodiment, the vaccine may contain recombinant CRCV or CRCV-like S protein, as well as other immunogenic coronavirus proteins such as the HE protein.

As discussed above, several viral and bacterial agents are known to be associated with respiratory disease in dogs, including canine parainfluenza virus (CPIV), canine adenovirus type 2 (CAV-2), canine herpesvirus (CHV), and *Bordetella bronchiseptica* (*B. bronchiseptica*).

In another preferred embodiment, the vaccine may contain recombinant CRCV or CRCV-like S or HE protein, as well as other pathogenic organisms involved in respiratory disease of dogs such as canine parainfluenzavirus, canine adenovirus type 2, the bacterium *Bordetella bronchiseptica*, canine herpesvirus, human reovirus and mycoplasma species, or immunogenic proteins therefrom. Thus the vaccine may contain an agent capable of raising an immune response, such as the production of antibodies against CRCV, as well as against other pathogenic organisms involved in respiratory disease of dogs such as CPIV, CAV-2, *B. bronchiseptica* and CHV.

In an embodiment, as well as containing an agent capable of stimulating the production of antibodies against CRCV, such as a CRCV or CRCV-like S or HE protein, the vaccine composition further comprises any one or more of:

(a) an agent capable of raising an immune response in a dog against CPIV;
(b) an agent capable of raising an immune response in a dog against CAV-2;
(c) an agent capable of raising an immune response in a dog against CHV; and
(d) an agent capable of raising an immune response in a dog against *B. bronchiseptica*.

Thus the vaccine composition can optionally also comprise any two, or any three or all four of these additional agents (a), (b), (c) and (d).

Typically, an agent capable of raising an immune response in a dog against CPIV comprises inactivated or attenuated CPIV, or an immunogenic fragment thereof, or a nucleic acid encoding said immunogenic fraction.

Typically, an agent capable of raising an immune response in a dog against CAV-2 comprises inactivated or attenuated CAV-2, or an immunogenic fragment thereof, or a nucleic acid encoding said immunogenic fraction.

Canine adenovirus type 1 causes infectious hepatitis; canine adenovirus type 2 causes respiratory disease. It has been shown that CAV-1 provides cross-protection against CAV-2 and vice versa. The agent that raises an immune response in a dog against CAV-2 may therefore contain either CAV-1 or CAV-2, or an immunogenic fragment thereof. The vaccines listed below contain CAV-2 except for EURICAN DHPPi, which does not specify the virus type used.

Suitable agents that raise an immune response in a dog against CPIV and CAV-2 are known to a person of skill in the art. For example, the following dog vaccines are licensed in the UK.

KAVAK DA$_2$PiP69 by Fort Dodge Animal Health is a live freeze dried vaccine containing attenuated strains of canine distemper virus, canine adenovirus type 2, canine parainfluenza type 2 and canine parvovirus grown in tissue culture.

KAVAK Parainfluenza by Fort Dodge Animal Health contains live freeze-dried vaccine derived from an attenuated strain of canine parainfluenza virus type 2 cultivated on an established homologous cell-line.

NOBIVAC DHPPi by Intervet UK Limited is a live attenuated freeze-dried, virus vaccine containing canine distemper virus, canine adenovirus type 2, canine parvovirus and canine parainfluenza virus grown in cell line tissue culture.

NOBIVAC KC by Intervet UK Limited is a modified live freeze-dried vaccine containing *Bordetella bronchiseptica* strain B-C2 and canine parainfluenza virus strain Cornell (this is an intranasal vaccine). Management authorisation number Vm 06376/4026.

EURICAN DHPPi by Merial Animal Health Ltd. is a combined live freeze-dried vaccine against canine distemper, infectious canine hepatitis, canine parvovirus and canine parainfluenza virus type 2.

VANGUARD 7 by Pfizer Ltd. contains live attenuated canine distemper virus (Snyder Hill strain), adenovirus (CAV-2 Manhattan strain), parainfluenza virus (NL-CPI-5 strain), canine parvovirus (NL-35-D) propagated in an established cell line, and an inactivated culture of *Leptospira canicola* and *Leptospira icterohaemorrhagiae*.

QUANTUM DOG 7 by Schering-Plough Animal Health contains canine distemper, adenovirus type 2, parvovirus, parainfluenza virus type 2 vaccine (living) and inactivated *Leptospira canicola* and *Leptospira icterohaemorrhagiae* vaccine.

CANIGEN DHPPi by Virbac Ltd. is a live attenuated, freeze-dried, virus vaccine containing canine distemper virus, canine adenovirus (CAV2), canine parvovirus and canine parainfluenza virus grown in cell line tissue culture.

CANIGEN Ppi by Virbac Ltd. is a live attenuated, freeze-dried virus vaccine containing canine parvovirus and canine parainfluenza virus grown in cell line tissue culture.

Typically, an agent capable of raising an immune response in a dog against CHV comprises inactivated or attenuated CHV, or an immunogenic fragment thereof, or a nucleic acid encoding said immunogenic fraction.

Suitable agents that raise an immune response in a dog against CHV are known to a person of skill in the art. For example, EURICAN Herpes 205 by Merial is a purified subunit vaccine against canine herpesvirus which is indicated for the active immunisation of pregnant bitches to prevent mortality, clinical signs and lesions in puppies resulting from canine herpesvirus infections acquired in the first days of life. It is not licensed for the vaccination of adult dogs for the prevention of respiratory disease.

Typically, an agent capable of raising an immune response in a dog against *B. bronchiseptica* comprises inactivated or attenuated *B. bronchiseptica*, or an immunogenic fragment thereof, or a nucleic acid encoding said immunogenic fraction.

Suitable agents that raise an immune response in a dog against *B. bronchiseptica* are known to a person of skill in the art. For example, the following dog vaccines are licensed for use.

COUGHGUARD-B® by Pfizer Animal Health (U.S. Vet. Lic. No.: 189) contains an inactivated culture of *B. bronchiseptica*. It is for the immunisation of healthy dogs against disease caused by *B. bronchiseptica*, in particular kennel cough. COUGHGUARD-B® is prepared from a highly antigenic strain of *B. bronchiseptica* which has been inactivated and processed to be nontoxic when administered to dogs. The production method is reported to leave the immunogenic properties of *B. bronchiseptica* intact.

VANGUARD® 5/B by Pfizer Animal Health (U.S. Vet. Lic. No.: 189) contains attenuated strains of canine distemper virus (CDV), CAV-2, CPIV, and canine parvovirus (CPV) propagated on an established canine cell line. The CPV antigen was attenuated by low passage on the canine cell line and at that passage level has immunogenic properties capable of overriding maternal antibodies. The vaccine is packaged in lyophilised form with inert gas in place of vacuum. The bacterin component containing inactivated whole cultures of *B. bronchiseptica* which is supplied as diluent. The *B. bronchiseptica* component in VANGUARD® 5/B is prepared from a highly antigenic strain which has been inactivated and processed to be nontoxic when administered to dogs.

NASAGUARD-B™ by Pfizer Animal Health (U.S. Vet. Lic. No.: 112) is composed of an avirulent live culture of *B. bronchiseptica* bacteria.

PROGARD®-KC by Intervet is a modified live intranasal vaccine containing attenuated canine parainfluenza virus and *Bordetella bronchiseptica* avirulent live culture. PROGARD®-KC is presented in a desiccated form with sterile diluent provided for reconstitution. PROGARD®-KC is for vaccination of healthy, susceptible puppies and dogs for prevention of canine infectious tracheobronchitis ("kennel cough") due to canine parainfluenza virus and *B. bronchiseptica*.

PROGARD®-KC PLUS by Intervet contains live culture of avirulent strains of *B. bronchiseptica*, attenuated canine adenovirus type 2 and parainfluenza virus for intranasal administration. Vaccination with PROGARD®-KC Plus stimulates rapid, local immunity in the respiratory tract, thereby inhibiting infection at the port of entry as well as preventing clinical signs. In addition to local immunity, it also stimulates systemic immunity within three weeks of intranasal administration. The small volume (0.4 ml) and one nostril application of PROGARD®-KC Plus provide for ease in vaccination, particularly in small breeds and young puppies. PROGARD®-KC Plus is presented in a desiccated form with sterile diluent provided for reconstitution. PROGARD®-KC Plus is for vaccination of healthy dogs and puppies three weeks of age or older for prevention of canine infectious tracheobronchitis ("kennel cough") due to canine adenovirus type 2, parainfluenza virus and *B. bronchiseptica*.

Intrac by Intervet is a freeze dried modified live vaccine, containing *B. bronchiseptica* strain S 55, for intranasal administration. Product license number PL 0201/4011

Nobivac KC, described above, also contains *B. bronchiseptica*.

Vaccination would be useful especially but not exclusively for dogs prior to entry into a boarding kennel or for the vaccination of dogs in breeding facilities.

A typical dose of a vaccine comprised of recombinant protein is about 5-µg. A typical dose of a vaccine comprised of inactivated virus is about 1-10 mg.

In a ninth aspect, the invention provides the use of (i) a coronavirus having an S protein with at least 75% amino acid identity with CRCV S protein, or (ii) a coronavirus having an S protein with at least 75% amino acid identity with BCV S protein, or (iii) a coronavirus having an HE protein with at least 90% amino acid identity with CRCV HE protein, or (iv) a coronavirus having an HE protein with at least 90% amino acid identity with BCV HE protein, or (v) a coronavirus protein having at least 75% amino acid identity with a CRCV protein or an immunogenic fragment thereof, or (vi) a coronaviral protein having at least 75% amino acid identity with a BCV protein, or an immunogenic fragment thereof, or (vii) a nucleic acid encoding said coronaviral protein or immunogenic fraction thereof, in the preparation of a medicament for stimulating an immune response against CRCV in a dog.

The invention includes the use of (i) a coronavirus having an S protein with at least 75% amino acid identity with CRCV S protein, or (ii) a coronavirus having an S protein with at least 75% amino acid identity with BCV S protein, or (iii) a coronavirus having an HE protein with at least 90% amino acid identity with CRCV HE protein, or (iv) a coronavirus having an HE protein with at least 90% amino acid identity with BCV HE protein, or (v) a coronavirus protein having at least 75% amino acid identity with a CRCV protein or an immunogenic fragment thereof, or (vi) a coronaviral protein having at least 75% amino acid identity with a BCV protein, or an immunogenic fragment thereof, or (vii) a nucleic acid encoding said coronaviral protein or immunogenic fraction thereof, in the preparation of a medicament for prophylaxis of respiratory disease in a dog, typically CIRD.

When a coronavirus protein, or an immunogenic fragment thereof, is used in the preparation of the medicament, the protein preferably has at least 80%, or at least 85%, or at least 90%, or at least 95% amino acid identity with the corresponding portion of a BCV protein. Preferably the protein has at least 80%, or at least 85%, or at least 90%, or at least 95% amino acid identity with the corresponding portion of a CRCV protein.

Preferably, the coronaviral protein used in the preparation of the medicament is a BCV, HCV, HEV or CRCV protein, or a modification thereof, as described above with reference to the eighth aspect of the invention.

More preferably, the coronaviral protein used in the preparation of the medicament is an S protein. Yet more preferably, the S protein comprises an CRCV or CRCV-like S protein as defined above in the first aspect of the invention or obtainable by the methods of the fourth aspect of the invention, a BCV S protein, an HCV S protein, or an immunogenic fragment thereof.

Most preferably, the coronaviral protein used in the preparation of the medicament comprises or consists of the amino acid sequence listed in FIG. 4, or an immunogenic fragment thereof having at least 97% identity with the sequence listed in FIG. 4. Preferably, the variant has at least 98%, or at least 99% amino acid sequence identity with the sequence listed in FIG. 4. More preferably the variant has at least 99.1%, or at least 99.2%, or at least 99.3%, or at least 99.4%, or at least 99.5%, or at least 99.6%, or at least 99.7%, or at least 99.8%, or at least 99.9% amino acid sequence identity with the sequence listed in FIG. 4.

Additionally or alternatively, the coronaviral protein used in the preparation of the medicament may comprise HE, E, M or N coronavirus proteins. In one embodiment, the HE, E, M or N proteins are BCV, HCV or HEV proteins. In another embodiment, the HE, E, M or N proteins are CRCV proteins.

Typically, the HE protein comprises an CRCV or CRCV-like HE protein as defined above in the third aspect of the invention or obtainable by the methods of the fourth aspect of the invention, a BCV HE protein, an HCV HE protein, or an immunogenic fragment thereof.

Preferably, the coronaviral HE protein used in the preparation of the medicament comprises or consists of the partial amino acid sequence listed in FIG. 14, or an immunogenic fragment thereof having at least 97% identity with the sequence listed in FIG. 14. Preferably, the variant has at least 98%, or at least 99% amino acid sequence identity with the sequence listed in FIG. 14. More preferably the variant has at least 99.1%, or at least 99.2%, or at least 99.3%, or at least 99.4%, or at least 99.5%, or at least 99.6%, or at least 99.7%, or at least 99.8%, or at least 99.9% amino acid sequence identity with the partial sequence listed in FIG. 14.

When a coronavirus is used in the preparation of the medicament, the coronavirus preferably comprises an S protein with at least 80%, or at least 85%, or at least 90%, or at least 95% amino acid identity with the BCV S protein. More preferably the coronavirus comprises an S protein with at least 80%, or at least 85%, or at least 90%, or at least 95% amino acid identity with the CRCV S protein.

Additionally or alternatively, the coronavirus may comprise an HE protein with at least 90%, or at least 95% amino acid identity with the BCV HE protein. More preferably the coronavirus comprises an HE protein with at least 96%, or at least 97%, or at least 98%, or at least 99% amino acid identity with the CRCV HE protein.

In a tenth aspect, the invention provides a CRCV or CRCV-like S protein as defined above in the first aspect of the invention or obtainable by the methods of the fourth aspect of the invention, for use in medicine. Typically, the S protein will be used in veterinary medicine.

The invention includes a CRCV or CRCV-like HE protein as defined above in the third aspect of the invention or obtainable by the methods of the fourth aspect of the invention, for use in medicine. Typically, the HE protein will be used in veterinary medicine.

In an eleventh aspect, the invention provides a method of vaccinating a dog against CRCV, the method comprising administering to the dog a vaccine composition as described above in the ninth aspect of the invention.

Typically, the vaccine will be administered via the intramuscular, subcutaneous or intranasal routes In another embodiment, a dog can passively acquire immunity against CRCV by being administered an antibody that reacts with CRCV. The antibody that reacts with CRCV may be an anti-BCV, anti-HCV antibody, but is preferably an anti-CRCV antibody. Preferably, the antibody that reacts with CRCV is an anti-S protein antibody an anti-HE protein antibody. Most preferably, the antibody that reacts with CRCV is an anti-CRCV S or HE protein antibody as described in the fifth aspect of the invention.

In a twelfth aspect, the invention provides a method for combating the spread of CRCV between dogs comprising determining whether a dog is infected with CRCV according to the methods as described above in the sixth aspect of the invention, or using the immunosorbent assay or solid substrate as described above in the seventh aspect of the invention, and, if the dog is infected with CRCV, quarantining the dog.

By "quarantining" a dog we include the meaning of keeping the dog separate from all other dogs. We also include the meaning of keeping the dog separate from dogs that have not been vaccinated against CRCV, which can be performed as described above. We also include the meaning of keeping the dog separate from dogs that have not been infected by CRCV, which can be determined as described above.

In a thirteenth aspect, the invention provides a method for combating the spread of CRCV between dogs comprising determining whether a dog is infected with CRCV according to the methods described above in the sixth aspect of the invention, or using the immunosorbent assay or solid substrate as described above in the seventh aspect of the invention, and, if the dog is infected with CRCV, vaccinating other dogs that have been, are, or are likely to be in contact with the dog.

A fourteenth aspect of the invention provides a method for identifying a test vaccine capable of preventing or reducing the incidence of canine infectious respiratory disease (CIRD) in dogs. The method comprises (a) determining whether a dog has been exposed to CRCV, typically according to the methods described above in the sixth aspect of the invention or using the immunosorbent assay or solid substrate as described above in the seventh aspect of the invention, (b) if the dog has not been exposed to CRCV, administering the test vaccine to the dog, (c) inoculating the dog with CRCV, and (d) determining whether the dog develops CIRD. The absence of CIRD in step (d) indicates that the test vaccine is capable of preventing CIRD.

Typically, this method is performed on a set of dogs.

Preferably, the method involves the use of a set of control dog which are not administered the test vaccine in step (b). The significantly lower incidence of CIRD in the set of dogs that has been administered the test vaccine than in the control set indicates that the test vaccine is capable of preventing or reducing the incidence of CIRD.

The invention also includes a vaccine identified by this method.

All of the documents referred to herein are incorporated herein, in their entirety, by reference.

The invention will now be described in more detail with the aid of the following Examples.

EXAMPLE 1

Detection of a Novel Coronavirus Associated with Canine Infectious Respiratory Disease Summary An investigation into the causes of canine infectious respiratory disease (CIRD) was carried out in a large re-homing kennel. Tissue samples taken from the respiratory tract of diseased dogs were tested for the presence of coronaviruses using RT-PCR with conserved primers for the polymerase gene. Sequence analysis of four positive samples showed the presence of a novel coronavirus with high similarity to both bovine and human coronavirus (strain OC43) in their polymerase and spike genes whereas there was a low similarity to comparable genes in the enteric canine coronavirus. This canine respiratory coronavirus (CRCV) was detected by RT-PCR in 32/119 tracheal and 20/119 lung samples with the highest prevalence being detected in dogs with mild clinical symptoms. Serological analysis showed that the presence of antibodies against CRCV on the day of entry into the kennel decreased the risk of developing respiratory disease.

Materials and Methods

Study Population

Dogs from a well-established re-homing kennel with a history of endemic respiratory disease were monitored for this study. On entry into the kennel, all dogs were vaccinated with KAVAK $DA_2$ PiP69 (Fort Dodge) a live attenuated vaccine for distemper virus, canine adenovirus type 2, canine parainfluenzavirus and canine parvovirus. Also, a killed leptospirosis vaccine was used (Fort Dodge). The health status of each dog was assessed twice a day by a veterinary clinician and the respiratory symptoms were graded as follows: 1: no respiratory signs, 2: mild cough, 3: cough and nasal discharge, 4: cough, nasal discharge and inappetence, 5: bronchopneumonia. The overall health status of the dogs was graded as follows: 1: good health, 2: poor health, 3: very poor health. The age, breed and sex of the dogs were recorded.

For 119 dogs a full post mortem examination was performed. The tissue samples were stored at −70° C. until further use.

Serum samples were collected from 111 dogs on day of entry into the re-homing kennel. For 81 dogs a follow-up serum was available on day 7 and for 111 dogs a serum was available on day 21 after entry.

Of the 111 dogs, 30 remained healthy during the 21 days between the first and the last serum sample whereas 81 dogs developed respiratory disease.

Sera from 35 dogs housed elsewhere were obtained from the diagnostic service of the Royal Veterinary College. These sera had been submitted for biochemical analysis for various reasons. Five of these sera were from 18-month-old beagles with no history of respiratory disease. Sera were routinely stored at −20° C.

RNA Extraction and RT-PCR

RNA was extracted from tracheal and lung tissue of 119 dogs using TriReagent (Sigma). Approximately 25-50 mg of homogenised tissue was used and RNA was extracted as recommended by the manufacturer.

Synthesis of cDNA was performed using Random Hexamers (Roche) and ImPromII reverse transcriptase (Promega).

The polymerase gene of coronaviruses is known to be highly conserved, and has previously been used for phylogenetic analysis of this virus family (Stephensen et al., 1999). For the detection of coronaviruses a modification of the primers 2 Bp and 4Bm directed against the polymerase gene as described by Stephensen et al. (1999) were used

```
(Conscoro5:
5'-ACT-CAR-ATG-AAT-TTG-AAA-TAT-GC;   (SEQ ID NO: 31)
and

Conscoro6:
5'-TCA-CAC-TTA-GGA-TAR-TCC-CA.       (SEQ ID NO: 32))
```

PCR was performed using Taq polymerase (Promega) in the provided reaction buffer containing a final concentration of 2.5 mM $MgCl_2$ and 0.5 µM of primers. For PCR with the primers Conscoro5 and Conscoro6 the following temperature profile was used: After denaturation at 95° C. for 5 min, 10 cycles were carried out at 95° C. for 1 min, annealing at 37° C. for 1 min and extension at 72° C. for 1 min. This was followed by 10 cycles using an annealing temperature of 45° C., 10 cycles at an annealing temperature of 50° C. and 10 cycles at an annealing temperature of 53° C. followed by a final extension at 72° C. for 10 min.

A 20 µl fraction of the PCR product was analysed on a 1.5% agarose gel and blotted onto a nylon membrane (Roche) after electrophoresis. The nylon membrane was hybridised with an oligonucleotide probe specific for the PCR product at 37° C. overnight (Probe Conscoro: AAG-TTT-TAT-GGY-GGY-TGG-GA (SEQ ID NO: 33)). The probe was 3'A-tailed with Digoxigenin-dUTP and was detected using anti-Digoxigenin conjugate and CSPD chemoluminescent substrate (Roche).

Primer sequences specific for the spike gene were derived from an alignment of the spike region of bovine coronavirus strain LY-138 (AF058942) and human coronavirus strain OC43 (L14643).

A PCR was performed with the primers Spike 1 and Spike 2, followed by a nested PCR using the primers Spike 3 and Spike 4 and 2 µl of the product of the first amplification. The numbers in brackets refer to the nucleotide position in the bovine coronavirus genome.

```
Spike 1:
5'-CTT-ATA-AGT-GCC-CCC-AAA-CTA-AAT     (25291-25314)

Spike 2:
5'-CCT-ACT-GTG-AGA-TCA-CAT-GTT-TG      (25912-25890)

Spike 3:
5'-GTT-GGC-ATA-GGT-GAG-CAC-CTG         (25320-25339)

Spike 4:
5'-GCA-ATG-CTG-GTT-CGG-AAG-AG          (25762-25742)
```

Oligonucleotide Spike 1 has SEQ ID NO: 34, Spike 2 has SEQ ID NO: 35, Spike 3 has SEQ ID NO: 36, Spike 4 has SEQ ID NO: 37.

The temperature profile used was denaturation at 95° C. for 5 min, followed by 35 cycles of denaturation at 95° C. for 1 min, annealing at 55° C. for 40 sec and elongation at 72° C. for 1 min. The final extension was performed at 72° C. for 10 min. The nested PCR produced a 442 bp fragment.

PCR products were cloned into the pGEM-T-easy vector (Promega) and sequenced using the Thermo sequenase fluorescent labelled primer cycle sequencing kit with 7-deaza-dGTP (Amersham Pharmacia) using Cy5 labelled primers.

Phylogenetic Analysis

An alignment of the 250 bp cDNA sequence from the polymerase gene to the corresponding sequences of 11 coronaviruses was performed using ClustalX (Thompson et al., 1997).

The phylogenetic relationship to known coronaviruses was analysed using the Phylip 3.6 package (Felsenstein, 1989). The alignments were followed by a bootstrap analysis using the Seqboot programme. The obtained data sets were used for a maximum parsimony analysis using the DNApars programme and a consensus tree was calculated using Consense. The resulting trees were drawn using the Treeview programme (Page, 1996).

ELISA

ELISA antigen for bovine coronavirus or enteric canine coronavirus (CECV) (the antigens are a preparation from virus infected cell cultures obtained from Churchill Applied Biosciences, Huntingdon, UK) was resuspended in PBS at the concentration recommended by the manufacturer and incubated on 96 well plates (Falcon) overnight at 37° C.

The plates were washed with PBS and blocked with PBS containing 5% skimmed milk powder for 30 min. The sera were diluted 1:100 in blocking buffer and incubated on the plates for 1 h. After washing with PBS/0.05% Tween 20 (Sigma), a peroxidase labelled rabbit anti-dog IgG conjugate (Sigma) was added (1:5000 in PBS/0.05% Tween 20) for 1 h. The plates were incubated with colour substrate (OPD, Sigma) for 10 min and the reaction was stopped by adding 2M $H_2SO_4$. The adsorption was determined in an ELISA photometer at 492 nm.

Virus Culture

Virus isolation is performed on canine adult lung fibroblasts (passage 3 to 7), MDCK and A72 cells. (It is appreciated, however, that virus isolation could be performed using primary cells or cell lines such as MDCK or A72 (canine), MDBK (bovine), HRT-18 (human rectal tumour cell line) and Vero (African Green Monkey). The lung fibroblasts are maintained in MEM with 20% fetal calf serum (FCS), MDCK and A72 cells are maintained in MEM with 5% FCS. Tracheal tissue samples (approx. 25 mg) are homogenised using a scalpel and mixed vigorously in 1 ml MEM containing Penicillin (100 U/ml), Streptomycin (0.1 mg/ml), Amphotericin B (2.5 µg/ml) and Trypsin (1 µg/ml). The samples are centrifuged at 13000 rpm for 10 min. and the supernatant is used to inoculate cell cultures. After 30 min. at 37° C. the supernatant is removed and maintenance medium added to the cultures. The cultures are passaged three times in the absence of a cytopathic effect. Then, RNA is extracted from the cells and RT-PCR to detect the presence of CRCV is performed.

Statistical Analysis

The data were analysed using the chi-square test or Fisher's exact test and p values below 0.05 were considered statistically significant.

Results

PCR Using Consensus Primers for the Coronavirus RNA Polymerase Gene

Using the primers Conscoro5 and Conscoro6, cDNA obtained from 40 tracheal samples was analysed by RT-PCR. Out of these, seven were found to be positive by PCR and subsequent hybridisation (17.5%).

The PCR products were cloned and sequenced (FIGS. 1 and 2) and the sequence data were compared to available viral sequences using the FASTA search program (Pearson, 1990).

Comparison of the coronavirus cDNA polymerase sequence obtained from four of the canine tracheal samples to other coronavirus sequences revealed that they were most similar to sequence data from BCV strain Quebec and LY138 (Genbank Accession Nos. AF220295 and AF058942, respectively) and human coronavirus strain OC43 (Genbank Accession No. AF124989). The similarity in the analysed 250 bp sequence was 98.8% for BCV Quebec, and 98.4% for BCV LY138 and the HCV pol genes, whereas it was only 68.53% for CCV strain 1-71 pol gene (FIGS. 6 and 7).

An alignment of the novel sequence with the corresponding sequences of 11 coronaviruses and phylogenetic analysis using the maximum parsimony method resulted in the consensus tree shown in FIG. 5. The cDNA sequence obtained from a tracheal sample (T101) was found on a common branch with bovine coronavirus, human coronavirus-OC43 and hemagglutinating encephalomyelitis virus.

The virus was called canine respiratory coronavirus (CRCV).

PCR Using Primers for the Spike Gene

Figure 11:
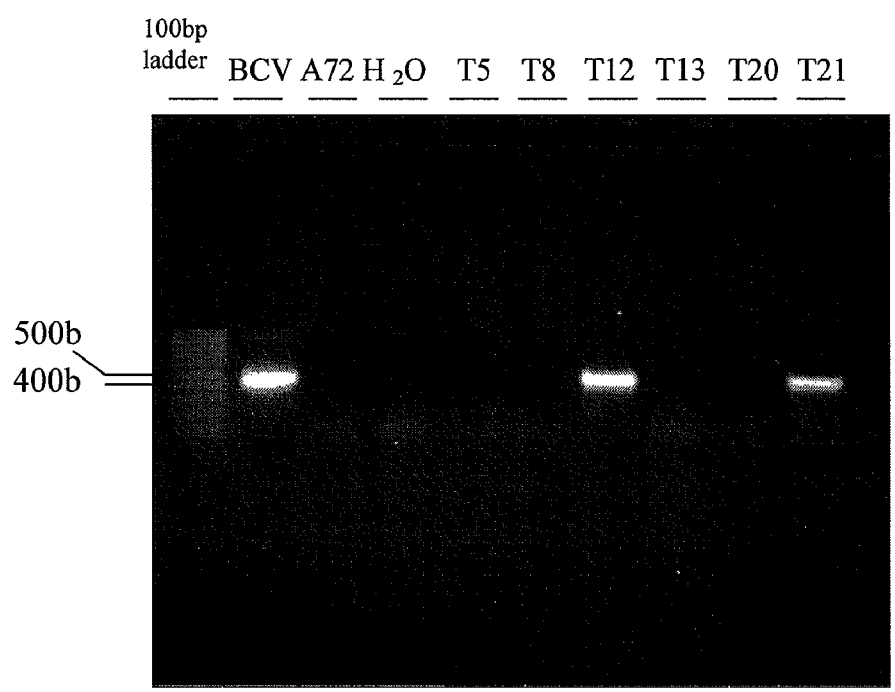
FIG. 11. RT-PCR using nested set of primers (Spike 1 and 2 (SEQ ID NOS: 34 and 35) followed by Spike 3 and 4 (SEQ ID NOS: 36 and 37)). BCV: Bovine coronavirus positive control sample; A72: Coronavirus negative A72 cells; $H_2O$: PCR mix without DNA; T5-T21: Tracheal samples of study dogs. The agarose gel electrophoresis shows PCR products of the expected size of 442 bp for the positive control (BCV) and samples T12 and T21.

For further analysis of the RNA sequence of CRCV, an alignment of the RNA for the spike gene of the bovine coronavirus LY 138 strain (AF058942) and the human coronavirus OC43 strain (L14643) was performed using Clustal X (Thompson et al., 1997). Consensus regions were chosen for the selection of the nested primer sets Spike 1-2 and Spike 3-4 (FIG. 11). PCR analysis was performed with the cDNA obtained from 119 tracheal and lung samples using these nested primers.

In total 32 tracheal samples (26.9%) and 20 lung samples (16.8%) were found positive by nested PCR. For eight dogs a positive PCR result was obtained for both, trachea and lung.

Sequence analysis of the PCR products obtained from tissues of six different dogs showed identical DNA sequences for these cDNAs (FIGS. 3 and 4). A comparison to known coronavirus spike sequences using the FASTA program revealed a 98.1% similarity to bovine coronavirus and a 97.8% similarity to human coronavirus OC43 (FIGS. 9 and 10).

PCR Using Primers for the HE Gene

Bovine coronavirus and other group II coronaviruses contain an additional structural protein, the hemagglutinin/esterase (HE). Because of the high similarity of CRCV with BCV, we analysed the presence of an HE gene in CRCV.

Figure 17:
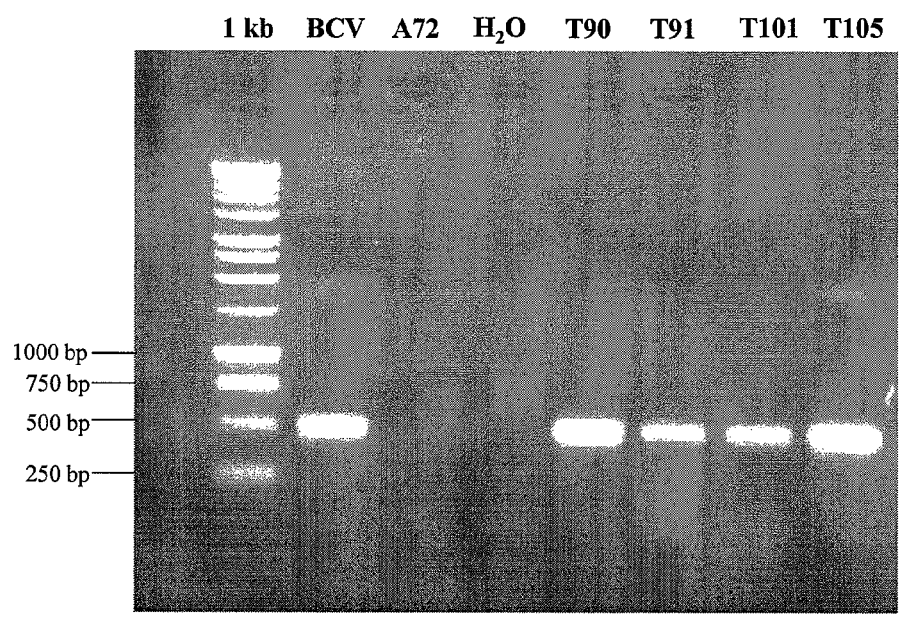
FIG. 17. RT-PCR using consensus primers HE1 (SEQ ID NO: 38) and HE2 (SEQ ID NO: 39) directed to the HE gene of BCV and HCV (strain OC43). The agarose gel electrophoresis shows a PCR product of the expected size of 497 bp for the BCV positive control and for four tracheal samples from study dogs (T90, T91, T101 and T105), and not for coronavirus-negative A72 cells or the PCR mix without DNA ($H_2O$). 1 kb indicates a molecular size standard (Promega).

An alignment of the HE genes sequences of BCV and HCv OC43 was used to design the primers HE1 and HE2 (Table 2). Four tracheal samples that had previously been identified as positive for coronavirus RNA by RT-PCR with primers for the S gene were tested by RT-PCR with the primer set for the HE gene. All four samples showed a PCR band of the expected size after agarose gel electrophoresis (FIG. 17).

TABLE 2

Primers designed from an alignment of the hemagglutinin/esterase genes of BCV (GenBank Accession No. M84486) and HCV OC43 (GenBank Accession No. M76373)

| Name | Sequence | Location in BCV HE gene |
|---|---|---|
| HE 1 | 5'-TAT-CGC-AGC-CTT-ACT-TTT-GT | 418-437 |
| HE 2 | 5'-ACC-GCC-GTC-ATG-TTA-TCA-G | 914-896 |

Primer HE1 has SEQ ID No: 38 and HE2 has SEQ ID No: 39. The sequence of the CRCV PCR product obtained using primers HE 1 and HE 2 is given in FIG. 13 (SEQ ID No: 21), and its predicted amino acid sequence is listed in FIG. 14 (SEQ ID No: 22). A comparison of these nucleotide and amino acid sequences with the corresponding fragments of other related coronaviruses is shown in FIGS. 15 and 16. Three amino acids were shown to be unique to CRCV, as shown in Table 3.

TABLE 3

Unique amino acids in CRCV HE gene

| Amino acid in CRCV | Amino acid in BCV/HECV/HCV/HEV | Position in BCV/HECV/HCV/HEV | Position in PCR product HE1-HE2 |
|---|---|---|---|
| F (Phe) | L (Leu) | 235 | 96 |
| N (Asn) | T (Thr) | 242 | 103 |
| L (Leu) | V (Val) | 253 | 114 |

The amino acid positions in BCV, HECV, HCV and HEV are numbered from the initial M (which is number 1) at the start of the BCV and HCV OC43 HE proteins (GenBank Accession Nos. M84486 and M76373, respectively).

Association of PCR Positive Samples with Respiratory Signs

Using primers for the spike gene, tracheal and lung samples from 119 dogs were analysed by RT-PCR for CRCV. Of these 42 were from dogs with no respiratory signs (grade 1), 18 dogs had shown mild respiratory signs (grade 2), 46 had shown moderate (grade 3) and 13 severe respiratory signs (grades 4 and 5). Grades 4 and 5 were merged due to the low case numbers in these groups.

Table 4 shows the PCR results for coronavirus in dogs with different grades of respiratory disease. Specifically, Table 4 shows the RT-PCR results from tracheal and lung samples of 119 dogs with different respiratory signs (none to severe) using a nested PCR directed against the coronavirus spike gene as well as the number of positive samples out of total sample number and the percentage of positive samples (in brackets).

TABLE 4

RT-PCR results for tracheal and lung samples

| Respiratory signs | Trachea: Positive samples | Lung Positive samples | Trachea and lung Positive samples |
|---|---|---|---|
| None | 11/42 (26.2%) | 8/42 (19.1%) | 2/42 |
| Mild | 10/18 (55.6%) | 4/18 (22.2%) | 4/18 |
| Moderate | 9/46 (19.6%) | 8/46 (17.4%) | 2/46 |
| Severe | 2/13 (15.4%) | 0/13 | 0/13 |

Establishment of a Serological Assay for CRCV

Because of the homology of the spike cDNA of CRCV to the spike region of bovine coronavirus, an ELISA antigen for BCV was used for serological analysis of CRCV.

Sera from five dogs with no history of infectious respiratory disease that had not been housed in the investigated kennel were tested. The OD values ranged from −0.013 to 0.39 with an average OD value of 0.154. Furthermore, sera from 30 dogs admitted to a veterinary clinic for various reasons were tested for antibodies to coronavirus. Of these, 20 samples showed an OD of <0.4 (−0.46 to 0.396) and 10 samples showed an OD of >1.0 (1.012 to 1.949). Samples with an OD of 0.6 or above were subsequently considered positive.

Comparison of the Immune Response to CRCV of Dogs with and without Respiratory Disease The BCV-antigen ELISA was performed using paired sera of 111 dogs from the study kennel. Of these, 81 dogs had shown symptoms of respiratory disease during a period of 21 days and 30 had remained healthy.

Of the group of dogs with respiratory disease, 17 were positive for antibodies to CRCV on the day of entry into the kennel and 64 were negative.

Of the 64 dogs with no detectable antibodies to BCV on day one, 63 tested positive on day 21. All 46 dogs out of these 63 for which a sample on day 7 was available tested negative on day 7. Therefore 63 dogs showed a seroconversion during the study-period whereas only one dog remained negative.

Of the 31 dogs that had remained healthy, 17 had antibodies to CRCV on the day of entry. All of the 13 dogs that were negative on day 1 tested negative on day 7 but showed a seroconversion by day 21.

Figure 12:
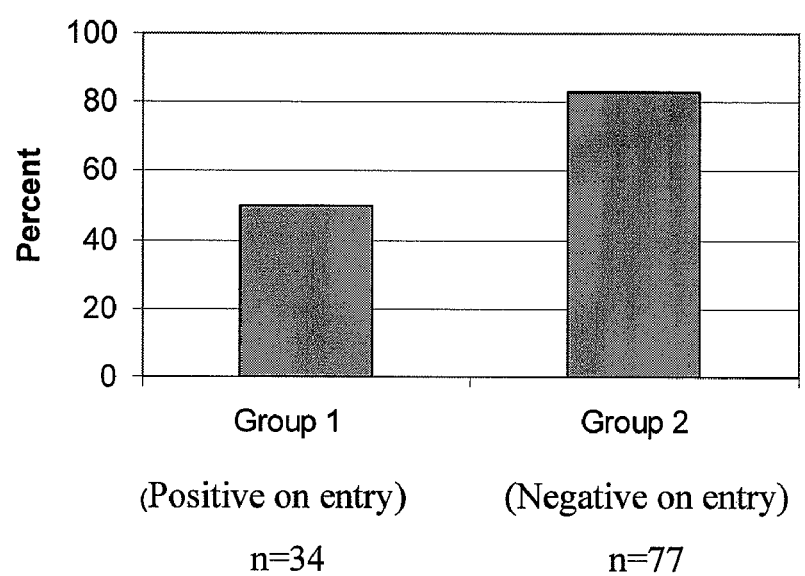
FIG. 12. Comparison of the prevalence of respiratory disease in two groups of dogs. Dogs in group 1 were positive for serum antibodies to respiratory coronavirus on day of entry into the kennel, dogs in group 2 were negative. The graph shows the percentage of dogs developing respiratory disease in group 1 compared to group2 ($p<0.001$). n is the total number of dogs in each group.

Thus, of 34 dogs that were positive for antibodies to CRCV on arrival in the kennel, 17 developed respiratory disease (50%) whereas of 77 dogs that were negative on arrival, 64 developed respiratory signs during the study-period (83.1%), (FIG. 12).

Therefore dogs that had no antibodies to CRCV on entry into the kennel had an increased probability of developing respiratory disease (p<0.001).

Only one out of the 77 dogs that were negative on arrival remained negative during the study period of 21 days whereas 76 dogs showed a seroconversion.

Serology Using Canine Enteric Coronavirus (CECV) Antigen

An ELISA assay using a canine coronavirus antigen was performed to investigate whether CRCV showed a serological cross reaction to canine enteric coronavirus. Sera from 27 dogs, previously tested for antibodies to CRCV using the BCV antigen were selected.

It was found that eight dogs had antibodies to CECV on the day of entry into the kennel, of these four also had antibodies to CRCV. Nineteen dogs were found to be negative for CECV on day 1, 17 of these were also negative for CRCV. Of the 19 negative dogs, five showed a seroconversion to CECV during the 21-day period of the investigation and 17 showed a seroconversion to CRCV.

Analysis of the prevalence of respiratory disease in this group showed that six out of the eight dogs (75%) that were positive for antibodies to CECV on day 1 developed respiratory disease. Out of the group of 19 dogs that had no detectable antibodies to CECV on day 1, 15 showed signs of respiratory disease (78.9%), (p=0.594).

Virus Isolation

Tracheal tissue samples from dogs that are identified as positive for CRCV RNA by RT-PCR are inoculated on cell cultures of canine adult lung fibroblasts and MDCK cells. For some samples, virus isolation is also performed on A72 cells. The cultures show no signs of a cytopathic effect during three passages. After several passage, RNA is extracted from the cultures and tested for the presence of CRCV RNA by RT-PCR.

Discussion

This study reports the detection of a novel coronavirus, CRCV, in kennelled dogs with respiratory disease.

Coronaviruses have been reported to cause respiratory disease of man, cattle, swine and poultry, but their presence in the respiratory tract of dogs and a possible association with canine infectious respiratory disease (CIRD) has not been determined.

Dogs were investigated from a kennel in which CIRD was endemic and could not be controlled by the use of vaccines recommended against CIRD. Samples taken from the respiratory tract of these dogs were examined using RT-PCR primers directed to the conserved polymerase gene of coronaviruses (Stephensen et al., 1999).

Initially, seven tracheal samples were found to be positive; the sequence of the RT-PCR products was determined and compared to all available coronavirus polymerase gene sequences. This analysis revealed that the cDNA sequence obtained from the canine samples had the highest similarity to the polymerase gene of bovine coronavirus (98.8%) and human coronavirus OC43 (98.4%) but only a very low similarity to the polymerase gene of the enteric canine coronavirus (strain 1-71, 68.53% similarity).

A phylogenetic analysis was performed using the polymerase sequences of eleven additional coronaviruses. The coronavirus detected in the respiratory tract of dogs (CRCV) was located on a common branch with three group 2 viruses: BCV, HCV strain OC43 and HEV. However, canine enteric coronavirus, a group 1 coronavirus, was shown to be only distantly related.

Canine respiratory coronavirus therefore is a novel coronavirus of dogs that is most closely related to BCV and HCV-OC43, both of which are known to cause respiratory disease.

To obtain more sequence information and to further determine the relationship to other coronaviruses using a more variable gene, a part of the spike gene was analysed. Since CRCV had been shown to be most similar to BCV and HCV-OC43, an alignment of the sequences of their spike genes was used to design a nested set of primers. Nested primers were chosen to achieve a more sensitive assay.

Sequencing of the products of this RT-PCR confirmed the high similarity of CRCV with BCV and HCV-OC43.

The presence of antibodies to CRCV was analysed using an ELISA based on a BCV antigen because of the high sequence similarity of the two viruses in the spike cDNA. The ELISA results confirmed the presence of a virus similar to BCV in the study population.

The prevalence of antibodies was 30% at the time of entry into the kennel and 99% after 21 days.

Interestingly and unexpectedly, serological analysis revealed that dogs with antibodies to CRCV on day of entry into the kennel developed respiratory disease less frequently than dogs without antibodies (p<0.001). Therefore the presence of antibodies to CRCV had a protective effect against respiratory disease in this population.

Almost all dogs negative on day of entry into the kennel showed a seroconversion to CRCV within three weeks, indicating that the virus is highly contagious. Serology using an antigen for canine enteric coronavirus (CECV) showed a much lower prevalence of antibodies to CECV on day 21. Therefore the BCV-ELISA results did not reflect an infection with canine enteric coronavirus and the cross-reactivity between the two antigens seems to be low.

Serum antibodies to CRCV were present in about 30% of dogs of various origins including dogs entering a re-homing kennel as well as pet dogs. The presence of CRCV is therefore not limited to the investigated kennel and the virus seems to be established in the dog population.

By PCR, CRCV was detected in tracheal tissue and lung tissue and therefore appears to infect the upper and lower respiratory tract of dogs. Within the kennelled population, CRCV-RNA was detected in 27.3% of dogs with all grades of respiratory disease as well as in 26.2% of dogs that were apparently healthy at the time of euthanasia.

CRCV-RNA was most frequently found in the trachea of dogs with mild cough (55%). Studies using the human coronavirus strain 229E have shown, that coronaviruses can cause disruption of the respiratory epithelium and ciliary dyskinesia (Chilvers et al., 2001). Without being bound by theory, we believe that an infection with CRCV has a similar effect, and that the virus plays an important role in the early stages of the pathogenesis of CIRD. By damaging the respiratory epithelium and disrupting ciliary clearance CRCV facilitates the entry of other viral or bacterial pathogens. Therefore while CRCV infection on its own may cause only mild respiratory symptoms, in conjunction with other pathogenic agents it could lead to severe respiratory disease.

The pathogenesis of CIRD has not been thoroughly investigated since the 1970s when *Bordetella bronchiseptica*, canine adenovirus type 2 and canine parainfluenza were determined to be the main causes of the disease. However the vaccination of all dogs against CPIV, CAV-2 and distemper virus did not help to control the disease in this kennel despite evidence that the majority of dogs responded to the vaccine within 21 days (data not shown).

This study shows an association of a novel canine respiratory coronavirus with CIRD. The aetiology of CIRD therefore needs to be re-evaluated and the role of novel microorganisms or microorganisms previously not associated with the disease has to be established.

REFERENCES

Appel, M., and Binn L. N. (1987) Canine infectious tracheobronchitis, Short review: kennel cough. In "Virus infections of carnivores" (M. Appel Ed.), 1st Edition, pp 201-211 Elsevier Science Publishers, Amsterdam).

Bemis, D. A., Carmichael, L. E., and Appel, M. J. (1977). Naturally occurring respiratory disease in a kennel caused by *Bordetella bronchiseptica*. Cornell Vet. 67, 282-93.

Binn, L. N., Alford, J. P., Marchwicki, R. H., Keefe, T. J., Beattie, R. J., and Wall, H. G. (1979). Studies of respiratory disease in random-source laboratory dogs: viral infections in unconditioned dogs. Lab Anim Sci. 29, 48-52

Binn, L. N., Eddy, G. A., Lazar, E. C., Helms, J., and Murnane, T. (1967). Viruses recovered from laboratory dogs with respiratory disease. Proc Soc Exp Biol Med 126, 140-5

Chilvers, M. A., McKean, M., Rutman, A., Myint, B. S., Silverman, M., and O'Callaghan, C. (2001). The effects of coronavirus on human nasal ciliated respiratory epithelium. Eur Respir J. 18, 965-70.

Ditchfield, J., Macpherson, L. W., and Zbitnew, A. (1962). Association of a canine adenovirus (Toronto A 26/61) with an outbreak of laryngotracheitis ("kennel cough"). Can. Vet. Jour. 3, 238-247

Felsenstein, J. (1989). PHYLIP-Phylogeny Inference Package (Version 3.2c). Cladistics 5, 164-166

Ignjatovic, J., and Sapats, S. (2000). Avian infectious bronchitis virus. Rev Sci Tech. 19, 493-508.

Karpas, A., King, N. W., Garcia, F. G., Calvo, F., and Cross, R. E. (1968). Canine tracheobronchitis: Isolation and characterization of the agent with experimental reproduction of the disease. Proc Soc Exp Biol Med. 127, 45-52.

Keil, D. J., and Fenwick, B. (1998). Role of *Bordetella bronchiseptica* in infectious tracheobronchitis in dogs. J Am Vet Med. Assoc. 15, 200-7.

Lou, T. Y., and Wenner, H. A. (1963). Natural and experimental infection of dogs with reovirus, type1: pathogenicity of the strain for other animals. Am. J. Hyg. 77, 293-304.

Makela, M. J., Puhakka, T., Ruuskanen, O., Leinonen, M., Saikku, P., Kimpimaki, M., Blomqvist, S., Hyypia, T., Arstila, P. (1998). Viruses and bacteria in the etiology of the common cold. J Clin Microbiol. 36, 539-42.

Page, R. D. M. Treeview: An application to display phylogenetic trees on personal computers. Computer Applications in the Biosciences 1996 12: 357-358

Pearson W R. Rapid and sensitive sequence comparison with FASTP and FASTA. Methods Enzymol. 1990; 183:63-98.

Pensaert M, Callebaut P, Vergote J. Isolation of a porcine respiratory, non-enteric coronavirus related to transmissible gastroenteritis. Vet Q. 1986 July; 8(3):257-61.

Randolph J F, Moise N S, Scarlett J M, Shin S J, Blue J T, Bookbinder P R. Prevalence of mycoplasmal and ureaplasmal recovery from tracheobronchial lavages and prevalence of mycoplasmal recovery from pharyngeal swab specimens in dogs with or without pulmonary disease. Am J Vet Res. 1993 March; 54(3):387-91.

Spaan W, Cavanagh D, Horzinek M C. Coronaviruses: structure and genome expression. J Gen Virol. 1988 December; 69 (Pt 12):2939-52.

Stephensen C B, Casebolt D B, Gangopadhyay N N. Phylogenetic analysis of a highly conserved region of the polymerase gene from 11 coronaviruses and development of a consensus polymerase chain reaction assay. Virus Res. 1999 April; 60(2): 181-9.

Storz J, Purdy C W, Lin X, Burrell M, Truax R E, Briggs R E, Frank G H, Loan R W Isolation of respiratory bovine coronavirus, other cytocidal viruses, and *Pasteurella* spp from cattle involved in two natural outbreaks of shipping fever. J Am Vet Med. Assoc. 2000 May 15; 216(10):1599-604.

Tennant B J, Gaskell R M, Jones R C, Gaskell C J. Studies on the epizootiology of canine coronavirus. Vet Rec. 1993 Jan. 2; 132(1):7-11.

Thompson J D, Gibson T J, Plewniak F, Jeanmougin F, Higgins D G The ClustalX windows interface: flexible strategies for multiple sequence alignment aided by quality analysis tools. Nucleic Acids Res. 1997 Dec. 15; 25(24):4876-82.

EXAMPLE 2

Cloning and Expression of CRCV Spike

Figure 18:
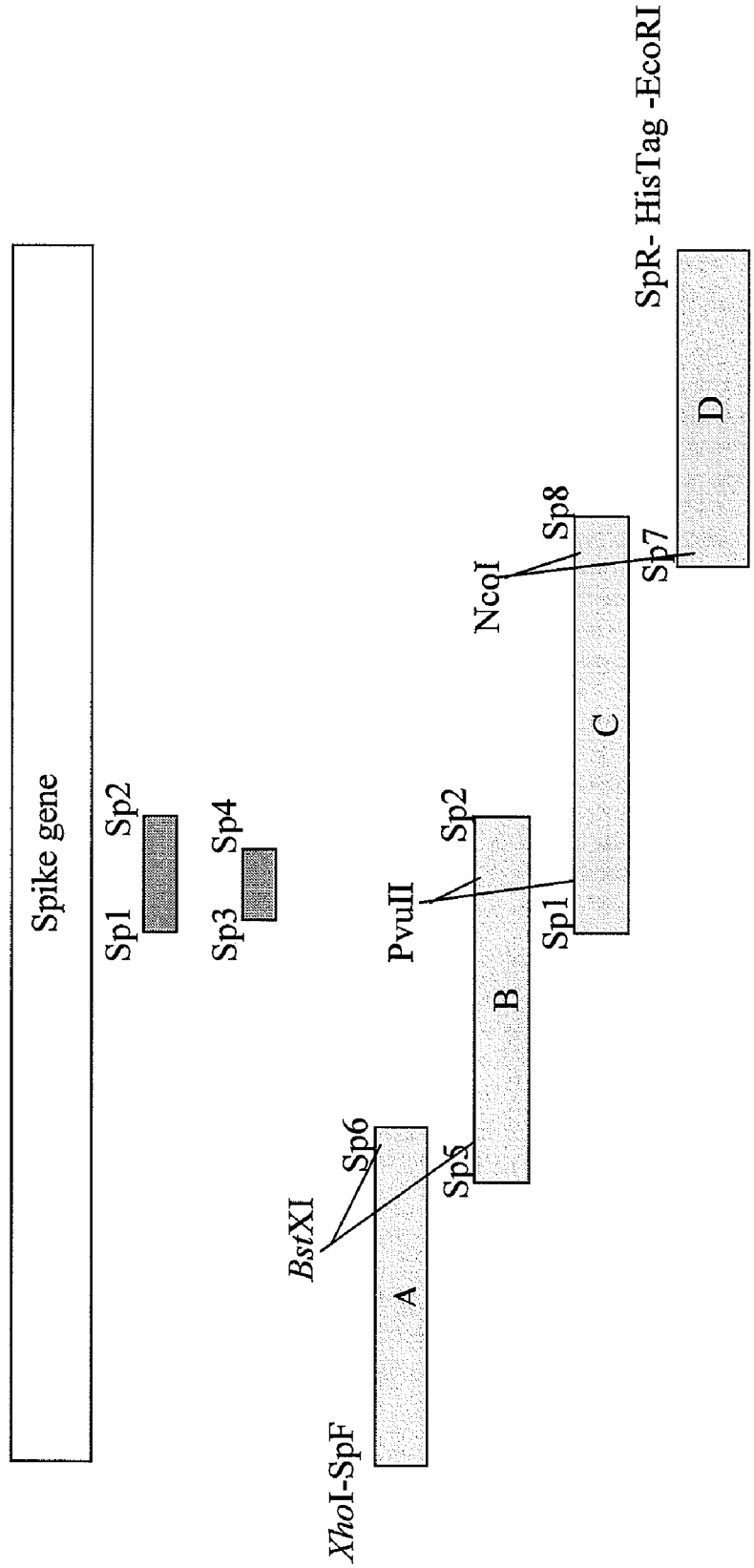
FIG. 18. CRCV Spike gene cloning strategy.

The CRCV Spike gene was cloned using the primers listed in Table 5 and using the following cloning strategy, which is illustrated in FIG. 18.

1. The spike gene was amplified in four overlapping fragments (A, B, C, D).
2. The PCR product Sp5-Sp2 (B) was joined to the product Sp1-Sp8 (C) using the PvuII site in the overlap.
3. This fragment was cloned into the pT7blue2 vector (Novagen) using the restriction sites NcoI and BstXI.
4. The PCR fragment SpFXho-Sp6 (A) was joined to BC using the restriction site BstXI in the overlap and the XhoI site that had been incorporated into the primer SpF-Xho.
5. Fragment ABC was moved into the baculovirus transfer vector pMelBacB (Invitrogen) using the restriction sites XhoI and NcoI.
6. The PCR fragment Sp7-SpR-HisTag-Eco (D) was joined to ABC using the restriction site NcoI in the overlap and the EcoRI site that had been incorporated into the primer SpR-Eco-HisTag resulting in the complete spike gene in pMelBacB (Spike MelBac). This construct contains a HisTag (6×His) at the C terminus of the expressed protein.
7. For mammalian expression the complete gene was moved to pSecTagA (Invitrogen) using the BamHI site in pMelBacB and the EcoRI site at the end of ABCD resulting in the plasmid SpikeSecTag.

Construction of a Recombinant Baculovirus

A co-transfection was performed in Sf9 cells using the Bac-N-Blue baculovirus DNA (Invitrogen) and Spike Mel-Bac. The resulting baculovirus (AcSpCRCV 1-11) was shown to contain a full-length insert by PCR using primers (Invitrogen) located upstream and downstream of the recombination site.

Expression in Mammalian Cells

The plasmid Spike SecTag was transfected into BHK-21 cells using Lipofectamine (Invitrogen). Expression of the Spike protein was analysed using a serum sample from a dog that had been shown to be positive for antibodies to CRCV using ELISA (BCV antigen obtained from Churchill) and a positive control serum for BCV obtained from Churchill (chicken anti BCV). The transfected cells showed a positive signal in an immunofluorescence assay using the canine or the chicken serum and a FITC labelled conjugate (FITC anti-dog IgG or FITC anti Chicken IgG).

TABLE 5

Primers designed from an alignment of the spike genes of bovine coronavirus (GenBank accession No. AF058942) and human coronavirus, OC43 (GenBank accession No. L14643)

| Name | Sequence | SEQ ID NO: | Location in BCV spike gene |
|---|---|---|---|
| Sp 1 | 5'-CTT-ATA-AGT-GCC-CCC-AAA-CTA-AAT | 40 | 1637-1660 |
| Sp 2 | 5'-CCT-ACT-GTG-AGA-TCA-CAT-GTT-TG | 41 | 2258-2236 |
| Sp 3 | 5'-GTT-GGC-ATA-GGT-GAG-CAC-TG | 42 | 1666-1686 |
| Sp 4 | 5'-GCA-ATG-CTG-GTT-CGG-AAG-AG | 43 | 2107-2088 |
| Sp 5 | 5'-AAC-GGT-TAC-ACT-GTT-CAG-CC | 44 | 931-950 |
| Sp 6 | 5'-CAA-GTA-AAT-GAG-TCT-GCC-TG | 45 | 1121-1102 |
| Sp 7 | 5'-GGC-TGC-CAC-CTC-TGC-TAG-TC | 46 | 2919-2938 |
| Sp 8 | 5'-ATT-GTT-AAA-TGC-ATT-AGC-AAT-AAG-C | 47 | 3069-3045 |
| SpF | 5'-TTT-TTG-ATA-CTT-TTA-ATT-TCC-TTA-CC | 48 | 4-29 |
| SpR | 5'-GTC-GTC-ATG-TGA-WGT-TTT-RAT-TAC | 49 | 4089-4066 |
| SpF-XhoI | 5'-AGC-TCG-AGC-TTT-TTG-ATA-CTT-TTA-ATT-TCC-TTA-CC | 50 | |
| SpR His-EcoRI | 5'-TTG-AAT-TCT-<ins>TAA</ins>-<u>TGA-TGA-TGA-TGA-TGA-TGG</u>-TCG-TCA-TGT-GAW-GTT-TTR-ATT-AC | 51 | |

SpF-XhoI contains a Xho I site (bold).
SpR-His-EcoR I contains a 6xHisTag (double-underlined), a stop codon (underlined) and an EcoR I site (bold)

What is claimed is:

1. An isolated coronavirus S protein having at least 97% amino acid sequence identity with SEQ ID NO:4.

2. An isolated polynucleotide that encodes the protein according to claim 1, or the complete complement thereof.

3. The polynucleotide according to claim 2 comprising SEQ ID NO:3.

4. A vector comprising the polynucleotide of claim 2.

5. An isolated host cell comprising the vector of claim 4.

6. An isolated host cell according to claim 5 wherein the vector is an expression vector comprising a eukaryotic promoter operatively linked to the polynucleotide, and wherein the host cell is a eukaryotic host cell.

7. The isolated coronavirus protein of claim 1, wherein said protein comprises at least one of: V at position 103; V at position 118; D at position 166; M at position 171; K at position 179; P at position 192; S at position 210; H at position 235; F at position 267; F at position 388; M at position 407; S at position 436; I at position 440; I at position 447; F at position 501; Y at position 525; N at position 528; L at position 540; K at position 582; G at position 608; G at position 692; S at position 695; W at position 757; G at position 758; Q at position 763; T at position 769; P at position 786; H at position 792; R at position 818; P at position 827; V at position 828; F at position 887; D at position 933; F at position 977; T at position 1011; S at position 1018; K at position 1063; L at position 1256; and M at position 1257, wherein the amino acid positions are from SEQ ID NO:4.

8. The isolated coronavirus protein of claim 1 comprising the amino acid sequence of SEQ ID NO:4.

* * * * *

SEQUENCE LISTING

<160> NUMBER OF SEQ ID NOS: 54

<210> SEQ ID NO 1
<211> LENGTH: 250
<212> TYPE: DNA
<213> ORGANISM: canine respiratory coronavirus

<400> SEQUENCE: 1

```
ctcagatgaa tttgaaatat gctattagtg ctaagaatag agcccgcact gttgctggtg     60
tttccatact tagtactatg actggcagaa tgtttcatca aaaatgtttg aaaagtatag    120
cagctacacg tggtgttcct gttgttatag gcaccactaa attttatggc ggctgggatg    180
atatgttacg tcgccttatt aaagatgttg acaatcctgt acttatgggt tgggattatc    240
ctaagtgtga                                                           250
```

<210> SEQ ID NO 2
<211> LENGTH: 83
<212> TYPE: PRT
<213> ORGANISM: canine respiratory coronavirus

<400> SEQUENCE: 2

Gln Met Asn Leu Lys Tyr Ala Ile Ser Ala Lys Asn Arg Ala Arg Thr
1               5                   10                  15

Val Ala Gly Val Ser Ile Leu Ser Thr Met Thr Gly Arg Met Phe His
            20                  25                  30

Gln Lys Cys Leu Lys Ser Ile Ala Ala Thr Arg Gly Val Pro Val Val

|  |  | 35 |  |  |  | 40 |  |  |  | 45 |  |
|--|--|--|--|--|--|--|--|--|--|--|--|

Ile Gly Thr Thr Lys Phe Tyr Gly Gly Trp Asp Asp Met Leu Arg Arg
50                       55                      60

Leu Ile Lys Asp Val Glu Asn Pro Val Leu Met Gly Trp Asp Tyr Pro
65                   70                      75                      80

Lys Cys Glu

<210> SEQ ID NO 3
<211> LENGTH: 4092
<212> TYPE: DNA
<213> ORGANISM: canine respiratory coronavirus

<400> SEQUENCE: 3

```
atgtttttga tacttttaat ttccttacca atggcttttg ctgttatagg agatttaaag     60
tgtactacgg tttccatcaa tgatgttgac accggtgctc cttctattag cactgatgtt    120
gtcgatgtta ctaatggttt aggtacttat tatgttttag atcgtgtgta tttaaatact    180
acattgttgc ttaatggtta ttatcctact tcaggttcta catatcgtaa tatggcactg    240
aagggaactt tactattgag cacactatgg tttaaaccac catttctttc tgattttatt    300
gatggtgttt ttgctaaggt aaaaaatacc aaggttatta agatggtgt agtgtatagt    360
gagtttcctg ctataactat aggtagtact tttgtaaata tcctatag tgtggtagta    420
caaccacata ctactaattt agataataaa ttacaaggtc tcttagagat ctctgtttgc    480
cagtatacta tgtgcgatta cccacatacg atgtgtcatc ctaatctggg taataaacgc    540
atagaactat ggcattggga tacaggtgtt gttccctgtt tatataagcg taatttcaca    600
tatgatgtga atgctgatta tttgtattcc cattttatc aagaaggtgg tactttttat    660
gcatatttta cagacactgg tgttgttact aagtttctgt ttcatgttta tttaggcacg    720
gtgctttcac attattatgt catgcccttg acttgtaata gtgctatgac tttagaatac    780
tgggttacac ctctcacttt taaacaatat ttactcgctt tcaatcaaga tggtgttatt    840
tttaatgctg ttgattgtaa gagtgatttt atgagtgaga ttaagtgtaa aacactatct    900
atagcaccat ctactggtgt ttatgaatta acggttaca ctgttcagcc aattgcagat    960
gtttaccgac gtataccta tcttcccgat gtaatatag aggcttggct taatgataag   1020
tcggtgcctt ctccattaaa ttgggaacgt aagacctttt caaattgtaa ttttaatatg   1080
agcagcctga tgtctttttat ccaggctgac tcgtttactt gtaataatat tgatgctgct   1140
aagatatacg gtatgtgttt tttcagcata actatagata agtttgctat acccaatggt   1200
aggaaggttg acctacaaat gggcaatttg gctatttgc agtcttttaa ctatagaatt   1260
gatactactg ctacaagttg tcagttgtat tataatttac ctgctagtaa tgtttctatt   1320
agcaggttta atccttctat ttggaatagg agatttggtt ttacagaaca atctgttttt   1380
aagcctcaac tgtaggtgt ttttactgat catgatgttg tttatgcaca acattgtttt   1440
aaagctccca caaatttctg tccgtgtaaa ttgaatgggt cttttgtgtgt aggtagtggt   1500
tttggtatag atgctggtta taaaatagt ggtataggca cttgtcctgc aggtactaat   1560
tatttaactt gttataatgc taaccaatgt gattgtttgt gcactccaga ccctatttta   1620
tctaaatcta cagggcctta taagtgcccc caaactaaat acttagttgg cataggtgag   1680
cactgttctg gtcttgctat taaagtgat tattgtggag gcaatccttg tacttgccaa   1740
ccaaagcat tttggggttg gtctgtggac tcttgtttac aagggatag gtgtaatatt   1800
tttgctaatt ttattttgca tggtgttaat agtggtacta cttgttctac tgatttacaa   1860
```

```
aaatcaaaca cagacataat tcttggtgtt tgtgttaatt atgatcttta tggtattaca    1920
ggccaaggta tttttgttga ggttaatgcg acttattata atagttggca gaaccttta     1980 tatgattcta atggtaatct ctatggtttt agggactact taacaaacag aactttatg     2040 attcgtagtt gctatagcgg tcgtgtttca gcgggctttc actctaactc ttccgaacca    2100
gcattgctat ttcggaatat taaatgcaat tacgttttta ataatactct ttcacgacag    2160
ctgcaaccta ttaactattt tgatagttat cttggttgtg ttgtcaatgc tgataatagt    2220
acttctagtt ctgttcaaac atgtgatctc acagtaggta gtggttactg ggggattac     2280 tctacacaaa gacgaagtcg tagaacgatt accactggtt atcggtttac taattttgag    2340
ccatttactg ttaatccagt aaatgatagt ttacaccctg taggtggttt gtatgaaatt    2400
caaataccct cagagtttac tataggtaat atggaggagt ttattcaaac aagatctcct    2460
aaagttacta ttgattgtcc tgtttttgtc tgtggtgatt atgcagcatg taaatcacag    2520
ttggttgaat atggtagttt ttgtgacaat attaatgcta tactcacaga agtaaatgaa    2580
ctacttgaca ctacacagtt gcaagtagct aatagtttaa tgaatggtgt cactcttagc    2640
actaagctta agatggctt taatttcaat gtagatgaca tcaattttc ccctgtatta      2700 ggttgtttag gaagcgaatg taataaagtt tccagtagat ctgctataga ggatttactt    2760
ttttctaaag taaagttatc tgatgttggt tttgttgatg cttataataa ttgtactgga    2820
ggtgccgaaa ttagggacct catttgtgtg caaagttata atggtatcaa agtgttgcct    2880
ccactgctct cagaaaatca gatcagtgga tacactttgg ctgccacctt tgctagtctg    2940
tttcctcctt ggtcagcagc agcaggcgta ccatttatt taaatgttca gtatcgtatt     3000
aatggtattg tgttaccat ggatgtgcta actcaaaatc aaaagcttat ttctaatgca     3060
tttaacaatg cccttgatgc tattcaggaa gggtttgatg ctaccaattc tgctttagtt    3120
aaaattcaag ctgttgttaa tgcaaatgct gaagctctta ataacttatt gcaacaactc    3180
tctaataaat ttggtgctat aagtgcttct ttacaagaaa ttctatctag acttgatgct    3240
cttgaagcgc aagctcagat agacagactt atcaatgggc gtcttaccgc tcttaatgct    3300
tatgtttctc aacagcttag tgattctaca ctagtaaaat ttagtgcagc acaagctatg    3360
gagaaggtta atgaatgtgt caaaagccaa tcatctagga taaattttg tggtaatggt    3420 aatcatatta tatcattagt gcagaatgct ccatatggtt tgtatttat ccactttagc     3480 tatgtcccta ctaagtatgt cactgcgaag gttagtcccg gtctgtgcat ygcaggtgat    3540
agaggtatag ctcctaagag tggttatttt gttaatgtaa ataacacttg gatgttcact    3600
ggtagtggtt attactaccc tgaacctata actggaaata tgtggttgt tatgagtacc     3660 tgtgctgtta actatactaa agcaccggat gtaatgctga acatttcaac acccaacctc    3720 cctgattta aggaagagtt ggatcaatgg tttaaaaacc aaacattaat ggcaccagat    3780
ttgtcacttg attatataaa tgttacattc ttggacctac aagatgaaat gaataggtta    3840
caggaggcaa taaagtttt aaatcatagc tacatcaatc tcaaggacat tggtacatat    3900
gaatattatg taaaatggcc ttggtatgta tggcttttaa ttggccttgc tggcgtagct    3960
atgcttgttt tactattctt catatgctgt tgtacaggat gtgggactag ttgttttaag    4020
aaatgcggtg gttgttgtga tgattatact ggacatcagg agttagtaat caaaacgtca    4080
catgacgact aa                                                         4092
```

<210> SEQ ID NO 4
<211> LENGTH: 1363
<212> TYPE: PRT

<213> ORGANISM: canine respiratory coronavirus

<400> SEQUENCE: 4

```
Met Phe Leu Ile Leu Leu Ile Ser Leu Pro Met Ala Phe Ala Val Ile
1               5                   10                  15

Gly Asp Leu Lys Cys Thr Thr Val Ser Ile Asn Asp Val Asp Thr Gly
                20                  25                  30

Ala Pro Ser Ile Ser Thr Asp Val Val Asp Val Thr Asn Gly Leu Gly
            35                  40                  45

Thr Tyr Tyr Val Leu Asp Arg Val Tyr Leu Asn Thr Thr Leu Leu Leu
        50                  55                  60

Asn Gly Tyr Tyr Pro Thr Ser Gly Ser Thr Tyr Arg Asn Met Ala Leu
65                  70                  75                  80

Lys Gly Thr Leu Leu Leu Ser Thr Leu Trp Phe Lys Pro Pro Phe Leu
                85                  90                  95

Ser Asp Phe Ile Asp Gly Val Phe Ala Lys Val Lys Asn Thr Lys Val
                100                 105                 110

Ile Lys Asp Gly Val Val Tyr Ser Glu Phe Pro Ala Ile Thr Ile Gly
            115                 120                 125

Ser Thr Phe Val Asn Thr Ser Tyr Ser Val Val Val Gln Pro His Thr
        130                 135                 140

Thr Asn Leu Asp Asn Lys Leu Gln Gly Leu Leu Glu Ile Ser Val Cys
145                 150                 155                 160

Gln Tyr Thr Met Cys Asp Tyr Pro His Thr Met Cys His Pro Asn Leu
                165                 170                 175

Gly Asn Lys Arg Ile Glu Leu Trp His Trp Asp Thr Gly Val Val Pro
                180                 185                 190

Cys Leu Tyr Lys Arg Asn Phe Thr Tyr Asp Val Asn Ala Asp Tyr Leu
            195                 200                 205

Tyr Ser His Phe Tyr Gln Glu Gly Gly Thr Phe Tyr Ala Tyr Phe Thr
        210                 215                 220

Asp Thr Gly Val Val Thr Lys Phe Leu Phe His Val Tyr Leu Gly Thr
225                 230                 235                 240

Val Leu Ser His Tyr Tyr Val Met Pro Leu Thr Cys Asn Ser Ala Met
                245                 250                 255

Thr Leu Glu Tyr Trp Val Thr Pro Leu Thr Phe Lys Gln Tyr Leu Leu
                260                 265                 270

Ala Phe Asn Gln Asp Gly Val Ile Phe Asn Ala Val Asp Cys Lys Ser
            275                 280                 285

Asp Phe Met Ser Glu Ile Lys Cys Lys Thr Leu Ser Ile Ala Pro Ser
        290                 295                 300

Thr Gly Val Tyr Glu Leu Asn Gly Tyr Thr Val Gln Pro Ile Ala Asp
305                 310                 315                 320

Val Tyr Arg Arg Ile Pro Asn Leu Pro Asp Cys Asn Ile Glu Ala Trp
                325                 330                 335

Leu Asn Asp Lys Ser Val Pro Ser Pro Leu Asn Trp Glu Arg Lys Thr
                340                 345                 350

Phe Ser Asn Cys Asn Phe Asn Met Ser Ser Leu Met Ser Phe Ile Gln
            355                 360                 365

Ala Asp Ser Phe Thr Cys Asn Asn Ile Asp Ala Ala Lys Ile Tyr Gly
        370                 375                 380

Met Cys Phe Phe Ser Ile Thr Ile Asp Lys Phe Ala Ile Pro Asn Gly
385                 390                 395                 400

Arg Lys Val Asp Leu Gln Met Gly Asn Leu Gly Tyr Leu Gln Ser Phe
```

```
                    405                 410                 415
Asn Tyr Arg Ile Asp Thr Thr Ala Thr Ser Cys Gln Leu Tyr Tyr Asn
                420                 425                 430

Leu Pro Ala Ser Asn Val Ser Ile Ser Arg Phe Asn Pro Ser Ile Trp
            435                 440                 445

Asn Arg Arg Phe Gly Phe Thr Glu Gln Ser Val Phe Lys Pro Gln Pro
        450                 455                 460

Val Gly Val Phe Thr Asp His Asp Val Val Tyr Ala Gln His Cys Phe
465                 470                 475                 480

Lys Ala Pro Thr Asn Phe Cys Pro Cys Lys Leu Asn Gly Ser Leu Cys
                485                 490                 495

Val Gly Ser Gly Phe Gly Ile Asp Ala Gly Tyr Lys Asn Ser Gly Ile
            500                 505                 510

Gly Thr Cys Pro Ala Gly Thr Asn Tyr Leu Thr Cys Tyr Asn Ala Asn
        515                 520                 525

Gln Cys Asp Cys Leu Cys Thr Pro Asp Pro Ile Leu Ser Lys Ser Thr
    530                 535                 540

Gly Pro Tyr Lys Cys Pro Gln Thr Lys Tyr Leu Val Gly Ile Gly Glu
545                 550                 555                 560

His Cys Ser Gly Leu Ala Ile Lys Ser Asp Tyr Cys Gly Gly Asn Pro
                565                 570                 575

Cys Thr Cys Gln Pro Lys Ala Phe Leu Gly Trp Ser Val Asp Ser Cys
            580                 585                 590

Leu Gln Gly Asp Arg Cys Asn Ile Phe Ala Asn Phe Ile Leu His Gly
        595                 600                 605

Val Asn Ser Gly Thr Thr Cys Ser Thr Asp Leu Gln Lys Ser Asn Thr
610                 615                 620

Asp Ile Ile Leu Gly Val Cys Val Asn Tyr Asp Leu Tyr Gly Ile Thr
625                 630                 635                 640

Gly Gln Gly Ile Phe Val Glu Val Asn Ala Thr Tyr Tyr Asn Ser Trp
                645                 650                 655

Gln Asn Leu Leu Tyr Asp Ser Asn Gly Asn Leu Tyr Gly Phe Arg Asp
            660                 665                 670

Tyr Leu Thr Asn Arg Thr Phe Met Ile Arg Ser Cys Tyr Ser Gly Arg
        675                 680                 685

Val Ser Ala Gly Phe His Ser Asn Ser Ser Glu Pro Ala Leu Leu Phe
690                 695                 700

Arg Asn Ile Lys Cys Asn Tyr Val Phe Asn Asn Thr Leu Ser Arg Gln
705                 710                 715                 720

Leu Gln Pro Ile Asn Tyr Phe Asp Ser Tyr Leu Gly Cys Val Val Asn
                725                 730                 735

Ala Asp Asn Ser Thr Ser Ser Val Gln Thr Cys Asp Leu Thr Val
            740                 745                 750

Gly Ser Gly Tyr Trp Gly Asp Tyr Ser Thr Gln Arg Arg Ser Arg Arg
        755                 760                 765

Thr Ile Thr Thr Gly Tyr Arg Phe Thr Asn Phe Glu Pro Phe Thr Val
    770                 775                 780

Asn Pro Val Asn Asp Ser Leu His Pro Val Gly Gly Leu Tyr Glu Ile
785                 790                 795                 800

Gln Ile Pro Ser Glu Phe Thr Ile Gly Asn Met Glu Glu Phe Ile Gln
                805                 810                 815

Thr Arg Ser Pro Lys Val Thr Ile Asp Cys Pro Val Phe Val Cys Gly
            820                 825                 830
```

-continued

Asp Tyr Ala Ala Cys Lys Ser Gln Leu Val Glu Tyr Gly Ser Phe Cys
        835                 840                 845

Asp Asn Ile Asn Ala Ile Leu Thr Glu Val Asn Glu Leu Leu Asp Thr
850                 855                 860

Thr Gln Leu Gln Val Ala Asn Ser Leu Met Asn Gly Val Thr Leu Ser
865                 870                 875                 880

Thr Lys Leu Lys Asp Gly Phe Asn Phe Asn Val Asp Asp Ile Asn Phe
                885                 890                 895

Ser Pro Val Leu Gly Cys Leu Gly Ser Glu Cys Asn Lys Val Ser Ser
                900                 905                 910

Arg Ser Ala Ile Glu Asp Leu Leu Phe Ser Lys Val Lys Leu Ser Asp
                915                 920                 925

Val Gly Phe Val Asp Ala Tyr Asn Asn Cys Thr Gly Gly Ala Glu Ile
        930                 935                 940

Arg Asp Leu Ile Cys Val Gln Ser Tyr Asn Gly Ile Lys Val Leu Pro
945                 950                 955                 960

Pro Leu Leu Ser Glu Asn Gln Ile Ser Gly Tyr Thr Leu Ala Ala Thr
                965                 970                 975

Phe Ala Ser Leu Phe Pro Pro Trp Ser Ala Ala Gly Val Pro Phe
        980                 985                 990

Tyr Leu Asn Val Gln Tyr Arg Ile Asn Gly Ile Gly Val Thr Met Asp
        995                 1000                1005

Val Leu Thr Gln Asn Gln Lys Leu Ile Ser Asn Ala Phe Asn Asn
    1010                1015                1020

Ala Leu Asp Ala Ile Gln Glu Gly Phe Asp Ala Thr Asn Ser Ala
    1025                1030                1035

Leu Val Lys Ile Gln Ala Val Val Asn Ala Asn Ala Glu Ala Leu
    1040                1045                1050

Asn Asn Leu Leu Gln Gln Leu Ser Asn Lys Phe Gly Ala Ile Ser
    1055                1060                1065

Ala Ser Leu Gln Glu Ile Leu Ser Arg Leu Asp Ala Leu Glu Ala
    1070                1075                1080

Gln Ala Gln Ile Asp Arg Leu Ile Asn Gly Arg Leu Thr Ala Leu
    1085                1090                1095

Asn Ala Tyr Val Ser Gln Gln Leu Ser Asp Ser Thr Leu Val Lys
    1100                1105                1110

Phe Ser Ala Ala Gln Ala Met Glu Lys Val Asn Glu Cys Val Lys
    1115                1120                1125

Ser Gln Ser Ser Arg Ile Asn Phe Cys Gly Asn Gly Asn His Ile
    1130                1135                1140

Ile Ser Leu Val Gln Asn Ala Pro Tyr Gly Leu Tyr Phe Ile His
    1145                1150                1155

Phe Ser Tyr Val Pro Thr Lys Tyr Val Thr Ala Lys Val Ser Pro
    1160                1165                1170

Gly Leu Cys Ile Ala Gly Asp Arg Gly Ile Ala Pro Lys Ser Gly
    1175                1180                1185

Tyr Phe Val Asn Val Asn Asn Thr Trp Met Phe Thr Gly Ser Gly
    1190                1195                1200

Tyr Tyr Tyr Pro Glu Pro Ile Thr Gly Asn Asn Val Val Val Met
    1205                1210                1215

Ser Thr Cys Ala Val Asn Tyr Thr Lys Ala Pro Asp Val Met Leu
    1220                1225                1230

Asn Ile Ser Thr Pro Asn Leu Pro Asp Phe Lys Glu Glu Leu Asp
    1235                1240                1245

```
Gln Trp Phe Lys Asn Gln Thr Leu Met Ala Pro Asp Leu Ser Leu
    1250                1255                1260

Asp Tyr Ile Asn Val Thr Phe Leu Asp Leu Gln Asp Glu Met Asn
    1265                1270                1275

Arg Leu Gln Glu Ala Ile Lys Val Leu Asn His Ser Tyr Ile Asn
    1280                1285                1290

Leu Lys Asp Ile Gly Thr Tyr Glu Tyr Tyr Val Lys Trp Pro Trp
    1295                1300                1305

Tyr Val Trp Leu Leu Ile Gly Leu Ala Gly Val Ala Met Leu Val
    1310                1315                1320

Leu Leu Phe Phe Ile Cys Cys Cys Thr Gly Cys Gly Thr Ser Cys
    1325                1330                1335

Phe Lys Lys Cys Gly Gly Cys Cys Asp Asp Tyr Thr Gly His Gln
    1340                1345                1350

Glu Leu Val Ile Lys Thr Ser His Asp Asp
    1355                1360

<210> SEQ ID NO 5
<211> LENGTH: 250
<212> TYPE: DNA
<213> ORGANISM: bovine coronavirus strain LY138

<400> SEQUENCE: 5
ctcaaatgaa tttgaaatat gctattagtg ctaagaatag agcccgcact gttgctggtg      60
tttccatact cagtactatg actggcagaa tgtttcatca aaaatgtttg aaaagtatag     120
cagctacacg tggtgttcct gttgttatag gcaccactaa gttttatggc ggctgggatg     180
atatgttacg tcgccttatt aaagatgttg ataatcctgt acttatgggt tgggattatc     240
ctaagtgtga                                                            250

<210> SEQ ID NO 6
<211> LENGTH: 250
<212> TYPE: DNA
<213> ORGANISM: human coronavirus strain OC43

<400> SEQUENCE: 6
ctcaaatgaa tttgaaatat gctattagtg ctaagaatag agcccgcact gttgctggtg      60
tttccatact tagtactatg actggcagaa tgtttcatca aaaatgtttg aaaagtatag     120
cagctacacg tggtgttcct gtagttatag gcaccactaa attttatggt ggctgggatg     180
atatgttacg ccgccttatt aaagatgttg acaatcctgt acttatgggt tgggattatc     240
ctaagtgtga                                                            250

<210> SEQ ID NO 7
<211> LENGTH: 250
<212> TYPE: DNA
<213> ORGANISM: hemagglutinating encephalomyelitis virus

<400> SEQUENCE: 7
ctcaaatgaa tttgaaatat gctattagtg ccaagaatag agcccgcact gttgctggtg      60
tttccatact tagtactatg actggcagaa tgtttcatca aaaatgcttg aaaagtatag     120
cagctacacg tggcgttcct gtggttatag gcaccactaa attttatggc ggctgggatg     180
atatgttacg ccgccttatt aaagatgttg ataatcctgt acttatgggt tgggattatc     240
caaagtgtga                                                            250
```

```
<210> SEQ ID NO 8
<211> LENGTH: 250
<212> TYPE: DNA
<213> ORGANISM: canine enteric coronavirus

<400> SEQUENCE: 8
ctcagatgaa tttgaaatat gctatttctg gaaaggctag agctcgtaca gtaggaggag     60
tttcacttct ttctaccatg actacgagac aataccacca gaagcatttg aagtcaattg    120
ctgcaacacg caatgccact gtggttattg gctcaaccaa gttttatggt ggttgggata    180
acatgcttaa aaatttaatg cgtgatgttg ataatggttg tttgatggga tgggactatc    240
ctaagtgtga                                                          250

<210> SEQ ID NO 9
<211> LENGTH: 81
<212> TYPE: PRT
<213> ORGANISM: human coronavirus strain OC43

<400> SEQUENCE: 9

Met Asn Leu Lys Tyr Ala Ile Ser Ala Lys Asn Arg Ala Arg Thr Val
1               5                   10                  15

Ala Gly Val Ser Ile Leu Ser Thr Met Thr Gly Arg Met Phe His Gln
            20                  25                  30

Lys Cys Leu Lys Ser Ile Ala Ala Thr Arg Gly Val Pro Val Val Ile
        35                  40                  45

Gly Thr Thr Lys Phe Tyr Gly Gly Trp Asp Asp Met Leu Arg Arg Leu
    50                  55                  60

Ile Lys Asp Val Asp Asn Pro Val Leu Met Gly Trp Asp Tyr Pro Lys
65                  70                  75                  80

Cys

<210> SEQ ID NO 10
<211> LENGTH: 81
<212> TYPE: PRT
<213> ORGANISM: hemagglutinating encephalomyelitis virus

<400> SEQUENCE: 10

Met Asn Leu Lys Tyr Ala Ile Ser Ala Lys Asn Arg Ala Arg Thr Val
1               5                   10                  15

Ala Gly Val Ser Ile Leu Ser Thr Met Thr Gly Arg Met Phe His Gln
            20                  25                  30

Lys Cys Leu Lys Ser Ile Ala Ala Thr Arg Gly Val Pro Val Val Ile
        35                  40                  45

Gly Thr Thr Lys Phe Tyr Gly Gly Trp Asp Asp Met Leu Arg Arg Leu
    50                  55                  60

Ile Lys Asp Val Asp Asn Pro Val Leu Met Gly Trp Asp Tyr Pro Lys
65                  70                  75                  80

Cys

<210> SEQ ID NO 11
<211> LENGTH: 81
<212> TYPE: PRT
<213> ORGANISM: bovine coronavirus strain LY138

<400> SEQUENCE: 11

Met Asn Leu Lys Tyr Ala Ile Ser Ala Lys Asn Arg Ala Arg Thr Val
1               5                   10                  15

Ala Gly Val Ser Ile Leu Ser Thr Met Thr Gly Arg Met Phe His Gln
            20                  25                  30
```

```
Lys Cys Leu Lys Ser Ile Ala Ala Thr Arg Gly Val Pro Val Ile
            35                  40                  45

Gly Thr Thr Lys Phe Tyr Gly Gly Trp Asp Asp Met Leu Arg Arg Leu
 50                  55                  60

Ile Lys Asp Val Asp Asn Pro Val Leu Met Gly Trp Asp Tyr Pro Lys
 65                  70                  75                  80

Cys

<210> SEQ ID NO 12
<211> LENGTH: 84
<212> TYPE: PRT
<213> ORGANISM: canine enteric coronavirus

<400> SEQUENCE: 12

Met Thr Gln Met Asn Leu Lys Tyr Ala Ile Ser Gly Lys Ala Arg Ala
 1               5                  10                  15

Arg Thr Val Gly Gly Val Ser Leu Leu Ser Thr Met Thr Thr Arg Gln
                20                  25                  30

Tyr His Gln Lys His Leu Lys Ser Ile Ala Ala Thr Arg Asn Ala Thr
            35                  40                  45

Val Val Ile Gly Ser Thr Lys Phe Tyr Gly Gly Trp Asp Asn Met Leu
 50                  55                  60

Lys Asn Leu Met Arg Asp Val Asp Asn Gly Cys Leu Met Gly Trp Asp
 65                  70                  75                  80

Tyr Pro Lys Cys

<210> SEQ ID NO 13
<211> LENGTH: 4363
<212> TYPE: DNA
<213> ORGANISM: canine enteric coronavirus

<400> SEQUENCE: 13
atgattgtgc tcgtaacttg cattttattg ttatgttcat accacactgc ttcgagtacg      60
tcaaataatg attgtagaca agttaacgta acacaattag atggcaatga aaacctcatt    120
agagactttt tgtttcaaaa ctttaaagaa gaaggaactg tagttgttgg tggttactac    180
cctacagagg tttggtataa ctgttctaga acagcaacaa ctactgccta tgagtatttc    240
agtaatatac acgcattcta tttttgatatg gaagccatgg agaatagtac tggtaatgca    300
cgtggtaaac ctttattatt tcatgttcat ggtgagcctg ttagtgtcat catatacata    360
tcttatagag atgatgtgca acataggcca cttttaaaac acggattagt gtgcataact    420
gaaagtcgca acattgacta taacagtttc accagtagcc agtggaattc catatgtacg    480
ggtaatgaca gaaaaattcc tttctctgtc atacccacgg acaatggaac aaaaatttat    540
ggtcttgagt ggaatgatga atttgttaca gcgtacatta gtggtcgttc ttataattgg    600
aacatcaata taattggtt taacaatgtc acgcttctgt atagtcgctc aagcactgcc    660
acatggcaac acagtgctgc atacgtttac caaggtgttt ctaacttcac ttattacaag    720
ttaaataaca ccaatggtct aaaaacctat gaattatgtg aagattatga atattgcact    780
ggctacgcca ctaacatctt tgccccaact gtgggaggtt acatacctga tggatttagt    840
tttaacaatt ggtttttgct tacaaacagc tccactttgt tagtggcag atttgtaaca    900 aatcaaccat tattagttaa ttgcttgtgg ccagttccta gttttggtgt tgcagcacaa    960 gaatttgtt tgaaggtgc acagtttagc caatgtaatg tgtgtttt aaataacaca    1020 gtagatgtca ttagattcaa ccttaatttt actgcagatg tacaatctgg catgggtgct    1080
```

```
acagtatttt cactgaatac aacaggtggt tgcattcttg agattcttg ttataatgat    1140 atagtgagcg agtcaagttt ctacagttat ggtgaaattc ccttcggcgt aactgatgga    1200
ccgcgttatt gttatgtcct ctataatggc acagctctta agtatttcgg cacattaccc    1260
cctagtgtca aggaaattgc tattagtaag tggggccaat tttatattaa tggttacaat    1320
ttctttagca cttttcctat tgattgtata tcttttaact taaccactgg tgatagtgga    1380
gcattttgga caattgctta cacatcgtac actgaagcat tagtacaagt tgaaaacaca    1440
gccattaaaa aggtgacgta ttgtaacagt cacattaata acatcaaatg ttctcaactt    1500
actgctaatt tgcaaaatgg cttttatcct gttgcttcaa gtgaagttgg tcttgtcaat    1560
aagagtgttg tgttactacc tagttttctat tcacatacca gtgttaatat aactattgat    1620
cttggtatga agcgtagtgg ttatggtcaa cccatagcct caacactaag taacatcaca    1680
ctaccaatgc aggataataa caccgatgtg tactgtattc gttctaacca attctcagtt    1740
tatgttcact ccacttgcaa aagttctta tgggacaaca attttaatca agattgcaca    1800
gatgttttat atgccacagc tgttataaaa actggtactt gccccttctc atttgataaa    1860
ttgaataatt acttaacttt taacaagctt tgtttgtcgt tgaatcctac tggtgccaac    1920
tgtaagtttg atgttgctgc ccgtacaaga accaatgagc aggttgttag aagtttatat    1980
gtaatatatg aagaaggaga caacatagtg ggtgtaccgt ctgataatag tggtcttcac    2040
gatttgtcag tgttacactt agactcctgt acagattaca atatatatgg tagaactggt    2100
gttggtatta ttagcaaaac taacagcaca atacttagtg gcttacatta tacatcacta    2160
tcaggtgatt tattaggttt taaaaatgtt agtgatggtg ttgtctattc tgtgacacca    2220
tgtgatgtaa gcgcacaagc ggctgttatt gatggggcca tagttggagc tatgacttcc    2280
attaatagtg aactgttagg tctaacacat tggacaacaa caccaaattt ttattactac    2340
tctatatata atacaacaaa tgagagaact cgtggcactg caatcgacag taacgatgta    2400
gattgtgaac ctatcataac ctattctaac ataggtgttt gtaaaaatgg tgcgttggtt    2460
tttattaacg tcacacattc tgatggagat gttcaaccaa ttagcactgg caatgtcacg    2520 atcccacaa actttaccat atctgtgcaa gttgaataca tccaggttta cactacaccg    2580
gtgtcaatag attgttctag atacgttgt aatggtaacc ctagatgtaa taattgtta    2640 acacaatatg tttctgcatg tcaaactatt gagcaagcgc ttgcaatgag tgccagcctt    2700
gaaaacatgg aagttgattc catgttgttt gtttcagaaa atgcccttaa attggcatct    2760
gttgaggcgt tcaatagtac agaacattta gatcctattt acaaagaatg gcctaacata    2820
ggtggttctt ggctaggagg tctaaaagac atacttccgt cccataatag caaacgtaag    2880
tatcgttctg ctatagaaga cttgcttttt gataaagttg taacttctgg tctaggtaca    2940
gttgatgaag attataaacg ttgtacaggt ggttatgaca tagctgactt agttgtgca    3000 caatattaca atggcatcat ggtctacct ggtgttgcta atgatgacaa gatgactatg    3060
tacacagcct ctcttgcagg tggtataaca ttaggtgcac taggtggtgg cgccgtggct    3120
ataccttttg cagtagcagt tcaggctaga cttaattatg ttgctctaca aactgatgta    3180
ttgaacaaaa accagcagat cctggctaat gctttcaacc aagctattgg taacattaca    3240
caggcatttg gtaaggttaa tgatgctata catcaaacat cacaaggtct tgccactgtt    3300
gctaaagcat tggcaaaagt gcaagatgtt gttaacacac aagggcaagc tttaagccac    3360
ctaacagtac aactgcaaaa tagcttccaa gccattagta gttctattag tgacatttat    3420
aataggcttg atgaactgag tgctgatgca caagttgata ggctgattac aggtagactt    3480
```

```
acagcactta atgcatttgt atctcagact ctaaccagac aagcggaggt tagggctagt    3540
agacaacttg ccaaagacaa ggttaatgaa tgtgttaggt ctcagtctca gagatttgga    3600
ttttgtggta atggtacaca tttgttttca cttgcaaatg cagcaccaaa tggcatggtt    3660
ttctttcaca cagtgctatt accaacagct tatgaaactg taacagcttg gtcaggtatt    3720
tgtgcttcag atggcgatcg cactttttgga cttgtcgtta agatgttca gttgacgttg    3780 tttcgtaatc tagatgacaa gttctatttg actcccagaa ctatgtatca gcctagagct    3840
gcaactagtt ctgattttgt tcagattgag gggtgcgacg tgttgtttgt caatgcaact    3900
gtaattgact tgcctagtat tatacctgac tatatcgaca ttaatcagac tgttcaagac    3960
atattagaaa actacagacc aaactggact gtacctgaat tgacaattga catttttaac    4020
gcaacctatt taaatctgac tggtgaaatt gatgacttag aatttaggtc agaaaagcta    4080
cataacacca cagtagagct tgccattctc attgacaata ttaacaatac attagtcaat    4140
cttgaatggc tcaatagaat tgaaacttat gtgaaatggc cttggtatgt gtggctacta    4200
ataggcttag tagtagtgtt ttgcataccg ctattgctat tttgctgttg tagtacaggt    4260
tgctgtggat gcataggttg tttgggaagt tgttgtcatt ctatttgtag tagaagacaa    4320
tttgaaaatt acgaaccaat tgaaaaagtg catgtccact aaa    4363
```

<210> SEQ ID NO 14
<211> LENGTH: 4049
<212> TYPE: DNA
<213> ORGANISM: bovine coronavirus strain LY138

<400> SEQUENCE: 14

```
atgttttga tacttttaat ttccttacca atggctcttg ctgttatagg agatttaaag      60
tgtactacgg tttccattaa tgatgttgac accggtgttc cttctgttag cactgatact     120
gtcgatgtta ctaatggttt aggtacttat tatgttttag atcgtgtgta tttaaatact     180
acgttgttgc ttaatggtta ctaccctact tcaggttcta catatcgtaa tatggcactg     240
aagggaactt tactattgag cacactatgg tttaaaccac ttttctttc tgattttatt     300 aatggtattt ttgctaaggt caaaaatacc aaggttatta aaaatggtgt aatgtatagt     360
gagtttcctg ctataactat aggtagtact tttgtaaata tcctctatag tgtggtagta     420
caaccacata ctaccaattt agataataaa ttacaaggtc tcttagagat ctctgtttgc     480
cagtatacta tgtgcgagta cccacatacg atttgtcatc ctaatttggg taatcggcgc     540
atagaactat ggcattggga tacaggtgtt gtttcctgtt tatataagcg taatttcaca     600
tatgatgtga atgctgatta tttgtatttc cattttttatc aagaaggtgg tacttttttat     660 gcatatttta cagacactgg tgttgttact aagtttctgt ttaatgttta tttaggcacg     720
gtgctttcac attattatgt catgcctttg acttgtaata gtgctatgac tttagaatat     780
tgggttacac ctctcacttc taaacaatat ttactcgctt tcaatcaaga tggtgttatt     840
tttaatgctg ttgattgtaa gagtgatttt atgagtgaga ttaagtgtaa aacactatct     900
atagcaccat ctactggtgt ttatgaatta aacggttaca ctgttcagcc aattgcagat     960
gtttaccgac gtatacctaa tcttcccgat tgtaatatag aggcttggct taatgataag    1020 tctgtgcccct ctccattaaa ttgggaacgt aagacctttt caaattgtaa ttttaatatg    1080
agcagcctga tgtctttttat tcaggcagac tcatttactt gtaataatat tgatgcagct    1140
aagatatatg gtatgtgttt ttccagcata actatagata agtttgctat acccaatggt    1200
aggaaggttg acctacaatt gggcaatttg ggctatttgc agtctttaa ctatagaatt    1260
```

```
gatactactg ctacaagttg tcagttgtat tataatttac ctgctgctaa tgtttctgtt    1320
agcaggttta atccttctac ttggaatagg agatttggtt ttacagaaca atctgttttt    1380
aagcctcaac ctgtaggtgt ttttactgat catgatgttg tttatgcaca acattgtttt    1440
aaagctccca caaatttctg tccgtgtaaa ttggatgggt ctttgtgtgt aggtagtggt    1500
tctggtatag atgctggtta taaaaatagt ggtataggca cttgtcctgc aggtactaat    1560
tatttaactt gtcataatgc tgcccaatgt aattgtttgt gcactccaga ccccattaca    1620
tctaaatcta cagggcctta taagtgcccc caaactaaat atttagttgg cataggtgag    1680
cactgttcgg gtcttgctat aaaagtgat tatttgtggag gtaatccttg tacttgccaa    1740
ccacaagcat ttttggggttg gtctgttgat tcttgtttac aaggggatag gtgtaatatc    1800
tttgctaatt ttattttgca tgatgttaat agtggtacta cttgttctac tgatttacaa    1860
aaatcaaaca cagacataat tcttggtgtt tgtgttaatt atgatcttta tggtattaca    1920
ggccaaggta tttttgttga ggttaatgcg acttattata atagttggca gaaccttta    1980 tatgattcta atggtaatct ctatggtttt agagactact taacaaacag aacttttatg    2040
attcgtagtt gctatagcgg tcgtgtttca gcggcctttc atgctaattc ttccgaacca    2100
gcattgctat ttcggaatat taaatgcaat tacgttttta ataatactct ttcacgacag    2160
ctgcaaccta ttaactattt tgatagttat cttggttgtg ttgtcaatgc tgataatagt    2220
acttctagtg ctgttcaaac atgtgatctc acagtaggta gtggttactg tgtggattac    2280
tctacaaaaa gacgaagtcg tagagcgatt accactggtt atcggtttac taattttgag    2340
ccatttactg ttaattcagt aaatgatagt ttagaacctg taggtggttt gtatgaaatt    2400 caaataccttt cagagtttac tataggtaat atggaggagt ttattcaaat aagctctcct    2460
aaagttacta ttgattgttc tgcttttgtc tgtggtgatt atgcagcatg taaatcacag    2520
ttggttgaat atggtagttt ctgtgacaat attaatgcta tactcacaga gtaaatgaa    2580 ctacttgaca ctacacagtt gcaagtagct aatagtttaa tgaatggtgt cactcttagc    2640
actaagctta aagatggcgt taatttcaat gtagacgaca tcaattttc ccctgtatta    2700 ggttgtttag gaagcgattg taataaagtt tccagtagat ctgctataga ggatttactt    2760
ttttctaaag taaagttatc tgatgtcggt tttgttgagg cttataataa ttgtactgga    2820
ggtgccgaaa ttagggacct catttgtgtg caaagttata atggtatcaa agtgttgcct    2880
ccactactct cagaaaatca gatcagtgga tacactttgg ctgctacctc tgctagtctg    2940
tttcctcctt ggtcagcagc agcaggcgta ccattttatt taaatgttca gtatcgtatt    3000
aatgggattg tgttaccat ggatgttcta agtcaaaatc aaaagcttat tgctaatgca    3060
tttaacaatg cccttgatgc tattcaggaa gggtttgatg ctaccaattc tgctttagtt    3120
aaaattcaag ctgttgttaa tgcaaatgct gaagctctta ataacttatt gcaacaactc    3180
tctaatagat ttggtgctat aagttcttct ttacaagaaa ttctatctag acttgatgct    3240
cttgaagcgc aagctcagat agacagactt attaatgggc gtcttaccgc tcttaatgct    3300
tatgtttctc aacagcttag tgattctaca ctagtaaaat ttagtgcagc acaagctatg    3360
gagaaggtta atgaatgtgt caaaagccaa tcatctagga taaattttg tggtaatggt    3420 aatcatatta tatcattagt gcagaatgct ccatatggtt tgtatttat ccactttagc    3480 tatgtcccta ctaagtatgt cactgcgaag gttagtcccg gtctgtgcat tgctggtgat    3540
agaggtatag cccctaagag tggttatttt gttaatgtaa ataacacttg gatgttcact    3600
ggtagtggtt attactaccc tgaacctata actggaaata atgttgttgt tatgagtacc    3660
```

| | |
|---|---|
| tgtgctgtta attacactaa agcaccggat gtaatgctga ac

```
ccacaagcat ttttgggttg gtctgttgac tcttgtttac aaggggatag gtgtaatatt    1800
tttgctaatt ttattttgca tgatgttaat agtggtacta cttgttctac tgatttacaa    1860
aaatcaaaca cagacataat tcttggtgtt tgtgttaatt atgatcttta tggtattaca    1920
ggccaaggta ttttttgttga ggttaatgcg ccttattata atagttggca gaaccttta    1980
tatgattcta atggtaatct ctatggtttt agagactact taacaaacag aacttttatg    2040
attcgtagtt gctatagcgg tcgtgtttca gcggcctttc atgctaactc ttccgaacca    2100
gcattgctat ttcggaatat aaatgcagt tacgttttta ataatactct ttcacgacag     2160
ctgcaaccta ttaactattt tgatagttat cttggttgtg ttgtcaatgc tgataatagt    2220
acttctagtg ttgttcaaac atgtgatctc acagtaggta gtggttactg tgtggattac    2280
tctacaaaaa gacgaagtcg tagagcgatt accactggtt atcggtttac taattttgag    2340
ccatttactg ttaattcagt aaatgatagt ttagaacctg taggtggttt gtatgaaatt    2400
caaataccct cagagtttac tataggtaat atggaggagt ttattcaaac aagctctcct    2460
aaagttacta ttgattgttc tgcttttgtc tgtggtgatt atgcagcatg taaatcacag    2520
ttggttgaat atggtagctt ctgtgacaat attaatgcta tactcacaga agtaaatgaa    2580
ctacttgaca ctacacagtt gcaagtagct aatagtttaa tgaatggtgt cactcttagc    2640
actaagctta aagatggcgt taatttcaat gtagacgaca tcaattttc ccctgtatta     2700
ggttgtttag gaagcgcttg taataaagtt tccagcagat ctgctataga ggatttactt    2760
ttttctaaag taaagttatc tgatgtcggt tcgttgagg cttataataa ttgtactgga     2820
ggtgccgaaa ttagggacct catttgtgtg caaagttata atggtatcaa agtgttgcct    2880
ccactgctct cagtaaatca gatcagtgga tacactttgg ctgccacctc tgctagtctg    2940
tttcctcctt ggtcagcagc agcaggtgta ccatttttatt taaatgttca gtatcgtatt    3000
aatgggattg tgttaccat ggatgtgtta agtcaaaatc aaaagcttat tgctaatgca     3060
tttagcaatg ctcttgatgc tattcaggaa gggtttgatg ctaccaattc tgctttagtt    3120
aaaattcaag ctgttgttaa tgcaaatgct gaagctctta ataacttatt gcaacaactc    3180
tctaatagat ttggtgctat aggttcttct ttacaagaaa ttcctatctag actggatgct    3240
cttgaagcgc aagctcagat agacagactt attaatgggc gtcttaccgc tcttaatgct    3300
tatgtttctc aacagcttag tgattctaca ctagtaaaat ttagtgcagc acaagctatg    3360
gagaaggtta atgaatgtgt caaaagccaa tcatctagga taaattttttg tggtaatggt    3420
aatcatatta tatcattagt gcagaatgct ccatatggtt tgtatttat ccactttagc     3480
tatgtcccta ctaagtatgt cactgcgaag gttagtcccg gtctgtgcat tgctggtgat    3540
agaggtatag cccctaagag tggttatttt gttaatgtaa ataatacttg gatgttcact    3600
ggtagtggtt attactaccc tgaacccata actggaaata atgttgttgt tatgagtacc    3660
tgtgctgtta actatactaa agcgccggat gtaatgctga acatttcaac acccaacctc    3720
catgatttta aggaagagtt ggatcaatgg tttaaaaacc aaacatcagt ggcaccagat    3780
ttgtcacttg attatataaa tgttacattc ttggacctac aagatgaaat gaataggtta    3840
caggaggcaa taaagttttt aaatcagagc tacatcaatc tcaaggacat tggtacatat    3900
gagtattatg taaaatggcc ttggtatgta tggcttttaa ttggctttgc tggtgtagct    3960
atgcttgttt tactattctt catatgctgt tgtacaggat gtgggactag ttgttttaag    4020
atatgtggtg gttgttgtga tgattatact ggacaccagg                          4060
```

```
<210> SEQ ID NO 16
<211> LENGTH: 4056
<212> TYPE: DNA
<213> ORGANISM: hemagglutinating encephalomyelitis virus

<400> SEQUENCE: 16 atgttttta  tacttttaat  caccctgcct  tctgttttg   cagttatagg  ggatttaaag     60
tgtaatactt catcaattaa tgacgttgac actggtgtgc catctattag ctctgaagtt        120
gttgatgtca ctaatggttt ggggactttc tatgttttag atcgtgtcta tttaaatacc        180
acattgttgc tcaatggtta ttacccaatt tcaggtgcta catttcgtaa tgtggctctg        240
aaaggaactc gattattgag caccttgtgg tttaagccgc cttttttatc acctttaat        300 gatggtattt ttgccaaggt taaaaacagc gattttcta aacatggtgt tatttatagt        360
gagtttcctg ctattactat aggtagtact tttgtaaata cttcctatag catagtagta       420
aagcctcata cctcatttat taatggtaat ttacaaggtt ttttgcaaat ttctgttttgt      480 caatatacta tgtgtgaata cccacagact atttgtcatc ctaatttggg taatcaacgc       540
atagaattat ggcatcatga cacagatgtt gtttcttgtt tatacaggcg taatttcaca       600
tatgatgtga atgctgatta tttatatttt cacttttatc aggaaggtgg cacttttttat     660 gcatacttta cagatactgg ttttgtgacc aagtttctgt ttaagttgta tttaggcact       720
gtgctgtcac actattatgt tatgccattg acttgtgata cgctttatc tttagaatat        780 tgggttacac ctctcactac tagacaattt cttctagcct ttgaccagga tggtgtttta       840
taccatgctg ttgattgtgc tagtgatttt atgagtgaga ttatgtgtaa aacttcttca       900
attacaccac ctactggtgt ttatgaacta aacggttaca cagttcaacc tgttgccact       960
gtgtatcgta gaatacctga cttacccaat tgcgatatcg aagcttggct taattctaag      1020
accgtttctt cgcctcttaa ttgggaacgt aaaatttttt ctaattgtaa ttttaacatg       1080
ggcaggctga tgtcttttat tcaggctgac tcttttggtt gtaacaatat tgatgcttct      1140
cgcttatatg gtatgtgttt tggtagcatt actattgaca agtttgctat acccaatagt       1200
agaaaggttg atctgcaagt gggtaaatct ggttatttac aatcttttaa ttataagatt       1260
gacactgctg ttagcagttg tcaactctat tatagtttgc ctgcagcaaa cgtatctgtc       1320
actcattata atccttcatc ttggaacaga aggtatgggt ttattaatca gagttttggt       1380
tccagaggcc ttcatgatgc tgtatattca cagcaatgtt ttaatacacc taatacatat       1440
tgtccttgta gaacaagtca atgcataggt ggtgctggca caggaacttg tcctgtaggc       1500
accactgtgc gcaagtgttt tgctgcagtt acaaacgcta ctaagtgtac ttgctggtgt       1560
caaccagatc cttccacata taaggtgta atgcctgga cttgtccgca atctaaagtt         1620
tctatacaac caggtcagca ttgccctggc ttgggtcttg tggaggatga ttgctctggt       1680
aatccttgca cttgtaaacc acaggctttc ataggctgga gttcagaaac ttgtttgcaa      1740
aatggtaggt gtaatatttt tgctaatttt attttgaatg atgttaatag cggtactacc       1800
tgttctactg atttacaaca gggtaatact aatattacta ctgatgtttg tgttaattat       1860
gacctatatg gcattacagg ccagggcata cttatagaag ttaatgccac gtattataat       1920
agttggcaga tcttcttta tgattctagt ggtaatctct atggctttag agattattta       1980
tcaaatagaa ccttttctta tcgtagctgc tatagtggaa gagtttcagc agtctttcat       2040
gctaactctt ctgaaccagc tttgatgttt cgtaatctta aatgcagcca cgttttaat        2100 tataccattt taagacaaat acagcttgtt aattattttg atagttacct tggttgtgtt       2160
gttaatgctt ataataatac agctagtgct gtaagtactt gtgatttaac cgttggtagc       2220
```

```
ggctattgtg ttgattatgt tacagcactt agatcacgta gatcttttac tacaggttat    2280
cgctttacta attttgaacc atttgccgct aatttggtaa atgatagtat agaacctgtt    2340
ggtggtttgt atgaaataca gataccttca gagtttacca ttggtaattt agaagaattc    2400
attcaaacga gttcccctaa ggttactata gattgtgcta catttgtttg tggtgactat    2460
gctgcatgta gacaacagtt agctgagtat ggtagttttt gtgagaacat taatgctata    2520
ctcatagaag taaatgaact acttgacact acacagttgc aagtagctaa tagtttaatg    2580
aatggagtca cccttagtac taagattaag gatgggatta atttcaatgt tgacgatatc    2640
aacttctcct ctgtattagg ttgtttagga agcgaatgta acagagcttc cactagatct    2700
gctatagagg atttactttt tgataaagta aaattgtctg atgtcggttt tgtacaggcc    2760
tataataact gcactggagg agccgaaatt agggatctca tttgtgtgca aagttataat    2820
ggtatcaaag tgttgcctcc attgttatct gaaaatcaga ttagtggtta cacttcggca    2880
gccaccgctg ctagcctatt tcctccctgg acagctgcag caggtgtacc attttatta    2940 aatgttcagt atcgtataaa tgggcttggc gtcaccatgg atgtgctaag ccaaaaccaa    3000
aagcttattg ctagtgcatt taacaacgct cttgattcta tccaggaagg ttcgacgca    3060 accaattctg ctttagttaa aattcaggct gttgttaatg caaatgctga agcacttaat    3120
aacttattgc agcaactctc taacagattt ggtgccataa gtgcctcttt acaagaaatt    3180
ttatccaggc tcgatgctct tgaagctaaa gctcagatag acagacttat taatgggcgt    3240
ctcaccgctc ttaatgctta tgtttctcag cagcttagtg attctacact agtaaaattt    3300
agtgcagcac aagctattga aaagttaat gaatgtgtta aaagccaatc atctaggata    3360
aatttctgtg gtaatggtaa tcatattata tcattagtac agaatgctcc atatggtttg    3420
tattttatcc attttagcta tgtccccacc aagtatgtta cagcaaaggt tagtcctggt    3480
ttgtgcattg ctggcgatat aggaatatcg cctaagagtg ttatttttat taatgtaaat    3540
aactcttgga tgttcactgg tagtggctat tactaccctg aacctataac ccaaaataat    3600
gttgttgtga tgagtacgtg tgctgttaat tatactaaag caccggatct aatgctgaac    3660
acatcgacac ccaaccttcc tgatttcaag gaagaattgt atcaatggtt taaaaaccaa    3720
tcttcattgg caccagattt gtcatttgat tatattaatg ttacgttctt ggacctacaa    3780
gatgaaatga ataggttaca agaagctata aaagttctaa atcatagcta catcaatctc    3840
aaggacattg gtacatatga gtattatgtg aaatggcctt ggtatgtatg ctttttaatt    3900
tgccttgctg gtgtagttat gcttgtttta ctattcttca tatgctgctg tacaggatgt    3960
gggactagtt gttttaagaa atgtggcggt tgttttgatg attatactgg acaccaggag    4020
tttgtaatca aaacttcaca tgacgattaa tttcgt                              4056
```

<210> SEQ ID NO 17
<211> LENGTH: 1363
<212> TYPE: PRT
<213> ORGANISM: bovine coronavirus strain LY138

<400> SEQUENCE: 17

Met Phe Leu Ile Leu Leu Ile Ser Leu Pro Met Ala Leu Ala Val Ile
1               5                   10                  15

Gly Asp Leu Lys Cys Thr Thr Val Ser Ile Asn Asp Val Asp Thr Gly
                20                  25                  30

Val Pro Ser Val Ser Thr Asp Thr Val Asp Val Thr Asn Gly Leu Gly
            35                  40                  45

-continued

Thr Tyr Tyr Val Leu Asp Arg Val Tyr Leu Asn Thr Leu Leu Leu
 50                  55                  60

Asn Gly Tyr Tyr Pro Thr Ser Gly Ser Thr Tyr Arg Asn Met Ala Leu
 65                  70                  75                  80

Lys Gly Thr Leu Leu Leu Ser Thr Leu Trp Phe Lys Pro Pro Phe Leu
                 85                  90                  95

Ser Asp Phe Ile Asn Gly Ile Phe Ala Lys Val Lys Asn Thr Lys Val
            100                 105                 110

Ile Lys Asn Gly Val Met Tyr Ser Glu Phe Pro Ala Ile Thr Ile Gly
        115                 120                 125

Ser Thr Phe Val Asn Thr Ser Tyr Ser Val Val Gln Pro His Thr
    130                 135                 140

Thr Asn Leu Asp Asn Lys Leu Gln Gly Leu Leu Glu Ile Ser Val Cys
145                 150                 155                 160

Gln Tyr Thr Met Cys Glu Tyr Pro His Thr Ile Cys His Pro Asn Leu
                165                 170                 175

Gly Asn Arg Arg Ile Glu Leu Trp His Trp Asp Thr Gly Val Val Ser
            180                 185                 190

Cys Leu Tyr Lys Arg Asn Phe Thr Tyr Asp Val Asn Ala Asp Tyr Leu
        195                 200                 205

Tyr Phe His Phe Tyr Gln Glu Gly Gly Thr Phe Tyr Ala Tyr Phe Thr
    210                 215                 220

Asp Thr Gly Val Val Thr Lys Phe Leu Phe Asn Val Tyr Leu Gly Thr
225                 230                 235                 240

Val Leu Ser His Tyr Tyr Val Met Pro Leu Thr Cys Asn Ser Ala Met
                245                 250                 255

Thr Leu Glu Tyr Trp Val Thr Pro Leu Thr Ser Lys Gln Tyr Leu Leu
            260                 265                 270

Ala Phe Asn Gln Asp Gly Val Ile Phe Asn Ala Val Asp Cys Lys Ser
        275                 280                 285

Asp Phe Met Ser Glu Ile Lys Cys Lys Thr Leu Ser Ile Ala Pro Ser
    290                 295                 300

Thr Gly Val Tyr Glu Leu Asn Gly Tyr Thr Val Gln Pro Ile Ala Asp
305                 310                 315                 320

Val Tyr Arg Arg Ile Pro Asn Leu Pro Asp Cys Asn Ile Glu Ala Trp
                325                 330                 335

Leu Asn Asp Lys Ser Val Pro Ser Pro Leu Asn Trp Glu Arg Lys Thr
            340                 345                 350

Phe Ser Asn Cys Asn Phe Asn Met Ser Ser Leu Met Ser Phe Ile Gln
        355                 360                 365

Ala Asp Ser Phe Thr Cys Asn Asn Ile Asp Ala Ala Lys Ile Tyr Gly
    370                 375                 380

Met Cys Phe Ser Ser Ile Thr Ile Asp Lys Phe Ala Ile Pro Asn Gly
385                 390                 395                 400

Arg Lys Val Asp Leu Gln Leu Gly Asn Leu Gly Tyr Leu Gln Ser Phe
                405                 410                 415

Asn Tyr Arg Ile Asp Thr Thr Ala Thr Ser Cys Gln Leu Tyr Tyr Asn
            420                 425                 430

Leu Pro Ala Ala Asn Val Ser Val Ser Arg Phe Asn Pro Ser Thr Trp
        435                 440                 445

Asn Arg Arg Phe Gly Phe Thr Glu Gln Ser Val Phe Lys Pro Gln Pro
    450                 455                 460

Val Gly Val Phe Thr Asp His Asp Val Val Tyr Ala Gln His Cys Phe
465                 470                 475                 480

```
Lys Ala Pro Thr Asn Phe Cys Pro Cys Lys Leu Asp Gly Ser Leu Cys
                485                 490                 495

Val Gly Ser Gly Ser Gly Ile Asp Ala Gly Tyr Lys Asn Ser Gly Ile
            500                 505                 510

Gly Thr Cys Pro Ala Gly Thr Asn Tyr Leu Thr Cys His Asn Ala Ala
            515                 520                 525

Gln Cys Asn Cys Leu Cys Thr Pro Asp Pro Ile Thr Ser Lys Ser Thr
            530                 535                 540

Gly Pro Tyr Lys Cys Pro Gln Thr Lys Tyr Leu Val Gly Ile Gly Glu
545                 550                 555                 560

His Cys Ser Gly Leu Ala Ile Lys Ser Asp Tyr Cys Gly Gly Asn Pro
                565                 570                 575

Cys Thr Cys Gln Pro Gln Ala Phe Leu Gly Trp Ser Val Asp Ser Cys
            580                 585                 590

Leu Gln Gly Asp Arg Cys Asn Ile Phe Ala Asn Phe Ile Leu His Asp
            595                 600                 605

Val Asn Ser Gly Thr Thr Cys Ser Thr Asp Leu Gln Lys Ser Asn Thr
            610                 615                 620

Asp Ile Ile Leu Gly Val Cys Val Asn Tyr Asp Leu Tyr Gly Ile Thr
625                 630                 635                 640

Gly Gln Gly Ile Phe Val Glu Val Asn Ala Thr Tyr Tyr Asn Ser Trp
                645                 650                 655

Gln Asn Leu Leu Tyr Asp Ser Asn Gly Asn Leu Tyr Gly Phe Arg Asp
            660                 665                 670

Tyr Leu Thr Asn Arg Thr Phe Met Ile Arg Ser Cys Tyr Ser Gly Arg
            675                 680                 685

Val Ser Ala Ala Phe His Ala Asn Ser Ser Glu Pro Ala Leu Leu Phe
690                 695                 700

Arg Asn Ile Lys Cys Asn Tyr Val Phe Asn Asn Thr Leu Ser Arg Gln
705                 710                 715                 720

Leu Gln Pro Ile Asn Tyr Phe Asp Ser Tyr Leu Gly Cys Val Val Asn
                725                 730                 735

Ala Asp Asn Ser Thr Ser Ser Ala Val Gln Thr Cys Asp Leu Thr Val
            740                 745                 750

Gly Ser Gly Tyr Cys Val Asp Tyr Ser Thr Lys Arg Arg Ser Arg Arg
            755                 760                 765

Ala Ile Thr Thr Gly Tyr Arg Phe Thr Asn Phe Glu Pro Phe Thr Val
770                 775                 780

Asn Ser Val Asn Asp Ser Leu Glu Pro Val Gly Gly Leu Tyr Glu Ile
785                 790                 795                 800

Gln Ile Pro Ser Glu Phe Thr Ile Gly Asn Met Glu Glu Phe Ile Gln
                805                 810                 815

Ile Ser Ser Pro Lys Val Thr Ile Asp Cys Ser Ala Phe Val Cys Gly
            820                 825                 830

Asp Tyr Ala Ala Cys Lys Ser Gln Leu Val Glu Tyr Gly Ser Phe Cys
            835                 840                 845

Asp Asn Ile Asn Ala Ile Leu Thr Glu Val Asn Glu Leu Leu Asp Thr
            850                 855                 860

Thr Gln Leu Gln Val Ala Asn Ser Leu Met Asn Gly Val Thr Leu Ser
865                 870                 875                 880

Thr Lys Leu Lys Asp Gly Val Asn Phe Asn Val Asp Asp Ile Asn Phe
                885                 890                 895

Ser Pro Val Leu Gly Cys Leu Gly Ser Asp Cys Asn Lys Val Ser Ser
```

```
                      900             905             910
Arg Ser Ala Ile Glu Asp Leu Leu Phe Ser Lys Val Lys Leu Ser Asp
        915             920             925
Val Gly Phe Val Glu Ala Tyr Asn Asn Cys Thr Gly Gly Ala Glu Ile
        930             935             940
Arg Asp Leu Ile Cys Val Gln Ser Tyr Asn Gly Ile Lys Val Leu Pro
945             950             955             960
Pro Leu Leu Ser Glu Asn Gln Ile Ser Gly Tyr Thr Leu Ala Ala Thr
            965             970             975
Ser Ala Ser Leu Phe Pro Pro Trp Ser Ala Ala Gly Val Pro Phe
            980             985             990
Tyr Leu Asn Val Gln Tyr Arg Ile Asn Gly Ile Gly Val Thr Met Asp
            995             1000            1005
Val Leu Ser Gln Asn Gln Lys Leu Ile Ala Asn Ala Phe Asn Asn
        1010            1015            1020
Ala Leu Asp Ala Ile Gln Glu Gly Phe Asp Ala Thr Asn Ser Ala
        1025            1030            1035
Leu Val Lys Ile Gln Ala Val Val Asn Ala Asn Ala Glu Ala Leu
        1040            1045            1050
Asn Asn Leu Leu Gln Gln Leu Ser Asn Arg Phe Gly Ala Ile Ser
        1055            1060            1065
Ser Ser Leu Gln Glu Ile Leu Ser Arg Leu Asp Ala Leu Glu Ala
        1070            1075            1080
Gln Ala Gln Ile Asp Arg Leu Ile Asn Gly Arg Leu Thr Ala Leu
        1085            1090            1095
Asn Ala Tyr Val Ser Gln Gln Leu Ser Asp Ser Thr Leu Val Lys
        1100            1105            1110
Phe Ser Ala Ala Gln Ala Met Glu Lys Val Asn Glu Cys Val Lys
        1115            1120            1125
Ser Gln Ser Ser Arg Ile Asn Phe Cys Gly Asn Gly Asn His Ile
        1130            1135            1140
Ile Ser Leu Val Gln Asn Ala Pro Tyr Gly Leu Tyr Phe Ile His
        1145            1150            1155
Phe Ser Tyr Val Pro Thr Lys Tyr Val Thr Ala Lys Val Ser Pro
        1160            1165            1170
Gly Leu Cys Ile Ala Gly Asp Arg Gly Ile Ala Pro Lys Ser Gly
        1175            1180            1185
Tyr Phe Val Asn Val Asn Asn Thr Trp Met Phe Thr Gly Ser Gly
        1190            1195            1200
Tyr Tyr Tyr Pro Glu Pro Ile Thr Gly Asn Asn Val Val Val Met
        1205            1210            1215
Ser Thr Cys Ala Val Asn Tyr Thr Lys Ala Pro Asp Val Met Leu
        1220            1225            1230
Asn Ile Ser Thr Pro Asn Leu Pro Asp Phe Lys Glu Glu Leu Asp
        1235            1240            1245
Gln Trp Phe Lys Asn Gln Thr Ser Val Ala Pro Asp Leu Ser Leu
        1250            1255            1260
Asp Tyr Ile Asn Val Thr Phe Leu Asp Leu Gln Asp Glu Met Asn
        1265            1270            1275
Arg Leu Gln Glu Ala Ile Lys Val Leu Asn Gln Ser Tyr Ile Asn
        1280            1285            1290
Leu Lys Asp Ile Gly Thr Tyr Glu Tyr Tyr Val Lys Trp Pro Trp
        1295            1300            1305
```

-continued

```
Tyr Val Trp Leu Leu Ile Gly Leu Ala Gly Val Ala Met Leu Val
    1310                1315                1320

Leu Leu Phe Phe Ile Cys Cys Cys Thr Gly Cys Gly Thr Ser Cys
    1325                1330                1335

Phe Lys Lys Cys Gly Gly Cys Cys Asp Asp Tyr Thr Gly His Gln
    1340                1345                1350

Glu Leu Val Ile Lys Thr Ser His Asp Asp
    1355                1360

<210> SEQ ID NO 18
<211> LENGTH: 1363
<212> TYPE: PRT
<213> ORGANISM: human coronavirus strain OC43

<400> SEQUENCE: 18

Met Phe Leu Ile Leu Leu Ile Ser Leu Pro Thr Ala Phe Ala Val Ile
1               5                   10                  15

Gly Asp Leu Lys Cys Thr Thr Val Ser Ile Asn Asp Ile Asp Thr Gly
            20                  25                  30

Ala Pro Ser Ile Ser Thr Asp Ile Val Asp Val Thr Asn Gly Leu Gly
        35                  40                  45

Thr Tyr Tyr Val Leu Asp Arg Val Tyr Leu Asn Thr Thr Leu Leu Leu
    50                  55                  60

Asn Gly Tyr Tyr Pro Thr Ser Gly Ser Thr Tyr Arg Asn Met Ala Leu
65                  70                  75                  80

Lys Gly Thr Leu Leu Leu Ser Arg Leu Trp Phe Lys Pro Pro Phe Leu
                85                  90                  95

Ser Asp Phe Ile Asn Gly Ile Phe Ala Lys Val Lys Asn Thr Lys Val
            100                 105                 110

Ile Lys Lys Gly Val Met Tyr Ser Glu Phe Pro Ala Ile Thr Ile Gly
        115                 120                 125

Ser Thr Phe Val Asn Thr Ser Tyr Ser Val Val Val Gln Pro His Thr
    130                 135                 140

Thr Asn Leu Asp Asn Lys Leu Gln Gly Leu Leu Glu Ile Ser Val Cys
145                 150                 155                 160

Gln Tyr Thr Met Cys Glu Tyr Pro His Thr Ile Cys His Pro Asn Leu
                165                 170                 175

Gly Asn Arg Arg Val Glu Leu Trp His Trp Asp Thr Gly Val Val Ser
            180                 185                 190

Cys Leu Tyr Lys Arg Asn Phe Thr Tyr Asp Val Asn Ala Asp Tyr Leu
        195                 200                 205

Tyr Phe His Phe Tyr Gln Glu Gly Gly Thr Phe Tyr Ala Tyr Phe Thr
    210                 215                 220

Asp Thr Gly Val Val Thr Lys Phe Leu Phe Asn Val Tyr Leu Gly Thr
225                 230                 235                 240

Val Leu Ser His Tyr Tyr Val Leu Pro Leu Thr Cys Asn Ser Ala Met
                245                 250                 255

Thr Leu Glu Tyr Trp Val Thr Pro Leu Thr Ser Lys Gln Tyr Leu Leu
            260                 265                 270

Ala Phe Asn Gln Asp Gly Val Ile Phe Asn Ala Val Asp Cys Lys Ser
        275                 280                 285

Asp Phe Met Ser Glu Ile Lys Cys Lys Thr Leu Ser Ile Ala Pro Ser
    290                 295                 300

Thr Gly Val Tyr Glu Leu Asn Gly Tyr Thr Val Gln Pro Ile Ala Asp
305                 310                 315                 320
```

```
Val Tyr Arg Arg Ile Pro Asn Leu Pro Asp Cys Asn Ile Glu Ala Trp
                325                 330                 335

Leu Asn Asp Lys Ser Val Pro Ser Pro Leu Asn Trp Glu Arg Lys Thr
            340                 345                 350

Phe Ser Asn Cys Asn Phe Asn Met Ser Ser Leu Met Ser Phe Ile Gln
        355                 360                 365

Ala Asp Ser Phe Thr Cys Asn Asn Ile Asp Ala Ala Lys Ile Tyr Gly
    370                 375                 380

Met Cys Phe Ser Ser Ile Thr Ile Asp Lys Phe Ala Ile Pro Asn Gly
385                 390                 395                 400

Arg Lys Val Asp Leu Gln Leu Gly Asn Leu Gly Tyr Leu Gln Ser Phe
                405                 410                 415

Asn Tyr Arg Ile Asp Thr Thr Ala Thr Ser Cys Gln Leu Tyr Tyr Asn
            420                 425                 430

Leu Pro Ala Ala Asn Val Ser Val Ser Arg Phe Asn Pro Ser Thr Trp
        435                 440                 445

Asn Arg Arg Phe Gly Phe Thr Glu Gln Ser Val Phe Lys Pro Gln Pro
    450                 455                 460

Val Gly Val Phe Thr His His Asp Val Val Tyr Ala Gln His Cys Phe
465                 470                 475                 480

Lys Ala Pro Thr Asn Phe Cys Pro Cys Lys Leu Asp Gly Ser Leu Cys
                485                 490                 495

Val Gly Asn Gly Pro Gly Ile Asp Ala Gly Tyr Lys Asn Ser Gly Ile
            500                 505                 510

Gly Thr Cys Pro Ala Gly Thr Asn Tyr Leu Thr Cys His Asn Ala Ala
        515                 520                 525

Gln Cys Asp Cys Leu Cys Thr Pro Asp Pro Ile Thr Ser Lys Ser Thr
    530                 535                 540

Gly Pro Tyr Lys Cys Pro Gln Thr Lys Tyr Leu Val Gly Ile Gly Glu
545                 550                 555                 560

His Cys Ser Gly Leu Ala Ile Lys Ser Asp Tyr Cys Gly Gly Asn Pro
                565                 570                 575

Cys Thr Cys Gln Pro Gln Ala Phe Leu Gly Trp Ser Val Asp Ser Cys
            580                 585                 590

Leu Gln Gly Asp Arg Cys Asn Ile Phe Ala Asn Phe Ile Leu His Asp
        595                 600                 605

Val Asn Ser Gly Thr Thr Cys Ser Thr Asp Leu Gln Lys Ser Asn Thr
    610                 615                 620

Asp Ile Ile Leu Gly Val Cys Val Asn Tyr Asp Leu Tyr Gly Ile Thr
625                 630                 635                 640

Gly Gln Gly Ile Phe Val Glu Val Asn Ala Pro Tyr Tyr Asn Ser Trp
                645                 650                 655

Gln Asn Leu Leu Tyr Asp Ser Asn Gly Asn Leu Tyr Gly Phe Arg Asp
            660                 665                 670

Tyr Leu Thr Asn Arg Thr Phe Met Ile Arg Ser Cys Tyr Ser Gly Arg
        675                 680                 685

Val Ser Ala Ala Phe His Ala Asn Ser Ser Glu Pro Ala Leu Leu Phe
    690                 695                 700

Arg Asn Ile Lys Cys Ser Tyr Val Phe Asn Asn Thr Leu Ser Arg Gln
705                 710                 715                 720

Leu Gln Pro Ile Asn Tyr Phe Asp Ser Tyr Leu Gly Cys Val Val Asn
                725                 730                 735

Ala Asp Asn Ser Thr Ser Ser Val Val Gln Thr Cys Asp Leu Thr Val
            740                 745                 750
```

```
Gly Ser Gly Tyr Cys Val Asp Tyr Ser Thr Lys Arg Arg Ser Arg Arg
            755                 760                 765

Ala Ile Thr Thr Gly Tyr Arg Phe Thr Asn Phe Glu Pro Phe Thr Val
            770                 775                 780

Asn Ser Val Asn Asp Ser Leu Glu Pro Val Gly Gly Leu Tyr Glu Ile
785                 790                 795                 800

Gln Ile Pro Ser Glu Phe Thr Ile Gly Asn Met Glu Glu Phe Ile Gln
                805                 810                 815

Thr Ser Ser Pro Lys Val Thr Ile Asp Cys Ser Ala Phe Val Cys Gly
                820                 825                 830

Asp Tyr Ala Ala Cys Lys Ser Gln Leu Val Glu Tyr Gly Ser Phe Cys
            835                 840                 845

Asp Asn Ile Asn Ala Ile Leu Thr Glu Val Asn Glu Leu Leu Asp Thr
850                 855                 860

Thr Gln Leu Gln Val Ala Asn Ser Leu Met Asn Gly Val Thr Leu Ser
865                 870                 875                 880

Thr Lys Leu Lys Asp Gly Val Asn Phe Asn Val Asp Asp Ile Asn Phe
                885                 890                 895

Ser Pro Val Leu Gly Cys Leu Gly Ser Ala Cys Asn Lys Val Ser Ser
                900                 905                 910

Arg Ser Ala Ile Glu Asp Leu Leu Phe Ser Lys Val Lys Leu Ser Asp
            915                 920                 925

Val Gly Phe Val Glu Ala Tyr Asn Asn Cys Thr Gly Gly Ala Glu Ile
            930                 935                 940

Arg Asp Leu Ile Cys Val Gln Ser Tyr Asn Gly Ile Lys Val Leu Pro
945                 950                 955                 960

Pro Leu Leu Ser Val Asn Gln Ile Ser Gly Tyr Thr Leu Ala Ala Thr
                965                 970                 975

Ser Ala Ser Leu Phe Pro Pro Trp Ser Ala Ala Gly Val Pro Phe
                980                 985                 990

Tyr Leu Asn Val Gln Tyr Arg Ile Asn Gly Ile Gly Val Thr Met Asp
            995                 1000                1005

Val Leu Ser Gln Asn Gln Lys Leu Ile Ala Asn Ala Phe Ser Asn
            1010                1015                1020

Ala Leu Asp Ala Ile Gln Glu Gly Phe Asp Ala Thr Asn Ser Ala
            1025                1030                1035

Leu Val Lys Ile Gln Ala Val Val Asn Ala Asn Ala Glu Ala Leu
            1040                1045                1050

Asn Asn Leu Leu Gln Gln Leu Ser Asn Arg Phe Gly Ala Ile Gly
            1055                1060                1065

Ser Ser Leu Gln Glu Ile Leu Ser Arg Leu Asp Ala Leu Glu Ala
            1070                1075                1080

Gln Ala Gln Ile Asp Arg Leu Ile Asn Gly Arg Leu Thr Ala Leu
            1085                1090                1095

Asn Ala Tyr Val Ser Gln Gln Leu Ser Asp Ser Thr Leu Val Lys
            1100                1105                1110

Phe Ser Ala Ala Gln Ala Met Glu Lys Val Asn Glu Cys Val Lys
            1115                1120                1125

Ser Gln Ser Ser Arg Ile Asn Phe Cys Gly Asn Gly Asn His Ile
            1130                1135                1140

Ile Ser Leu Val Gln Asn Ala Pro Tyr Gly Leu Tyr Phe Ile His
            1145                1150                1155

Phe Ser Tyr Val Pro Thr Lys Tyr Val Thr Ala Lys Val Ser Pro
```

-continued

```
                1160                1165                1170

Gly Leu Cys Ile Ala Gly Asp Arg Gly Ile Ala Pro Lys Ser Gly
            1175                1180                1185

Tyr Phe Val Asn Val Asn Asn Thr Trp Met Phe Thr Gly Ser Gly
            1190                1195                1200

Tyr Tyr Tyr Pro Glu Pro Ile Thr Gly Asn Asn Val Val Val Met
            1205                1210                1215

Ser Thr Cys Ala Val Asn Tyr Thr Lys Ala Pro Asp Val Met Leu
            1220                1225                1230

Asn Ile Ser Thr Pro Asn Leu His Asp Phe Lys Glu Glu Leu Asp
            1235                1240                1245

Gln Trp Phe Lys Asn Gln Thr Ser Val Ala Pro Asp Leu Ser Leu
            1250                1255                1260

Asp Tyr Ile Asn Val Thr Phe Leu Asp Leu Gln Asp Glu Met Asn
            1265                1270                1275

Arg Leu Gln Glu Ala Ile Lys Val Leu Asn Gln Ser Tyr Ile Asn
            1280                1285                1290

Leu Lys Asp Ile Gly Thr Tyr Glu Tyr Tyr Val Lys Trp Pro Trp
            1295                1300                1305

Tyr Val Trp Leu Leu Ile Gly Phe Ala Gly Val Ala Met Leu Val
            1310                1315                1320

Leu Leu Phe Phe Ile Cys Cys Cys Thr Gly Cys Gly Thr Ser Cys
            1325                1330                1335

Phe Lys Ile Cys Gly Gly Cys Cys Asp Asp Tyr Thr Gly His Gln
            1340                1345                1350

Glu Leu Val Ile Lys Thr Ser His Asp Asp
            1355                1360

<210> SEQ ID NO 19
<211> LENGTH: 1349
<212> TYPE: PRT
<213> ORGANISM: hemagglutinating encephalomyelitis virus

<400> SEQUENCE: 19

Met Phe Phe Ile Leu Leu Ile Thr Leu Pro Ser Val Phe Ala Val Ile
1               5                   10                  15

Gly Asp Leu Lys Cys Asn Thr Ser Ile Asn Asp Val Asp Thr Gly
            20                  25                  30

Val Pro Ser Ile Ser Ser Glu Val Val Asp Val Thr Asn Gly Leu Gly
        35                  40                      45

Thr Phe Tyr Val Leu Asp Arg Val Tyr Leu Asn Thr Thr Leu Leu Leu
50                  55                      60

Asn Gly Tyr Tyr Pro Ile Ser Gly Ala Thr Phe Arg Asn Val Ala Leu
65                  70                      75                  80

Lys Gly Thr Arg Leu Leu Ser Thr Leu Trp Phe Lys Pro Pro Phe Leu
                85                  90                      95

Ser Pro Phe Asn Asp Gly Ile Phe Ala Lys Val Lys Asn Ser Arg Phe
            100                 105                 110

Ser Lys His Gly Val Ile Tyr Ser Glu Phe Pro Ala Ile Thr Ile Gly
        115                 120                     125

Ser Thr Phe Val Asn Thr Ser Tyr Ser Ile Val Val Lys Pro His Thr
    130                 135                     140

Ser Phe Ile Asn Gly Asn Leu Gln Gly Phe Leu Gln Ile Ser Val Cys
145                 150                     155                 160

Gln Tyr Thr Met Cys Glu Tyr Pro Gln Thr Ile Cys His Pro Asn Leu
```

```
                    165                 170                 175
Gly Asn Gln Arg Ile Glu Leu Trp His His Asp Thr Asp Val Val Ser
            180                 185                 190

Cys Leu Tyr Arg Arg Asn Phe Thr Tyr Asp Val Asn Ala Asp Tyr Leu
            195                 200                 205

Tyr Phe His Phe Tyr Gln Glu Gly Thr Phe Tyr Ala Tyr Phe Thr
            210                 215                 220

Asp Thr Gly Phe Val Thr Lys Phe Leu Phe Lys Leu Tyr Leu Gly Thr
225                 230                 235                 240

Val Leu Ser His Tyr Tyr Val Met Pro Leu Thr Cys Asp Ser Ala Leu
                245                 250                 255

Ser Leu Glu Tyr Trp Val Thr Pro Leu Thr Thr Arg Gln Phe Leu Leu
                260                 265                 270

Ala Phe Asp Gln Asp Gly Val Leu Tyr His Ala Val Asp Cys Ala Ser
                275                 280                 285

Asp Phe Met Ser Glu Ile Met Cys Lys Thr Ser Ile Thr Pro Pro
            290                 295                 300

Thr Gly Val Tyr Glu Leu Asn Gly Tyr Thr Val Gln Pro Val Ala Thr
305                 310                 315                 320

Val Tyr Arg Arg Ile Pro Asp Leu Pro Asn Cys Asp Ile Glu Ala Trp
                325                 330                 335

Leu Asn Ser Lys Thr Val Ser Ser Pro Leu Asn Trp Glu Arg Lys Ile
                340                 345                 350

Phe Ser Asn Cys Asn Phe Asn Met Gly Arg Leu Met Ser Phe Ile Gln
            355                 360                 365

Ala Asp Ser Phe Gly Cys Asn Asn Ile Asp Ala Ser Arg Leu Tyr Gly
            370                 375                 380

Met Cys Phe Gly Ser Ile Thr Ile Asp Lys Phe Ala Ile Pro Asn Ser
385                 390                 395                 400

Arg Lys Val Asp Leu Gln Val Gly Lys Ser Gly Tyr Leu Gln Ser Phe
                405                 410                 415

Asn Tyr Lys Ile Asp Thr Ala Val Ser Ser Cys Gln Leu Tyr Tyr Ser
                420                 425                 430

Leu Pro Ala Ala Asn Val Ser Val Thr His Tyr Asn Pro Ser Ser Trp
            435                 440                 445

Asn Arg Arg Tyr Gly Phe Ile Asn Gln Ser Phe Gly Ser Arg Gly Leu
            450                 455                 460

His Asp Ala Val Tyr Ser Gln Gln Cys Phe Asn Thr Pro Asn Thr Tyr
465                 470                 475                 480

Cys Pro Cys Arg Thr Ser Gln Cys Ile Gly Gly Ala Gly Thr Gly Thr
                485                 490                 495

Cys Pro Val Gly Thr Thr Val Arg Lys Cys Phe Ala Ala Val Thr Asn
            500                 505                 510

Ala Thr Lys Cys Thr Cys Trp Cys Gln Pro Asp Pro Ser Thr Tyr Lys
            515                 520                 525

Gly Val Asn Ala Trp Thr Cys Pro Gln Ser Lys Val Ser Ile Gln Pro
530                 535                 540

Gly Gln His Cys Pro Gly Leu Gly Leu Val Glu Asp Asp Cys Ser Gly
545                 550                 555                 560

Asn Pro Cys Thr Cys Lys Pro Gln Ala Phe Ile Gly Trp Ser Ser Glu
                565                 570                 575

Thr Cys Leu Gln Asn Gly Arg Cys Asn Ile Phe Ala Asn Phe Ile Leu
                580                 585                 590
```

-continued

```
Asn Asp Val Asn Ser Gly Thr Thr Cys Ser Thr Asp Leu Gln Gln Gly
        595                 600                 605

Asn Thr Asn Ile Thr Thr Asp Val Cys Val Asn Tyr Asp Leu Tyr Gly
610                 615                 620

Ile Thr Gly Gln Gly Ile Leu Ile Glu Val Asn Ala Thr Tyr Tyr Asn
625                 630                 635                 640

Ser Trp Gln Asn Leu Leu Tyr Asp Ser Gly Asn Leu Tyr Gly Phe
            645                 650                 655

Arg Asp Tyr Leu Ser Asn Arg Thr Phe Leu Ile Arg Ser Cys Tyr Ser
                660                 665                 670

Gly Arg Val Ser Ala Val Phe His Ala Asn Ser Ser Glu Pro Ala Leu
                675                 680                 685

Met Phe Arg Asn Leu Lys Cys Ser His Val Phe Asn Tyr Thr Ile Leu
690                 695                 700

Arg Gln Ile Gln Leu Val Asn Tyr Phe Asp Ser Tyr Leu Gly Cys Val
705                 710                 715                 720

Val Asn Ala Tyr Asn Asn Thr Ala Ser Ala Val Ser Thr Cys Asp Leu
                725                 730                 735

Thr Val Gly Ser Gly Tyr Cys Val Asp Tyr Val Thr Ala Leu Arg Ser
            740                 745                 750

Arg Arg Ser Phe Thr Thr Gly Tyr Arg Phe Thr Asn Phe Glu Pro Phe
        755                 760                 765

Ala Ala Asn Leu Val Asn Asp Ser Ile Glu Pro Val Gly Gly Leu Tyr
770                 775                 780

Glu Ile Gln Ile Pro Ser Glu Phe Thr Ile Gly Asn Leu Glu Glu Phe
785                 790                 795                 800

Ile Gln Thr Ser Ser Pro Lys Val Thr Ile Asp Cys Ala Thr Phe Val
            805                 810                 815

Cys Gly Asp Tyr Ala Ala Cys Arg Gln Gln Leu Ala Glu Tyr Gly Ser
                820                 825                 830

Phe Cys Glu Asn Ile Asn Ala Ile Leu Ile Glu Val Asn Glu Leu Leu
                835                 840                 845

Asp Thr Thr Gln Leu Gln Val Ala Asn Ser Leu Met Asn Gly Val Thr
    850                 855                 860

Leu Ser Thr Lys Ile Lys Asp Gly Ile Asn Phe Asn Val Asp Asp Ile
865                 870                 875                 880

Asn Phe Ser Ser Val Leu Gly Cys Leu Gly Ser Glu Cys Asn Arg Ala
            885                 890                 895

Ser Thr Arg Ser Ala Ile Glu Asp Leu Leu Phe Asp Lys Val Lys Leu
                900                 905                 910

Ser Asp Val Gly Phe Val Gln Ala Tyr Asn Asn Cys Thr Gly Gly Ala
            915                 920                 925

Glu Ile Arg Asp Leu Ile Cys Val Gln Ser Tyr Asn Gly Ile Lys Val
930                 935                 940

Leu Pro Pro Leu Leu Ser Glu Asn Gln Ile Ser Gly Tyr Thr Ser Ala
945                 950                 955                 960

Ala Thr Ala Ala Ser Leu Phe Pro Pro Trp Thr Ala Ala Ala Gly Val
                965                 970                 975

Pro Phe Tyr Leu Asn Val Gln Tyr Arg Ile Asn Gly Leu Gly Val Thr
            980                 985                 990

Met Asp Val Leu Ser Gln Asn Gln  Lys Leu Ile Ala Ser  Ala Phe Asn
        995                 1000                1005

Asn Ala  Leu Asp Ser Ile Gln  Glu Gly Phe Asp Ala  Thr Asn Ser
    1010                1015                1020
```

```
Ala Leu Val Lys Ile Gln Ala Val Asn Ala Asn Ala Glu Ala
    1025                1030                1035
Leu Asn Asn Leu Leu Gln Gln Leu Ser Asn Arg Phe Gly Ala Ile
1040                1045                1050
Ser Ala Ser Leu Gln Glu Ile Leu Ser Arg Leu Asp Ala Leu Glu
    1055                1060                1065
Ala Lys Ala Gln Ile Asp Arg Leu Ile Asn Gly Arg Leu Thr Ala
    1070                1075                1080
Leu Asn Ala Tyr Val Ser Gln Gln Leu Ser Asp Ser Thr Leu Val
    1085                1090                1095
Lys Phe Ser Ala Ala Gln Ala Ile Glu Lys Val Asn Glu Cys Val
    1100                1105                1110
Lys Ser Gln Ser Ser Arg Ile Asn Phe Cys Gly Asn Gly Asn His
    1115                1120                1125
Ile Ile Ser Leu Val Gln Asn Ala Pro Tyr Gly Leu Tyr Phe Ile
    1130                1135                1140
His Phe Ser Tyr Val Pro Thr Lys Tyr Val Thr Ala Lys Val Ser
    1145                1150                1155
Pro Gly Leu Cys Ile Ala Gly Asp Ile Gly Ile Ser Pro Lys Ser
    1160                1165                1170
Gly Tyr Phe Ile Asn Val Asn Asn Ser Trp Met Phe Thr Gly Ser
    1175                1180                1185
Gly Tyr Tyr Tyr Pro Glu Pro Ile Thr Gln Asn Asn Val Val Val
    1190                1195                1200
Met Ser Thr Cys Ala Val Asn Tyr Thr Lys Ala Pro Asp Leu Met
    1205                1210                1215
Leu Asn Thr Ser Thr Pro Asn Leu Pro Asp Phe Lys Glu Glu Leu
    1220                1225                1230
Tyr Gln Trp Phe Lys Asn Gln Ser Ser Leu Ala Pro Asp Leu Ser
    1235                1240                1245
Phe Asp Tyr Ile Asn Val Thr Phe Leu Asp Leu Gln Asp Glu Met
    1250                1255                1260
Asn Arg Leu Gln Glu Ala Ile Lys Val Leu Asn His Ser Tyr Ile
    1265                1270                1275
Asn Leu Lys Asp Ile Gly Thr Tyr Glu Tyr Tyr Val Lys Trp Pro
    1280                1285                1290
Trp Tyr Val Trp Leu Leu Ile Cys Leu Ala Gly Val Val Met Leu
    1295                1300                1305
Val Leu Leu Phe Phe Ile Cys Cys Cys Thr Gly Cys Gly Thr Ser
    1310                1315                1320
Cys Phe Lys Lys Cys Gly Gly Cys Phe Asp Asp Tyr Thr Gly His
    1325                1330                1335
Gln Glu Phe Val Ile Lys Thr Ser His Asp Asp
    1340                1345

<210> SEQ ID NO 20
<211> LENGTH: 1453
<212> TYPE: PRT
<213> ORGANISM: canine enteric coronavirus

<400> SEQUENCE: 20

Met Ile Val Leu Val Thr Cys Ile Leu Leu Leu Cys Ser Tyr His Thr
1               5                   10                  15

Ala Ser Ser Thr Ser Asn Asn Asp Cys Arg Gln Val Asn Val Thr Gln
            20                  25                  30
```

Leu Asp Gly Asn Glu Asn Leu Ile Arg Asp Phe Leu Phe Gln Asn Phe
         35                  40                  45

Lys Glu Glu Gly Thr Val Val Gly Gly Tyr Tyr Pro Thr Glu Val
 50                  55                  60

Trp Tyr Asn Cys Ser Arg Thr Ala Thr Thr Ala Tyr Glu Tyr Phe
 65                  70                  75                  80

Ser Asn Ile His Ala Phe Tyr Phe Asp Met Glu Ala Met Glu Asn Ser
                 85                  90                  95

Thr Gly Asn Ala Arg Gly Lys Pro Leu Leu Phe His Val His Gly Glu
             100                 105                 110

Pro Val Ser Val Ile Ile Tyr Ile Ser Tyr Arg Asp Val Gln His
         115                 120                 125

Arg Pro Leu Leu Lys His Gly Leu Val Cys Ile Thr Glu Ser Arg Asn
         130                 135                 140

Ile Asp Tyr Asn Ser Phe Thr Ser Ser Gln Trp Asn Ser Ile Cys Thr
145                 150                 155                 160

Gly Asn Asp Arg Lys Ile Pro Phe Ser Val Ile Pro Thr Asp Asn Gly
                 165                 170                 175

Thr Lys Ile Tyr Gly Leu Glu Trp Asn Asp Glu Phe Val Thr Ala Tyr
             180                 185                 190

Ile Ser Gly Arg Ser Tyr Asn Trp Asn Ile Asn Asn Asn Trp Phe Asn
             195                 200                 205

Asn Val Thr Leu Leu Tyr Ser Arg Ser Ser Thr Ala Thr Trp Gln His
         210                 215                 220

Ser Ala Ala Tyr Val Tyr Gln Gly Val Ser Asn Phe Thr Tyr Tyr Lys
225                 230                 235                 240

Leu Asn Asn Thr Asn Gly Leu Lys Thr Tyr Glu Leu Cys Glu Asp Tyr
                 245                 250                 255

Glu Tyr Cys Thr Gly Tyr Ala Thr Asn Ile Phe Ala Pro Thr Val Gly
             260                 265                 270

Gly Tyr Ile Pro Asp Gly Phe Ser Phe Asn Asn Trp Phe Leu Leu Thr
             275                 280                 285

Asn Ser Ser Thr Phe Val Ser Gly Arg Phe Val Thr Asn Gln Pro Leu
         290                 295                 300

Leu Val Asn Cys Leu Trp Pro Val Pro Ser Phe Gly Val Ala Ala Gln
305                 310                 315                 320

Glu Phe Cys Phe Glu Gly Ala Gln Phe Ser Gln Cys Asn Gly Val Phe
                 325                 330                 335

Leu Asn Asn Thr Val Asp Val Ile Arg Phe Asn Leu Asn Phe Thr Ala
                 340                 345                 350

Asp Val Gln Ser Gly Met Gly Ala Thr Val Phe Ser Leu Asn Thr Thr
             355                 360                 365

Gly Gly Cys Ile Leu Glu Ile Ser Cys Tyr Asn Asp Ile Val Ser Glu
         370                 375                 380

Ser Ser Phe Tyr Ser Tyr Gly Glu Ile Pro Phe Gly Val Thr Asp Gly
385                 390                 395                 400

Pro Arg Tyr Cys Tyr Val Leu Tyr Asn Gly Thr Ala Leu Lys Tyr Phe
                 405                 410                 415

Gly Thr Leu Pro Pro Ser Val Lys Glu Ile Ala Ile Ser Lys Trp Gly
             420                 425                 430

Gln Phe Tyr Ile Asn Gly Tyr Asn Phe Phe Ser Thr Phe Pro Ile Asp
             435                 440                 445

Cys Ile Ser Phe Asn Leu Thr Thr Gly Asp Ser Gly Ala Phe Trp Thr

```
              450                 455                 460
Ile Ala Tyr Thr Ser Tyr Thr Glu Ala Leu Val Gln Val Glu Asn Thr
465                 470                 475                 480

Ala Ile Lys Lys Val Thr Tyr Cys Asn Ser His Ile Asn Asn Ile Lys
                485                 490                 495

Cys Ser Gln Leu Thr Ala Asn Leu Gln Asn Gly Phe Tyr Pro Val Ala
                500                 505                 510

Ser Ser Glu Val Gly Leu Val Asn Lys Ser Val Leu Leu Pro Ser
                515                 520                 525

Phe Tyr Ser His Thr Ser Val Asn Ile Thr Ile Asp Leu Gly Met Lys
                530                 535                 540

Arg Ser Gly Tyr Gly Gln Pro Ile Ala Ser Thr Leu Ser Asn Ile Thr
545                 550                 555                 560

Leu Pro Met Gln Asp Asn Thr Asp Val Tyr Cys Ile Arg Ser Asn
                565                 570                 575

Gln Phe Ser Val Tyr Val His Ser Thr Cys Lys Ser Ser Leu Trp Asp
                580                 585                 590

Asn Asn Phe Asn Gln Asp Cys Thr Asp Val Leu Tyr Ala Thr Ala Val
                595                 600                 605

Ile Lys Thr Gly Thr Cys Pro Phe Ser Phe Asp Lys Leu Asn Asn Tyr
                610                 615                 620

Leu Thr Phe Asn Lys Leu Cys Leu Ser Leu Asn Pro Thr Gly Ala Asn
625                 630                 635                 640

Cys Lys Phe Asp Val Ala Ala Arg Thr Arg Thr Asn Glu Gln Val Val
                645                 650                 655

Arg Ser Leu Tyr Val Ile Tyr Glu Glu Gly Asp Asn Ile Val Gly Val
                660                 665                 670

Pro Ser Asp Asn Ser Gly Leu His Asp Leu Ser Val Leu His Leu Asp
                675                 680                 685

Ser Cys Thr Asp Tyr Asn Ile Tyr Gly Arg Thr Gly Val Gly Ile Ile
                690                 695                 700

Arg Gln Thr Asn Ser Thr Ile Leu Ser Gly Leu His Tyr Thr Ser Leu
705                 710                 715                 720

Ser Gly Asp Leu Leu Gly Phe Lys Asn Val Ser Asp Gly Val Val Tyr
                725                 730                 735

Ser Val Thr Pro Cys Asp Val Ser Ala Gln Ala Ala Val Ile Asp Gly
                740                 745                 750

Ala Ile Val Gly Ala Met Thr Ser Ile Asn Ser Glu Leu Leu Gly Leu
                755                 760                 765

Thr His Trp Thr Thr Thr Pro Asn Phe Tyr Tyr Tyr Ser Ile Tyr Asn
770                 775                 780

Thr Thr Asn Glu Arg Thr Arg Gly Thr Ala Ile Asp Ser Asn Asp Val
785                 790                 795                 800

Asp Cys Glu Pro Ile Ile Thr Tyr Ser Asn Ile Gly Val Cys Lys Asn
                805                 810                 815

Gly Ala Leu Val Phe Ile Asn Val Thr His Ser Asp Gly Asp Val Gln
                820                 825                 830

Pro Ile Ser Thr Gly Asn Val Thr Ile Pro Thr Asn Phe Thr Ile Ser
                835                 840                 845

Val Gln Val Glu Tyr Ile Gln Val Tyr Thr Thr Pro Val Ser Ile Asp
                850                 855                 860

Cys Ser Arg Tyr Val Cys Asn Gly Asn Pro Arg Cys Asn Lys Leu Leu
865                 870                 875                 880
```

```
Thr Gln Tyr Val Ser Ala Cys Gln Thr Ile Glu Gln Ala Leu Ala Met
            885                 890                 895

Ser Ala Ser Leu Glu Asn Met Glu Val Asp Ser Met Leu Phe Val Ser
            900                 905                 910

Glu Asn Ala Leu Lys Leu Ala Ser Val Glu Ala Phe Asn Ser Thr Glu
            915                 920                 925

His Leu Asp Pro Ile Tyr Lys Glu Trp Pro Asn Ile Gly Gly Ser Trp
            930                 935                 940

Leu Gly Gly Leu Lys Asp Ile Leu Pro Ser His Asn Ser Lys Arg Lys
945                 950                 955                 960

Tyr Arg Ser Ala Ile Glu Asp Leu Leu Phe Asp Lys Val Val Thr Ser
            965                 970                 975

Gly Leu Gly Thr Val Asp Glu Asp Tyr Lys Arg Cys Thr Gly Gly Tyr
            980                 985                 990

Asp Ile Ala Asp Leu Val Cys Ala Gln Tyr Tyr Asn Gly Ile Met Val
            995                 1000                1005

Leu Pro Gly Val Ala Asn Asp Asp Lys Met Thr Met Tyr Thr Ala
        1010                1015                1020

Ser Leu Ala Gly Gly Ile Ala Leu Gly Ala Leu Gly Gly Gly Ala
        1025                1030                1035

Val Ala Ile Pro Phe Ala Val Ala Val Gln Ala Arg Leu Asn Tyr
        1040                1045                1050

Val Ala Leu Gln Thr Asp Val Leu Asn Lys Asn Gln Gln Ile Leu
        1055                1060                1065

Ala Asn Ala Phe Asn Gln Ala Ile Gly Asn Ile Thr Gln Ala Phe
        1070                1075                1080

Gly Lys Val Asn Asp Ala Ile His Gln Thr Ser Gln Gly Leu Ala
        1085                1090                1095

Thr Val Ala Lys Ala Leu Ala Lys Val Gln Asp Val Val Asn Thr
        1100                1105                1110

Gln Gly Gln Ala Leu Ser His Leu Thr Val Gln Leu Gln Asn Ser
        1115                1120                1125

Phe Gln Ala Ile Ser Ser Ser Ile Ser Asp Ile Tyr Asn Arg Leu
        1130                1135                1140

Asp Glu Leu Ser Ala Asp Ala Gln Val Asp Arg Leu Ile Thr Gly
        1145                1150                1155

Arg Leu Thr Ala Leu Asn Ala Phe Val Ser Gln Thr Leu Thr Arg
        1160                1165                1170

Gln Ala Glu Val Arg Ala Ser Arg Gln Leu Ala Lys Asp Lys Val
        1175                1180                1185

Asn Glu Cys Val Arg Ser Gln Ser Gln Arg Phe Gly Phe Cys Gly
        1190                1195                1200

Asn Gly Thr His Leu Phe Ser Leu Ala Asn Ala Ala Pro Asn Gly
        1205                1210                1215

Met Val Phe Phe His Thr Val Leu Leu Pro Thr Ala Tyr Glu Thr
        1220                1225                1230

Val Thr Ala Trp Ser Gly Ile Cys Ala Ser Asp Gly Asp Arg Thr
        1235                1240                1245

Phe Gly Leu Val Val Lys Asp Val Gln Leu Thr Leu Phe Arg Asn
        1250                1255                1260

Leu Asp Asp Lys Phe Tyr Leu Thr Pro Arg Thr Met Tyr Gln Pro
        1265                1270                1275

Arg Ala Ala Thr Ser Ser Asp Phe Val Gln Ile Glu Gly Cys Asp
        1280                1285                1290
```

Val Leu Phe Val Asn Ala Thr Val Ile Asp Leu Pro Ser Ile Ile
    1295                1300                1305

Pro Asp Tyr Ile Asp Ile Asn Gln Thr Val Gln Asp Ile Leu Glu
    1310                1315                1320

Asn Tyr Arg Pro Asn Trp Thr Val Pro Glu Leu Thr Ile Asp Ile
    1325                1330                1335

Phe Asn Ala Thr Tyr Leu Asn Leu Thr Gly Glu Ile Asp Asp Leu
    1340                1345                1350

Glu Phe Arg Ser Glu Lys Leu His Asn Thr Thr Val Glu Leu Ala
    1355                1360                1365

Ile Leu Ile Asp Asn Ile Asn Asn Thr Leu Val Asn Leu Glu Trp
    1370                1375                1380

Leu Asn Arg Ile Glu Thr Tyr Val Lys Trp Pro Trp Tyr Val Trp
    1385                1390                1395

Leu Leu Ile Gly Leu Val Val Phe Cys Ile Pro Leu Leu Leu
    1400                1405                1410

Phe Cys Cys Cys Ser Thr Gly Cys Cys Gly Cys Ile Gly Cys Leu
    1415                1420                1425

Gly Ser Cys Cys His Ser Ile Cys Ser Arg Arg Gln Phe Glu Asn
    1430                1435                1440

Tyr Glu Pro Ile Glu Lys Val His Val His
    1445                1450

<210> SEQ ID NO 21
<211> LENGTH: 496
<212> TYPE: DNA
<213> ORGANISM: canine respiratory coronavirus

<400> SEQUENCE: 21
tatcgcagcc ttactttgt taatgtacca tatgtttata atggctctgc acaatctaca      60
gctctttgta aatctggtag tttagttctt aataaccctg catatatagc tcgtgaagct    120
aattttgggg attattatta taaggttgaa gctgatttct atttgtcagg ttgtgacgag    180
tatatcgtac cactttgtat ttttaacggc aagttttgt cgaatacaaa gtattatgat    240
gatagtcaat attatttaa taaagacact ggtgttattt atggtttcaa ttctactgaa    300
accattaaca ctggttttga ttttaattgt cattatttac ttttaccctc tggtaattat    360
ttagccattt caaatgagct attgttaact gttcctacga aagcaatctg tcttaataag    420
cgtaaggatt ttacgcctgt acaggttgtt gactcgcggt ggaacaatgc caggcagtct    480
gataacatga cggcgg                                                    496

<210> SEQ ID NO 22
<211> LENGTH: 165
<212> TYPE: PRT
<213> ORGANISM: canine respiratory coronavirus

<400> SEQUENCE: 22

Tyr Arg Ser Leu Thr Phe Val Asn Val Pro Tyr Val Tyr Asn Gly Ser
1               5                   10                  15

Ala Gln Ser Thr Ala Leu Cys Lys Ser Gly Ser Leu Val Leu Asn Asn
            20                  25                  30

Pro Ala Tyr Ile Ala Arg Glu Ala Asn Phe Gly Asp Tyr Tyr Lys
        35                  40                  45

Val Glu Ala Asp Phe Tyr Leu Ser Gly Cys Asp Glu Tyr Ile Val Pro
    50                  55                  60

Leu Cys Ile Phe Asn Gly Lys Phe Leu Ser Asn Thr Lys Tyr Tyr Asp
65                  70                  75                  80

Asp Ser Gln Tyr Tyr Phe Asn Lys Asp Thr Gly Val Ile Tyr Gly Phe
                85                  90                  95

Asn Ser Thr Glu Thr Ile Asn Thr Gly Phe Asp Phe Asn Cys His Tyr
            100                 105                 110

Leu Leu Leu Pro Ser Gly Asn Tyr Leu Ala Ile Ser Asn Glu Leu Leu
            115                 120                 125

Leu Thr Val Pro Thr Lys Ala Ile Cys Leu Asn Lys Arg Lys Asp Phe
            130                 135                 140

Thr Pro Val Gln Val Val Asp Ser Arg Trp Asn Asn Ala Arg Gln Ser
145                 150                 155                 160

Asp Asn Met Thr Ala
            165

<210> SEQ ID NO 23
<211> LENGTH: 497
<212> TYPE: DNA
<213> ORGANISM: bovine coronavirus strain LY138

<400> SEQUENCE: 23
tatcgcagcc ttactttgt taatgtacca tatgtttata atggctctgc acaatctaca      60
gctctttgta atctggtag tttagttctt aataaccctg catatatagc tcgtgaagct     120
aattttgggg attattatta taaggttgaa gctgattttt atttgtcagg ttgtgacgag    180
tatatcgtac cactttgtat ttttaacggc aagttttttgt cgaatacaaa gtattatgat    240
gatagtcaat attattttaa taaagacact ggtgttattt atggtctcaa ttctactgaa    300
accattacca ctggttttga ttttaattgt cattatttag ttttacccct tggtaattat    360
ttagccattt caaatgagct attgttaact gttcctacga aagcaatctg tcttaataag    420
cgtaaggatt ttacgcctgt acaggttgtt gactctcggt ggaacaatgc caggcagtct    480
gataacatga cggcggt                                                    497

<210> SEQ ID NO 24
<211> LENGTH: 497
<212> TYPE: DNA
<213> ORGANISM: human coronavirus strain OC43

<400> SEQUENCE: 24
tatcgcagcc ttactttgt taatgtacca tatgtttata atggctctgc acaatctaca      60
gctctttgta atctggtag tttagtcctt aataaccctg catatatagc tcctcaagct     120
aactctgggg attattatta taaggttgaa gctgattttt atttgtcagg ttgtgacgag    180
tatatcgtac cactttgtat ttttaacggc aagttttttgt cgaatacaaa gtattatgat    240
gatagtcaat attattttaa taaagacact ggtgttattt atggtctcaa ttctacagaa    300
accattacca ctggttttga tcttaattgt tattatttag ttttacccct tggtaattat    360
ttagccattt caaatgagct attgttaact gttcctacga aagcaatctg tcttaataag    420
cgtaaggatt ttacgcctgt acaggttgtt gattcgcggt ggaacaatgc caggcagtct    480
gataacatga cggcggt                                                    497

<210> SEQ ID NO 25
<211> LENGTH: 497
<212> TYPE: DNA
<213> ORGANISM: human enteric coronavirus

<400> SEQUENCE: 25

-continued

```
tatcgcagcc ttactttgt taatgtacca tatgtttaca atggctctgc acaatctaca      60
gctctttgta aatctggtag tttagttctt aataaccctg catatatagc tcgtgaagct    120
aattttgggg attattatta taaggttgaa gctgattttt atttgtcagg ttgtgacgag    180
tatatcgtac cactttgtat ttttaacggc aagttttgt cgaatacaaa gtattatgat     240
gatagtcaat attatttaa taaagacact ggtgttattt atggtctcaa ttctactgaa     300
accattacca ctggttttga ttttaattgt cattatttag ttctaccctc tggcaattat    360
ttagccattt caaatgagct attgttaact gttcctacta aagcaatctg tcttaataag    420
cgtaaggatt ttacgcctgt acaggttgtt gactcgcggt ggaacaatgc caggcagtct    480
gataacatga cggcagt                                                   497
```

<210> SEQ ID NO 26
<211> LENGTH: 497
<212> TYPE: DNA
<213> ORGANISM: hemagglutinating encephalomyelitis virus

<400> SEQUENCE: 26

```
tatcgcagtc ttactttagt taatgtgcca tacgtttaca atgggtcagc tcaacccacc    60
gcactttgta agtctggcag tttaattctt aacaatcctg catatatagc ccgtgaggct    120
aatgtgggtg attattatta taagtctgaa gcagattttt ctctctcagg ttgtgacgag    180
tatatcgtac cactttgtat ttttaatggc aagttttgt cgaatacaaa gtattatgat     240
gatagtcaat attatttaa taaagacact ggtgttattt atggtctcaa ttctactgaa     300
accattacca ctggttttga ttttaattgt cattatttag ttctaccctc tggtaattat    360
ctagccattt caaatgagct attgttaact gttcctacta aagcaatctg tcttaataag    420
cgtaaggttt ttacgcctgt acaggttgtt gattcgcggt ggaacaatgc caggcaatct    480
gataacatga cggcagt                                                   497
```

<210> SEQ ID NO 27
<211> LENGTH: 165
<212> TYPE: PRT
<213> ORGANISM: bovine coronavirus strain LY138

<400> SEQUENCE: 27

```
Tyr Arg Ser Leu Thr Phe Val Asn Val Pro Tyr Val Tyr Asn Gly Ser
 1               5                  10                  15

Ala Gln Ser Thr Ala Leu Cys Lys Ser Gly Ser Leu Val Leu Asn Asn
            20                  25                  30

Pro Ala Tyr Ile Ala Arg Glu Ala Asn Phe Gly Asp Tyr Tyr Tyr Lys
        35                  40                  45

Val Glu Ala Asp Phe Tyr Leu Ser Gly Cys Asp Glu Tyr Ile Val Pro
    50                  55                  60

Leu Cys Ile Phe Asn Gly Lys Phe Leu Ser Asn Thr Lys Tyr Tyr Asp
65                  70                  75                  80

Asp Ser Gln Tyr Tyr Phe Asn Lys Asp Thr Gly Val Ile Tyr Gly Leu
                85                  90                  95

Asn Ser Thr Glu Thr Ile Thr Thr Gly Phe Asp Phe Asn Cys His Tyr
            100                 105                 110

Leu Val Leu Pro Ser Gly Asn Tyr Leu Ala Ile Ser Asn Glu Leu Leu
        115                 120                 125

Leu Thr Val Pro Thr Lys Ala Ile Cys Leu Asn Lys Arg Lys Asp Phe
    130                 135                 140
```

```
Thr Pro Val Gln Val Val Asp Ser Arg Trp Asn Asn Ala Arg Gln Ser
145                 150                 155                 160

Asp Asn Met Thr Ala
                165

<210> SEQ ID NO 28
<211> LENGTH: 165
<212> TYPE: PRT
<213> ORGANISM: human coronavirus strain OC43

<400> SEQUENCE: 28

Tyr Arg Ser Leu Thr Phe Val Asn Val Pro Tyr Val Tyr Asn Gly Ser
1               5                   10                  15

Ala Gln Ser Thr Ala Leu Cys Lys Ser Gly Ser Leu Val Leu Asn Asn
                20                  25                  30

Pro Ala Tyr Ile Ala Pro Gln Ala Asn Ser Gly Asp Tyr Tyr Tyr Lys
                35                  40                  45

Val Glu Ala Asp Phe Tyr Leu Ser Gly Cys Asp Glu Tyr Ile Val Pro
50                  55                  60

Leu Cys Ile Phe Asn Gly Lys Phe Leu Ser Asn Thr Lys Tyr Tyr Asp
65                  70                  75                  80

Asp Ser Gln Tyr Tyr Phe Asn Lys Asp Thr Gly Val Ile Tyr Gly Leu
                85                  90                  95

Asn Ser Thr Glu Thr Ile Thr Thr Gly Phe Asp Leu Asn Cys Tyr Tyr
                100                 105                 110

Leu Val Leu Pro Ser Gly Asn Tyr Leu Ala Ile Ser Asn Glu Leu Leu
            115                 120                 125

Leu Thr Val Pro Thr Lys Ala Ile Cys Leu Asn Lys Arg Lys Asp Phe
130                 135                 140

Thr Pro Val Gln Val Val Asp Ser Arg Trp Asn Asn Ala Arg Gln Ser
145                 150                 155                 160

Asp Asn Met Thr Ala
                165

<210> SEQ ID NO 29
<211> LENGTH: 165
<212> TYPE: PRT
<213> ORGANISM: human enteric coronavirus

<400> SEQUENCE: 29

Tyr Arg Ser Leu Thr Phe Val Asn Val Pro Tyr Val Tyr Asn Gly Ser
1               5                   10                  15

Ala Gln Ser Thr Ala Leu Cys Lys Ser Gly Ser Leu Val Leu Asn Asn
                20                  25                  30

Pro Ala Tyr Ile Ala Arg Glu Ala Asn Phe Gly Asp Tyr Tyr Tyr Lys
                35                  40                  45

Val Glu Ala Asp Phe Tyr Leu Ser Gly Cys Asp Glu Tyr Ile Val Pro
50                  55                  60

Leu Cys Ile Phe Asn Gly Lys Phe Leu Ser Asn Thr Lys Tyr Tyr Asp
65                  70                  75                  80

Asp Ser Gln Tyr Tyr Phe Asn Lys Asp Thr Gly Val Ile Tyr Gly Leu
                85                  90                  95

Asn Ser Thr Glu Thr Ile Thr Thr Gly Phe Asp Phe Asn Cys His Tyr
                100                 105                 110

Leu Val Leu Pro Ser Gly Asn Tyr Leu Ala Ile Ser Asn Glu Leu Leu
            115                 120                 125

Leu Thr Val Pro Thr Lys Ala Ile Cys Leu Asn Lys Arg Lys Asp Phe
```

```
                130                 135                 140
Thr Pro Val Gln Val Val Asp Ser Arg Trp Asn Asn Ala Arg Gln Ser
145                 150                 155                 160

Asp Asn Met Thr Ala
            165

<210> SEQ ID NO 30
<211> LENGTH: 165
<212> TYPE: PRT
<213> ORGANISM: hemagglutinating encephalomyelitis virus

<400> SEQUENCE: 30

Tyr Arg Ser Leu Thr Leu Val Asn Val Pro Tyr Val Tyr Asn Gly Ser
1               5                   10                  15

Ala Gln Pro Thr Ala Leu Cys Lys Ser Gly Ser Leu Ile Leu Asn Asn
            20                  25                  30

Pro Ala Tyr Ile Ala Arg Glu Ala Asn Val Gly Asp Tyr Tyr Tyr Lys
        35                  40                  45

Ser Glu Ala Asp Phe Ser Leu Ser Gly Cys Asp Glu Tyr Ile Val Pro
    50                  55                  60

Leu Cys Ile Phe Asn Gly Lys Phe Leu Ser Asn Thr Lys Tyr Tyr Asp
65                  70                  75                  80

Asp Ser Gln Tyr Tyr Phe Asn Lys Asp Thr Gly Val Ile Tyr Gly Leu
                85                  90                  95

Asn Ser Thr Glu Thr Ile Thr Thr Gly Phe Asp Phe Asn Cys His Tyr
            100                 105                 110

Leu Val Leu Pro Ser Gly Asn Tyr Leu Ala Ile Ser Asn Glu Leu Leu
        115                 120                 125

Leu Thr Val Pro Thr Lys Ala Ile Cys Leu Asn Lys Arg Lys Val Phe
    130                 135                 140

Thr Pro Val Gln Val Val Asp Ser Arg Trp Asn Asn Ala Arg Gln Ser
145                 150                 155                 160

Asp Asn Met Thr Ala
            165

<210> SEQ ID NO 31
<211> LENGTH: 23
<212> TYPE: DNA
<213> ORGANISM: artificial
<220> FEATURE:
<223> OTHER INFORMATION: Consensus oligonucleotide primer for
      coronavirus polymerase gene

<400> SEQUENCE: 31
actcaratga atttgaaata tgc                                          23

<210> SEQ ID NO 32
<211> LENGTH: 20
<212> TYPE: DNA
<213> ORGANISM: artificial
<220> FEATURE:
<223> OTHER INFORMATION: Consensus oligonucleotide primer for
      coronavirus polymerase gene

<400> SEQUENCE: 32
tcacacttag gatartccca                                              20

<210> SEQ ID NO 33
<211> LENGTH: 20
<212> TYPE: DNA
<213> ORGANISM: artificial
```

```
<220> FEATURE:
<223> OTHER INFORMATION: Consensus oligonucleotide probe for coronavirus
      polymerase gene

<400> SEQUENCE: 33 aagttttat

<211> LENGTH: 23
<212> TYPE: DNA
<213> ORGANISM: bovine coronavirus strain LY138

<400> SEQUENCE: 41
cctactgtga gatcacatgt ttg 23

<210> SEQ ID NO 42
<211> LENGTH: 20
<212> TYPE: DNA
<213> ORGANISM: bovine coronavirus strain LY138

<400> SEQUENCE: 42
gttggcatag gtgagcactg 20

<210> SEQ ID NO 43
<211> LENGTH: 20
<212> TYPE: DNA
<213> ORGANISM: bovine coronavirus strain LY138

<400> SEQUENCE: 43
gcaatgctgg ttcggaagag 20

<210> SEQ ID NO 44
<211> LENGTH: 20
<212> TYPE: DNA
<213> ORGANISM: bovine coronavirus strain LY138

<400> SEQUENCE: 44
aacggttaca ctgttcagcc 20

<210> SEQ ID NO 45
<211> LENGTH: 20
<212> TYPE: DNA
<213> ORGANISM: bovine coronavirus strain LY138

<400> SEQUENCE: 45
caagtaaatg agtctgcctg 20

<210> SEQ ID NO 46
<211> LENGTH: 20
<212> TYPE: DNA
<213> ORGANISM: bovine coronavirus strain LY138

<400> SEQUENCE: 46
ggctgccacc tctgctagtc 20

<210> SEQ ID NO 47
<211> LENGTH: 25
<212> TYPE: DNA
<213> ORGANISM: bovine coronavirus strain LY138

<400> SEQUENCE: 47
attgttaaat gcattagcaa taagc 25

<210> SEQ ID NO 48
<211> LENGTH: 26
<212> TYPE: DNA
<213> ORGANISM: bovine coronavirus strain LY138

<400> SEQUENCE: 48
tttttgatac ttttaatttc cttacc 26

<210> SEQ ID NO 49

```
<211> LENGTH: 24
<212> TYPE: DNA
<213> ORGANISM: bovine coronavirus strain LY138

<400> SEQUENCE: 49
gtcgtcatgt gawgttttra ttac                                              24

<210> SEQ ID NO 50
<211> LENGTH: 35
<212> TYPE: DNA
<213> ORGANISM: artificial
<220> FEATURE:
<223> OTHER INFORMATION: Oligonucleotide primer for cloning canine
      respiartory coronavirus Spike gene

<400> SEQUENCE: 50
agctcgagct ttttgatact tttaatttcc ttacc                                  35

<210> SEQ ID NO 51
<211> LENGTH: 53
<212> TYPE: DNA
<213> ORGANISM: artificial
<220> FEATURE:
<223> OTHER INFORMATION: Oligonucleotide primer for cloning canine
      respiartory coronavirus Spike gene

<400> SEQUENCE: 51
ttgaattctt aatgatgatg atgatgatgg tcgtcatgtg awgttttrat tac              53

<210> SEQ ID NO 52
<211> LENGTH: 11
<212> TYPE: PRT
<213> ORGANISM: Unknown
<220> FEATURE:
<223> OTHER INFORMATION: Presumed T cell epitope

<400> SEQUENCE: 52

Thr Ala Ser Gly Val Ala Glu Thr Thr Asn Cys
1               5                   10

<210> SEQ ID NO 53
<211> LENGTH: 424
<212> TYPE: PRT
<213> ORGANISM: Bovine coronavirus (Strain LY-138)

<400> SEQUENCE: 53

Met Phe Leu Leu Pro Arg Phe Val Leu Val Ser Cys Ile Ile Gly Ser
1               5                   10                  15

Leu Gly Phe Asp Asn Pro Pro Thr Asn Val Val Ser His Leu Asn Gly
                20                  25                  30

Asp Trp Phe Leu Phe Gly Asp Ser Arg Ser Asp Cys Asn His Val Val
            35                  40                  45

Asn Thr Asn Pro Arg Asn Tyr Ser Tyr Met Asp Leu Asn Pro Ala Leu
        50                  55                  60

Cys Asp Ser Gly Lys Ile Ser Ser Lys Ala Gly Asn Ser Ile Phe Arg
65                  70                  75                  80

Ser Phe His Phe Thr Asp Phe Tyr Asn Tyr Thr Gly Glu Gly Gln Gln
                85                  90                  95

Ile Ile Phe Tyr Glu Gly Val Asn Phe Thr Pro Tyr His Ala Phe Lys
            100                 105                 110

Cys Thr Thr Ser Gly Ser Asn Asp Ile Trp Met Gln Asn Lys Gly Leu
        115                 120                 125

Phe Tyr Thr Gln Val Tyr Lys Asn Met Ala Val Tyr Arg Ser Leu Thr
```

```
    130                 135                 140

Phe Val Asn Val Pro Tyr Val Tyr Asn Gly Ser Ala Gln Ser Thr Ala
145                 150                 155                 160

Leu Cys Lys Ser Gly Ser Leu Val Leu Asn Asn Pro Ala Tyr Ile Ala
                165                 170                 175

Arg Glu Ala Asn Phe Gly Asp Tyr Tyr Tyr Lys Val Glu Ala Asp Phe
            180                 185                 190

Tyr Leu Ser Gly Cys Asp Glu Tyr Ile Val Pro Leu Cys Ile Phe Asn
        195                 200                 205

Gly Lys Phe Leu Ser Asn Thr Lys Tyr Tyr Asp Asp Ser Gln Tyr Tyr
    210                 215                 220

Phe Asn Lys Asp Thr Gly Val Ile Tyr Gly Leu Asn Ser Thr Glu Thr
225                 230                 235                 240

Ile Thr Thr Gly Phe Asp Phe Asn Cys His Tyr Leu Val Leu Pro Ser
                245                 250                 255

Gly Asn Tyr Leu Ala Ile Ser Asn Glu Leu Leu Leu Thr Val Pro Thr
            260                 265                 270

Lys Ala Ile Cys Leu Asn Lys Arg Lys Asp Phe Thr Pro Val Gln Val
        275                 280                 285

Val Asp Ser Arg Trp Asn Asn Ala Arg Gln Ser Asp Asn Met Thr Ala
    290                 295                 300

Val Ala Cys Gln Pro Pro Tyr Cys Tyr Phe Arg Asn Ser Thr Thr Asn
305                 310                 315                 320

Tyr Val Gly Val Tyr Asp Ile Asn His Gly Asp Ala Gly Phe Thr Ser
                325                 330                 335

Ile Leu Ser Gly Leu Leu Tyr Asp Ser Pro Cys Phe Ser Gln Gln Gly
            340                 345                 350

Val Phe Arg Tyr Asp Asn Val Ser Ser Val Trp Pro Leu Tyr Pro Tyr
        355                 360                 365

Gly Arg Cys Pro Thr Ala Ala Asp Ile Asn Asn Pro Asp Val Pro Ile
    370                 375                 380

Cys Val Tyr Asp Pro Leu Pro Leu Ile Leu Leu Gly Ile Leu Leu Gly
385                 390                 395                 400

Val Ala Val Ile Ile Ile Val Val Leu Leu Leu Tyr Phe Met Val Asp
                405                 410                 415

Asn Gly Thr Arg Leu His Asp Ala
            420

<210> SEQ ID NO 54
<211> LENGTH: 7094
<212> TYPE: PRT
<213> ORGANISM: Bovine enteric coronavirus (strain 98TXSF-110-ENT)

<400> SEQUENCE: 54

Met Ser Lys Ile Asn Lys Tyr Gly Leu Glu Leu His Trp Ala Pro Glu
1               5                   10                  15

Phe Pro Trp Met Phe Glu Asp Ala Glu Glu Lys Leu Asp Asn Pro Ser
            20                  25                  30

Ser Ser Glu Val Asp Ile Val Cys Ser Thr Thr Ala Gln Lys Leu Glu
        35                  40                  45

Thr Gly Gly Ile Cys Pro Glu Asn His Val Met Val Asp Cys Arg Arg
    50                  55                  60

Leu Leu Lys Gln Glu Cys Cys Val Gln Ser Ser Leu Ile Arg Glu Ile
65                  70                  75                  80

Val Met Asn Thr Arg Pro Tyr Asp Leu Glu Val Leu Leu Gln Asp Ala
```

```
                  85                  90                  95
Leu Gln Ser Arg Glu Ala Val Leu Val Thr Pro Pro Leu Gly Met Ser
            100                 105                 110
Leu Glu Ala Cys Tyr Val Arg Gly Cys Asn Pro Asn Gly Trp Thr Met
            115                 120                 125
Gly Leu Phe Arg Arg Ser Val Cys Asn Thr Gly Arg Cys Ala Val
            130                 135                 140
Asn Lys His Val Ala Tyr Gln Leu Tyr Met Ile Asp Pro Ala Gly Val
145                 150                 155                 160
Cys Phe Gly Ala Gly Gln Phe Val Gly Trp Val Ile Pro Leu Ala Phe
                165                 170                 175
Met Pro Val Gln Ser Arg Lys Phe Ile Val Pro Trp Val Met Tyr Leu
            180                 185                 190
Arg Lys Cys Gly Glu Lys Gly Ala Tyr Asn Lys Asp His Lys Arg Gly
                195                 200                 205
Gly Phe Glu His Val Tyr Asn Phe Lys Val Glu Asp Ala Tyr Asp Leu
            210                 215                 220
Val His Asp Glu Pro Lys Gly Lys Phe Ser Lys Lys Ala Tyr Ala Leu
225                 230                 235                 240
Ile Arg Gly Tyr Arg Gly Val Lys Pro Leu Leu Tyr Val Asp Gln Tyr
                245                 250                 255
Gly Cys Asp Tyr Thr Gly Gly Leu Ala Asp Gly Leu Glu Ala Tyr Ala
                260                 265                 270
Asp Lys Thr Leu Gln Glu Met Lys Ala Leu Phe Pro Ile Trp Ser Gln
            275                 280                 285
Glu Leu Pro Phe Asp Val Thr Val Ala Trp His Val Val Arg Asp Pro
            290                 295                 300
Arg Tyr Val Met Arg Leu Gln Ser Ala Ser Thr Ile Arg Ser Val Ala
305                 310                 315                 320
Tyr Val Ala Asn Pro Thr Glu Asp Leu Cys Asp Gly Ser Val Val Ile
                325                 330                 335
Lys Glu Pro Val His Val Tyr Ala Asp Asp Ser Ile Ile Leu Arg Gln
            340                 345                 350
His Asn Leu Val Asp Ile Met Ser Cys Phe Tyr Met Glu Ala Asp Ala
            355                 360                 365
Val Val Asn Ala Phe Tyr Gly Val Asp Leu Lys Asp Cys Gly Phe Val
            370                 375                 380
Met Gln Phe Gly Tyr Ile Asp Cys Glu Gln Asp Leu Cys Asp Phe Lys
385                 390                 395                 400
Gly Trp Val Pro Gly Asn Met Ile Asp Gly Phe Ala Cys Thr Thr Cys
                405                 410                 415
Gly His Val Tyr Glu Thr Gly Asp Leu Leu Ala Gln Ser Ser Gly Val
            420                 425                 430
Leu Pro Val Asn Pro Val Leu His Thr Lys Ser Ala Ala Gly Tyr Gly
            435                 440                 445
Gly Phe Gly Cys Lys Asp Ser Phe Thr Leu Tyr Gly Gln Thr Val Val
            450                 455                 460
Tyr Phe Gly Gly Cys Val Tyr Trp Ser Pro Ala Arg Asn Ile Trp Ile
465                 470                 475                 480
Pro Ile Leu Lys Ser Ser Val Lys Ser Tyr Asp Gly Leu Val Tyr Thr
                485                 490                 495
Gly Val Val Gly Cys Lys Ala Ile Val Lys Glu Thr Asn Leu Ile Cys
            500                 505                 510
```

```
Lys Ala Leu Tyr Leu Asp Tyr Val Gln His Lys Cys Gly Asn Leu His
        515                 520                 525

Gln Arg Glu Leu Leu Gly Val Ser Asp Val Trp His Lys Gln Leu Leu
        530                 535                 540

Leu Asn Arg Gly Val Tyr Lys Pro Leu Leu Glu Asn Ile Asp Tyr Phe
545                 550                 555                 560

Asn Met Arg Arg Ala Lys Phe Ser Leu Glu Thr Phe Thr Val Cys Ala
                565                 570                 575

Asp Gly Phe Met Pro Phe Leu Leu Asp Asp Leu Val Pro Arg Ala Tyr
            580                 585                 590

Tyr Leu Ala Val Ser Gly Gln Ala Phe Cys Asp Tyr Ala Asp Lys Ile
        595                 600                 605

Cys His Ala Val Val Ser Lys Ser Lys Glu Leu Leu Asp Val Ser Leu
    610                 615                 620

Asp Ser Leu Ser Ala Ala Ile His Tyr Leu Asn Ser Lys Ile Val Asp
625                 630                 635                 640

Leu Ala Gln His Phe Ser Asp Phe Gly Thr Ser Phe Val Ser Lys Ile
                645                 650                 655

Val His Phe Phe Lys Thr Phe Thr Ser Thr Ala Leu Ala Phe Ala
            660                 665                 670

Trp Val Leu Phe His Val Leu His Gly Ala Tyr Ile Val Glu Ser
    675                 680                 685

Asp Ile Tyr Phe Val Lys Asn Ile Pro Arg Tyr Ala Ser Ala Val Ala
    690                 695                 700

Gln Ala Phe Arg Ser Val Ala Lys Val Val Leu Asp Ser Leu Arg Val
705                 710                 715                 720

Thr Phe Ile Asp Gly Leu Ser Cys Phe Lys Ile Gly Arg Arg Ile
                725                 730                 735

Cys Leu Ser Gly Ser Lys Ile Tyr Glu Val Glu Arg Gly Leu Leu His
            740                 745                 750

Ser Ser Gln Leu Pro Leu Asp Val Tyr Asp Leu Thr Met Pro Ser Gln
        755                 760                 765

Val Gln Lys Ala Lys Gln Lys Pro Ile Tyr Leu Lys Gly Ser Gly Ser
    770                 775                 780

Asp Phe Ser Leu Ala Asp Ser Val Val Glu Val Thr Thr Ser Leu
785                 790                 795                 800

Thr Pro Cys Gly Tyr Ser Glu Pro Pro Lys Val Ala Asp Lys Ile Cys
                805                 810                 815

Ile Val Asp Asn Val Tyr Met Ala Lys Ala Gly Asp Lys Tyr Tyr Pro
            820                 825                 830

Val Val Val Asp Gly His Val Gly Leu Leu Asp Gln Ala Trp Arg Val
        835                 840                 845

Pro Cys Ala Gly Arg Arg Val Thr Phe Lys Glu Gln Pro Thr Val Asn
850                 855                 860

Glu Ile Ala Ser Thr Pro Lys Thr Ile Lys Val Phe Tyr Glu Leu Asp
865                 870                 875                 880

Lys Asp Phe Asn Thr Ile Leu Asn Thr Ala Cys Gly Val Phe Glu Val
                885                 890                 895

Asp Asp Thr Val Asp Met Glu Glu Phe Tyr Ala Val Ile Asp Ala
            900                 905                 910

Ile Glu Glu Lys Leu Ser Pro Cys Lys Glu Leu Glu Gly Val Gly Ala
        915                 920                 925

Lys Val Ser Ala Phe Leu Gln Lys Leu Glu Asp Asn Ser Leu Phe Leu
    930                 935                 940
```

```
Phe Asp Glu Ala Gly Glu Val Leu Ala Ser Lys Leu Tyr Cys Ala
945                 950                 955                 960

Phe Thr Ala Pro Glu Asp Asp Phe Leu Glu Glu Ser Gly Val Glu
            965                 970                 975

Glu Asp Asp Val Glu Gly Glu Thr Asp Leu Thr Val Thr Ser Ala
                980                 985                 990

Gly Glu Pro Cys Val Ala Ser Glu Gln Glu Glu Ser Ser Glu Ile Leu
        995                 1000                1005

Glu Asp Thr Leu Asp Asp Gly Pro Cys Val Glu Thr Ser Asp Ser
    1010                1015                1020

Gln Val Glu Glu Asp Val Glu Met Ser Asp Phe Ala Asp Leu Glu
    1025                1030                1035

Ser Val Ile Gln Asp Tyr Glu Asn Val Cys Phe Glu Phe Tyr Thr
    1040                1045                1050

Thr Glu Pro Glu Phe Val Lys Val Leu Asp Leu Tyr Val Pro Lys
    1055                1060                1065

Ala Thr Arg Asn Asn Cys Trp Leu Arg Ser Val Leu Ala Val Met
    1070                1075                1080

Gln Lys Leu Pro Cys Gln Phe Lys Asp Lys Asn Leu Gln Asp Leu
    1085                1090                1095

Trp Val Leu Tyr Lys Gln Gln Tyr Ser Gln Leu Phe Val Asp Thr
    1100                1105                1110

Leu Val Asn Lys Ile Pro Ala Asn Ile Val Val Pro Gln Gly Gly
    1115                1120                1125

Tyr Val Ala Asp Phe Ala Tyr Trp Phe Leu Thr Leu Cys Asp Trp
    1130                1135                1140

Gln Cys Val Ala Tyr Trp Lys Cys Ile Lys Cys Asp Leu Ala Leu
    1145                1150                1155

Lys Leu Lys Gly Leu Asp Ala Met Phe Phe Tyr Gly Asp Val Val
    1160                1165                1170

Ser His Val Cys Lys Cys Gly Glu Ser Met Val Leu Ile Asp Val
    1175                1180                1185

Asp Val Pro Phe Thr Ala His Phe Ala Leu Lys Asp Lys Leu Phe
    1190                1195                1200

Cys Ala Phe Ile Thr Lys Arg Ser Val Tyr Lys Ala Ala Cys Val
    1205                1210                1215

Val Asp Val Asn Asp Ser His Ser Met Ala Val Val Asp Gly Lys
    1220                1225                1230

Gln Ile Asp Asp His Arg Val Thr Ser Ile Thr Ser Asp Lys Phe
    1235                1240                1245

Asp Phe Ile Ile Gly His Gly Met Ser Phe Ser Met Thr Thr Phe
    1250                1255                1260

Glu Ile Ala Gln Leu Tyr Gly Ser Cys Ile Thr Pro Asn Val Cys
    1265                1270                1275

Phe Val Lys Gly Asp Ile Ile Lys Val Ser Lys Arg Val Lys Ala
    1280                1285                1290

Glu Val Val Asn Pro Ala Asn Gly His Met Ala His Gly Gly
    1295                1300                1305

Gly Val Ala Lys Ala Ile Ala Val Ala Ala Gly Gln Gln Phe Val
    1310                1315                1320

Lys Glu Thr Thr Asp Met Val Lys Ser Lys Gly Val Cys Ala Thr
    1325                1330                1335

Gly Asp Cys Tyr Val Ser Thr Gly Gly Lys Leu Cys Lys Thr Val
```

```
            1340                1345                1350
Leu Asn Val Val Gly Pro Asp Ala Arg Thr Gln Gly Lys Gln Ser
        1355                1360                1365
Tyr Ala Leu Leu Glu Arg Val Tyr Lys His Leu Asn Lys Tyr Asp
        1370                1375                1380
Cys Val Val Thr Thr Leu Ile Ser Ala Gly Ile Phe Ser Val Pro
        1385                1390                1395
Ser Asp Val Ser Leu Thr Tyr Leu Leu Gly Thr Ala Glu Lys Gln
        1400                1405                1410
Val Val Leu Val Ser Asn Asn Gln Glu Asp Phe Asp Leu Ile Ser
        1415                1420                1425
Lys Cys Gln Ile Thr Ala Val Glu Gly Thr Lys Lys Leu Ala Glu
        1430                1435                1440
Arg Leu Ser Phe Asn Val Gly Arg Ser Ile Val Tyr Glu Thr Asp
        1445                1450                1455
Ala Asn Lys Leu Ile Leu Ser Asn Asp Val Ala Phe Val Ser Thr
        1460                1465                1470
Phe Asn Val Leu Gln Asp Val Leu Ser Leu Arg His Asp Ile Ala
        1475                1480                1485
Leu Asp Asp Asp Ala Arg Thr Phe Val Gln Ser Asn Val Asp Val
        1490                1495                1500
Val Pro Glu Gly Trp Arg Val Val Asn Lys Phe Tyr Gln Ile Asn
        1505                1510                1515
Gly Val Arg Thr Val Lys Tyr Phe Glu Cys Pro Gly Gly Ile Asp
        1520                1525                1530
Ile Cys Ser Gln Asp Lys Val Phe Gly Tyr Val Gln Gln Gly Ser
        1535                1540                1545
Phe Asn Lys Ala Thr Val Ala Gln Ile Lys Ala Leu Phe Leu Asp
        1550                1555                1560
Lys Val Asp Ile Leu Leu Thr Val Asp Gly Val Asn Phe Thr Asn
        1565                1570                1575
Arg Phe Val Pro Val Gly Glu Ser Phe Gly Lys Ser Leu Gly Asn
        1580                1585                1590
Val Phe Cys Asp Gly Val Asn Val Thr Lys His Lys Cys Asp Ile
        1595                1600                1605
Asn Tyr Lys Gly Lys Val Phe Phe Gln Phe Asp Asn Leu Ser Ser
        1610                1615                1620
Glu Asp Leu Lys Ala Val Arg Ser Ser Phe Asn Phe Asp Gln Lys
        1625                1630                1635
Glu Leu Leu Ala Tyr Tyr Asn Met Leu Val Asn Cys Ser Lys Trp
        1640                1645                1650
Gln Val Val Phe Asn Gly Lys Tyr Phe Thr Phe Lys Gln Ala Asn
        1655                1660                1665
Asn Asn Cys Phe Val Asn Val Ser Cys Leu Met Leu Gln Ser Leu
        1670                1675                1680
Asn Leu Lys Phe Lys Ile Val Gln Trp Gln Glu Ala Trp Leu Glu
        1685                1690                1695
Phe Arg Ser Gly Arg Pro Ala Arg Phe Val Ser Leu Val Leu Ala
        1700                1705                1710
Lys Gly Gly Phe Lys Phe Gly Asp Pro Ala Asp Ser Arg Asp Phe
        1715                1720                1725
Leu Arg Val Val Phe Ser Gln Val Asp Leu Thr Gly Ala Ile Cys
        1730                1735                1740
```

-continued

```
Asp Phe Glu Ile Ala Cys Lys Cys Gly Val Lys Gln Glu Gln Arg
     1745                1750                1755
Thr Gly Val Asp Ala Val Met His Phe Gly Thr Leu Ser Arg Glu
     1760                1765                1770
Asp Leu Glu Ile Gly Tyr Thr Val Asp Cys Ser Cys Gly Lys Lys
     1775                1780                1785
Leu Ile His Cys Val Arg Phe Asp Val Pro Phe Leu Ile Cys Ser
     1790                1795                1800
Asn Thr Pro Ala Ser Val Lys Leu Pro Lys Gly Val Gly Ser Ala
     1805                1810                1815
Asn Ile Phe Lys Gly Asp Lys Val Gly His Tyr Val His Val Lys
     1820                1825                1830
Cys Glu Gln Ser Tyr Gln Leu Tyr Asp Ala Ser Asn Val Lys Lys
     1835                1840                1845
Val Thr Asp Val Thr Gly Asn Leu Ser Asp Cys Leu Tyr Leu Lys
     1850                1855                1860
Asn Leu Lys Gln Thr Phe Lys Ser Val Leu Thr Thr Tyr Tyr Leu
     1865                1870                1875
Asp Asp Val Lys Lys Ile Glu Tyr Asn Pro Asp Leu Ser Gln Tyr
     1880                1885                1890
Tyr Cys Asp Gly Gly Lys Tyr Tyr Thr Gln Arg Ile Ile Lys Ala
     1895                1900                1905
Gln Phe Lys Thr Phe Glu Lys Val Asp Gly Val Tyr Thr Asn Phe
     1910                1915                1920
Lys Leu Ile Gly His Thr Ile Cys Asp Ile Leu Asn Ala Lys Leu
     1925                1930                1935
Gly Phe Asp Ser Ser Lys Glu Phe Val Glu Tyr Lys Val Thr Glu
     1940                1945                1950
Trp Pro Thr Ala Thr Gly Asp Val Val Leu Ala Thr Asp Asp Leu
     1955                1960                1965
Tyr Val Lys Arg Tyr Glu Arg Gly Cys Ile Thr Phe Gly Lys Pro
     1970                1975                1980
Val Ile Trp Leu Ser His Glu Gln Ala Ser Leu Asn Ser Leu Thr
     1985                1990                1995
Tyr Phe Asn Arg Pro Leu Leu Val Asp Glu Asn Lys Phe Asp Val
     2000                2005                2010
Leu Lys Val Asp Asp Val Asp Asp Gly Gly Asp Ile Ser Glu Ser
     2015                2020                2025
Asp Ala Lys Glu Ser Lys Glu Ile Asn Ile Ile Lys Leu Ser Gly
     2030                2035                2040
Val Lys Lys Pro Phe Lys Val Glu Asp Ser Val Ile Val Asn Asp
     2045                2050                2055
Asp Thr Ser Glu Ile Lys Tyr Val Lys Ser Leu Ser Ile Val Asp
     2060                2065                2070
Val Tyr Asp Met Trp Leu Thr Gly Cys Arg Tyr Val Val Arg Thr
     2075                2080                2085
Ala Asn Ala Leu Ser Met Ala Val Asn Val Pro Thr Ile Arg Lys
     2090                2095                2100
Phe Ile Lys Phe Gly Met Thr Leu Val Ser Ile Pro Ile Asp Leu
     2105                2110                2115
Leu Asn Leu Arg Glu Ile Lys Pro Val Phe Asn Val Val Lys Ala
     2120                2125                2130
Val Arg Asn Lys Ile Ser Ala Cys Phe Asn Phe Ile Lys Trp Leu
     2135                2140                2145
```

```
Phe Val Leu Leu Phe Gly Trp Ile Lys Ile Ser Ala Asp Asn Lys
2150                2155                2160

Val Ile Tyr Thr Thr Glu Val Ala Ser Lys Leu Thr Cys Lys Leu
2165                2170                2175

Val Ala Leu Ala Phe Lys Asn Ala Phe Leu Thr Phe Lys Trp Ser
2180                2185                2190

Val Val Ala Arg Gly Ala Cys Ile Ile Ala Thr Ile Phe Leu Leu
2195                2200                2205

Trp Phe Asn Phe Ile Tyr Ala Asn Val Ile Phe Ser Asp Phe Tyr
2210                2215                2220

Leu Pro Lys Ile Gly Phe Leu Pro Thr Phe Val Gly Lys Ile Ala
2225                2230                2235

Gln Trp Ile Lys Ser Thr Phe Ser Leu Val Thr Ile Cys Asp Leu
2240                2245                2250

Tyr Ser Ile Gln Asp Val Gly Phe Lys Asn Gln Tyr Cys Asn Gly
2255                2260                2265

Ser Ile Ala Cys Gln Phe Cys Leu Ala Gly Phe Asp Met Leu Asp
2270                2275                2280

Asn Tyr Lys Ala Ile Asp Val Val Gln Tyr Glu Ala Asp Arg Arg
2285                2290                2295

Ala Phe Val Asp Tyr Thr Gly Val Leu Lys Ile Val Ile Glu Leu
2300                2305                2310

Ile Val Ser Tyr Ala Leu Tyr Thr Ala Trp Phe Tyr Pro Leu Phe
2315                2320                2325

Ala Leu Ile Ser Ile Gln Ile Leu Thr Thr Trp Leu Pro Glu Leu
2330                2335                2340

Phe Met Leu Ser Thr Leu His Trp Ser Val Arg Leu Leu Val Ser
2345                2350                2355

Leu Ala Asn Met Leu Pro Ala His Val Phe Met Arg Phe Tyr Ile
2360                2365                2370

Ile Ile Ala Ser Phe Ile Lys Leu Phe Ile Leu Phe Arg His Val
2375                2380                2385

Ala Tyr Gly Cys Ser Lys Pro Gly Cys Leu Phe Cys Tyr Lys Arg
2390                2395                2400

Asn Arg Ser Leu Arg Val Lys Cys Ser Thr Ile Val Gly Gly Met
2405                2410                2415

Ile Arg Tyr Tyr Asp Val Met Ala Asn Gly Gly Thr Gly Phe Cys
2420                2425                2430

Ser Lys His Gln Trp Asn Cys Ile Asp Cys Asp Ser Tyr Lys Pro
2435                2440                2445

Gly Asn Thr Phe Ile Thr Val Glu Ala Ala Leu Asp Leu Ser Lys
2450                2455                2460

Glu Leu Lys Arg Pro Ile Gln Pro Thr Asp Val Ala Tyr His Thr
2465                2470                2475

Val Thr Asp Val Lys Gln Val Gly Cys Tyr Met Arg Leu Phe Tyr
2480                2485                2490

Glu Arg Asp Gly Gln Arg Thr Tyr Asp Asp Val Asn Ala Ser Leu
2495                2500                2505

Phe Val Asp Tyr Ser Asn Leu Leu His Ser Lys Val Lys Gly Val
2510                2515                2520

Pro Asn Met His Val Val Val Glu Asn Asp Ala Asp Lys Ala
2525                2530                2535

Asn Phe Leu Asn Ala Ala Val Phe Tyr Ala Gln Ser Leu Phe Arg
```

```
                2540                2545                2550

Pro Ile Leu Met Val Asp Lys Asn Leu Ile Thr Thr Ala Asn Thr
    2555                2560                2565

Gly Thr Ser Val Thr Glu Thr Met Phe Asp Val Tyr Val Asp Thr
    2570                2575                2580

Phe Leu Ser Met Phe Asp Val Asp Lys Lys Ser Leu Asn Ala Leu
    2585                2590                2595

Ile Ala Thr Ala His Ser Ser Ile Lys Gln Gly Thr Gln Ile Cys
    2600                2605                2610

Lys Val Leu Asp Thr Phe Leu Ser Cys Ala Arg Lys Ser Cys Ser
    2615                2620                2625

Ile Asp Ser Asp Val Asp Thr Lys Cys Leu Ala Asp Ser Val Met
    2630                2635                2640

Ser Ala Val Ser Ala Gly Leu Glu Leu Thr Asp Glu Ser Cys Asn
    2645                2650                2655

Asn Leu Val Pro Thr Tyr Leu Lys Gly Asp Asn Ile Val Ala Ala
    2660                2665                2670

Asp Leu Gly Val Leu Ile Gln Asn Ser Ala Lys His Val Gln Gly
    2675                2680                2685

Asn Val Ala Lys Ile Ala Gly Val Ser Cys Ile Trp Ser Val Asp
    2690                2695                2700

Ala Phe Asn Gln Leu Ser Ser Asp Phe Gln His Lys Leu Lys Lys
    2705                2710                2715

Ala Cys Cys Lys Thr Gly Leu Lys Leu Lys Leu Thr Tyr Asn Lys
    2720                2725                2730

Gln Met Ala Asn Val Ser Val Leu Thr Thr Pro Phe Ser Leu Lys
    2735                2740                2745

Gly Gly Ala Val Phe Ser Tyr Phe Val Tyr Val Cys Phe Leu Leu
    2750                2755                2760

Ser Leu Val Cys Phe Ile Gly Leu Trp Cys Leu Met Pro Thr Tyr
    2765                2770                2775

Thr Val His Lys Ser Asp Phe Gln Leu Pro Val Tyr Ala Ser Tyr
    2780                2785                2790

Lys Val Leu Asp Asn Gly Val Ile Arg Asp Val Ser Val Glu Asp
    2795                2800                2805

Val Cys Phe Ala Asn Lys Phe Glu Gln Phe Asp Gln Trp Tyr Glu
    2810                2815                2820

Ser Thr Phe Gly Leu Ser Tyr Tyr Ser Asn Ser Met Ala Cys Pro
    2825                2830                2835

Ile Val Val Ala Val Val Asp Gln Asp Leu Gly Ser Thr Val Phe
    2840                2845                2850

Asn Val Pro Thr Lys Val Leu Arg Tyr Gly Tyr His Val Leu His
    2855                2860                2865

Phe Ile Thr His Ala Leu Ser Ala Asp Gly Val Gln Cys Tyr Thr
    2870                2875                2880

Pro His Ser Gln Ile Ser Tyr Ser Asn Phe Tyr Ala Ser Gly Cys
    2885                2890                2895

Val Leu Ser Ser Ala Cys Thr Met Phe Ala Met Ala Asp Gly Ser
    2900                2905                2910

Pro Gln Pro Tyr Cys Tyr Thr Glu Gly Leu Met Gln Asn Ala Ser
    2915                2920                2925

Leu Tyr Ser Ser Leu Val Pro His Val Arg Tyr Asn Leu Ala Asn
    2930                2935                2940
```

-continued

| | | | | | | | | | | | |
|---|---|---|---|---|---|---|---|---|---|---|---|
| Ala | Lys | Gly | Phe | Ile | Arg | Phe | Pro | Glu | Val | Leu | Arg | Glu | Gly | Leu |
| 2945 | | | | | 2950 | | | | | 2955 | | | | |

Ala Lys Gly Phe Ile Arg Phe Pro Glu Val Leu Arg Glu Gly Leu
2945                 2950                2955

Val Arg Ile Val Arg Thr Arg Ser Met Ser Tyr Cys Arg Val Gly
2960                 2965                2970

Leu Cys Glu Glu Ala Asp Glu Gly Ile Cys Phe Asn Phe Asn Gly
2975                 2980                2985

Ser Trp Val Leu Asn Asn Asp Tyr Tyr Arg Ser Leu Pro Gly Thr
2990                 2995                3000

Phe Cys Gly Arg Asp Val Phe Asp Leu Ile Tyr Gln Leu Phe Lys
3005                 3010                3015

Gly Leu Ala Gln Pro Val Asp Phe Leu Ala Leu Thr Ala Ser Ser
3020                 3025                3030

Ile Ala Gly Ala Ile Leu Ala Val Ile Val Val Leu Val Phe Tyr
3035                 3040                3045

Tyr Leu Ile Lys Leu Lys Arg Ala Phe Gly Asp Tyr Thr Ser Ile
3050                 3055                3060

Val Phe Val Asn Val Ile Val Trp Cys Val Asn Phe Met Met Leu
3065                 3070                3075

Phe Val Phe Gln Val Tyr Pro Thr Leu Ser Cys Val Tyr Ala Ile
3080                 3085                3090

Cys Tyr Phe Tyr Ala Thr Leu Tyr Phe Pro Ser Glu Ile Ser Val
3095                 3100                3105

Ile Met His Leu Gln Trp Leu Val Met Tyr Gly Thr Ile Met Pro
3110                 3115                3120

Leu Trp Phe Cys Leu Leu Tyr Ile Ser Val Val Ser Asn His
3125                 3130                3135

Ala Phe Trp Val Phe Ala Tyr Cys Arg Arg Leu Gly Thr Ser Val
3140                 3145                3150

Arg Ser Asp Gly Thr Phe Glu Glu Met Ala Leu Thr Thr Phe Met
3155                 3160                3165

Ile Thr Lys Asp Ser Tyr Cys Lys Leu Lys Asn Ser Leu Ser Asp
3170                 3175                3180

Val Ala Phe Asn Arg Tyr Leu Ser Leu Tyr Asn Lys Tyr Arg Tyr
3185                 3190                3195

Tyr Ser Gly Lys Met Asp Thr Ala Ala Tyr Arg Glu Ala Ala Cys
3200                 3205                3210

Ser Gln Leu Ala Lys Ala Met Asp Thr Phe Thr Asn Asn Asn Gly
3215                 3220                3225

Ser Asp Val Leu Tyr Gln Pro Pro Thr Ala Ser Val Ser Thr Ser
3230                 3235                3240

Phe Leu Gln Ser Gly Ile Val Lys Met Val Asn Pro Thr Ser Lys
3245                 3250                3255

Val Glu Pro Cys Ile Val Ser Val Thr Tyr Gly Asn Met Thr Leu
3260                 3265                3270

Asn Gly Leu Trp Leu Asp Asp Lys Val Tyr Cys Pro Arg His Val
3275                 3280                3285

Ile Cys Ser Ala Ser Asp Met Thr Asn Pro Asp Tyr Thr Asn Leu
3290                 3295                3300

Leu Cys Arg Val Thr Ser Ser Asp Phe Thr Val Leu Phe Asp Arg
3305                 3310                3315

Leu Ser Leu Thr Val Met Ser Tyr Gln Met Gln Gly Cys Met Leu
3320                 3325                3330

Val Leu Thr Val Thr Leu Gln Asn Ser Arg Thr Pro Lys Tyr Thr
3335                 3340                3345

```
Phe Gly Val Val Lys Pro Gly Glu Thr Phe Thr Val Leu Ala Ala
    3350             3355             3360

Tyr Asn Gly Lys Pro Gln Gly Ala Phe His Val Thr Met Arg Ser
    3365             3370             3375

Ser Tyr Thr Ile Lys Gly Ser Phe Leu Cys Gly Ser Cys Gly Ser
    3380             3385             3390

Val Gly Tyr Val Leu Met Gly Asp Cys Val Lys Phe Val Tyr Met
    3395             3400             3405

His Gln Leu Glu Leu Ser Thr Gly Cys His Thr Gly Thr Asp Phe
    3410             3415             3420

Asn Gly Asp Phe Tyr Gly Pro Tyr Lys Asp Ala Gln Val Val Gln
    3425             3430             3435

Leu Pro Val Gln Asp Tyr Ile Gln Ser Val Asn Phe Val Ala Trp
    3440             3445             3450

Leu Tyr Ala Ala Ile Leu Asn Asn Cys Asn Trp Phe Val Gln Ser
    3455             3460             3465

Asp Lys Cys Ser Val Glu Asp Phe Asn Val Trp Ala Leu Ser Asn
    3470             3475             3480

Gly Phe Ser Gln Val Lys Ser Asp Leu Val Ile Asp Ala Leu Ala
    3485             3490             3495

Ser Met Thr Gly Val Ser Leu Glu Thr Leu Leu Ala Ala Ile Lys
    3500             3505             3510

Arg Leu Lys Asn Gly Phe Gln Gly Arg Gln Ile Met Gly Ser Cys
    3515             3520             3525

Ser Phe Glu Asp Glu Leu Thr Pro Ser Asp Val Tyr Gln Gln Leu
    3530             3535             3540

Ala Gly Ile Lys Leu Gln Ser Lys Arg Thr Arg Leu Val Lys Gly
    3545             3550             3555

Ile Val Cys Trp Ile Met Ala Ser Thr Phe Leu Phe Ser Cys Ile
    3560             3565             3570

Ile Thr Ala Phe Val Lys Trp Thr Met Phe Met Tyr Val Thr Thr
    3575             3580             3585

Asn Met Leu Ser Ile Thr Phe Cys Ala Leu Cys Val Ile Ser Leu
    3590             3595             3600

Ala Met Leu Leu Val Lys His Lys His Leu Tyr Leu Thr Met Tyr
    3605             3610             3615

Ile Ile Pro Val Leu Phe Thr Leu Leu Tyr Asn Asn Tyr Leu Val
    3620             3625             3630

Val Tyr Lys Gln Thr Phe Arg Gly Tyr Val Tyr Ala Trp Leu Ser
    3635             3640             3645

Tyr Tyr Val Pro Ser Val Glu Tyr Thr Tyr Thr Asp Glu Val Ile
    3650             3655             3660

Tyr Gly Met Leu Leu Leu Ile Gly Met Val Phe Val Thr Leu Arg
    3665             3670             3675

Ser Ile Asn His Asp Leu Phe Ser Phe Ile Met Phe Val Gly Arg
    3680             3685             3690

Val Ile Ser Val Val Ser Leu Trp Tyr Met Gly Ser Asn Leu Glu
    3695             3700             3705

Glu Glu Ile Leu Leu Met Leu Ala Ser Leu Phe Gly Thr Tyr Thr
    3710             3715             3720

Trp Thr Thr Ala Leu Ser Met Ala Ala Ala Lys Val Ile Ala Lys
    3725             3730             3735

Trp Val Ala Val Asn Val Leu Tyr Phe Thr Asp Ile Pro Gln Ile
```

```
               3740            3745              3750
Lys Ile Val Leu Val Cys Tyr Leu Phe Ile Gly Tyr Ile Ile Ser
    3755            3760              3765

Cys Tyr Trp Gly Leu Phe Ser Leu Met Asn Ser Leu Phe Arg Met
    3770            3775              3780

Pro Leu Gly Val Tyr Asn Tyr Lys Ile Ser Val Gln Glu Leu Arg
    3785            3790              3795

Tyr Met Asn Ala Asn Gly Leu Arg Pro Pro Lys Asn Ser Phe Glu
    3800            3805              3810

Ala Leu Met Leu Asn Phe Lys Leu Leu Gly Ile Gly Gly Val Pro
    3815            3820              3825

Ile Ile Glu Val Ser Gln Phe Gln Ser Lys Leu Thr Asp Val Lys
    3830            3835              3840

Cys Ala Asn Val Val Leu Leu Asn Cys Leu Gln His Leu His Val
    3845            3850              3855

Ala Ser Asn Ser Lys Leu Trp Gln Tyr Cys Ser Thr Leu His Asn
    3860            3865              3870

Glu Ile Leu Ala Thr Ser Asp Leu Gly Val Ala Phe Glu Lys Leu
    3875            3880              3885

Ala Gln Leu Leu Ile Val Leu Phe Ala Asn Pro Ala Ala Val Asp
    3890            3895              3900

Ser Lys Cys Leu Thr Ser Ile Glu Glu Val Cys Asp Asp Tyr Ala
    3905            3910              3915

Lys Asp Asn Thr Val Leu Gln Ala Leu Gln Ser Glu Phe Val Asn
    3920            3925              3930

Met Ala Ser Phe Val Glu Tyr Glu Val Ala Lys Lys Asn Leu Asp
    3935            3940              3945

Glu Ala Arg Ser Ser Gly Ser Ala Asn Gln Gln Gln Leu Lys Gln
    3950            3955              3960

Leu Glu Lys Ala Cys Asn Ile Ala Lys Ser Ala Tyr Glu Arg Asp
    3965            3970              3975

Arg Ala Val Ala Arg Lys Leu Glu Arg Met Ala Asp Leu Ala Leu
    3980            3985              3990

Thr Asn Met Tyr Lys Glu Ala Arg Ile Asn Asp Lys Lys Ser Lys
    3995            4000              4005

Val Val Ser Ala Leu Gln Thr Met Leu Phe Ser Met Val Arg Lys
    4010            4015              4020

Leu Asp Asn Gln Ala Leu Asn Ser Ile Leu Asp Asn Ala Val Lys
    4025            4030              4035

Gly Cys Val Pro Leu Asn Ala Ile Pro Ser Leu Ala Ala Asn Thr
    4040            4045              4050

Leu Thr Ile Ile Val Pro Asp Lys Ser Val Tyr Asp Gln Val Val
    4055            4060              4065

Asp Asn Val Tyr Val Thr Tyr Ala Gly Asn Val Trp Gln Ile Gln
    4070            4075              4080

Thr Ile Gln Asp Ser Asp Gly Thr Asn Lys Gln Leu Asn Glu Ile
    4085            4090              4095

Ser Asp Asp Cys Asn Trp Pro Leu Val Ile Ile Ala Asn Arg His
    4100            4105              4110

Asn Glu Val Ser Ala Thr Val Leu Gln Asn Asn Glu Leu Met Pro
    4115            4120              4125

Ala Lys Leu Lys Thr Gln Val Val Asn Ser Gly Pro Asp Gln Thr
    4130            4135              4140
```

```
Cys Asn Thr Pro Thr Gln Cys Tyr Tyr Asn Asn Ser Asn Asn Gly
    4145            4150                4155

Lys Ile Val Tyr Ala Ile Leu Ser Asp Val Asp Gly Leu Lys Tyr
    4160            4165                4170

Thr Lys Ile Leu Lys Asp Asp Gly Asn Phe Val Val Leu Glu Leu
    4175            4180                4185

Asp Pro Pro Cys Lys Phe Thr Val Gln Asp Val Lys Gly Leu Lys
    4190            4195                4200

Ile Lys Tyr Leu Tyr Phe Val Lys Gly Cys Asn Thr Leu Ala Arg
    4205            4210                4215

Gly Trp Val Val Gly Thr Ile Ser Ser Thr Val Arg Leu Gln Ala
    4220            4225                4230

Gly Thr Ala Thr Glu Tyr Ala Ser Asn Ser Ser Ile Leu Ser Leu
    4235            4240                4245

Cys Ala Phe Ser Val Asp Pro Lys Lys Thr Tyr Leu Asp Phe Ile
    4250            4255                4260

Gln Gln Gly Gly Thr Pro Ile Ala Asn Cys Val Lys Met Leu Cys
    4265            4270                4275

Asp His Ala Gly Thr Gly Met Ala Ile Thr Val Lys Pro Asp Ala
    4280            4285                4290

Thr Thr Asn Gln Asp Ser Tyr Gly Gly Ala Ser Val Cys Ile Tyr
    4295            4300                4305

Cys Arg Ala Arg Val Glu His Pro Asp Val Asp Gly Leu Cys Lys
    4310            4315                4320

Leu Arg Gly Lys Phe Val Gln Val Pro Val Gly Ile Lys Asp Pro
    4325            4330                4335

Val Ser Tyr Val Leu Thr His Asp Val Cys Gln Val Cys Gly Phe
    4340            4345                4350

Trp Arg Asp Gly Ser Cys Ser Cys Val Ser Thr Asp Thr Thr Val
    4355            4360                4365

Gln Ser Lys Asp Thr Asn Phe Leu Asn Arg Val Arg Gly Thr Ser
    4370            4375                4380

Val Asp Ala Arg Leu Val Pro Cys Ala Ser Gly Leu Ser Thr Asp
    4385            4390                4395

Val Gln Leu Arg Ala Phe Asp Ile Cys Asn Ala Ser Val Ala Gly
    4400            4405                4410

Ile Gly Leu His Leu Lys Val Asn Cys Cys Arg Phe Gln Arg Val
    4415            4420                4425

Asp Glu Asn Gly Asp Lys Leu Asp Gln Phe Phe Val Val Lys Arg
    4430            4435                4440

Thr Asp Leu Thr Ile Tyr Asn Arg Glu Met Glu Cys Tyr Glu Arg
    4445            4450                4455

Val Lys Asp Cys Lys Phe Val Ala Glu His Asp Phe Phe Thr Phe
    4460            4465                4470

Asp Val Glu Gly Ser Arg Val Pro His Ile Val Arg Lys Asp Leu
    4475            4480                4485

Thr Lys Tyr Thr Met Leu Asp Leu Cys Tyr Ala Leu Arg His Phe
    4490            4495                4500

Asp Arg Asn Asp Cys Met Leu Leu Cys Asp Ile Leu Ser Ile Tyr
    4505            4510                4515

Ala Gly Cys Glu Gln Ser Tyr Phe Thr Lys Lys Asp Trp Tyr Asp
    4520            4525                4530

Phe Val Glu Asn Pro Asp Ile Ile Asn Val Tyr Lys Lys Leu Gly
    4535            4540                4545
```

```
Pro Ile Phe Asn Arg Ala Leu Val Ser Ala Thr Glu Phe Ala Asp
    4550                4555                4560

Lys Leu Val Glu Val Gly Leu Val Gly Ile Leu Thr Leu Asp Asn
    4565                4570                4575

Gln Asp Leu Asn Gly Lys Trp Tyr Asp Phe Gly Asp Tyr Val Ile
    4580                4585                4590

Ala Ala Pro Gly Cys Gly Val Ala Ile Ala Asp Ser Tyr Tyr Ser
    4595                4600                4605

Tyr Met Met Pro Met Leu Thr Met Cys His Ala Leu Asp Cys Glu
    4610                4615                4620

Leu Tyr Val Asn Asn Ala Tyr Arg Leu Phe Asp Leu Val Gln Tyr
    4625                4630                4635

Asp Phe Thr Asp Tyr Lys Leu Glu Leu Phe Asn Lys Tyr Phe Lys
    4640                4645                4650

His Trp Ser Met Pro Tyr His Pro Asn Thr Val Asp Cys Gln Asp
    4655                4660                4665

Asp Arg Cys Ile Ile His Cys Ala Asn Phe Asn Ile Leu Phe Ser
    4670                4675                4680

Met Val Leu Pro Asn Thr Cys Phe Gly Pro Leu Val Arg Gln Ile
    4685                4690                4695

Phe Val Asp Gly Val Pro Phe Val Val Ser Ile Gly Tyr His Tyr
    4700                4705                4710

Lys Glu Leu Gly Ile Val Met Asn Met Asp Val Asp Thr His Arg
    4715                4720                4725

Tyr Arg Leu Ser Leu Lys Asp Leu Leu Leu Tyr Ala Ala Asp Pro
    4730                4735                4740

Ala Leu His Val Ala Ser Ala Ser Ala Leu Tyr Asp Leu Arg Thr
    4745                4750                4755

Cys Cys Phe Ser Val Ala Ala Ile Thr Ser Gly Val Lys Phe Gln
    4760                4765                4770

Thr Val Lys Pro Gly Asn Phe Asn Gln Asp Phe Tyr Asp Phe Ile
    4775                4780                4785

Leu Ser Lys Gly Leu Leu Lys Glu Gly Ser Ser Val Asp Leu Lys
    4790                4795                4800

His Phe Phe Phe Thr Gln Asp Gly Asn Ala Ala Ile Thr Asp Tyr
    4805                4810                4815

Asn Tyr Tyr Lys Tyr Asn Leu Pro Thr Met Val Asp Ile Lys Gln
    4820                4825                4830

Leu Leu Phe Val Leu Glu Val Val Tyr Lys Tyr Phe Glu Ile Tyr
    4835                4840                4845

Asp Gly Gly Cys Ile Pro Ala Ser Gln Val Ile Val Asn Asn Tyr
    4850                4855                4860

Asp Lys Ser Ala Gly Tyr Pro Phe Asn Lys Phe Gly Lys Ala Arg
    4865                4870                4875

Leu Tyr Tyr Glu Ala Leu Ser Phe Glu Glu Gln Asp Glu Ile Tyr
    4880                4885                4890

Ala Tyr Thr Lys Arg Asn Val Leu Pro Thr Leu Thr Gln Met Asn
    4895                4900                4905

Leu Lys Tyr Ala Ile Ser Ala Lys Asn Arg Ala Arg Thr Val Ala
    4910                4915                4920

Gly Val Ser Ile Leu Ser Thr Met Thr Gly Arg Met Phe His Gln
    4925                4930                4935

Lys Cys Leu Lys Ser Ile Ala Ala Thr Arg Gly Val Pro Val Val
```

```
                    4940              4945              4950

Ile Gly Thr Thr Lys Phe Tyr Gly Gly Trp Asp Asp Met Leu Arg
    4955              4960              4965

Arg Leu Ile Lys Asp Val Asp Asn Pro Val Leu Met Gly Trp Asp
    4970              4975              4980

Tyr Pro Lys Cys Asp Arg Ala Met Pro Asn Ile Leu Arg Ile Val
    4985              4990              4995

Ser Ser Leu Val Leu Ala Arg Lys His Glu Ala Cys Cys Ser Gln
    5000              5005              5010

Ser Asp Arg Phe Tyr Arg Leu Ala Asn Glu Cys Ala Gln Val Leu
    5015              5020              5025

Ser Glu Ile Val Met Cys Gly Gly Cys Tyr Tyr Val Lys Pro Gly
    5030              5035              5040

Gly Thr Ser Ser Gly Asp Ala Thr Thr Ala Phe Ala Asn Ser Val
    5045              5050              5055

Phe Asn Ile Cys Gln Ala Val Ser Ala Asn Val Cys Ala Leu Met
    5060              5065              5070

Ser Cys Asn Gly Asn Lys Ile Glu Asp Leu Ser Ile Arg Ala Leu
    5075              5080              5085

Gln Lys Arg Leu Tyr Ser His Val Tyr Arg Ser Asp Met Val Asp
    5090              5095              5100

Ser Thr Phe Val Thr Glu Tyr Tyr Glu Phe Leu Asn Lys His Phe
    5105              5110              5115

Ser Met Met Ile Leu Ser Asp Asp Gly Val Val Cys Tyr Asn Ser
    5120              5125              5130

Asp Tyr Ala Ser Lys Gly Tyr Ile Ala Asn Ile Ser Ala Phe Gln
    5135              5140              5145

Gln Val Leu Tyr Tyr Gln Asn Asn Val Phe Met Ser Glu Ser Lys
    5150              5155              5160

Cys Trp Val Glu Asn Asp Ile Asn Asn Gly Pro His Glu Phe Cys
    5165              5170              5175

Ser Gln His Thr Met Leu Val Lys Met Asp Gly Asp Asp Val Tyr
    5180              5185              5190

Leu Pro Tyr Pro Asp Pro Ser Arg Ile Leu Gly Ala Gly Cys Phe
    5195              5200              5205

Val Asp Asp Leu Leu Lys Thr Asp Ser Val Leu Leu Ile Glu Arg
    5210              5215              5220

Phe Val Ser Leu Ala Ile Asp Ala Tyr Pro Leu Val Tyr His Glu
    5225              5230              5235

Asn Glu Glu Tyr Gln Lys Val Phe Arg Val Tyr Leu Glu Tyr Ile
    5240              5245              5250

Lys Lys Leu Tyr Asn Asp Leu Gly Asn Gln Ile Leu Asp Ser Tyr
    5255              5260              5265

Ser Val Ile Leu Ser Thr Cys Asp Gly Gln Lys Phe Thr Asp Glu
    5270              5275              5280

Ser Phe Tyr Lys Asn Met Tyr Leu Arg Ser Ala Val Met Gln Ser
    5285              5290              5295

Val Gly Ala Cys Val Val Cys Ser Ser Gln Thr Ser Leu Arg Cys
    5300              5305              5310

Gly Ser Cys Ile Arg Lys Pro Leu Leu Cys Cys Lys Cys Cys Tyr
    5315              5320              5325

Asp His Val Met Ala Thr Asp His Lys Tyr Val Leu Ser Val Ser
    5330              5335              5340
```

-continued

Pro Tyr Val Cys Asn Ala Pro Gly Cys Asp Val Asn Asp Val Thr
5345                5350                5355

Lys Leu Tyr Leu Gly Gly Met Ser Tyr Tyr Cys Glu Asp His Lys
5360                5365                5370

Pro Gln Tyr Ser Phe Lys Leu Val Met Asn Gly Met Val Phe Gly
5375                5380                5385

Leu Tyr Lys Gln Ser Cys Thr Gly Ser Pro Tyr Ile Asp Asp Phe
5390                5395                5400

Asn Arg Ile Ala Ser Cys Lys Trp Thr Asp Val Asp Asp Tyr Ile
5405                5410                5415

Leu Ala Asn Glu Cys Thr Glu Arg Leu Lys Leu Phe Ala Ala Glu
5420                5425                5430

Thr Gln Lys Ala Thr Glu Glu Ala Phe Lys Gln Ser Tyr Ala Ser
5435                5440                5445

Ala Thr Ile Gln Glu Ile Val Ser Glu Arg Glu Leu Ile Leu Ser
5450                5455                5460

Trp Glu Ile Gly Lys Val Lys Pro Pro Leu Asn Lys Asn Tyr Val
5465                5470                5475

Phe Thr Gly Tyr His Phe Thr Lys Asn Gly Lys Thr Val Leu Gly
5480                5485                5490

Glu Tyr Val Phe Asp Lys Ser Glu Leu Thr Asn Gly Val Tyr Tyr
5495                5500                5505

Arg Ala Thr Thr Thr Tyr Lys Leu Ser Val Gly Asp Val Phe Val
5510                5515                5520

Leu Thr Ser His Ser Val Ala Asn Leu Ser Ala Pro Thr Leu Val
5525                5530                5535

Pro Gln Glu Asn Tyr Ser Ser Ile Arg Phe Ala Ser Val Tyr Ser
5540                5545                5550

Val Leu Glu Thr Phe Gln Asn Asn Val Val Asn Tyr Gln His Ile
5555                5560                5565

Gly Met Lys Arg Tyr Cys Thr Val Gln Gly Pro Pro Gly Thr Gly
5570                5575                5580

Lys Ser His Leu Ala Ile Gly Leu Ala Val Tyr Tyr Cys Thr Ala
5585                5590                5595

Arg Val Val Tyr Thr Ala Ala Ser His Ala Ala Val Asp Ala Leu
5600                5605                5610

Cys Glu Lys Ala Tyr Lys Phe Leu Asn Ile Asn Asp Cys Thr Arg
5615                5620                5625

Ile Val Pro Ala Lys Val Arg Val Glu Cys Tyr Asp Lys Phe Lys
5630                5635                5640

Ile Asn Asp Thr Thr Arg Lys Tyr Val Phe Thr Thr Ile Asn Ala
5645                5650                5655

Leu Pro Glu Met Val Thr Asp Ile Val Val Val Asp Glu Val Ser
5660                5665                5670

Met Leu Thr Asn Tyr Glu Leu Ser Val Ile Asn Ala Arg Ile Arg
5675                5680                5685

Ala Lys His Tyr Val Tyr Ile Gly Asp Pro Ala Gln Leu Pro Ala
5690                5695                5700

Pro Arg Val Leu Leu Ser Lys Gly Thr Leu Glu Pro Lys Tyr Phe
5705                5710                5715

Asn Thr Val Thr Lys Leu Met Cys Cys Leu Gly Pro Asp Ile Phe
5720                5725                5730

Leu Gly Thr Cys Tyr Arg Cys Pro Lys Glu Ile Val Asp Thr Val
5735                5740                5745

Ser Ala Leu Val Tyr Glu Asn Lys Leu Lys Ala Lys Asn Glu Ser
5750                5755                5760

Ser Ser Leu Cys Phe Lys Val Tyr Tyr Lys Gly Val Thr Thr His
5765                5770                5775

Glu Ser Ser Ser Ala Val Asn Met Gln Gln Ile Tyr Leu Ile Asn
5780                5785                5790

Lys Phe Leu Lys Ala Asn Pro Leu Trp His Lys Ala Val Phe Ile
5795                5800                5805

Ser Pro Tyr Asn Ser Gln Asn Phe Ala Ala Lys Arg Val Leu Gly
5810                5815                5820

Leu Gln Thr Gln Thr Val Asp Ser Ala Gln Gly Ser Glu Tyr Asp
5825                5830                5835

Tyr Val Ile Tyr Ser Gln Thr Ala Glu Thr Ala His Ser Val Asn
5840                5845                5850

Val Asn Arg Phe Asn Val Ala Ile Thr Arg Ala Lys Lys Gly Ile
5855                5860                5865

Leu Cys Val Met Ser Asn Met Gln Leu Phe Glu Ala Leu Gln Phe
5870                5875                5880

Thr Thr Leu Thr Leu Asp Lys Val Pro Gln Ala Val Glu Thr Arg
5885                5890                5895

Val Gln Cys Ser Thr Asn Leu Phe Lys Asp Cys Ser Lys Ser Tyr
5900                5905                5910

Ser Gly Tyr His Pro Ala His Ala Pro Ser Phe Leu Ala Val Asp
5915                5920                5925

Asp Lys Tyr Lys Ala Thr Gly Asp Leu Ala Val Cys Leu Gly Ile
5930                5935                5940

Gly Asp Ser Ala Val Thr Tyr Ser Arg Leu Ile Ser Leu Met Gly
5945                5950                5955

Phe Lys Leu Asp Val Thr Leu Asp Gly Tyr Cys Lys Leu Phe Ile
5960                5965                5970

Thr Lys Glu Glu Ala Val Lys Arg Val Arg Ala Trp Val Gly Phe
5975                5980                5985

Asp Ala Glu Gly Ala His Ala Thr Arg Asp Ser Ile Gly Thr Asn
5990                5995                6000

Phe Pro Leu Gln Leu Gly Phe Ser Thr Gly Ile Asp Phe Val Val
6005                6010                6015

Glu Ala Thr Gly Leu Phe Ala Asp Arg Asp Gly Tyr Ser Phe Lys
6020                6025                6030

Lys Ala Val Ala Lys Ala Pro Pro Gly Glu Gln Phe Lys His Leu
6035                6040                6045

Ile Pro Leu Met Thr Arg Gly Gln Arg Trp Asp Val Val Arg Pro
6050                6055                6060

Arg Ile Val Gln Met Phe Ala Asp His Leu Ile Asp Leu Ser Asp
6065                6070                6075

Cys Val Val Leu Val Thr Trp Ala Ala Asn Phe Glu Leu Thr Cys
6080                6085                6090

Leu Arg Tyr Phe Ala Lys Val Gly Arg Glu Ile Ser Cys Asn Val
6095                6100                6105

Cys Thr Lys Arg Ala Thr Ala Tyr Asn Ser Arg Thr Gly Tyr Tyr
6110                6115                6120

Gly Cys Trp Arg His Ser Val Thr Cys Asp Tyr Leu Tyr Asn Pro
6125                6130                6135

Leu Ile Val Asp Ile Gln Gln Trp Gly Tyr Ile Gly Ser Leu Ser

|  |  |  |
| --- | --- | --- |
| 6140 | 6145 | 6150 |

Ser Asn His Asp Leu Tyr Cys Ser Val His Lys Gly Ala His Val
6155                6160                6165

Ala Ser Ser Asp Ala Ile Met Thr Arg Cys Leu Ala Val Tyr Asp
6170                6175                6180

Cys Phe Cys Asn Asn Ile Asn Trp Asn Val Glu Tyr Pro Ile Ile
6185                6190                6195

Ser Asn Glu Leu Ser Ile Asn Thr Ser Cys Arg Val Leu Gln Arg
6200                6205                6210

Val Met Leu Lys Ala Ala Met Leu Cys Asn Arg Tyr Thr Leu Cys
6215                6220                6225

Tyr Asp Ile Gly Asn Pro Lys Ala Ile Ala Cys Val Lys Asp Phe
6230                6235                6240

Asp Phe Lys Phe Tyr Asp Ala Gln Pro Ile Val Lys Ser Val Lys
6245                6250                6255

Thr Leu Leu Tyr Ser Phe Glu Ala His Lys Asp Ser Phe Lys Asp
6260                6265                6270

Gly Leu Cys Met Phe Trp Asn Cys Asn Val Asp Lys Tyr Pro Pro
6275                6280                6285

Asn Ala Val Val Cys Arg Phe Asp Thr Arg Val Leu Asn Asn Leu
6290                6295                6300

Asn Leu Pro Gly Cys Asn Gly Gly Ser Leu Tyr Val Asn Lys His
6305                6310                6315

Ala Phe His Thr Lys Pro Phe Ser Arg Ala Ala Phe Glu His Leu
6320                6325                6330

Lys Pro Met Pro Phe Phe Tyr Tyr Ser Asp Thr Pro Cys Val Tyr
6335                6340                6345

Met Asp Gly Met Asp Ala Lys Gln Val Asp Tyr Val Pro Leu Lys
6350                6355                6360

Ser Ala Thr Cys Ile Thr Arg Cys Asn Leu Gly Gly Ala Val Cys
6365                6370                6375

Leu Lys His Ala Glu Glu Tyr Arg Glu Tyr Leu Glu Ser Tyr Asn
6380                6385                6390

Thr Ala Thr Thr Ala Gly Phe Thr Phe Trp Val Tyr Lys Thr Phe
6395                6400                6405

Asp Phe Tyr Asn Leu Trp Asn Thr Phe Thr Lys Leu Gln Ser Leu
6410                6415                6420

Glu Asn Val Val Tyr Asn Leu Val Lys Thr Gly His Tyr Thr Gly
6425                6430                6435

Gln Ala Gly Glu Met Pro Cys Ala Ile Ile Asn Asp Lys Val Val
6440                6445                6450

Ala Lys Ile Asp Lys Glu Asp Val Val Ile Phe Ile Asn Asn Thr
6455                6460                6465

Thr Tyr Pro Thr Asn Val Ala Val Glu Leu Phe Ala Lys Arg Ser
6470                6475                6480

Ile Arg His His Pro Glu Leu Lys Leu Phe Arg Asn Leu Asn Ile
6485                6490                6495

Asp Val Cys Trp Lys His Val Ile Trp Asp Tyr Ala Arg Glu Ser
6500                6505                6510

Ile Phe Cys Ser Asn Thr Tyr Gly Val Cys Met Tyr Thr Asp Leu
6515                6520                6525

Lys Phe Ile Asp Lys Leu Asn Val Leu Phe Asp Gly Arg Asp Asn
6530                6535                6540

-continued

```
Gly Ala Leu Glu Ala Phe Lys Arg Ser Asn Asn Gly Val Tyr Ile
6545                6550                6555

Ser Thr Thr Lys Val Lys Ser Leu Ser Met Ile Lys Gly Pro Pro
6560                6565                6570

Arg Ala Glu Leu Asn Gly Val Val Val Asp Lys Val Gly Asp Thr
6575                6580                6585

Asp Cys Val Phe Tyr Phe Ala Val Arg Lys Glu Gly Gln Asp Val
6590                6595                6600

Ile Phe Ser Gln Phe Asp Ser Leu Arg Val Ser Ser Asn Gln Ser
6605                6610                6615

Pro Gln Gly Asn Leu Gly Ser Asn Glu Pro Gly Asn Val Gly Gly
6620                6625                6630

Asn Asp Ala Leu Ala Thr Ser Thr Ile Phe Thr Gln Ser Arg Val
6635                6640                6645

Ile Ser Ser Phe Thr Cys Arg Thr Asp Met Glu Lys Asp Phe Ile
6650                6655                6660

Ala Leu Asp Gln Asp Leu Phe Ile Gln Lys Tyr Gly Leu Glu Asp
6665                6670                6675

Tyr Ala Phe Glu His Ile Val Tyr Gly Asn Phe Asn Gln Lys Ile
6680                6685                6690

Ile Gly Gly Leu His Leu Leu Ile Gly Leu Tyr Arg Arg Gln Gln
6695                6700                6705

Thr Ser Asn Leu Val Ile Gln Glu Phe Val Ser Tyr Asp Ser Ser
6710                6715                6720

Ile His Ser Tyr Phe Ile Thr Asp Glu Lys Ser Gly Gly Ser Lys
6725                6730                6735

Ser Val Cys Thr Val Ile Asp Ile Leu Leu Asp Asp Phe Val Ala
6740                6745                6750

Leu Val Lys Ser Leu Asn Leu Asn Cys Val Ser Lys Val Val Asn
6755                6760                6765

Val Asn Val Asp Phe Lys Asp Phe Gln Phe Met Leu Trp Cys Asn
6770                6775                6780

Asp Glu Lys Val Met Thr Phe Tyr Pro Arg Leu Gln Ala Ala Ser
6785                6790                6795

Asp Trp Lys Pro Gly Tyr Ser Met Pro Val Leu Tyr Lys Tyr Leu
6800                6805                6810

Asn Ser Pro Met Glu Arg Val Ser Leu Trp Asn Tyr Gly Lys Pro
6815                6820                6825

Val Thr Leu Pro Thr Gly Cys Met Met Asn Val Ala Lys Tyr Thr
6830                6835                6840

Gln Leu Cys Gln Tyr Leu Asn Thr Thr Thr Leu Ala Val Pro Val
6845                6850                6855

Asn Met Arg Val Leu His Leu Gly Ala Gly Ser Glu Lys Gly Val
6860                6865                6870

Ala Pro Gly Ser Ala Val Leu Arg Gln Trp Leu Pro Ala Gly Thr
6875                6880                6885

Ile Leu Val Asp Asn Asp Leu Tyr Pro Phe Val Ser Asp Ser Val
6890                6895                6900

Ala Thr Tyr Phe Gly Asp Cys Ile Thr Leu Pro Phe Asp Cys Gln
6905                6910                6915

Trp Asp Leu Ile Ile Ser Asp Met Tyr Asp Pro Ile Thr Lys Asn
6920                6925                6930

Ile Gly Glu Tyr Asn Val Ser Lys Asp Gly Phe Phe Thr Tyr Ile
6935                6940                6945
```

-continued

```
Cys His Met Ile Arg Asp Lys Leu Ala Leu Gly Gly Ser Val Ala
    6950             6955             6960

Ile Lys Ile Thr Glu Phe Ser Trp Asn Ala Glu Leu Tyr Lys Leu
    6965             6970             6975

Met Gly Tyr Phe Ala Phe Trp Thr Val Phe Cys Thr Asn Ala Asn
    6980             6985             6990

Ala Ser Ser Ser Glu Gly Phe Leu Ile Gly Ile Asn Tyr Leu Gly
    6995             7000             7005

Lys Pro Lys Val Glu Ile Asp Gly Asn Val Met His Ala Asn Tyr
    7010             7015             7020

Leu Phe Trp Arg Asn Ser Thr Val Trp Asn Gly Gly Ala Tyr Ser
    7025             7030             7035

Leu Phe Asp Met Ala Lys Phe Pro Leu Lys Leu Ala Gly Thr Ala
    7040             7045             7050

Val Ile Asn Leu Arg Ala Asp Gln Ile Asn Asp Met Val Tyr Ser
    7055             7060             7065

Leu Leu Glu Lys Gly Lys Leu Leu Val Arg Asp Thr Asn Lys Glu
    7070             7075             7080

Val Phe Val Gly Asp Ser Leu Val Asn Val Ile
    7085             7090
```